(12) United States Patent
Chen et al.

(10) Patent No.: US 9,416,179 B2
(45) Date of Patent: Aug. 16, 2016

(54) PDGF RECEPTOR BETA BINDING POLYPEPTIDES

(71) Applicant: X-Body, Inc., Waltham, MA (US)

(72) Inventors: Yan Chen, Lexington, MA (US); Richard W. Wagner, Cambridge, MA (US); Csaba Pazmany, Cambridge, MA (US)

(73) Assignee: X-Body, Inc., Waltham, MA (US)

( * ) Notice: Subject to any disclaimer, the term of this patent is extended or adjusted under 35 U.S.C. 154(b) by 193 days.

(21) Appl. No.: 13/705,978

(22) Filed: Dec. 5, 2012

(65) Prior Publication Data

US 2013/0177572 A1 Jul. 11, 2013

Related U.S. Application Data

(60) Provisional application No. 61/566,778, filed on Dec. 5, 2011, provisional application No. 61/610,905, filed on Mar. 14, 2012.

(51) Int. Cl.
| | |
|---|---|
| *C07K 16/28* | (2006.01) |
| *A61K 39/00* | (2006.01) |
| *C07K 16/22* | (2006.01) |
| *C07K 14/49* | (2006.01) |
| *C07K 14/71* | (2006.01) |

(52) U.S. Cl.
CPC .............. *C07K 16/22* (2013.01); *C07K 14/49* (2013.01); *C07K 14/71* (2013.01); *C07K 16/2863* (2013.01); *A61K 39/00* (2013.01); *C07K 16/28* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 5,817,310 A | 10/1998 | Ramakrishnan et al. |
| 2011/0183863 A1 | 7/2011 | Wagner |

FOREIGN PATENT DOCUMENTS

| WO | 2008130704 A2 | 10/2008 |
| WO | 2010011944 A2 | 1/2010 |

OTHER PUBLICATIONS

Paul, W.E. Fundamental Immunology, Third Edition (textbook), "Fv Structure and Diversity in Three Dimensions" pp. 292-295; Raven Press, New York (1993).*
Casset et al. A peptide mimetic of an anti-CD4 monoclonal antibody by rational design. Biochemical and Biophysical Research Communications. 307:198-205 (2003).*
MacCallum et al. Antibody-antigen interactions: Contact analysis and binding site topography. J Mol Biol. vol. 262:732-745 (1996).*
Vajdos et al. Comprehensive functional maps of the antigen-binding site of an anti-ErbB2 antibody obtained with shotgun scanning mutagenesis. J Mol Biol. 320(2):415-428 (2002).*
Holm et al. Functional mapping and single chain construction of the anti-cytokeratin 8 monoclonal antibody TS1. Mol Immunol. 2007; 44(6):1075-1084 (2007).*
Lokker, et al., "Functional Importance of Platelet-derived Growth Factor (PDGF) Receptor Extracellular Immunoglobulin-like Domains", Journal of Biological Chemistry, vol. 272, No. 52, pp. 33037-33044, (1997).
Giese, et al., "The Role of Alpha and Beta Platelet-Derived Growth Factor Teceptor in the Vascular Response to Injury in Nonhuman Primates", Arteriosclerosis, Thrombosis, and Vascular Biology, Apr. 1999, vol. 19, pp. 900-909.
International Search Report and Written Opinion in related application PCT/US2012/067909, mailed Apr. 30, 2013, 14 pages.
Shen et al. (2007) "An antibody directed against PDGF receptor beta enhances the antitumor and the anti-angiogenic activities of an anti-VEGF receptor 2 antibody," Biochem. Biophys. Res. Comm. 357(4):1142-1147.
Shen et al. (2009) "Development of a Fully Human Anti-PDGFRβ Antibody That Suppresses Growth of Human Tumor Xenografts and Enhances Antitumor Activity of an Anti-VEGFR2 Antibody," Neoplasia. 11(6):594-604.
Extended European Search Report of corresponding application EP 12856569.4, dated Apr. 7, 2015.

* cited by examiner

*Primary Examiner* — Elizabeth C Kemmerer
*Assistant Examiner* — Regina M Deberry
(74) *Attorney, Agent, or Firm* — Lathrop & Gage LLP; James H. Velema

(57) ABSTRACT

The present invention provides binding polypeptides (e.g., antibodies or fragments thereof) that specifically bind to a target antigen (e.g., a human antigen, e.g., human PDGFRβ) with high affinity. The invention also provides, libraries of binding polypeptides, pharmaceutical compositions, as well as nucleic acids encoding binding polypeptides, recombinant expression vectors and host cells for making such binding polypeptides. Methods of using binding polypeptide of the invention to diagnose and treat disease are also encompassed by the invention.

26 Claims, 16 Drawing Sheets

PDGF RECEPTOR BETA BINDING POLYPEPTIDES

RELATED APPLICATIONS

This application claims priority to U.S. provisional application 61/566,778 filed on Dec. 5, 2011, and U.S. provisional application 61/610,905 filed on Mar. 14, 2012, both of which are hereby incorporated by reference in their entirety.

INTRODUCTION

Platelet derived growth factor (PDGF) is a potent mitogen and chemoattractant in cells of mesenchymal origin and is involved in the pathologies of many diseases. PDGF exists as a disulfide-linked dimer consisting of two homologous chains, A or B, that can combine to form three distinct PDGF isoforms, AA, BB or AB. All isoforms of PDGF mediate their mitogenic effect by binding to a cell surface PDGF receptor (PDGFR).

PDGF receptors belong to the tyrosine kinase family and consist of two receptor isoforms, alpha and beta. The alpha and beta isoforms can be distinguished by their distinct ligand binding specificities. PDGF beta receptor can bind to only B-chain (isoforms BB and AB), while PDGF alpha receptor can bind to all isoforms of PDGF.

Binding of PDGF to a cell surface PDGFR causes receptor dimerization and trans-autophosphorylation which, in turn, results in intracellular signalling events that cause, inter alia, cell proliferation and cell migration. Accordingly, PDGFR antagonists that block PDGF binding and/or receptor dimerization can be used to treat or prevent diseases associated with PDGFR activation.

There is a therefore a need in the art for novel PDGFR antagonists that can be used to treat diseases associated with PDGFR activation.

SUMMARY OF THE INVENTION

The present invention provides binding polypeptides (e.g., antibodies or fragments thereof) that specifically bind to a target antigen (e.g., a human antigen, e.g., human PDGF) with high affinity. In a preferred embodiment, the invention provides binding polypeptides that bind to PDGFRβ (e.g., human PDGFRβ) with high affinity and antagonize PDGFRβ activation. Such binding polypeptides are particularly useful for treating PDGFRβ-associated diseases or disorders (e.g., age-related macular degeneration (AMD)). The invention also provides, libraries of binding polypeptides, pharmaceutical compositions, as well as nucleic acids encoding binding polypeptides, recombinant expression vectors and host cells for making such binding polypeptides. Methods of using binding polypeptides of the invention to detect PDGFRβ and to modulate PDGFRβ activity are also encompassed by the invention.

Accordingly, in one aspect the invention provides an isolated binding polypeptide comprising a VH domain, wherein, as an isolated domain, the VH domain binds to an antigen with a Kd of less than 100 μM.

In another aspect, the invention provides an isolated binding polypeptide that specifically binds to PDGFRβ, comprising the CDR3 sequence set forth in SEQ ID NO: 1.

In certain embodiments, the binding polypeptide comprises a VH domain comprising the HCDR3 amino acid sequence set forth in SEQ ID NO: 1. The VH domain may further comprise a HCDR2 comprising an amino acid sequence selected from the group consisting of SEQ ID NOs: 2-32, and/or a HCDR1 comprising an amino acid sequence selected from the group consisting of SEQ ID NOs: 33-62.

In certain embodiments, the polypeptide comprises a VH domain comprising an amino acid sequence sharing at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) amino acid identity with a VH domain amino acid sequence selected from the group consisting of SEQ ID NOs: 318-368.

In certain embodiments, the polypeptide comprises a VH domain comprising an am amino acid sequence selected from the group consisting of SEQ ID NOs: 318-368

In certain embodiments, the binding polypeptide comprises a VL domain. The VH domain may further comprise a LCDR3 comprising an amino acid sequence selected from the group consisting of SEQ ID NOs: 63-147, a LCDR2 comprising an amino acid sequence selected from the group consisting of SEQ ID NOs: 148-232, and/or a LCDR1 comprising an amino acid sequence selected from the group consisting of SEQ ID NOs: 233-317.

In certain embodiments, the polypeptide comprises a VL domain comprising an amino acid sequence sharing at least 80% (e.g., 80%, 81%, 82%, 83%, 84%, 85%, 86%, 87%, 88%, 89%, 90%, 91%, 92%, 93%, 94%, 95%, 96%, 97%, 98%, or 99%) amino acid identity with a VL domain amino acid sequence selected from the group consisting of SEQ ID NOs: 369-453.

In certain embodiments, the polypeptide comprises a VL domain comprising an amino acid sequence selected from the group consisting of SEQ ID NOs: 369-453.

In further aspect, the invention provides a binding polypeptide that binds to the same epitope on PDGFRβ as a binding polypeptide comprising the VH domain amino acid sequence set forth in SEQ ID No: 318. In a preferred embodiment, the binding polypeptide comprises a VH domain amino acid sequence sharing at least 80% amino acid identity (e.g., 80%, 81%, 82%, 83%, 84%, 85%, 86%, 87%, 88%, 89%, 90%, 91%, 92%, 93%, 94%, 95%, 96%, 97%, 98%, or 99%) with a VH domain amino acid sequence selected from the group consisting of SEQ ID NOs: 318-368.

In a further aspect, the invention provides a binding polypeptide that competes for binding to PDGFRβ with a binding polypeptide comprising the VH domain amino acid sequence set forth in SEQ ID No: 318. In a preferred embodiment, the binding polypeptide comprises a VH domain amino acid sequence sharing at least 80% amino acid identity with a VH domain amino acid sequence selected from the group consisting of SEQ ID NOs: 318-368.

In certain embodiments, the binding polypeptides of the invention inhibit the activity of PDGFRβ. In one embodiment, the activity of PDGFRβ is inhibited by antagonizing PDGF binding to PDGFRβ. In another embodiment, the activity of PDGFRβ is inhibited by antagonizing PDGFRβ dimerization.

In certain embodiments, the binding polypeptides of the invention bind to PDGFRβ with a Kd of less than 100 pM and/or with an off-rate of less than $10^{-3}$ $s^{-1}$.

In certain embodiments, the binding polypeptides of the invention bind specifically to mouse and human PDGFRβ.

In certain embodiments, the binding polypeptides of the invention antagonize PDGF binding to the PDGFRβ with an IC50 of less than 5 nM, inhibit ligand induced tyrosine phosphorylation of PDGFRβ with an IC50 of less than 4 nM, inhibit retinal pericyte migration with an IC50 of less than 6 nM, and/or have a melting temperature (Tm) of at least 68° C.

In a further aspect, the invention provides an isolated nucleic acid encoding a binding polypeptide of the invention.

In a further aspect, the invention provides a recombinant expression vector comprising an isolated nucleic acid encoding a binding polypeptide of the invention.

In a further aspect, the invention provides a host cell expressing a binding polypeptide of the invention.

In a further aspect, the invention provides a method of producing a binding polypeptide that binds specifically to human PDGFRβ, comprising culturing a host cell capable of expressing a binding polypeptide of the invention under conditions such that the binding polypeptide is produced by the host cell.

In a further aspect, the invention provides a pharmaceutical composition comprising a binding polypeptide of the invention and one or more pharmaceutically acceptable carrier.

In a further aspect, the invention provides a method for treating a disease or disorder PDGFRβ-associated disease or disorder (e.g., age-related macular degeneration (AMD) or cancer), the method comprising administering to a subject in need of thereof a pharmaceutical composition of the invention.

In a further aspect, the invention provides a diverse library of unpaired VH domains wherein each member of the library binds to human PDGFRβ. In one preferred embodiment, each member of the library comprises the CDR3 amino acid sequence set forth in SEQ ID NO: 1 and diversity lies in the FR1-FR3 regions. In one preferred embodiment, the library is a nucleic acid display library (e.g., a DNA display library).

In a further aspect, the invention provides a diverse library of stable VH/VL pairs wherein each member of the library binds to human PDGFRβ. In one preferred embodiment, each member of the library comprises a VH domain comprising the CDR3 amino acid sequence set forth in SEQ ID NO: 1. In one preferred embodiment, the VL domains are human VL domains. In one preferred embodiment, the library is a nucleic acid display library (e.g., a DNA display library).

DETAILED DESCRIPTION

Figure 1:
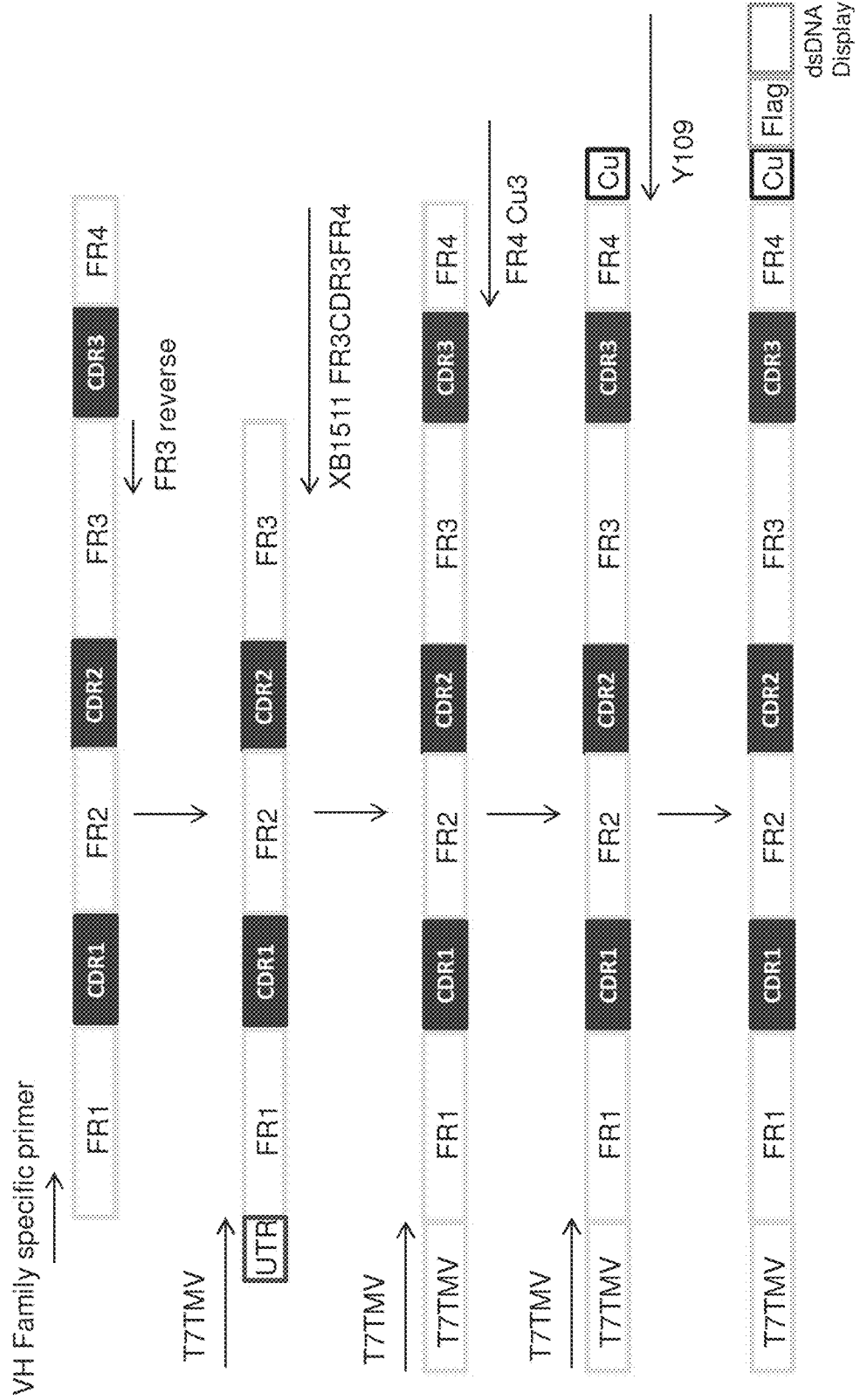
FIG. 1 is a schematic representation of the construction of exemplary VH domain nucleic acid display libraries for use in the disclosed methods.

The present invention provides binding polypeptides (e.g., antibodies or fragments thereof) that specifically bind to a target antigen (e.g., a human antigen) with high affinity. In a preferred embodiment, the binding polypeptides of the invention bind to PDGFRβ (e.g., human PDGFRβ) with high affinity and inhibit the activity of PDGFRβ. Such binding polypeptides are particularly useful for treating PDGFRβ-associated diseases or disorders (e.g., age-related macular degeneration (AMD)). The invention also provides, libraries of binding polypeptides, pharmaceutical compositions, as well as nucleic acids encoding binding polypeptides, recombinant expression vectors and host cells for making such binding polypeptides. Methods of using binding polypeptides of the invention to detect PDGFRβ and to modulate PDGFRβ activity are also encompassed by the invention.

I. DEFINITIONS

In order that the present invention may be more readily understood, certain terms are first defined.

As used herein, the term "PDGFRβ" refers to platelet-derived growth factor receptor beta. PDGFRβ nucleotide and polypeptide sequences are well known in the art. An exemplary human PDGFRβ amino sequence is set forth in GenBank deposit GI:4505683 and an exemplary mouse PDGFRβ amino sequence is set forth in GenBank deposit GI: 226371752.

As used herein, the term "PDGF" refers to platelet-derived growth factor. PDGF nucleotide and polypeptide sequences are well known in the art. An exemplary human PDGF amino sequence is set forth in GenBank deposit GI:4505681 and an exemplary mouse PDGF amino sequence is set forth in GenBank deposit GI:400744.

As used herein, the term "binding polypeptide" refers to a polypeptide that contains all or a part of the antigen binding site of an antibody (e.g., all or part of the heavy and/or light chain variable domain, e.g., at least HCDR3 of the heavy chain variable domain) such that the binding polypeptide specifically recognizes a target antigen. Non-limiting examples of binding polypeptides include antibodies, or fragments thereof, and immunoglobulin-like domains (e.g., fibronectin domains) that have been altered to comprise all or a part of the antigen binding site of an antibody.

As used herein, the term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2 and CH3. Each light chain comprises a light chain variable region (abbreviated VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR).

As used herein, the term "antigen-binding portion" of an antibody includes any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding portion."

As used herein, the terms "VH domain" and "VL domain" refer to single antibody variable heavy and light domains, respectively, comprising FR (Framework Regions) 1, 2, 3 and 4 and CDR (Complementary Determinant Regions) 1, 2 and 3 (see Kabat et al. (1991) Sequences of Proteins of Immunological Interest. (NIH Publication No. 91-3242, Bethesda).

As used herein, the term "FR1-FR3" refers to the region of a VH encompassing FR1, CDR2, FR2, CDR2 and FR3, but excluding the CDR3 and FR4 regions.

As used herein, the term "unpaired" refers to VH or VL that are not linked (either covalently or non-covalently) to a complementary VL or VH domain, respectively.

As used herein, the term "complementary VL or VH domain" refers to a VL or VH domain that associates with a VH or VL domain, respectively, to form a VH/VL pair.

As used herein, the term "VH/VL pair" refers to a non-covalent dimer of a single VH and a single VL domain, wherein the VL and VH domain are associated in a similar manner to that observed in a complete, tetrameric immunogobulin molecule, and the dimer can bind specifically to at least one target antigen. A "stable VH/VL pair" is a VH/VL pair that does not exhibit significant dissociation of the substituent VH and VL domains under physiological conditions.

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196: 901-917 (1987) and by MacCallum et al., J. Mol. Biol. 262: 732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat, based on sequence comparisons.

As used herein the term "framework (FR) amino acid residues" refers to those amino acids in the framework region of an immunogobulin chain. The term "framework region" or "FR region" as used herein, includes the amino acid residues that are part of the variable region, but are not part of the CDRs (e.g., using the Kabat definition of CDRs).

As used herein, the term "specifically binds to" refers to the ability of a binding polypeptide to bind to an antigen with an Kd of at least about $1\times10^{-6}$M, $1\times10^{-7}$M, $1\times10^{-8}$M, $1\times10^{-9}$M, $1\times10^{-10}$M, $1\times10^{-11}$M, $1\times10^{-12}$M, or more, and/or bind to an antigen with an affinity that is at least two-fold greater than its affinity for a nonspecific antigen. It shall be understood, however, that the binding polypeptide are capable of specifically binding to two or more antigens which are related in sequence. For example, the binding polypeptides of the invention can specifically bind to both human and a non-human (e.g., mouse or non-human primate) PDGFRβ.

As used herein, the term "antigen" refers to the binding site or epitope recognized by a binding polypeptide.

As used herein, the term "nucleic acid display library" refers to any art recognized in vitro cell-free phenotype-genotype linked display, including, without limitation those set forth in, for example, U.S. Pat. Nos. 7,195,880; 6,951,725; 7,078,197; 7,022,479; 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315, and in WO2010/011944, which are all hereby incorporated by reference in their entirety.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a recombinant expression vector has been introduced. It should be understood that this term is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "treat," "treating," and "treatment" refer to therapeutic or preventative measures described herein. The methods of "treatment" employ administration to a subject, an antibody or antigen binding portion of the present invention, for example, a subject having a PDGFRβ-associated disease or disorder (e.g. AMD) or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "PDGFRβ-associated disease or disorder" includes disease states and/or symptoms associated with PDGFRβ activity. Exemplary PDGFRβ-associated diseases or disorders include, but are not limited to, age-related macular degeneration (AMD) and cancer.

As used herein, the term "effective amount" refers to that amount of a binding polypeptide that is sufficient to effect treatment, prognosis or diagnosis of a PDGFRβ-associated disease or disorder, as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 1 ug to about 5,000 mg, about 1 mg to about 1,000 mg, about 10 mg to about 100 mg, of a binding polypeptide according to the invention. Dosage regiments may be adjusted to provide the optimum therapeutic response. An effective amount is also one in which any toxic or detrimental effects (i.e., side effects) of a binding polypeptide are minimized and/or outweighed by the beneficial effects.

As used herein, the term "subject" includes any human or non-human animal.

As used herein, the term "surface plasmon resonance" refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

As used herein, the term "$K_D$" refers to the equilibrium dissociation constant of a particular binding polypeptide/antigen interaction.

As used herein, the term "off-rate" is refers to the dissociation rate ($K_{off}$) for a particular binding polypeptide/antigen interaction.

As used herein, the term "epitope" refers to an antigenic determinant that interacts with the specific antigen binding site in a binding molecule of the invention. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain.

II. BINDING POLYPEPTIDES

In one aspect, the invention provides binding polypeptides comprising a VH domain, wherein, as an isolated domain, the VH domain binds to an antigen with a Kd of less than about 200 pM (e.g., about 200, 190, 180, 175, 170, 160, 150, 140, 130, 120, 110, 100, 95, 90, 80, 75, 70, 65, 60, 55, 50, 40, 30, 20, 10, 5, or 1 pM or less).

In another aspect, the invention provides binding polypeptides (e.g., antibodies, or antigen binding fragments thereof) that specifically bind to PDGFRβ and inhibit PDGFRβ activity. Such binding polypeptides are particularly useful for treating PDGFRβ-associated disease or disorders (e.g., age-related macular degeneration or AMD).

In general, PDGFRβ binding polypeptides of the invention comprise a heavy chain CDR3 (HCDR3) amino acid sequence that specifically binds to PDGFRβ. One, non-limiting, HCDR3 sequence suitable for use in the binding polypeptides of the invention is the heavy chain CDR3 amino acid sequence set forth in SEQ ID NO: 1 (HGGDRSY)). In other embodiments, the heavy chain CDR3 sequence is a variant of SEQ ID NO:1 which comprises at least one (e.g., one, two, or three) conservative amino acid substitutions relative to SEQ ID NO:1.

Any binding polypeptide that can incorporate a heavy chain CDR3 amino acid sequence that specifically binds to PDGFRβ (e.g., the CDR3 amino acid sequence set forth in SEQ ID NO: 1 (HGGDRSY)) can be used in the binding polypeptides of the invention including, without limitation antibodies, or fragments thereof, and immunoglobulin-like domains. Suitable immunoglobulin-like domains include, without limitation, fibronectin domains (see, for example, Koide et al. (2007), *Methods Mol. Biol.* 352: 95-109, which is incorporated by reference herein in its entirety), DARPin (see, for example, Stumpp et al. (2008) *Drug Discov. Today* 13 (15-16): 695-701, which is incorporated by reference herein in its entirety), Z domains of protein A (see, Nygren et al. (2008) *FEBS J.* 275 (11): 2668-76, which is incorporated by reference herein in its entirety), Lipocalins (see, for example, Skerra et al. (2008) *FEBS J.* 275 (11): 2677-83, which is incorporated by reference herein in its entirety), Affilins (see, for example, Ebersbach et al. (2007) *J. Mol. Biol.* 372 (1): 172-85, which is incorporated by reference herein in its entirety), Affitins (see, for example, Krehenbrink et al. (2008). *J. Mol. Biol.* 383 (5): 1058-68, which is incorporated by reference herein in its entirety), Avimers (see, for example, Silverman et al. (2005) *Nat. Biotechnol.* 23 (12): 1556-61, which is incorporated by reference herein in its entirety), Fynomers, (see, for example, Grabulovski et al. (2007) *J Biol Chem* 282 (5): 3196-3204, which is incorporated by reference herein in its entirety), and Kunitz domain peptides (see, for example, Nixon et al. (2006) *Curr Opin Drug Discov Devel* 9 (2): 261-8, which is incorporated by reference herein in its entirety).

In a preferred embodiment, the PDGFRβ binding polypeptides are antibodies, or antigen binding fragment thereof, comprising a VH domain and/or a VL domain. Exemplary CDR, VH, and VL amino acid sequences suitable for use in the invention are set forth in Tables 1-4. Accordingly, in certain embodiments, the binding polypeptides may comprise HCDR3 (SEQ ID NO:1) together with HCDR2 and/or HCDR1 sequences which are independently selected from any one of the heavy chain HCDR2 or HCDR1 sequences set forth in Table 1. In certain embodiments, the binding polypeptides of the invention may further comprise light chain CDRs which are independently selected from any one of the light chain CDR1, CDR2 or CDR3 sequences set forth in Table 2. For example, the binding polypeptide of the invention may comprise any one of the heavy chain variable (VH) domains set forth in Table 3, optionally paired with any one of the light chain variable (VL) domains set forth in Table 4.

TABLE 1

Heavy chain CDR amino acid sequences of exemplary anti-PDGFRβ ntibodies.

| Clone name | CDR3 | SEQ ID NO. | CDR2 | SEQ ID NO. | CDR1 | SEQ ID NO. |
|---|---|---|---|---|---|---|
| XB1511 | HGGDRSY | 1 | GIIPIFGTANYAQKFQG | 2 | SYAIS | 33 |
| G2 | HGGDRSY | 1 | GIIPIFGTANYAQKFQG | 2 | GYAIS | 34 |
| XB2202 | HGGDRSY | 1 | GILPILKTPNYAQRFQG | 3 | RHAIS | 35 |
| C05. | HGGDRSY | 1 | GVLPILKTPNYAQRFQG | 4 | RHAIS | 35 |
| E2. | HGGDRSY | 1 | WINPNSGNTGYAQKFQG | 5 | DYYIQ | 36 |
| A3. | HGGDRSY | 1 | WINPNSGGTYFAQKFQG | 6 | DYYIQ | 36 |
| C3. | HGGDRSY | 1 | GILPILKTPNYAQRFQG | 3 | DYYIQ | 36 |
| F10. | HGGDRSY | 1 | WINPDSGGTYFAQKFQG | 7 | DYYIQ | 36 |
| C12. | HGGDRSY | 1 | WMNPDSGGTIYAQKFQG | 8 | DYYIQ | 36 |
| H2. | HGGDRSY | 1 | WLNPNSGDTHSAQKFQG | 9 | AYYIQ | 37 |
| B1. | HGGDRSY | 1 | WINPNNGNTTYAQKFQG | 10 | DYYIH | 38 |
| E11. | HGGDRSY | 1 | GIIPIFGTANYAQKFQG | 2 | DYYIH | 38 |
| H1. | HGGDRSY | 1 | WINPNSGGTNSAPKFQG | 11 | DYHLH | 39 |
| E6. | HGGDRSY | 1 | WINPNSGGTNYAQKFQG | 12 | DYYLH | 40 |
| A1. | HGGDRSY | 1 | WIVVGSGNTNYAQKFQE | 13 | SSAVQ | 41 |
| H7. | HGGDRSY | 1 | WIVVGSGNTNYAQKFQE | 13 | SSAMQ | 42 |
| G04. | HGGDRSY | 1 | WIVVGSGNTNYAQKFQE | 13 | SYAIS | 33 |
| B2. | HGGDRSY | 1 | VINTGVGSTNYAQKFQG | 14 | NYQVQ | 43 |
| A7. | HGGDRSY | 1 | VINTGVGSTNYAQKFQG | 14 | NYPVQ | 44 |
| H3. | HGGDRSY | 1 | LSNPSGDYTVYAPKFQG | 15 | NSFMQ | 45 |
| B4. | HGGDRSY | 1 | LSNPSGDYTVYAPKLQG | 16 | NSFMQ | 45 |
| D06. | HGGDRSY | 1 | VISYDGSNKYYADSVKG | 17 | SYGMH | 46 |
| F3. | HGGDRSY | 1 | WISADNGNTNYAQKFQE | 18 | SHGMS | 47 |
| A12. | HGGDRSY | 1 | WISADNGNTKYAQKFQD | 19 | SHGMS | 47 |
| G3. | HGGDRSY | 1 | GFDPEDGETIYAQKFQG | 20 | ELSMH | 48 |
| H12. | HGGDRSY | 1 | GIIPIFGTANYAQKFQG | 2 | DNYVH | 49 |
| G12. | HGGDRSY | 1 | GIIPVSGTPNYAQKFQG | 21 | AYPIS | 50 |
| C06. | HGGDRSY | 1 | GIIPIFGTANYAQKFQG | 2 | GHYIH | 51 |
| C11. | HGGDRSY | 1 | GIIPIFGTANYAQKFQG | 2 | NDYIH | 52 |
| F08. | HGGDRSY | 1 | GIIPIFGTANYAQKFQG | 2 | SSYIH | 53 |
| E9. | HGGDRSY | 1 | ITYPADSTTVYSPSFQG | 22 | NYWIG | 54 |
| E11. | HGGDRSY | 1 | RINNDGSSTSYADSVKG | 23 | SYWMH | 55 |
| C08. | HGGDRSY | 1 | RISIDGTTTTYADSVQG | 24 | AFWMH | 56 |
| XB2708 | HGGDRSY | 1 | FILFDGNNKYYADSVKG | 25 | SYGMH | 46 |
| D03. | HGGDRSY | 1 | RINADGTSTAYAESVKG | 26 | NDWMH | 57 |

TABLE 1-continued

Heavy chain CDR amino acid sequences of exemplary anti-PDGFRβ ntibodies.

| Clone name | CDR3 | SEQ ID NO. | CDR2 | SEQ ID NO. | CDR1 | SEQ ID NO. |
|---|---|---|---|---|---|---|
| A10. | HGGDRSY | 1 | LIYSDGSTYYADSVKG | 27 | DYAMN | 58 |
| C09. | HGGDRSY | 1 | AIDGSGGTTYYAGSVKG | 28 | NNAMS | 59 |
| A06. | HGGDRSY | 1 | HISNDGSITRYADSVKG | 29 | GHWMH | 60 |
| C05. | HGGDRSY | 1 | RIKTDGSSTSYADSVKG | 30 | SNWMH | 61 |
| H01. | HGGDRSY | 1 | RISSDGSTTAYADSVRG | 31 | SDWMH | 62 |
| G07. | HGGDRSY | 1 | RISSDGSSTAYADSVKG | 32 | SDWMH | 62 |

TABLE 2

Light chain CDR amino acid sequences of exemplary anti-PDGFRβ antibodies.

| Clone name | CDR3 | SEQ ID NO. | CDR2 | SEQ ID NO. | CDR1 | SEQ ID NO. |
|---|---|---|---|---|---|---|
| B10. | HQSSSLPWT | 63 | AYQSVS | 148 | RASQTIGSTLH | 233 |
| H10. | HQSSSLPHT | 64 | SSQSFS | 149 | RASQSIGSSLH | 234 |
| F10. | RASQSIGSGLH | 65 | ASQSMS | 150 | HQSSSLPWT | 235 |
| B12. | HQTSSLPLT | 66 | ASQPFS | 151 | RASQSIGIKLH | 236 |
| B11. | QQYGSSPWT | 67 | GASSRAS | 152 | RASQSVSSNYLA | 237 |
| E7. | QQYGSSPQT | 68 | GASSRAT | 153 | RASQSVSSSYLA | 238 |
| E8. | QQYGSSPPYT | 69 | GASSRAT | 154 | RASQSVSSSYLA | 239 |
| H8. | QQYAGSPFT | 70 | GASSRAT | 155 | RASQSVSSNYLA | 240 |
| H12. | QQFGSSPWT | 71 | GASRRAT | 156 | RASQSVRSSYVA | 241 |
| F8. | QQYGSSPLT | 72 | VASRRVT | 157 | SGGRSNIGGNAVN | 242 |
| D11. | QQYGASPRT | 73 | GASSRAT | 158 | RASQNITSNFFA | 243 |
| G8. | QQYGSALLT | 74 | DASNRAA | 159 | RASQSLSGTYLA | 244 |
| H9. | QQYGNSWT | 75 | RASTRAT | 160 | RASEDIYNNYLA | 245 |
| H11. | HQSRNLPFT | 76 | ASQSFS | 161 | RASQSIGSSLH | 246 |
| G12. | HQSRSFPLT | 77 | SSQSIS | 162 | RASESIGTALH | 247 |
| E11. | QQYETSWT | 78 | RASTRAT | 163 | RTSQILHSQYLA | 248 |
| F12. | RDGLNHLV | 79 | GENNRPS | 164 | QGDTLRTCYAS | 249 |
| C8. | GTWDSSLSVVI | 80 | YDNYQRFS | 165 | SGSTSNIGKNFVS | 250 |
| A8. | HQTGSFPYT | 81 | LASQSFS | 166 | RASRYIGSNLH | 251 |
| B8. | LLSYSGPRVV | 82 | DTSNKQS | 167 | GSSTGAVTSGHSPF | 252 |
| F7. | QQSYRTPFS | 83 | WASTRES | 168 | KSSXSLLYRSNNKNYLA | 253 |
| B7. | QVWDSSSVI | 84 | RDSNRPS | 169 | GGANIANKNVH | 254 |
| G9. | KSRDSSAMRWV | 85 | GKDNRPS | 170 | QGDSLRTYYAS | 255 |
| A9. | LLYFNPTRV | 86 | DTHNRHS | 171 | GSSTGAVTSGHYPY | 256 |

TABLE 2-continued

Light chain CDR amino acid sequences of exemplary anti-PDGFRβ antibodies.

| Clone name | CDR3 | SEQ ID NO. | CDR2 | SEQ ID NO. | CDR1 | SEQ ID NO. |
|---|---|---|---|---|---|---|
| A11. | GADHGRV | 87 | GIVGSKGD | 172 | TLSSGYSNYKVD | 257 |
| E12. | QVWHSGVI | 88 | FDSDRPS | 173 | GGNNIGSKSVH | 258 |
| H7. | HQSRSSHT | 89 | YASQSFS | 174 | RASQNIGNSLH | 259 |
| A10. | QSFDVYSHEVV | 90 | GNNQRPS | 175 | TRCTGNIASHFVQ | 260 |
| C11. | MQSTHFPFT | 91 | EVSKRFS | 176 | KSSQSLLNSDDGKTYLY | 261 |
| D10. | QQYDSPPWT | 92 | DASHLEA | 177 | QASHDISNYLN | 262 |
| D12. | QQHDTSQWT | 93 | GASSRAA | 178 | RASQSVSRTYLA | 263 |
| C7. | MQGLHIPHT | 94 | EVSGRFS | 179 | KSSQSLLHSDGKTHLF | 264 |
| D7. | MQSTHQWT | 95 | SVSKRDS | 180 | RSSHSLVHSDGNIYLN | 265 |
| C9. | QQYDSYSRT | 96 | EASRLES | 181 | RASQSISSWLA | 266 |
| C12. | QQSFSMRT | 97 | GASGLQS | 182 | RTSQGIRNYLS | 267 |
| D8. | QQYVNSRT | 98 | DASNRAT | 183 | RASQSVTSNYLA | 268 |
| D9. | QQYNDFFT | 99 | GASTRAT | 184 | RASQSVSSKLA | 269 |
| G7. | MQATQFPS | 100 | KISNRMS | 185 | RSSESPVHSDGNIYLS | 270 |
| G11. | QQYGDSVFT | 101 | GGSIRAS | 186 | RASQSVSSRNLA | 271 |
| F9. | QQSYSTPRT | 102 | AASTLHY | 187 | RASDNIGNYLN | 272 |
| E9. | QESYSTLLYT | 103 | AASRLQS | 188 | RASESISNYLN | 273 |
| B1. | QVWESGSEHYV | 104 | DDSDRPS | 189 | GGNNIGYDSVH | 274 |
| E6. | QVWESTSDHPT | 105 | YDNDRPS | 190 | GGNNIGATTV | 275 |
| F3. | QVWDSSSDHWV | 106 | YDSDRPS | 191 | GGNNIGSKSVH | 276 |
| H4. | QVWDSSSGHRGV | 107 | DDSDRPS | 192 | GGNNIVSKGVH | 277 |
| H5. | QVWDSATDHVV | 108 | SDRDRPS | 193 | GGNNLGSKIVH | 278 |
| B5. | QVWDSDRHHVV | 109 | DDYGRPS | 194 | AGNNIGGKSVQ | 279 |
| G6. | QVWDINDDYAV | 110 | QDTKRPS | 195 | SGDNLGHTNAC | 280 |
| C1. | QQYVSSPPMYT | 111 | GASSRAT | 196 | TASQSVSSTYLT | 281 |
| F1. | QQYVTYPLT | 112 | GASNLEG | 197 | RASQNIDYDLA | 282 |
| A3. | QQYDSVPLT | 113 | GASTLES | 198 | QASQVIDKYVN | 283 |
| B4. | QQYEDLPSF | 114 | EASNLET | 199 | QASQDIFHYLN | 284 |
| B6. | QQYGSFPYS | 115 | AASNRAT | 200 | RASQSFGSNYLA | 285 |
| F2. | QQYQNPPFT | 116 | GASNLER | 201 | QASQFIHIYLN | 286 |
| D3. | QQYKTFPHT | 117 | AASYLQT | 202 | RASQDVGIYVA | 287 |
| G2. | QQYHSYPYT | 118 | KVSTLES | 203 | RASQDINTWLA | 288 |
| A4. | QQYNNVLRT | 119 | EASNLET | 204 | QASQDISNWLN | 289 |
| G4. | QQYNKWPTF | 120 | GASTRAT | 205 | RVSQNVFSDLA | 290 |
| D5. | QQYYNWPPWT | 121 | AASTLHY | 206 | RASDNIGNYLN | 291 |
| A1. | QQRSNGVTF | 122 | EASTRAT | 207 | RASQSVSSFLA | 292 |

TABLE 2-continued

Light chain CDR amino acid sequences of exemplary anti-PDGFRβ antibodies.

| Clone name | CDR3 | SEQ ID NO. | CDR2 | SEQ ID NO. | CDR1 | SEQ ID NO. |
|---|---|---|---|---|---|---|
| H2. | QHYHTYPFT | 123 | QASSLKT | 208 | RATESISIWLA | 293 |
| E2. | QQYYLTPTFTVT | 124 | WASTRES | 209 | KSSQSVLYSSNNKNYLA | 294 |
| F4. | QQTNTFPLT | 125 | RATNLQS | 210 | RASQDISSWLA | 295 |
| C5. | QQYHTTPYT | 126 | WASTRES | 211 | KSSQSVLYSSNNRNYLA | 296 |
| E5. | QQSFSSPWT | 127 | AASNLQS | 212 | RASQTFTSHLN | 297 |
| F6. | QQSFTTLVT | 128 | SASTLQS | 213 | RASQSVNVYLN | 298 |
| G5. | CQQFNSYPLS | 129 | DASTLQT | 214 | RASQDISSSLA | 299 |
| A5. | GADHGSGSNLVYV | 130 | VGTGGIVGSRGD | 215 | TVSSGYRSYEVD | 300 |
| D6. | GADHGSGSDFVYV | 131 | VGTGGIVGSRGD | 216 | TLSSDYSSYNVD | 301 |
| E4. | AAWDDSLNGPV | 132 | TNNQRPS | 217 | SGSSTNIGSNAVN | 302 |
| F5. | AAWDDRLSGPV | 133 | TTDRRPS | 218 | SGGGSNIGSNFGY | 303 |
| G1. | ATWDDDLSNPKWV | 134 | TTNQRPS | 219 | SGSSSNIGSNSVD | 304 |
| E3. | MQALQTSWT | 135 | LGSNRAS | 220 | RSSQSLLHSNGYNFLD | 305 |
| A2. | MQGTHWPYT | 136 | QVSTRDS | 221 | CDDTVSTLPARHP | 306 |
| D1. | MQSRNLPKT | 137 | EASSRFS | 222 | KSSQSLVHRDGKTYLY | 307 |
| C4. | MVWYSAWV | 138 | RSDSDRHQGS | 223 | TLSSGFNVVSYNIY | 308 |
| E1. | HVLDSSTIVI | 139 | RDTNRPS | 224 | AGNNIGTYYVH | 309 |
| A6. | HQYNNWPLYT | 140 | GASTRAT | 225 | RASQSVSSNLA | 310 |
| H1. | NSRDSSGYLLL | 141 | GKNTRPS | 226 | QGDSLRTYYAS | 311 |
| B2. | LLSYSGAGV | 142 | DASNKHS | 227 | GSSTGAVTSGHYPY | 312 |
| C2. | LQDYSFPYT | 143 | DSSTLQS | 228 | RPSQDIGTDLG | 313 |
| G3. | QAWDSSHAV | 144 | QDTKRPS | 229 | SGDELKYKYTC | 314 |
| H3. | QSEDSRGPV | 145 | KDTERPS | 230 | SGSTFPKLYSF | 315 |
| D4. | VQATHFPVT | 146 | KISNRFS | 231 | RSSESVVHDDGNTYLS | 316 |
| C6. | CSYTTGSTLYL | 147 | DVNRRPS | 232 | TGTSDDVGRYDYVS | 317 |

TABLE 3

Heavy chain variable domain (VH) amino acid sequences of exemplary anti-PDGFRβ antibodies.

| Clone name | VH Amino Acid Sequence | SEQ ID NO. |
|---|---|---|
| | Sequences of VH Primary Selection on recombinant human PDGFRβ | |
| A4 XB1511 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCAIHGGDRSYWGQGTLVTVSS | 318 |
| B4 | QVQLVQSGAEVKKPGASVKVSCKASGYTFTSYAISWVRQAPGQGLEWMGGIIPIFGTANYAQKFQGRVTITADESTSTAYMELSSLRSEDTAVYYCAIHGGDRSYWGQGTLVTVSS | 319 |

TABLE 3-continued

Heavy chain variable domain (VH) amino acid sequences of exemplary anti-PDGFRβ antibodies.

| Clone name | VH Amino Acid Sequence | SEQ ID NO. |
|---|---|---|
| G2 | QVQLVQSGAEVKKPGASVKVSCKASGYTFTGYAISWVRQAPGQGLEWMG GIIPIFGTANYAQKFQGRVTITADESTSTAYMELSSLRSKDTAVYYCAI HGGDRSYWGQGTLVTVSS | 320 |
| | (XB1511) Framework Shuffled and selected with 2 rounds on human and 2 rounds on mouse PDGFRβ targets | |
| XB2202 | QVQLVQSGAEVKKPGSSVRVSCKASGGTFSRHAISWVRQAPGQGLEWIG GILPILKTPNYAQRFQGRVTINADESTSTVYMEMSSLRSEDTAVYYCAT HGGDRSYWGQGTLVTVSS | 321 |
| C4. | QMQLVQSGAEVKKPGSSVRVSCKASGGTFSRHAISWVRQAPGQGLEWIG GILPILKTPNYAQRFQGRVTINADESTSTVYMEMSGLRSEDTAVYYCAT HGGDRSYWGQGTLVTVSS | 322 |
| B12. | QMQLVQSGAEVKKPGSSVRVSCKASGGTFSRHAISWVRQAPGQGLEWIG GILPILKTPNYAQRFQGRVTINADESTSTVYMEMSSLRSENTAVYYCAT HGGDRSYWGQGTLVTVSS | 323 |
| D07. | QMQLVQSGAEVKKPGSSVRVSCKASGGTFSRHAISWVRQAPGQGLEWIG GILPILKTPNYAQRFQGRVTINADESTSTVYMEMSSLRSDDTAVYYCAT HGGDRSYWGQGTLVTVSS | 324 |
| C05. | QMQLVQSGAEVKKPGSSVRVSCKASGGTFSRHAISWVRQAPGQGLEWIG GVLPILKTPNYAQRFQGRVTINADESTSTVYMELSSLRSEDTAVYYCAT HGGDRSYWGQGTLVTVSS | 325 |
| E05. | QVQLVQSGPKVKKPGSSVRVSCKASGGTFSRHAISWVRQAPGQGLEWIG GILPILKTPNYAQRFQGRVTINADESTSTVYMEMSSLRSEDTAVYYCAT HGGDRSYWGQGTLVTVSS | 326 |
| E2. | QMQLVQSGAEVKKPGASVKISCKTSGYTFTDYYIQWVRQAPGQGLEWVG WINPNSGNTGYAQKFQGRVTMTRDTSISTAYMELSSLRSEDTAVYYCAT HGGDYSYWGQGTLVTVSS | 327 |
| A3. | QVQLVQSGAEVKKPGASVRVSCKASGYTFSDYYIQWVRQAPGQGLEWMG WINPNSGGTYFAQKFQGRVTMTRDTSISTAYMELSSLTSDDTAVYYCAT HGGDRGYWGQGTLVTVSS | 328 |
| C3. | QMQLVQSGAEVKKPGASVKVSCKASGYTFTDYYIQWVRQAPGQGLEWIG GILPILKTPNYAQRFQGRVTINADESTSTVYMEMSSLRSEDTAVYYCAT HGGDRSYWGQGTLVTVSS | 329 |
| F10. | QMQLVQSGAEVKKPGASVKVSCKASGYTFTDYYIQWVRQAPGQGLEWMG WINPDSGGTYFAQKFQGRVAMTRDTSINTAYMELSSLRSDDTAVYYCAT HGGDRSYWGQGTLVTVSS | 330 |
| C12. | QVQLVQSGAEVKKPGASVKVSCKASGYTFTDYYIQWVRQAPGEGLEWMG WMNPDSGGTIYAQKFQGRVTMTRDTSISTAYMELSRLRPDDTAVYYCAT HGGDRSYWGQGTLVTVSS | 331 |
| H2. | QMQLVQSGAEVKNPGASVKVSCKASGYPFSAYYIQWVRQAPGQGLEWMG WLNPNSGDTHSAQKFQGRVTMTRDTSISTAYMELSGLTSDDTAVYYCAT HGGDRSYWGQGTLVTVSS | 332 |
| F11. | QMQLVQSGAEVKNPGASVKVSCKASGYPFSAYYIQWVRQAPGQGLEWMG WLNPNSGDTHSAQKFQGRVTMTRDTSISTAYMELSGPTSDDTAVYYCAT HGGDRSYWGQGTLVTVSS | 333 |
| B1. | QMQLVQSGAEVRKPGASVKVSCKASGYSFSDYYIHWVRQAPGQGLEWIG WINPNNGNTTYAQKFQGRVTMTRDTSISTAYMELSELRSDDTAVYYCAT HGGDRSYWGQGTLVTVSS | 334 |
| E11. | QVQLVQSGAEVEKPGASVKVSCKASGYTFTDYYIHWVRQAPGQGLEWMR GIIPIFGTANYAQKFQGRVTITADESTSTAYMELSSLRSEDTAVYYCAT HGGDRSYWGQGTLVTVSS | 335 |
| H1. | EVQLLESGAEVKQPGASVKVSCKTSGYTFTDYHLHWVRQAPGQGLEWMG WINPNSGGTNSAPKFQGRVTMTRDTSISTAYMELSGLTSDDTAVYYCAT HGGDRSYWGQGTLVTVSS | 336 |

TABLE 3-continued

Heavy chain variable domain (VH) amino acid sequences of exemplary anti-PDGFRβ antibodies.

| Clone name | VH Amino Acid Sequence | SEQ ID NO. |
|---|---|---|
| E6. | QMQLVQSGAEVKRPGASVKVPCKASGYTFTDYYLHWVRQAPGQGLKWMG WINPNSGGTNYAQKFQGRVTMTRDTSISTAYMELSRLRSEDTAVYYCAT HGGDRSYWGQGTLVTVSS | 337 |
| A1. | QVQLVQSGPEVKKPGTSVKVSCKASGFTFTSSAVQWVRQARGQRLEWIG WIVVGSGNTNYAQKFQERVTITRDMSTSTAYMELSSLRSEDTAVYYCAT HGGDRSYWGQGTLVTVSS | 338 |
| H7. | QVQLVQSGPEVKKPGTSVKVSCKASGFTFTSSAMQWVRQARGQRLEWIG WIVVGSGNTNYAQKFQERVTITRDMSTSTAYMELSSLRSEDTAVYYCAT HGGDRSYWGQGTLVTVSS | 339 |
| G04. | QVQLVQSGAEVKKPGASVKVSCKASGFTFTSYAISWVRQARGQRLEWIG WIVVGSGNTNYAQKFQERVTITRDMSTSTAYMELSSLRSEDTAVYYCAT HGGDRSYWGQGTLVTVSS | 340 |
| B2. | QVQLVQSGAEVKKPGASVKVSCKASGYSFTNYQVQWVRQAPGQGLEWLG VINTGVGSTNYAQKFQGRVTMTRDTATSTVYMELSSLRSEDTAVYYCAT HGGDRSYWGQGTLVTVSS | 341 |
| A7. | QVQLVQSGAEVKKPGASVKVSCKASGYSFTNYPVQWVRQAPGQGLEWLG VINTGVGSTNYAQKFQGRVTMTRDTATSIVYMELSSLRSEDTAVYYCAT HGGDRSYWGQGTLVTVSS | 342 |
| H3. | QVQLVQSGAEVKKPGASVKVSCRASGYTFTNSFMQWVRQVPGQRLEWVG LSNPSGDYTVYAPKFQGRVTMTTDTATSTFYMELFSLRSDDTAVYYCAT HGGDRSYWGQGTLVTVSS | 343 |
| B4. | QVQLVQSGAEVKKPGASVKVSCRASGYTFTNSFMQWVRQVPGQRLEWVG LSNPSGDYTVYAPKLQGRVTMTTDTATGTFYMELFSLRSDDTAVYYCAT HGGDRSYWGQGTLVTVSS | 344 |
| H05. | EVQLVQSGGGVVQPGGSLRLSCAASGFTFRSYGMHWVRQAPGKGLEWVA FILFDGNNKYYADSVKGRFTISSDNSKNTLYLQMNSLRAEDTAVYYCAT HGGDRSYWGQGTLVTVSS | 345 |
| D06. | QVQLVQSGGGVVQPGRSLRLSCAASGFTFSSYGMHWVRQAPGKGLEWVA VISYDGSNKYYADSVKGRFTISRDNSKNTLYLQMNSLRAEDTAVYYCAK HGGDRSYWGQGTLVTVSS | 346 |
| F3. | QVQLVQSGAEVKKPGASVKVSCKASGYTFISHGMSWVRQAPGQGLEWMG WISADNGNTNYAQKFQERVTITRDMSTSTAYMELSSLRSEDTAVYYCAT HGGDRSYWGQGTLVTVSS | 347 |
| A12. | QVQLVQSGAEVKKPGASVKVSCKASGYTFISHGMSWVRQAPGQGLEWMG WISADNGNTKYAQKFQDRVTLTTDTSTSTAYLELRSLRSDDTAVYYCAT HGGDRSYWGQGTLVTVSS | 348 |
| G3. | QVQLVQSGAEVKKPGASVKVSCKVSGYTLTELSMHWVRQAPGKGLEWMG GFDPEDGETIYAQKFQGRVTMTRDTSISTAYMELSRLRSDDTAVYYCAT HGGDRSYWGQGTLVTVSS | 349 |
| F05. | QVQLVQSGAEVKRPGASVKVSCKASGYTLTELSMHWVRQAPGKGLEWMG GFDPEDGETIYAQKFQGRVTMTEDTSTDTAYMELSSLRSEDTAVYYCAT HGGDRSYWGQGTLVTVSS | 350 |
| H12. | QVQLVQSGAEVKKPGASVKVSCKASGYTFTDNYVHWVRQAPGQGLEWMG GIIPIFGTANYAQKFQGRVTITADESTSTAYMELSSLRSEDTAVYYCAT HGGDRSYWGQGTLVTVSS | 351 |
| G12. | QVQLVQSGAEVKKPGSSVKVSCKASGGAFNAYPISWVRQAPGQGLEWMG GIIPVSGTPNYAQKFQGRVTITADKSTYTAYMELSSLRSEDTAVYYCAT HGGDRSYWGQGTLVTVSS | 352 |
| C06. | QMQLVQSGAEVKKPGASVKVSCMASGYTFTGHYIHWVRQAPGQGLEWMG GIIPIFGTANYAQKFQGRVTITADESTSTAYTELSSLRSEDTAVYYCAT HGGDRSYWGQGTLVTVSS | 353 |
| C11. | QVQLVQSGAAVKKPGASVKVSRKASGYTFTNDYIHWVRQAPGQGLEWMG GIIPIFGTANYAQKFQGRVTITADESTSTAYMELSSLRSEDTAVYYCAT HGGDRSYWGQGTLVTVSS | 354 |

TABLE 3-continued

Heavy chain variable domain (VH) amino acid sequences of exemplary anti-PDGFRβ antibodies.

| Clone name | VH Amino Acid Sequence | SEQ ID NO. |
|---|---|---|
| F08. | QVQLVQSGAEVKKPGASVKVSCKASGYTFTSSYIHWVRQAPGQGLEWMGGIIPIFGTANYAQKFQGRVTITADKSTSTAYMELSSLRSEDTAMYYCATHGGDRSYWGQGTLVTVSS | 355 |
| E9. | QVQLVESGAEVRKPGESLQISCKASGYRFTNYWIGWVRQMPGKGLEWMGITYPADSTTVYSPSFQGQVTISADKSISTVFLQWSSLRSEDTAVYYCATHGGDRSYWGQGTLVTVSS | 356 |
| E11. | QVQLVESGGGVVQPGRSLRLSCAASGFTFSSYWMHWVRQAPGKGLVWVSRINNDGSSTSYADSVKGRFTISRDTAKNTLYLQMNSLRAEDTAVYYCATHGGDRSYWGQGTLVTVSS | 357 |
| H11. | QVQLLESGAEVKNPGASVKVSCKASGYPFSAYYIQWVRQAPGQGLEWMGWLNPNSGDTHSAQKFQGRVTMTRDTSISTAYMELSGLTSDDTAVYYCATHGGDRSYWGQGTLVTVSS | 358 |
| C08. | EVQLLESEGGLVQPGGSLRLSCTASGFSFNAFWMHWVRQAPGKGLEWVSRISIDGTTTTYADSVQGRFTISRDNARNTLYLQMNSLRAEDAAVYYCATHGGDRSYWSQGTLVTVSS | 359 |

(XB1511) Framework Shuffled and selected with human PDGFRβ and off rate selection

| Clone name | VH Amino Acid Sequence | SEQ ID NO. |
|---|---|---|
| XB2708 | QVQLVQSGGGVVQPGGSLRLSCAASGFISRSYGMHWVRQAPGKGLEWVAFILFDGNNKYYADSVKGRFTISSDNSKNTLYLQMNSLRAEDTAVYYCATHGGDRSYWGQGTLVTVSS | 360 |
| D03. | QVQLVQSGGGLVQPGGSLRLSCVASGFTFGNDWMHWVRQAPGKGLVWVSRINADGTSTAYAESVKGRFTVSRDNAKNTLYLQMNGLRAEDTAVYYCATHGGDRSYWGQGTLVTVSS | 361 |
| A10. | QVQLVQSGGGLVQPGRSLRLSCAASGFTFDDYAMNWVRQAPGKGLEWVSLIYSDGSTYYADSVKGRFTISRDNSKKTLYLQMNNLRVEDTAVYYCATHGGDRSYWGQGTLVTVSS | 362 |
| C09. | QVQLVQSGGALVQPGGSLRLSCAASGFTLSNNAMSWVRQAPGKRLEWVSAIDGSGGTTYYAGSVKGRFTISSDNSKNTVFLQMNSLRAEDTAVYYCATHGGDRSYWGQGTLVTVSS | 363 |
| A06. | QVQLVQSGGGLVQPGGSLRLSCAASGFTFSGHWMHWVRQVPGKGLVWVSHISNDGSITRYADSVKGRFTVARDNAKNTMYLQMNSLRAEDTAVYYCATHGGDRSYWGQGTLVTVSS | 364 |
| C05. | QVQLVQSGGGLVKPGGSLRLSCAASGFIFSSNWMHWVRQVPGKGLEWVSRIKTDGSSTSYADSVKGRFTISRDNAKNTLYLQMNSLRAEDTAVYYCATHGGDRSYWGQGTLVTVSS | 365 |
| H01. | QVQLVQSGGGLVQPGGSLRLSCAASGFTLSSDWMHWVRQAPGKGLVWVSRISSDGSTTAYADSVRGRFTISRDNAKNTLYLQMNSLRAEDTAVYYCATHGGDRSYWGQGTLVTVSS | 366 |
| G04. | QVQLVQSGGGLVQPGGSLRLSCAASGFTLSSDWMHWVRQAPGKGLVWVSRISSDGSTTAYADSVRGRFTISRDNTKNTLYLQMNSLRAEDTAVYYCATHGGDRSYWGQGTLVTVSS | 367 |
| G07. | QVQLVQSGGGLVQPGGSLRLSCAASGFTFSSDWMHWVRQAPGEGLVWVSRISSDGSSTAYADSVKGRFTISRDNAKNTVSLQMNSLRAEDTAVYYCATHGGDRSYWGQGTLVTVSS | 368 |

TABLE 4

Light chain variable domain (VL) amino acid sequences of exemplary anti-PDGFRβ antibodies.

| Clone name | VL Amino Acid Sequence | SEQ ID NO. |
|---|---|---|
| | PR2 VL sequences from XB1511 pairing | |
| B10. | QSVLTQSPDLQSVTPREKLTITCRASQTIGSTLHWYQQKPGQSPRLVIKYAYQSVSGVPSRFSGSGSGTEFTLTINGLEAEDAATYYCHQSSSLPWTFGQGTKLTVL | 369 |
| H10. | QSVLTQSPDFQSVSPKDKVTITCRASQSIGSSLHWYQQKPGQSPKLLIKYSSQSFSGVPSRFSGSASGTEFTLTITGLEAEDAATYYCHQSSSLPHTFGQGTKVTVL | 370 |
| F10. | QSVLTQSPEFQSVTPKEKVTITCRASQSIGSGLHWYQQKPHQSPKLLIRYASQSMSGVPSRFSGSGSGTDFTLTISRLEVEDAAMYYCHQSSSLPWTFGQGTKVTVL | 371 |
| B12. | QSVLTQSPDFQSVTPKQNVTFTCRASQSIGIKLHWYQQKPDQSPKVLIKYASQPFSGVPSRFSGRGSGTDFTLTINSLEAEDAATYYCHQTSSLPLTFGGGTKVTVL | 372 |
| B11. | QSVLTQSPGTLSLSPGERATLSCRASQSVSSNYLAWYQQKPGQAPRLLIYGASSRASGIPVRVSGSGSGTDFTLTISRLEPEDFAVYYCQQYGSSPWTFGQGTKLTVL | 373 |
| E7. | QSVLTQSPGTLSLSPGERATLSCRASQSVSSSYLAWYQQKPGQAPRLLIYGASSRATGIPDRFSGSGSGTDFTLTISRLEPEDFAVYYCQQYGSSPQTFGQGTKLTVL | 374 |
| E8. | QSVLTQSPGTLSLSPGERATLSCRASQSVSSSYLAWYQQKPGQAPRLLIYGASSRATGIPDRFSGSGSGTDFTLTISRLEPEDFAVYYCQQYGSSPPYTFGQGTKLTVL | 375 |
| H8. | QSVLTQSPGTLSLSPGERATLSCRASQSVSSNYLAWYLQKPGQAPRLLISGASSRATGIPDRFSGSGSGTDFTLTISRLEPEDFAVYYCQQYAGSPFTFGPGTKLTVL | 376 |
| H12. | QSVLTQSPGTLSLSPGERATLSCRASQSVRSSYVAWYQQKPGQAPRLLISGASRRATGIPDRFTGSGSGTDFTLTISRLEPEDFAVHCQQFGSSPWTFGQGTKLTVL | 377 |
| F8. | QSVLTQPPSASGTPGQRVTISCSGGRSNIGGNAVNWYQQKPGQAPRLLIHVASRRVTGIPDRFSGSGSGTDFTLTISRLEPEDFAIYYCQQYGSSPLTFGGGTKLTVL | 378 |
| D11. | QSVLTQSPGTLSLSPGERATLSCRASQNITSNFFAWYQQKPGQAPRLLIYGASSRATGIPDRISGSGSGTDFTLTISRLEPEDFALYYCQQYGASPRTFGQGTQLTVL | 379 |
| G8. | QSVLTQSPGTLSLSPGDRATLSCRASQSLSGTYLAWYQQKPGQAPRLLIYDASNRAAGIPKRFSGSGSRTDFTLTISRVDPADSAVYYCQQYGSALLTFGGGTKVTVL | 380 |
| H9. | QSVLTQSPGTLSLSPGESATLSCRASEDIYNNYLAWYQHKRGQPPRLLIFRASTRATGIPTRFSGSGSGRDFVLTINRLEPEDFAVYYCQQYGNSWTFGQGTKLTVL | 381 |
| H11. | QSVLTQSPDFQSVTPKEKVTITCRASQSIGSSLHWYQQKPDQSPKLLITFASQSFSGVPSRFSGSGSGTDFTLTINSLEAEDAATYYCHQSRNLPFTFGPGTKLTVL | 382 |
| G12. | QSVLTQSPDFQSVTPKEEVTITCRASESIGTALHWYQQKPDQSPKLLIKYSSQSISGVPSRFVGRGSETEFTLTINSLEAENAATYYCHQSRSFPLTFGQGTQLTVL | 383 |
| E11. | QSVLTQSPGTLSLSPGERATLSCRTSQILHSQYLAWYQQKRGQAPRLLIFRASTRATGIPERFSGSGSGRDFVLTISRLEPEDSAVYYCQQYETSWTFGQGTKVTVL | 384 |
| F12. | QSVLTQDPVVSVALGQTVRITCQGDTLRTCYASWYQQRPRQAPILVIYGENNRPSGIPARFSGSSSGSTASLTITGAQAEDEGDYYCHCRDGLNHLVFGGGTKVTVL | 385 |
| C8. | QSVLTQPPSVSAAPGQKVTISCSGSTSNIGKNFVSWYQHLPGTAPKLLIYDNYQRFSGIPDRFSGFKSGTSATLSITGLQTADEADYYCGTWDSSLSVVIFGGGTKLTVL | 386 |

TABLE 4-continued

Light chain variable domain (VL) amino acid sequences of exemplary anti-PDGFRβ antibodies.

| Clone name | VL Amino Acid Sequence | SEQ ID NO. |
|---|---|---|
| A8. | QAGLTQSPDFQSVTPKERVTITCRASRYIGSNLHWYQQKPDQPPKLLIKL ASQSFSGVPPRFSGGGSGTDFTLTINGLEAEDAATYYCHQTGSFPYTFGQ GTKLTVL | 387 |
| B8. | QAVLTQEPSLTVSPGGTVTLTCGSSTGAVTSGHSPFWFQQRPGQAPRTLI YDTSNKQSWTPARFSGSLLGGKAALTLSGAQPEDEAEYYCLLSYSGPRVV FGGGTKVTVL | 388 |
| F7. | QAVVTQSPDSLAVSLGERATISCKSSXSLLYRSNNKNYLAWYQQKPGQPP RLLISWASTRESGVPDRFSGSGSGTDFTLTVSRLRAEDAAVYYCQQSYRT PFSFGPGTKVTVL | 389 |
| B7. | SYVLTQPLSVSVALGQTARISCGGANIANKNVHWYQLPGQAPVLVIYRD SNRPSGIPERFSGSNSGNTATLTITRAQARDEADYYCQVWDSSSVIIGGG TKVTVL | 390 |
| G9. | SYVLTQDPAVSVALGQTVRITCQGDSLRTYYASWYRQKPGQAPVLVFYGK DNRPSGIPDRFSGSSSGNTASLTITGAQAEDEADYYCKSRDSSAMRWVFG GGTKLTVL | 391 |
| A9. | NFMLTQEPSLTVSPGGTVTLTCGSSTGAVTSGHYPYWFQQKPGQVPRTFI YDTHNRHSWTPVRFSGSLFGGKAALTLSGAQPEDEAEYYCLLYFNPTRVF GGGTKLTV | 392 |
| A11. | NFMLTQPPSASASLGASVTLTCTLSSGYSNYKVDWYQQRPGKGPRFVMRV GTGGIVGSKGDGIPDRFSVLGSGLNRYLTIKNIQEEDESDYHCGADHGRV FGGGTKLTVL | 393 |
| E12. | QPVLTQPPSVSVAPGKTARITCGGNNIGSKSVHWYHLRPGQAPVLVIYFD SDRPSGIPERFSGSNSGNTATLTISRVEAGDEADYYCQVWHSGVIFGGGT KLTVL | 394 |
| H7. | QPVLTQSLDFQSVTPKEKVTITCRASQNIGNSLHWYQQKPNQSPKVLIKY ASQSFSGVPSRFSGSGFGTDFTLTINSLEPEDAATYYCHQSRSSHTFGQG TKLTVL | 395 |
| A10. | EIVLTQSPGNLSLSPGERATLSCTRCTGNIASHFVQWYQQRPGSSPTTVI FGNNQRPSGVSDRFSGSIDSSSNSASLTISRLKTEDEADYYCQSFDVYSH EVVFGGGTKLTVL | 396 |
| C11. | QTVVTQTPVSLSVTPGQPASISCKSSQSLLNSDDGKTYLYWYLQRPGQPP HLLIYEVSKRFSGVPDRFSGSGSGTDFTLRISRVEAEDVGVFYCMQSTHF PFTFGPGTKVTVL | 397 |
| D10. | NIQMTQSPVSLSASLGDTVSITCQASHDISNYLNWYQQKPGKAPKLLIYD ASHLEAGVPSRFRGSGSGTDFTLTINRLEPEDFAVYYCQQYDSPPWTFGQ GTKLTVL | 398 |
| D12. | DVVLTQSPGTMSLSPGERATLSCRASQSVSRTYLAWHQQKPGQAPRLLIY GASSRAAGIPDRFSGSGSGTDFTLSISRLEPEDFAVYYCQQHDTSQWTFG QGTKLTVL | 399 |
| C7. | DIVMTQTPLSLSVTPGQPASISCKSSQSLLHSDGKTHLFWYLQRPGQSPQ LLIYEVSGRFSGVSERFSGSGSGTDFTLKISRVEAEDVGVYYCMQGLHIP HTFGQGTKVEIK | 400 |
| D7. | DIVMTQSPLSLPVTLGQPASISCRSSHSLVHSDGNIYLNWYHQRPGQSPR RLIYSVSKRDSGVPDRFSGSGSRTDFTLKISRVEAEDVGVYFCMQSTHQW TFGQGTKVEIK | 401 |
| C9. | VIWMTQSPSTVSASVGDRVTITCRASQSISSWLAWYQQKPGKAPNLLIYE ASRLESGIPSRFSGSGSGTEFTLTXSSLQPDDFATYYCQQYDSYSRTFGQ GTKVAIK | 402 |
| C12. | DVVMTQSPSSLSASVGDRVTITCRTSQGIRNYLSWYQQKPAKAPKLLIHG ASGLQSGVPSRFSGSGSGTNFTLTISSLQPEDFATYYCQQSFSMRTFGQG TKVEIK | 403 |
| D8. | EIVMTQSPGTLTLSPGEGATLSCRASQSVTSNYLAWYQQRPGASSLQSGQ APRLLIYDASNRATGIPDRFSGSGFGTDFTLTISRLEPEDFAVYYCQQYV NSRTFGQGTKVEIK | 404 |

TABLE 4-continued

Light chain variable domain (VL) amino acid sequences of exemplary anti-PDGFRβ antibodies.

| Clone name | VL Amino Acid Sequence | SEQ ID NO. |
|---|---|---|
| D9. | EIVMTQSPVTLSVSPGERATLSCRASQSVSSKLAWYQQKPGQAPRLLIYG ASTRATGIPARFSGSGSGTEFTLTISSLQSEDFAIYYCQQYNDFFTFGPG TKVDIK | 405 |
| G7. | EIVLTQTPLSSPVTLGQPASISCRSSESPVHSDGNIYLSWLHQRPGQPPR LLLYKISNRMSGVPDRFSGSGAGTDFTLKISRVEAEDVGVYYCMQATQFP SFGQGTKLEIK | 406 |
| G11. | EIVLTQSPGTLSLSPGEGATLSCRASQSVSSRNLAWYQQKPGQAPRLLIY GGSIRASGTSTRFSGSGSGTDFTLTINRLEPEDFAVYYCQQYGDSVFTFG PGTKVDIK | 407 |
| F9. | NIQMTQSPSSLSASVGDRVNITCRASDNIGNYLNWYQHKPGKAPTVLIYA ASTLHYGVPSRFSGRGSGTDFTVTISSLQPEDSATYYCQQSYSTPRTFGQ GTRVELK | 408 |
| E9. | AIQMTQSPSSLSASVGDRVTITCRASESISNYLNWYQQKPGKAPKLLLSA ASRLQSGVPSRFSGSGSGTDFTLTITSLQPEDLATYYCQESYSTLLYTFG QGTKLEIK | 409 |
| | VL sequences from XB2202 VL pairing | |
| B1. | SYELIQPPSVSVAPGKTASITCGGNNIGYDSVHWYQQKPGQAPVLVVFDD SDRPSGIPERFSGSNSGNTATLTISRVEAGDEADYYCQVWESGSEHYVFG TGTQLTVL | 410 |
| E6. | LPVLTQPPSVSVAPGQTARISCGGNNIGATTVHWYQHRPGQAPVSVIFYD NDRPSGIPERFSGSNSGNTATLTISRVEAGDEADYYCQVWESTSDHPTFG GGTQLTVL | 411 |
| F3. | QSVLTQPPSVSVAPGKTARITCGGNNIGSKSVHWYQQKPGQAPVLVIYYD SDRPSGIPERFSGSNSGNTATLTISRVEAGDEADYYCQVWDSSSDHWVFG GGTKLTVL | 412 |
| H4. | SYELTQPSPSVSVPPGQTARITCGGNNIVSKGVHWYQQRPGQAPVLVVYDD SDRPSGIPERFAGFNSGNTATLTISRVEAGDEADYYCQVWDSSSGHRGVF GGGTKVTVL | 413 |
| H5. | SYELTQPPSVSMAPGKTARITCGGNNLGSKIVHWYQQKPGQAPVVVIYSD RDRPSGVPERFSGSNSGNSATLTISGVEAGDEADYYCQVWDSATDHVVFG GGTKLTVL | 414 |
| B5. | SYELTQPPSVSVAPGQTATITCAGNNIGGKSVQWYQQKPGQAPVVVVYDD YGRPSGIPERVSGSNSGNTATLTLTRVEAGDEADYYCQVWDSDRHHVVFG GGTKLTVL | 415 |
| G6. | QLVLTQPPSVSVSPGQTASITCSGDNLGHTNACWYQQNPGQSPVLVIYQD TKRPSGIPERFSGSNSGNPATLTIXRVXAGDEANYYCQVWDINDDYAVFG TGTXLTVL | 416 |
| C1. | QSVLTQSPGTLSLSPGERATLSCTASQSVSSTYLTWYQQKPGQAPRLLIY GASSRATGIPDRFSGSGSGTDFTLTISRLEPEDFAVYYCQQYVSSPPMYT FGQL | 417 |
| F1. | DIQMTQSPSTLSASVGDRVTISCRASQNIDYDLAWYQXKPGKAPXLLIYG ASNLEGGVPSXFSGXGSGTEFTLTISSLQPDXSATYYCQQYVTYPLTFGQ GTRLEIK | 418 |
| A3. | AIQMTQSPSSLSASVGDRVTMTCQASQVIDKYVNWYRQRPGKAPELLIYG ASTLESGVPSRFSGSGSGTQFTFSITSVQPEDFATYICQQYDSVPLTFGP GTILDVKRTVA | 419 |
| B4. | DIQLTQSPSSLSASIGDRVTITCQASQDIFHYLNWFQQKPGKAPKLLIYE ASNLETGVPSRFSGSGSVTDFTFTISSLQPEDIATYYCQQYEDLPSFGGG TKVDIKRTVA | 420 |
| B6. | EIVLTQSPGTLSLSPGERATLSCRASQSFGSNYLAWYQHKPGQAPRLLIF AASNRATGIPDRFTGSASGTDFTLTINRVEPEDLAVYYCQQYGSFPYSFG QGTKLEIK | 421 |
| F2. | NIQMTQSPSSLSASVGDRVTITCQASQFIHIYLNWYQQKLGKAPKLLIYG ASNLERGVPSRFSGRGSETDFTFTIDSLQPEDIATYFCQQYQNPPFTFGG GTKVEINGTVA | 422 |

TABLE 4-continued

Light chain variable domain (VL) amino acid sequences of exemplary anti-PDGFRβ antibodies.

| Clone name | VL Amino Acid Sequence | SEQ ID NO. |
|---|---|---|
| D3. | AIRMTQSPSSLSASIGDRISVTCRASQDVGIYVAWFQQKPGKPPRSLIYA ASYLQTAVPPKFRGSGSGTDFTLTISDLQPDDFATYYCQQYKTFPHTFGQ GTKLDFKRTVA | 423 |
| G2. | VIWMTQSPSTLSASVGDRVTITCRASQDINTWLAWYQQKPGKAPKLLMFK VSTLESGDFSRFSGSGSGTEFTLTVSSLQPDDSAIYYCQQYHSYPYTFGQ GTRLEIK | 424 |
| A4. | DVVMTQSPSSLSASVGDRVTITCQASQDISNWLNWYQQKPGKAPKLLIYE ASNLETGVPSRFSGSGSGTDFTFTISSLQPEDIATYYCQQYNNVLRTFGQ GTKVEIK | 425 |
| G4. | EIVMTXSPATLSVSPGERVTLSCRVSQNVFSDLAWYQRKTGQSPRLLIHG ASTRATGIPTRFSGSGSGTEFTLTISSLXSDDFAVYYCQQYNKWPTFGQG TKVEIK | 426 |
| D5. | AIQLTQSPSSLSASVGDRVNITCRASDNIGNYLNWYQHKPGKAPTVLIYA ASTLHYGVPSRFSGRGSGTDFTVTISSLRSDDFAVYYCQQYYNWPPWTFG QGTTVDIKRTVA | 427 |
| A1. | EIVLTQSPATLSLSPGERATLSCRASQSVSSFLAWYQQKPGQAPRLLIFE ASTRATGISARFSGSGSGTDFTLTISTLEPEDFAVYYCQQRSNGVTFGQG TRLEIK | 428 |
| H2. | DIQMTQSPSTLSASVGDTVTITCRATESISIWLAWYQQEPGKAPNLLVSQ ASSLKTGVPSRFSASGSGTEFTLTISSLHPDDFATYVCQHYHTYPFTFGP GTKVDMKRTVA | 429 |
| E2. | EIVLTQSPDSXAVSLGERATINCKSSQSVLYSSNNKNYLAWYQQKPGQPP RLLIYWASTRESGVPDRFSGSGSGTDFTLTISRLQAEDVAVYYCQQYYLT PTFTVTFGQGTKLEIK | 430 |
| F4. | DIQLTQSPSSVSASVGDRVTITCRASQDISSWLAWYQQKPGKAPKFLIYR ATNLQSGVPSRFSGSGSGTDFTLTISSLQPGDFATYYCQQTNIFPLTFGG GTKVEVKRTVA | 431 |
| C5. | DIVMTQSPDSLAVSLGERATINCKSSQSVLYSSNNRNYLAWYQKKPGQPP KLLFYWASTRESGVSDRFSGSGSGTDFTLTISSLQAEDVAVYYCQQYHTT PYTFGQGTKLEIK | 432 |
| E5. | VIWMTQSPSSLSASVGDRVSITCRASQTFTSHLNWYQQKPGQPPKLLIFA ASNLQSGVPSRFSGSGSGTDFTLTINGLQATDFATYYCQQSFSSPWTFGQ GTTVDVKGTVA | 433 |
| F6. | DIQMTQSPSSLSASVGDRVTITCRASQSVNVYLNWYQQKPGKAPKLLIYS ASTLQSGVPSRFTGSGSRTDFTLTINGLQPEDFATYYCQQSFTTLVTFGP GTRVDVTRTVA | 434 |
| G5. | DIQMTQSPSSLSASVGDRVTITCRASQDISSSLAWYQQKPGKAPKPLIYD ASTLQTGVPSRFSGRASGTDFTLTIDSLQPEDFATYCCQQFNSYPLSFGG GTKVELKRTVA | 435 |
| A5. | SYELTQPPSASASLGASVTLTCTVSSGYRSYEVDWFQQRPGKGPRFVMRV GTGGIVGSRGDGIPDRFSVWGSGLNRYLTIEDIQEEDESDYYCGADHGSG SNLVYVFGTGTKVTVL | 436 |
| D6. | QLVLTQPPSASASLGASVTLTCTLSSDYSSYNVDWYQQRPGMGPRFLMRV GTGGIVGSRGDGIPDRFSVKGSGLNRYLTIKNIQEEDESDYYCGADHGSG SDFVYVFGIGTKLTVL | 437 |
| E4. | QSVLTQPPSASGTPGQRVTISCSGSSTNIGSNAVNWYQQLPRIAPKLLIY TNNQRPSGVPDRFSGSKSGTSASLAISGLQSEDEANYYCAAWDDSLNGPV FGGGTQLTVL | 438 |
| F5. | QSVLTQPPSASGTPGQTVIISCSGGGSNIGSNFGYWYQQFPGTAPKLLIY TTDRRPSGVPDRFSGSKSGTTASLAISGLRSEDEADYYCAAWDDRLSGPV FGGGTQLTVL | 439 |
| G1. | QTVVTQPPSVSGTPGQRVTISCSGSSSNIGSNSVDWYQQFPGSAPKLLIY TNNQRPSGVPDRFSGSKSGTSASLAISGLRSEDEADYYCATWDDDLSNPK WVFGGGTKLTVL | 440 |

TABLE 4-continued

Light chain variable domain (VL) amino acid sequences of exemplary anti-PDGFRβ antibodies.

| Clone name | VL Amino Acid Sequence | SEQ ID NO. |
|---|---|---|
| E3. | DIVMTQSPLSLPVTPGEPASISCRSSQSLLHSNGYNFLDWYLQKPGQSPQ LLIYLGSNRASGVPDRFSGSGSGTDFTLKISRVEAEDVGIYYCMQALQTS WTFGQGTKLEIK | 441 |
| A2. | DICRIRPLIRLTIGTITIYNYNGCCDDTVSTLPARHPWTAGLHLQSPRRL MYQVSTRDSGVPDRFSGSGSGTDFTLRISRVEAEDVGVYYCMQGTHWPYT FGQGTKLEIRRTVA | 442 |
| D1. | DIVMTQTPLSLSVTPGQPAAISCKSSQSLVHRDGKTYLYWYLQKPGHSPQ LLVYEASSRFSGVPDRISGSASGTQFTLNISRVEAEDVGLYYCMQSRNLP KTFGQGTKVEIK | 443 |
| C4. | SYELTQPTSLSASPGASASLTCTLSSGFNVVSYNIYWYQQKPGSPPQYLL RYRSDSDRHQGSGVPSRFSGSKDASANAGILVISALQSDDEADYYCMVWY SAWVFGGG | 444 |
| E1. | SYELTQPLSVSVALGQTATITCAGNNIGTYYVHWYQQRPGQAPVLVMYRD TNRPSGISDRFSGSNSGDTATLTICGVQVGDEADYYCHVLDSSTIVIFGG GTQLTVL | 445 |
| A6. | QSVLTQSPATLSVSPGERASLSCRASQSVSSNLAWYQQKPGQAPRLLIYG ASTRATGIPARFSGSGSGTEFTLTISSLQSEDFAVYYCHQYNNWPLYTFG QGTKLTVL | 446 |
| H1. | QSVLTQDPAVPVALGQTVRITCQGDSLRTYYASWYQQKPGQAPLLVIYGK NTRPSGIPVRFSGSSSGNTASLTITGAQAEDEADYYCNSRDSSGYLLLFG TGTKLTVL | 447 |
| B2. | QAVLTQEPSLTVSPGGTVTLTCGSSTGAVTSGHYPYWFQQKPGQAPRTLI YDASNKHSWTPARFSGSLLGGKAALTLSGAQPEDEAEYYCLLSYSGAGVF GTGTKVTVL | 448 |
| C2. | DIQMTQSPSSLSASVGDRVAIACRPSQDIGTDLGWYQQKPGKAPKLLIFD SSTLQSGVPSRFSGSLSGTDFILTITNLQPEDFATYYCLQDYSFPYTFGQ GTKLQIKRTVA | 449 |
| G3. | SYVLTQPPSVSVSPGQTASITCSGDELKYKYTCWYHQKPGQSPVLLIYQD TKRPSGIPERFSGSRSENTATLTISGTQAMDEADYYCQAWDSSHAVFGRG TQLTVL | 450 |
| H3. | H3SYVLTQPPSVSVFPGQTARITCSGSTFPKLYSFWYQQKTGQAPLLVIY KDTERPSGIPERFSGSTSGTTVTLIISGVQPEDDADYYCQSEDSRGPVFG GGTKVTVL | 451 |
| D4. | GVVMTQTPLSSLVTLGQPASISCRSSESVVHDDGNTYLSWLQQRPGQPPR LLIYKISNRFSGVPDRFSGSGAGTDFTLKISRVEPEDVGVYYCVQATHFP VTFGGGTRVEIK | 452 |
| C6. | QSALTQPASVSASPGQSVTISCTGTSDDVGRYDYVSWYQQHPGGAPKLIL YDVNRRPSGVSDRFSGSKSANKASLTISGLQADDEGDYYCCSYTTGSTLY LFGTGTQLTVL | 453 |

In certain embodiments, the antibody, or antigen binding fragment thereof, comprises a heavy chain CDR3 sequence of SEQ ID NO:1 together with one or more CDR region amino acid sequences selected from the group consisting of SEQ ID NOs: 2-317. In exemplary embodiments, the antibody, or antigen binding fragment thereof, comprises HCDR3, HCDR2 and HCDR1 amino acid sequences selected from the group consisting of SEQ ID NO: 1, 2 and 3; 1, 2 and 34; 1, 3 and 35; 1, 4 and 35; 1, 5 and 36; 1, 6 and 36; 1, 3 and 36; 1, 7 and 36; 1, 8 and 36; 1, 9 and 36; 1, 10 and 38; 1, 2 and 38; 1, 11 and 39; 1, 12 and 40; 1, 13 and 41; 1, 13 and 42; 1, 13 and 33; 1, 14 and 43; 1, 14 and 44; 1, 15 and 45; 1, 16 and 45; 1, 17 and 46; 1, 18 and 47; 1, 19 and 47; 1, 20 and 48; 1, 2 and 49; 1, 21 and 50; 1, 2 and 51; 1, 2 and 52; 1, 2 and 53; 1, 22 and 54; 1, 23 and 55; 1, 24 and 56; 1, 25 and 46; 1, 26 and 57; 1, 27 and 58; 1, 28 and 59; 1, 29 and 60; 1, 30 and 61; 1, 31 and 62; and, 1, 32 and 62, respectively.

In other embodiments, the antibody, or antigen binding fragment thereof, further comprises the LCDR3, LCDR2 and LCDR1 amino acid sequences selected from the group consisting of SEQ ID NO: 63, 148 and 233; 64, 149 and 234; 65, 150 and 235; 66, 151 and 236; 67, 152 and 237; 68, 153 and 238; 69, 154 and 239; 70, 155 and 240; 71, 156 and 241; 72, 157 and 242; 73, 158 and 243; 741, 159 and 244; 75, 160 and 245; 76, 161 and 246; 77, 162 and 247; 78, 163 and 248; 79, 164 and 249; 80, 165 and 250; 81, 166 and 251; 82, 167 and 252; 83, 168 and 253; 84, 169 and 254; 85, 170 and 255; 86, 171 and 256; 87, 172 and 257; 88, 173 and 258; 89, 174 and 259; 90, 175 and 260; 91, 176 and 261; 92, 177 and 262; 93, 178 and 263; 94, 179 and 264; 95, 180 and 265; 96, 181 and 266; 97, 182 and 267; 98, 183 and 268; 99, 184 and 269; 100, 185 and 270; 101, 186 and 271; 102, 187 and 272; 103, 188 and 273; 104, 189 and 274; 105, 190 and 275; 106, 191 and 276; 107, 192 and 277; 108, 193 and 278; 109, 194 and 279; 110, 195 and 280; 111, 196 and 281; 112, 197 and 282; 113, 198 and 283; 114, 199 and 284; 115, 200 and 285; 116, 201 and 286; 117, 202 and 287; 118, 203 and 288; 119, 204 and 289; 120, 205 and 290; 121, 206 and 291; 122, 207 and 292; 123, 208 and 293; 124, 209 and 294; 125, 210 and 295; 126, 211 and 296; 127, 212 and 297; 128, 213 and 298; 129, 214 and 299; 130, 215 and 300; 131, 216 and 301; 132, 217 and 302; 133, 218 and 303; 134, 219 and 304; 135, 220 and 305; 136, 221 and 306; 137, 222 and 307; 138, 223 and 308; 139, 224 and 309; 140, 225 and 310; 141, 226 and 311; 142, 227 and 312; 143, 228 and 313; 144, 229 and 314; 145, 220 and 315; 146, 231 and 316; and, 147, 232 and 317, respectively.

In other embodiments, the antibody, or antigen binding fragment thereof, comprises the HCDR3 amino acid sequence set forth in SEQ ID NO: 1, and LCDR3, LCDR2 and LCDR1 amino acid sequences selected from the group consisting of SEQ ID NO: 63, 148 and 233; 64, 149 and 234; 65, 150 and 235; 66, 151 and 236; 67, 152 and 237; 68, 153 and 238; 69, 154 and 239; 70, 155 and 240; 71, 156 and 241; 72, 157 and 242; 73, 158 and 243; 741, 159 and 244; 75, 160 and 245; 76, 161 and 246; 77, 162 and 247; 78, 163 and 248; 79, 164 and 249; 80, 165 and 250; 81, 166 and 251; 82, 167 and 252; 83, 168 and 253; 84, 169 and 254; 85, 170 and 255; 86, 171 and 256; 87, 172 and 257; 88, 173 and 258; 89, 174 and 259; 90, 175 and 260; 91, 176 and 261; 92, 177 and 262; 93, 178 and 263; 94, 179 and 264; 95, 180 and 265; 96, 181 and 266; 97, 182 and 267; 98, 183 and 268; 99, 184 and 269; 100, 185 and 270; 101, 186 and 271; 102, 187 and 272; 103, 188 and 273; 104, 189 and 274; 105, 190 and 275; 106, 191 and 276; 107, 192 and 277; 108, 193 and 278; 109, 194 and 279; 110, 195 and 280; 111, 196 and 281; 112, 197 and 282; 113, 198 and 283; 114, 199 and 284; 115, 200 and 285; 116, 201 and 286; 117, 202 and 287; 118, 203 and 288; 119, 204 and 289; 120, 205 and 290; 121, 206 and 291; 122, 207 and 292; 123, 208 and 293; 124, 209 and 294; 125, 210 and 295; 126, 211 and 296; 127, 212 and 297; 128, 213 and 298; 129, 214 and 299; 130, 215 and 300; 131, 216 and 301; 132, 217 and 302; 133, 218 and 303; 134, 219 and 304; 135, 220 and 305; 136, 221 and 306; 137, 222 and 307; 138, 223 and 308; 139, 224 and 309; 140, 225 and 310; 141, 226 and 311; 142, 227 and 312; 143, 228 and 313; 144, 229 and 314; 145, 220 and 315; 146, 231 and 316; and, 147, 232 and 317, respectively.

In other embodiments, the antibody, or antigen binding fragment thereof, comprises HCDR3, HCDR2 and HCDR1 amino acid sequences selected from the group consisting of SEQ ID NO: 1, 2 and 3; 1, 2 and 34; 1, 3 and 35; 1, 4 and 35; 1, 5 and 36; 1, 6 and 36; 1, 3 and 36; 1, 7 and 36; 1, 8 and 36; 1, 9 and 36; 1, 10 and 38; 1, 2 and 38; 1, 11 and 39; 1, 12 and 40; 1, 13 and 41; 1, 13 and 42; 1, 13 and 33; 1, 14 and 43; 1, 14 and 44; 1, 15 and 45; 1, 16 and 45; 1, 17 and 46; 1, 18 and 47; 1, 19 and 47; 1, 20 and 48; 1, 2 and 49; 1, 21 and 50; 1, 2 and 51; 1, 2 and 52; 1, 2 and 53; 1, 22 and 54; 1, 23 and 55; 1, 24 and 56; 1, 25 and 46; 1, 26 and 57; 1, 27 and 58; 1, 28 and 59; 1, 29 and 60; 1, 30 and 61; 1, 31 and 62; and, 1, 32 and 62, respectively, and LCDR3, LCDR2 and LCDR1 amino acid sequences selected from the group consisting of SEQ ID NO: 63, 148 and 233; 64, 149 and 234; 65, 150 and 235; 66, 151 and 236; 67, 152 and 237; 68, 153 and 238; 69, 154 and 239; 70, 155 and 240; 71, 156 and 241; 72, 157 and 242; 73, 158 and 243; 741, 159 and 244; 75, 160 and 245; 76, 161 and 246; 77, 162 and 247; 78, 163 and 248; 79, 164 and 249; 80, 165 and 250; 81, 166 and 251; 82, 167 and 252; 83, 168 and 253; 84, 169 and 254; 85, 170 and 255; 86, 171 and 256; 87, 172 and 257; 88, 173 and 258; 89, 174 and 259; 90, 175 and 260; 91, 176 and 261; 92, 177 and 262; 93, 178 and 263; 94, 179 and 264; 95, 180 and 265; 96, 181 and 266; 97, 182 and 267; 98, 183 and 268; 99, 184 and 269; 100, 185 and 270; 101, 186 and 271; 102, 187 and 272; 103, 188 and 273; 104, 189 and 274; 105, 190 and 275; 106, 191 and 276; 107, 192 and 277; 108, 193 and 278; 109, 194 and 279; 110, 195 and 280; 111, 196 and 281; 112, 197 and 282; 113, 198 and 283; 114, 199 and 284; 115, 200 and 285; 116, 201 and 286; 117, 202 and 287; 118, 203 and 288; 119, 204 and 289; 120, 205 and 290; 121, 206 and 291; 122, 207 and 292; 123, 208 and 293; 124, 209 and 294; 125, 210 and 295; 126, 211 and 296; 127, 212 and 297; 128, 213 and 298; 129, 214 and 299; 130, 215 and 300; 131, 216 and 301; 132, 217 and 302; 133, 218 and 303; 134, 219 and 304; 135, 220 and 305; 136, 221 and 306; 137, 222 and 307; 138, 223 and 308; 139, 224 and 309; 140, 225 and 310; 141, 226 and 311; 142, 227 and 312; 143, 228 and 313; 144, 229 and 314; 145, 220 and 315; 146, 231 and 316; and, 147, 232 and 317, respectively.

In other embodiments, the antibody, or antigen binding fragment thereof, comprises at least one of the VH amino acid sequences set forth in SEQ ID NO: 318-368.

In other embodiments, the antibody, or antigen binding fragment thereof, comprises at least one of the VL amino acid sequences set forth in SEQ ID NO: 369-453.

In other embodiments, the antibody, or antigen binding fragment thereof, comprises the VH region amino acid sequence set forth in SEQ ID NO: 318, 321, or 360 paired with a VL region amino acid sequences selected from the group consisting of: SEQ ID NO: 369-453.

In certain embodiments, the antibody, or antigen binding fragment thereof, comprises one or more CDR amino acid sequence selected from the group consisting of SEQ ID NO: 1-317, wherein the one or more CDR region amino acid sequences comprises at least one or more conservative amino acid substitutions (e.g., 1, 2, 3, 4, or 5 conservative amino acid substitutions). Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted non-essential amino acid residue in an anti-PDGFRβ antibody is preferably replaced with another amino acid residue from the same class. Methods of identifying amino acid conservative substitutions which do not eliminate antigen binding are well-known in the art (see, e.g., Brummell et al., Biochem. 32:1180-1187 (1993); Kobayashi et al. Protein Eng. 12(10): 879-884 (1999); and Burks et al. Proc. Natl. Acad. Sci. USA 94:412-417 (1997)).

In another embodiment, the present invention provides anti-PDGFRβ antibodies, or antigen binding fragment thereof, that comprise a VH and/or VL region amino acid sequence with about 80%, 85%, 86%, 87%, 88%, 89%, 90%, 91%, 92%, 93%, 94%, 95%, 96%, 97%, 98%, or 99%, identity to the VH region amino acid sequence set forth in SEQ ID NO: 318-368, and/or the VL region amino acid sequence set forth in SEQ ID NO: 369-453, respectively.

In another aspect, the present invention provides anti-PDGFRβ antibodies that bind to the same epitope and/or cross compete with an antibody, or antigen binding fragment thereof comprising the VH domain amino acid sequence set forth in SEQ ID NO: 318. Such antibodies can be identified using routine competition binding assays including, for example, surface plasmon resonance (SPR)-based competition assays.

In another aspect, the present invention provides a diverse library of unpaired VH domains wherein each member of the library binds specifically to human PDGFRβ and wherein diversity lies in the FR1-FR3 regions. In a preferred embodiment, each member of the library comprises an identical heavy chain CDR3 (e.g., the amino acid sequence set forth in SEQ ID NO: 1) amino acid sequence that binds specifically to human PDGFRβ, and wherein diversity lies in the FR1-FR3 regions.

In another aspect, the present invention provides a diverse library of stable VH/VL pairs wherein each member of the library binds to human PDGFRβ Preferably each member of the library comprises a VH domain comprising the CDR3 amino acid sequence set forth in SEQ ID NO: 1. The stable VH/VL pairs can be selected using any methods known in the art including, without limitation those set forth in U.S. provisional patent application 61/453,106, which is hereby incorporated by reference in its entirety.

Any type of VH or VL domain expression library can be employed in the methods of the invention. Suitable expression libraries include, without limitation, nucleic acid display, phage display, and cell surface display libraries (e.g., yeast, mammalian, and bacterial cells). In a preferred embodiment, the library is a nucleic acid display library generated according to the methods set forth in WO2010/011944, which is hereby incorporated by reference in its entirety. Methods for screening expression libraries are well known in the art. See, for example, Antibody Engineering: Methods and Protocols. Methods in Molecular Biology Volume 248, (B.K.C. Lo, Ed) Humana Press, 2004 (ISBN: 1-58829-092-1), which is hereby incorporated by reference in its entirety.

III. MODIFIED BINDING POLYPEPTIDES

In certain embodiments, binding polypeptides of the invention may comprise one or more modifications. Modified forms of binding polypeptides of the invention can be made using any techniques known in the art.

i) Reducing Immunogenicity

In certain embodiments, binding polypeptides (e.g., antibodies or antigen binding fragments thereof) of the invention are modified to reduce their immunogenicity using art-recognized techniques. For example, antibodies, or fragments thereof, can be chimericized, humanized, and/or deimmunized.

In one embodiment, an antibody, or antigen binding fragments thereof, of the invention may be chimeric. A chimeric antibody is an antibody in which different portions of the antibody are derived from different animal species, such as antibodies having a variable region derived from a murine monoclonal antibody and a human immunoglobulin constant region. Methods for producing chimeric antibodies, or fragments thereof, are known in the art. See, e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entireties. Techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) may be employed for the synthesis of said molecules. For example, a genetic sequence encoding a binding specificity of a mouse anti-PDGFRβ antibody molecule may be fused together with a sequence from a human antibody molecule of appropriate biological activity. As used herein, a chimeric antibody is a molecule in which different portions are derived from different animal species, such as those having a variable region derived from a murine monoclonal antibody and a human immunoglobulin constant region, e.g., humanized antibodies.

In another embodiment, an antibody, or antigen binding portion thereof, of the invention is humanized. Humanized antibodies have a binding specificity comprising one or more complementarity determining regions (CDRs) from a non-human antibody and framework regions from a human antibody molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

In some embodiments, de-immunization can be used to decrease the immunogenicity of PDGFRβ binding polypeptides (e.g., antibody, or antigen binding portion thereof). As used herein, the term "de-immunization" includes alteration of polypeptide (e.g., an antibody, or antigen binding portion thereof) to modify T cell epitopes (see, e.g., WO9852976A1, WO0034317A2). For example, VH and VL sequences from the starting PDGFRβ-specific antibody, or antigen binding portion thereof, of the invention may be analyzed and a human T cell epitope "map" may be generated from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of PDGFRβ-specific antibodies or fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

ii) Effector Functions and Fc Modifications

Binding polypeptides of the invention may comprise an antibody constant region (e.g. an IgG constant region e.g., a human IgG constant region, e.g., a human IgG1 or IgG4 constant region) which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In preferred embodiments, the binding polypeptides (e.g., antibodies or antigen binding fragments thereof) of the invention bind to an Fc-gamma receptor. In alternative embodiments, binding polypeptides of the invention may comprise a constant region which is devoid of one or more effector functions (e.g., ADCC activity) and/or is unable to bind Fcγ receptor.

Certain embodiments of the invention include anti-PDG-FRβ antibodies in which at least one amino acid in one or more of the constant region domains has been deleted or otherwise altered so as to provide desired biochemical characteristics such as reduced or enhanced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies, or fragments thereof, for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain other embodiments, binding polypeptides comprise constant regions derived from different antibody isotypes (e.g., constant regions from two or more of a human IgG1, IgG2, IgG3, or IgG4). In other embodiments, binding polypeptides comprises a chimeric hinge (i.e., a hinge comprising hinge portions derived from hinge domains of different antibody isotypes, e.g., an upper hinge domain from an IgG4 molecule and an IgG1 middle hinge domain). In one embodiment, binding polypeptides comprise an Fc region or portion thereof from a human IgG4 molecule and a Ser228Pro mutation (EU numbering) in the core hinge region of the molecule.

In certain embodiments, the Fc portion may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, biodistribution and serum half-life, may easily be measured and quantified using well know immunological techniques without undue experimentation.

In certain embodiments, an Fc domain employed in an antibody of the invention is an Fc variant. As used herein, the term "Fc variant" refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

The binding polypeptides of the invention may employ any art-recognized Fc variant which is known to impart an improvement (e.g., reduction or enhancement) in effector function and/or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein. In one exemplary embodiment, a binding polypeptide of the invention may comprise an Fc variant comprising an amino acid substitution at EU position 268 (e.g., H268D or H268E). In another exemplary embodiment, a binding polypeptide of the invention may comprise an amino acid substitution at EU position 239 (e.g., S239D or S239E) and/or EU position 332 (e.g., I332D or I332Q).

In certain embodiments, a binding polypeptide of the invention may comprise an Fc variant comprising an amino acid substitution which alters the antigen-independent effector functions of the antibody, in particular the circulating half-life of the binding polypeptide. Such binding polypeptides exhibit either increased or decreased binding to FcRn when compared to binding polypeptides lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the altered binding polypeptides (e.g., antibodies or antigen binding fragments thereof) of the invention exhibit reduced transport across the epithelium of kidney glomeruli from the vasculature. In another embodiment, the altered binding polypeptides (e.g., antibodies or antigen binding fragments thereof) of the invention exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047327 which is incorporated by reference herein. In certain exemplary embodiments, the binding polypeptides (e.g., antibodies or antigen binding fragments thereof) of the invention comprise an Fc domain having one or more of the following substitutions: V284E, H285E, N286D, K290E and S304D (EU numbering).

In other embodiments, binding polypeptides, for use in the diagnostic and treatment methods described herein have a constant region, e.g., an IgG1 or IgG4 heavy chain constant region, which is altered to reduce or eliminate glycosylation. For example, a binding polypeptides (e.g., antibodies or antigen binding fragments thereof) of the invention may also comprise an Fc variant comprising an amino acid substitution which alters the glycosylation of the antibody Fc. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

Exemplary amino acid substitutions which confer reduce or altered glycosylation are disclosed in International PCT Publication No. WO05/018572, which is incorporated by reference herein. In preferred embodiments, the antibodies, or fragments thereof, of the invention are modified to eliminate glycosylation. Such antibodies, or fragments thereof, may be referred to as "agly" antibodies, or fragments thereof, (e.g. "agly" antibodies). While not being bound by theory, it is believed that "agly" antibodies, or fragments thereof, may have an improved safety and stability profile in vivo. Exemplary agly antibodies, or fragments thereof, comprise an aglycosylated Fc region of an IgG4 antibody which is devoid of Fc-effector function thereby eliminating the potential for Fc mediated toxicity to the normal vital organs that express PDGFRβ. In yet other embodiments, antibodies, or fragments thereof, of the invention comprise an altered glycan. For example, the antibody may have a reduced number of fucose residues on an N-glycan at Asn297 of the Fc region, i.e., is afucosylated. In another embodiment, the antibody may have an altered number of sialic acid residues on the N-glycan at Asn297 of the Fc region.

iii) Covalent Attachment

Binding polypeptides of the invention may be modified, e.g., by the covalent attachment of a molecule to the binding polypeptide such that covalent attachment does not prevent the binding polypeptide from specifically binding to its cognate epitope. For example, but not by way of limitation, the antibodies, or fragments thereof, of the invention may be modified by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Binding polypeptide (e.g., antibodies, or fragments thereof) of the invention may further be recombinantly fused to a heterologous polypeptide at the N- or C-terminus or chemically conjugated (including covalent and non-covalent conjugations) to polypeptides or other compositions. For example, anti-PDGFRβ antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Binding polypeptides may be fused to heterologous polypeptides to increase the in vivo half life or for use in immunoassays using methods known in the art. For example, in one embodiment, PEG can be conjugated to the binding polypeptides of the invention to increase their half-life in vivo. Leong, S. R., et al., Cytokine 16:106 (2001); Adv. in Drug Deliv. Rev. 54:531 (2002); or Weir et al., Biochem. Soc. Transactions 30:512 (2002).

Moreover, binding polypeptides of the invention can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Binding polypeptides of the invention may be used in non-conjugated form or may be conjugated to at least one of a variety of molecules, e.g., to improve the therapeutic properties of the molecule, to facilitate target detection, or for imaging or therapy of the patient. Binding polypeptides of the invention can be labeled or conjugated either before or after purification, when purification is performed. In particular, binding polypeptides of the invention may be conjugated to therapeutic agents, prodrugs, peptides, proteins, enzymes, viruses, lipids, biological response modifiers, pharmaceutical agents, or PEG.

The present invention further encompasses binding polypeptides of the invention conjugated to a diagnostic or therapeutic agent. The binding polypeptides can be used diagnostically to, for example, monitor the development or progression of a immune cell disorder (e.g., CLL) as part of a clinical testing procedure to, e.g., determine the efficacy of a given treatment and/or prevention regimen. Detection can be facilitated by coupling the binding polypeptides to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Binding polypeptides for use in the diagnostic and treatment methods disclosed herein may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG.

In another embodiment, an anti-PDGFRβ antibody for use in the diagnostic and treatment methods disclosed herein can be conjugated to a molecule that decreases tumor cell growth. In other embodiments, the disclosed compositions may comprise antibodies, or fragments thereof, coupled to drugs or prodrugs. Still other embodiments of the present invention comprise the use of antibodies, or fragments thereof, conjugated to specific biotoxins or their cytotoxic fragments such as ricin, gelonin, *Pseudomonas* exotoxin or diphtheria toxin. The selection of which conjugated or unconjugated antibody to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy tumor cells in animal models, and in some cases in humans. Exemplary radioisotopes include: 90Y, 125I, 131I, 123I, 111In, 105Rh, 153Sm, 67Cu, 67Ga, 166Ho, 177Lu, 186Re and 188Re. The radionuclides act by producing ionizing radiation which causes multiple strand breaks in nuclear DNA, leading to cell death. The isotopes used to produce therapeutic conjugates typically produce high energy alpha- or beta-particles which have a short path length. Such radionuclides kill cells to which they are in close proximity, for example neoplastic cells to which the conjugate has attached or has entered. They have little or no effect on non-localized cells. Radionuclides are essentially non-immunogenic.

IV. EXPRESSION OF BINDING POLYPEPTIDES

Following manipulation of the isolated genetic material to provide binding polypeptides of the invention as set forth above, the genes are typically inserted in an expression vector for introduction into host cells that may be used to produce the desired quantity of the claimed antibodies, or fragments thereof.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals. In particularly preferred embodiments the cloned variable region genes are inserted into an expression vector along with the heavy and light chain constant region genes (preferably human) synthetic as discussed above.

In other preferred embodiments the binding polypeptides, or fragments thereof, of the invention may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193, 980 which is incorporated herein. Those skilled in the art will appreciate that such expression systems may be used to effectively produce the full range of polypeptides disclosed in the instant application.

More generally, once a vector or DNA sequence encoding an antibody, or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472. Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for antibody expression is of mammalian origin; those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (Potelligent® Cells) (Biowa, Princeton, N.J.)). In one embodiment NS0 cells may be used. CHO cells are particularly preferred. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-)affinity chromatography.

Genes encoding the binding polypeptides, or fragments thereof, of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides can become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

V. PHARMACEUTICAL FORMULATIONS AND METHODS OF ADMINISTRATION OF BINDING POLYPEPTIDES

In another aspect, the invention provides pharmaceutical compositions comprising an anti-PDGFRβ antibody, or fragment thereof.

Methods of preparing and administering antibodies, or fragments thereof, of the invention to a subject are well known to or are readily determined by those skilled in the art. The route of administration of the antibodies, or fragments thereof, of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an antibody by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders.

Effective doses of the stabilized antibodies, or fragments thereof, of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

For passive immunization with an antibody of the invention, the dosage may range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered may fall within the ranges indicated.

Antibodies, or fragments thereof, of the invention can be administered on multiple occasions. Intervals between single dosages can be, e.g., daily, weekly, monthly or yearly. Intervals can also be irregular as indicated by measuring blood levels of polypeptide or target molecule in the patient. In some methods, dosage is adjusted to achieve a certain plasma antibody or toxin concentration, e.g., 1-1000 ug/ml or 25-300 ug/ml. Alternatively, antibodies, or fragments thereof, can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies. In one embodiment, the antibodies, or fragments thereof, of the invention can be administered in unconjugated form. In another embodiment, the antibodies of the invention can be administered multiple times in conjugated form. In still another embodiment, the antibodies, or fragments thereof, of the invention can be administered in unconjugated form, then in conjugated form, or vise versa.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 ug to 10 mg, or 30-300 ug DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. Intramuscular injection or intravenous infusion are preferred for administration of a antibody of the invention. In some methods, therapeutic antibodies, or fragments thereof, are injected directly into the cranium. In some methods, antibodies, or fragments thereof, are administered as a sustained release composition or device, such as a Medipad™ device.

Agents of the invention can optionally be administered in combination with other agents that are effective in treating the disorder or condition in need of treatment (e.g., prophylactic or therapeutic). Preferred additional agents are those which are art recognized and are standardly administered for a particular disorder.

Effective single treatment dosages (i.e., therapeutically effective amounts) of 90Y-labeled antibodies of the invention range from between about 5 and about 75 mCi, more preferably between about 10 and about 40 mCi. Effective single treatment non-marrow ablative dosages of 131I-labeled antibodies range from between about 5 and about 70 mCi, more preferably between about 5 and about 40 mCi. Effective single treatment ablative dosages (i.e., may require autologous bone marrow transplantation) of 131I-labeled antibodies range from between about 30 and about 600 mCi, more preferably between about 50 and less than about 500 mCi. In conjunction with a chimeric modified antibody, owing to the longer circulating half life vis-a-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the 111In label, are typically less than about 5 mCi.

While a great deal of clinical experience has been gained with 131I and. 90Y, other radiolabels are known in the art and have been used for similar purposes. Still other radioisotopes are used for imaging. For example, additional radioisotopes which are compatible with the scope of the instant invention include, but are not limited to, 123I, 125I, 32P, 57Co, 64Cu, 67Cu, 77Br, 81Rb, 81Kr, 87Sr, 113In, 127Cs, 129Cs, 132I, 197Hg, 203Pb, 206Bi, 177Lu, 186Re, 212Pb, 212Bi, 47Sc, 105Rh, 109Pd, 153Sm, 188Re, 199Au, 225Ac, 211A 213Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include 125I, 123I, 99Tc, 43K, 52Fe, 67Ga, 68Ga, as well as 111In. Antibodies have also been labeled with a variety of radionuclides for potential use in targeted immunotherapy (Peirersz et al. Immunol. Cell Biol. 65: 111-125 (1987)). These radionuclides include 188Re and 186Re as well as 199Au and 67Cu to a lesser extent. U.S. Pat. No. 5,460,785 provides additional data regarding such radioisotopes and is incorporated herein by reference.

As previously discussed, the antibodies, or fragments thereof, of the invention, can be administered in a pharmaceutically effective amount for the in vivo treatment of mammalian disorders. In this regard, it will be appreciated that the disclosed antibodies, or fragments thereof, will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a antibody of the invention, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the antibodies of the invention may be administered to a human or other animal in accordance with the aforementioned methods of treatment in an amount sufficient to produce a therapeutic or prophylactic effect. The polypeptides of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VI. METHODS OF TREATING PDGFRβ-ASSOCIATED DISEASE OR DISORDERS

The binding polypeptides, or fragments thereof, of the invention are useful for antagonizing PDGFRβ activity. Accordingly, in another aspect, the invention provides methods for treating PDGFRβ-associated diseases or disorders by administering to a subject in need of thereof a pharmaceutical composition comprising one or more anti-PDGFRβ antibody, or antigen binding fragment thereof of the invention.

PDGFRβ-associated diseases or disorders amenable to treatment include, without limitation: Age related macular degeneration (AMD); restenosis, including coronary restenosis after angioplasty, atherectomy, or other invasive methods of plaque removal, and renal or peripheral artery restenosis after the same procedures; vascular proliferative phenomena and fibrosis associated with other forms of acute injury such as: pulmonary fibrosis associated with adult respiratory distress syndrome, renal fibrosis associated with nephritis, coronary stenosis associated with Kawasake's disease, and vascular narrowings associated with other arteritides such as Takayasha's disease; fibrotic processes, such as scleroderma, myofibrosis; and cancer (e.g., tumor cell proliferation and neovascularization)

One skilled in the art would be able, by routine experimentation, to determine what an effective, non-toxic amount of antibody (or additional therapeutic agent) would be for the purpose of treating a PDGFRβ-associated disease or disorder. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

VII. EXAMPLES

The present invention is further illustrated by the following examples which should not be construed as further limiting. The contents of Sequence Listing, figures and all references, patents and published patent applications cited throughout this application are expressly incorporated herein by reference.

Example 1

Isolation of VH domains that Bind Specifically to Human PDGFRβ

VH domains that bind specifically to human PDGFRβ were selected using DNA display as set forth in WO2010/011944, which is hereby incorporated by reference in its entirety. Specifically, a naïve, human VH domain DNA display library derived from ten bone marrow donors was subject to six rounds of selection against human PDGFRβ. The selected binders were cloned and sequenced. From this screen, VH domain clones A4, B4 and G2 were selected, the amino acid sequences of which are set forth in Table 3.

Example 2

HCDR3 Shuffling

A. VH Library Construction

To screen for VH domains with improved binding characteristics, the HCDR3 sequence of clone A4 (designated XB1511) was shuffled into a naïve human VH library, which was further selected for binding to human and mouse PDGFRβ. Specifically, the DNA sequence coding for the HCDR3 of clone A4 (SEQ ID NO: 1) was synthesized and assembled into a library comprising framework regions 1-3 of naïve human VH domains amplified from bone marrow B cells and PBMCs using framework specific oligonucleotides. Human VH framework regions 1-3 were amplified using 5' VH family-specific and 3' generic FR3 reverse primers to create separate libraries of VH family framework regions. The VH family framework libraries and the XB1511 HCDR3 were shuffled by further PCR amplification using 5' T7TMV and 3' XB1511 FR3CDR3FR4 oligos. This also added a T7TMV promoter sequence at the 5' end for in vitro transcription/translation. A C-terminal Cμ3 sequence and a FLAG tag (for purification after translation) were also added by PCR using FR4Cu3 Reverse and Y109 primers, respectively, together with the 5' T7TMV primer. The nucleic acid sequences of the oligonucleotides used for preparation of the HCDR3-shuffled VH library are set forth in Table 5. A schematic representation of the VH library construction is set forth in FIG. 1.

TABLE 5

Oligonucleotides for constructing HCDR3 shuffled VH libraries

| Oligo | Sequence | SEQ ID NO. |
|---|---|---|
| FR3 Reverse | CGCACAGTAATACACGGC | 454 |
| VH1a | CAATTACTATTTACAATTACAATGCAGGTKCAGCTGGTGCAGTCTG | 455 |
| VH1b | CAATTACTATTTACAATTACAATGCAGGTCCAGCTTGTGCAGTCTG | 456 |
| VH1c | CAATTACTATTTACAATTACAATGSAGGTCCAGCTGGTACAGTCTG | 457 |
| VH1d | CAATTACTATTTACAATTACAATGCARATGCAGCTGGTGCAGTCTG | 458 |
| VH2 | CAATTACTATTTACAATTACAATGCAGRTCACCTTGAAGGAGTCTG | 459 |
| VH3a | CAATTACTATTTACAATTACAATGGARGTGCAGCTGGTGGAGTCTG | 460 |
| VH3b | CAATTACTATTTACAATTACAATGCAGGTGCAGCTGGTGGAGTCTG | 461 |
| VH3c | CAATTACTATTTACAATTACAATGGAGGTGCAGCTGTTGGAGTCTG | 462 |
| VH4a | CAATTACTATTTACAATTACAATGCAGSTGCAGCTGCAGGAG | 463 |
| VH4b | CAATTACTATTTACAATTACAATGCAGGTGCAGCTACAGCAGTGG | 464 |
| VH5 | CAATTACTATTTACAATTACAATGGARGTGCAGCTGGTGCAGTCTG | 465 |
| VH6 | CAATTACTATTTACAATTACAATGCAGGTACAGCTGCAGCAGTCAG | 466 |
| VH7 | CAATTACTATTTACAATTACAATGCAGGTGCAGCTGGTGCAATCTG | 467 |
| T7TMVUTR | TAATACGACTCACTATAGGGACAATTACTATTTACAATTACA | 468 |
| XB1511 FR3CDR3FR4 Reverse | TGAGGAGACGGTGACCAGGGTTCCCTGGCCCCAGTAGCTCCTGTCG CCCCCATGTKTCGCACAGTAATACACGGC | 469 |
| FR4 Cu3 Reverse | GGAGACGAGGGGAAAAGGGTTGAGGAGACGGTGACCAG | 470 |
| Y109 | TTTTTTTTTTTTTTTTTTAAATAGCGGATGCTAAGGACGACTTG TCGTCGTCGTCCTTGTAGTCGGAGACGAGGGGAAAAGGGT | 471 |

B. Library Screening

The HCDR3 shuffled VH domain library was then transcribed into an mRNA library and subjected to selection with dsDNA display technology as set forth in WO2010/011944. The selection was carried out with human and mouse PDGFRβ at alternate round for 4 rounds. Kinetic controlled on- and off-rate selection was applied at successive rounds to increase the stringency of selection, and thus select for VH domains with high affinity for PDGFRβ. Specifically, selection was performed as follows: Round 1 (R1) with 10 nM of immobilized human PDGFRβ; R2 with immobilized 100 nM mouse PDGFRβ; R3 with 10 nM soluble human PDGFRβ and competed with 200 nM immobilized human PDGFRβ for 24 hours and 120 hours; and R4 with 10 nM mouse PDGFRβ. The R4 binding pool was subcloned for DNA sequencing. Analysis of the sequences of the R4 binding pool showed that the HCDR3 of XB1511 was present in a variety of different framework contexts. No wild type parental sequence was obtained from the set of sequences analyzed. The amino acid sequences of the selected VH domains are set forth in Table 3, herein.

C. Binding Specificity of Selected HCDR3 Shuffled VH Domains

Figure 2:
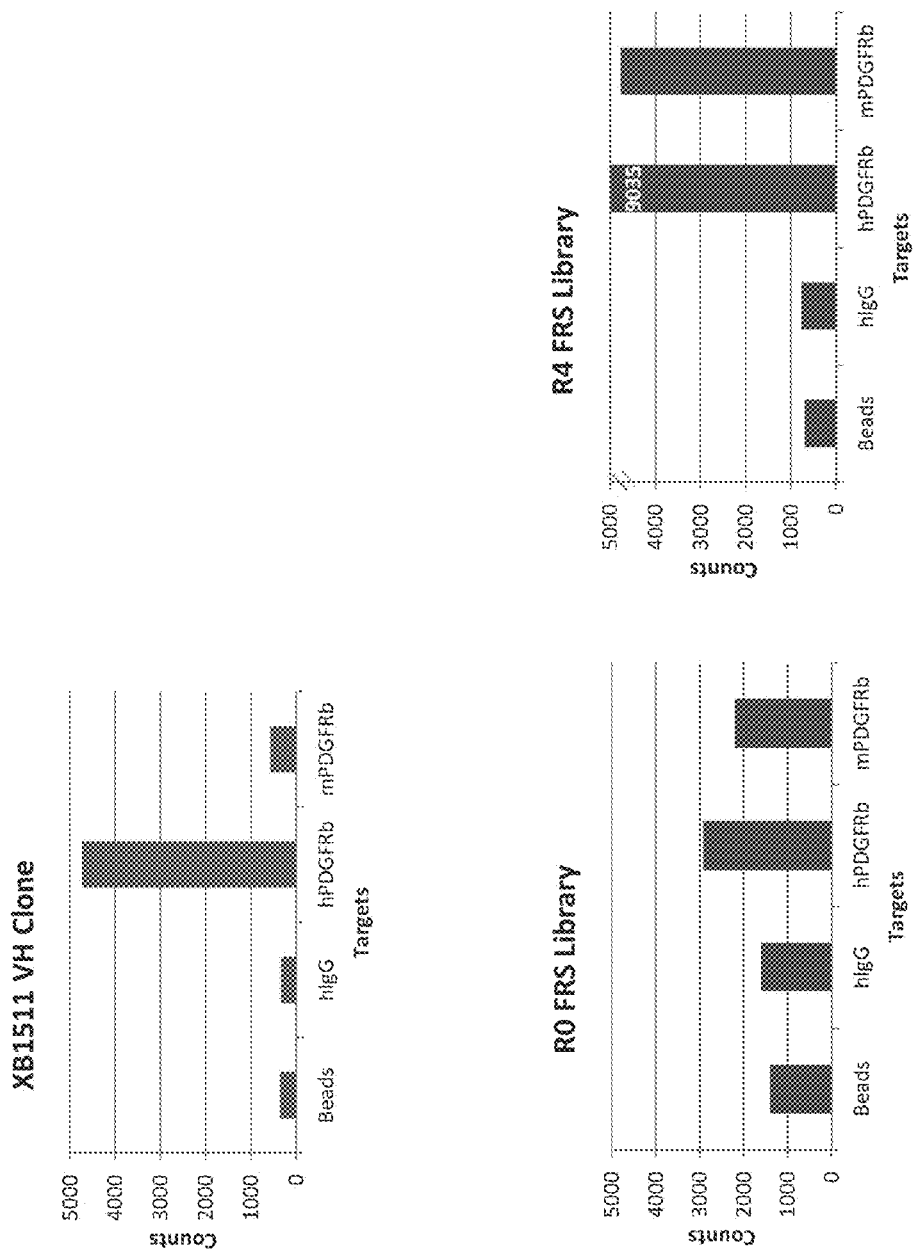
FIG. 2 depicts the results of in vitro binding assays measuring the binding to human or mouse PDGFRβ of the XB1511VH domain, an unselected XB1511 CDR3/framework shuffled DNA display library (R0), and an XB1511 CDR3/framework shuffled DNA display library pool after four rounds of selection (R4).

The R4 binding pool selected above was assessed for binding to both human and mouse PDGFRβ using a $^{35}$S Met-labelled in vitro translated library. Specifically, binding of the pool to epoxy beads, 100 nM of human IgG, human PDGFRβ and mouse PDGFRβ were assessed. As shown in FIG. 2, the parental XB1511 VH domain showed specific binding to human PDGFRβ, and undetectable binding to mouse PDGFRβ. The framework shuffled pre-selected library showed weak binding to human PDGFRβ. However, in contrast, the R4 framework shuffled library showed significant binding to both human and mouse PDGFRβ.

Example 3

Identification of Stable VL/VH Pairs

A. Construction of VL DNA Libraries

Figure 3:
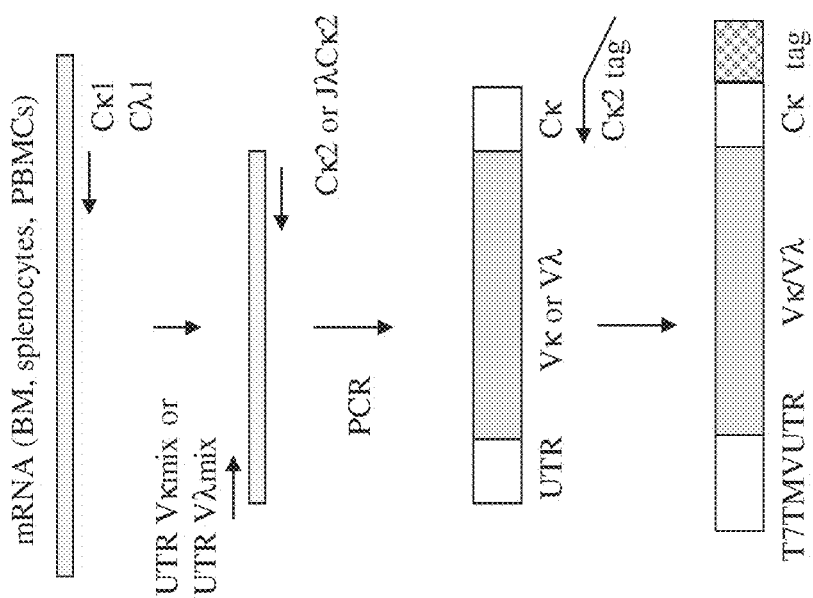
FIG. 3 depicts the results of surface Plasmon resonance binding studies measuring the binding kinetics of XB1511 and the framework shuffled derivatives XB2202 and XB2708 to human PDGFRβ.

Human VL libraries (Vkappa and Vlamda) were constructed from B cells of young healthy donors (Allcells) by RT-PCR. To ensure the diversity of the library, 300 million bone marrow mononuclear cells and 100 million peripheral blood mononuclear cells were obtained from ten donors and used for naive VH and VL library construction. A schematic of the library generation method is set forth in FIG. 3.

Oligonucleotide primers for cDNA synthesis and subsequent PCR amplification of the Vkappa and Vlamda sequences were designed as set forth in Table 4. Specifically, multiple sense primers were designed from the Vκ and Vλ FR1 regions of each family with an upstream UTR sequence. The anti-sense primers for κ and λ, gene amplification were designed from the constant regions nested to Cκ1 (Cκ2) or Jλ with the same Cκ2 downstream (JμCκ2). The Vκ and Vλ libraries carry the same C-terminal sequence for PCR amplification during the selection cycles.

mRNA was prepared from individual donors using a Fast-Track mRNA preparation kit (Invitrogen) following the protocol provided by the kit. First strand cDNA was synthesized from the isolated mRNA using primers specific for the light chain kappa and lambda constant regions (Cκ1 and Cλ1).

PCR amplification of the Vkappa and Vlamda sequences was performed with Cκ2 and Vκ family specific or JλCκ2 mix and Vλ family specific primers using cDNA as a template. The PCR was performed for individual Vκ and Vλ families and individual donors for 18-20 cycles. After gel purification, Vκ and Vλ libraries from each different source were pooled to generate the final Vκ and Vλ libraries.

TABLE 6

Oligonucleotides for constructing human Vλ and Vκ DNA display libraries

| Oligo | Sequence | SEQ ID NO. |
|---|---|---|
| Cκ1 | CAACTGCTCATCAGATGGCGG | 472 |
| Cl1 | CAGTGTGGCCTTGTTGGCTTG | 473 |
| Cκ2 | AGATGGTGCAGCCACAGTTCG | 474 |
| J11-3Cκ2 | AGATGGTGCAGCCACAGTTCGTAGACGGTSASCTTGGTCCC | 475 |
| J17Cκ2 | AGATGGTGCAGCCACAGTTCGGAGACGGTCAGCTGGGTGCC | 476 |
| T7TMVUTR | TAATACGACTCACTATAGGGACAATTACTATTTACAATTACA | 477 |
| Vκ oligos | | |
| UTRVκ1a | CAATTACTATTTACAATTACAATGRACATCCAGATGACCCAG | 478 |
| UTRVκ1b | CAATTACTATTTACAATTACAATGGMCATCCAGTTGACCCAG | 479 |
| UTRVκ1c | CAATTACTATTTACAATTACAATGGCCATCCRGATGACCCAG | 480 |
| UTRVκ1d | CAATTACTATTTACAATTACAATGGTCATCTGGATGACCCAG | 481 |
| UTRVκ2a | CAATTACTATTTACAATTACAATGGATATTGTGATGACCCAG | 482 |
| UTRVκ2b | CAATTACTATTTACAATTACAATGGATRTTGTGATGACTCAG | 483 |
| UTRVκ3a | CAATTACTATTTACAATTACAATGGAAATTGTGTTGACRCAG | 484 |
| UTRVκ3b | CAATTACTATTTACAATTACAATGGAAATAGTGATGACGCAG | 485 |

TABLE 6-continued

Oligonucleotides for constructing human Vλ and Vκ DNA display libraries

| | Sequence | SEQ ID NO. |
|---|---|---|
| UTRVk3c | CAATTACTATTTACAATTACAATGGAAATTGTAATGACACAG | 486 |
| UTRVk4a | CAATTACTATTTACAATTACAATGGACATCGTGATGACCCAG | 487 |
| UTRVk5a | CAATTACTATTTACAATTACAATGGAAACGACACTCACGCAG | 488 |
| UTRVk6a | CAATTACTATTTACAATTACAATGGAAATTGTGCTGACTCAG | 489 |
| UTRVk6b | CAATTACTATTTACAATTACAATGGATGTTGTGATGACACAG | 490 |
| UTRVL1a | CAATTACTATTTACAATTACAATGCAGTCTGTGCTGACKCAG | 491 |
| UTRVL1b | CAATTACTATTTACAATTACAATGCAGTCTGTGYTGACGCAG | 492 |
| UTRVL2 | CAATTACTATTTACAATTACAATGCAGTCTGCCCTGACTCAG | 493 |
| UTRVL3a | CAATTACTATTTACAATTACAATGTCCTATGWGCTGACTCAG | 494 |
| UTRVL3b | CAATTACTATTTACAATTACAATGTCCTATGAGCTGACACAG | 495 |
| UTRVL3c | CAATTACTATTTACAATTACAATGTCTTCTGAGCTGACTCAG | 496 |
| UTRVL3d | CAATTACTATTTACAATTACAATGTCCTATGAGCTGATGCAG | 497 |
| UTRVL4 | CAATTACTATTTACAATTACAATGCAGCYTGTGCTGACTCAA | 498 |
| UTRVL5 | CAATTACTATTTACAATTACAATGCAGSCTGTGCTGACTCAG | 499 |
| UTRVL6 | CAATTACTATTTACAATTACAATGAATTTTATGCTGACTCAG | 500 |
| UTRVL7 | CAATTACTATTTACAATTACAATGCAGRCTGTGGTGACTCAG | 501 |
| UTRVL8 | CAATTACTATTTACAATTACAATGCAGACTGTGGTGACCCAG | 502 |
| UTRVL4/9 | CAATTACTATTTACAATTACAATGCWGCCTGTGCTGACTCAG | 503 |
| UTRVL10 | CAATTACTATTTACAATTACAATGCAGGCAGGGCTGACTCAG | 504 |

R = A/G, Y = C/T, K = G/T, M = A/C, S = G/C, W = A/T

B. Generation of VL Fusion Libraries by dsDNA Display

Vκ and Vλ DNA libraries generated using the methods set forth in this Example were transcribed into mRNA libraries using the T7 Megascript kit (Invitrogen, Cat# AM1334). The mRNA was purified with RNeasy MinElute Cleanup Kit (Qiagen, Cat#74204) following protocol provided by the kit. A total of 600 pmol of RNA (300 pmol of Vκ and Vλ libraries) was ligated and assembled with dsDNA display linkers and components as described in WO2010/011944. The assembled VL library was subjected to in vitro translation to create a fusion library in which each VL domain (phenotype) is stably fused to its coding sequence (genotype). $^{35}$S Met was incorporated in the translation process to radiolabel the fusions. The library was then purified with oligo dT cellulose, converted into a dsDNA display library using the standard molecular biology techniques of reverse transcription, RNaseH digestion, $2^{nd}$ strand DNA synthesis, followed by flag tag purification.

C. Identification of VL Pairs for XB1511, and XB2202 VH Domains

XB1511 VH domain was translated as free protein (with incorporation of $^{35}$S Met in the translation reaction) and affinity purified through a c-terminal flag tag. The XB1511 VH domain and a purified VL domain fusion library (prepared as above) were then mixed at an equal molar ratio and incubated at 25 C overnight to allow for in vitro association of VH and VL fusion domains through their hydrophobic patch. The mixture was then contacted with PDGFRβ target pre-immobilized on Epoxy-450 beads or in solution and captured by protein A beads, Complexes that bound to the immobilized PDGFRβ target were washed and eluted with 0.1N KOH. PCR was performed with VL specific primer sets to recover the VLs that bound to the PDGFRβ target, both as VH-VL pairs and as unpaired VL domains. The VL pairing was performed for 3 rounds, with low stringency (100 nM PDGFRβ) for the first 2 rounds and higher stringency (10 nM PDGFRβ) for the third round. The XB2202 VH domain was also paired with the VL library similarly for two rounds. For each round of XB2202/VL pairing and selection, the stringency was increased by kinetic controlled on and off rate strategy to identify VL domains that paired stably with XB2202 VH domain and enhance the VH binding.

VL domain pools identified above were then cloned into Blunt Zero TOPO vector (Invitrogen) and VL-encoding DNA sequences were amplified from the resultant bacterial colonies by PCR using M13 forward and reverse primers. The individual amplified VL-encoding DNA sequences were then sequenced. The sequence data obtained from VL pools showed that a diverse repertoire of VLs was enriched through the process. Multiple families and frameworks were present in the pool. Several VLs were present as replicates or families Distinct VL families could be identified and several VLs were present more than once. Exemplary VL sequences identified using the methods of the invention that pair with the PDGFRβ-binding VH domains XB1511 and XB2202 are set forth in Table 4 herein.

D. Evaluation of Identified VH and VL Pairs

To evaluate the characteristics of the identified VH-VL pairs, 10-12 scFVs from each pool were constructed and produced by either in vitro translation or by E. coli expression, followed by affinity purification.

Figure 4:
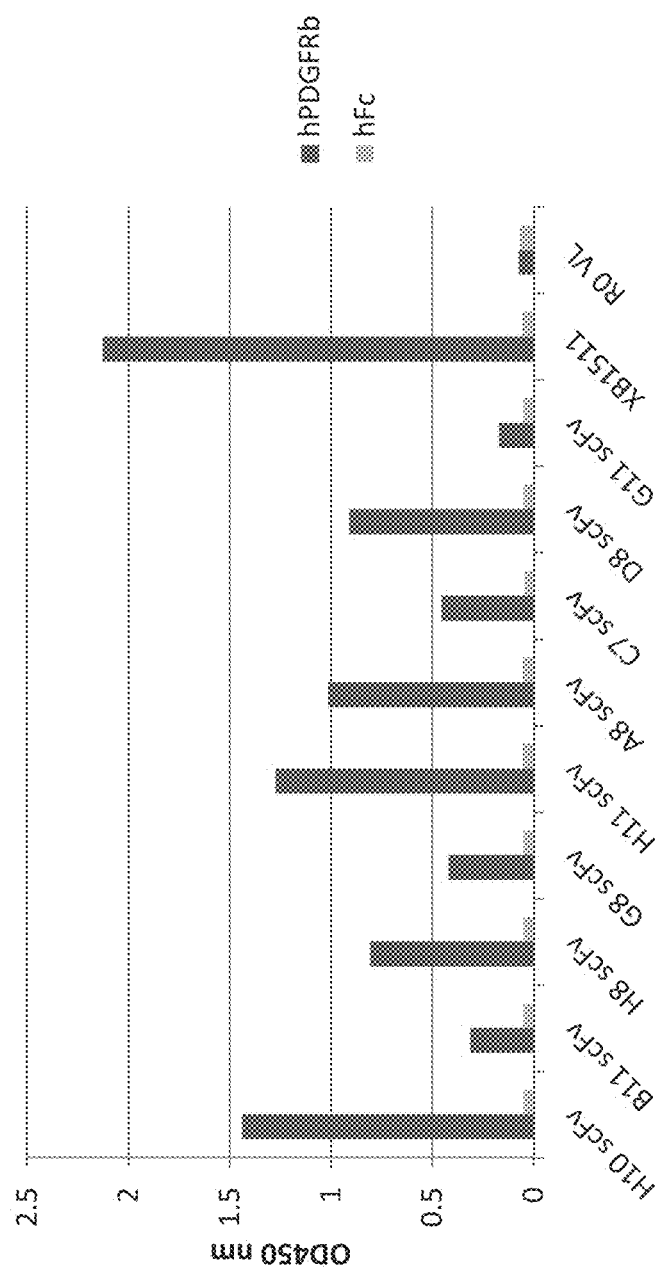
FIG. 4 depicts the results of surface plasmon resonance binding assays measuring the binding kinetics of XB2202 to human (A) and mouse (B) PDGFRβ.
Figure 5:
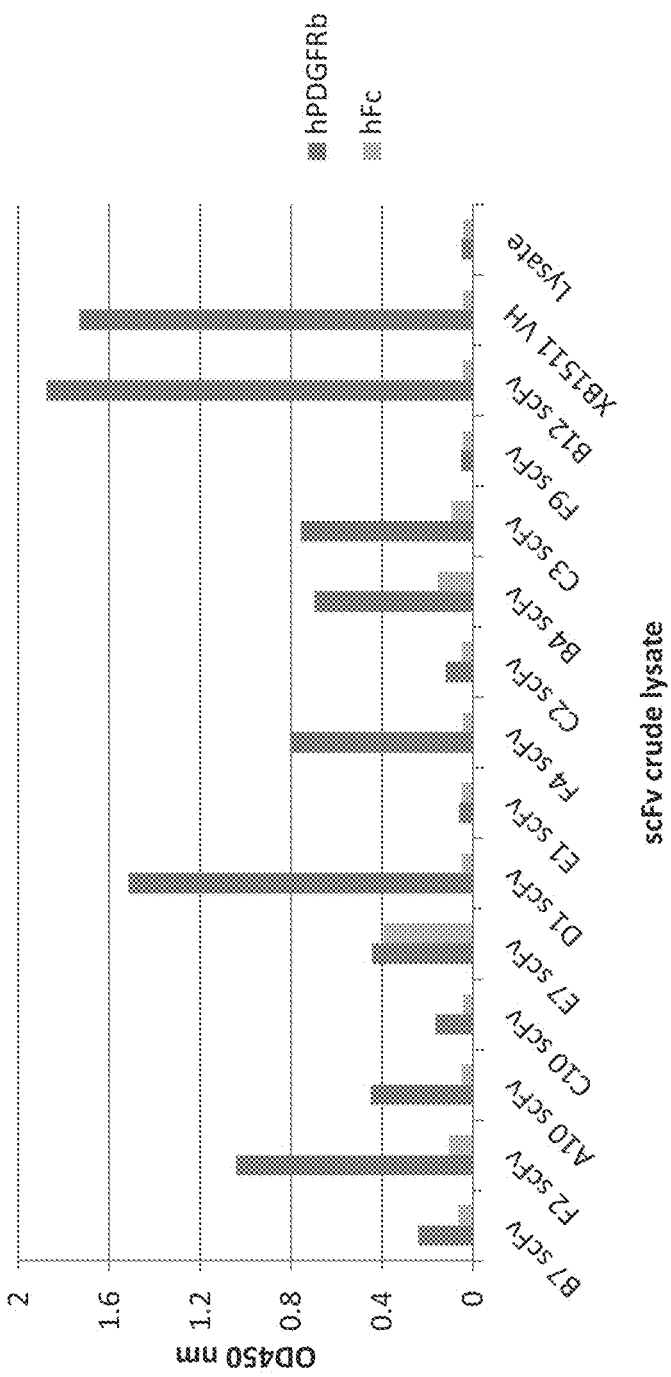
FIG. 5 depicts the results of surface plasmon resonance binding assays measuring the binding kinetics of XB2708 to human (A) and mouse (B) PDGFRβ.
Figure 6:
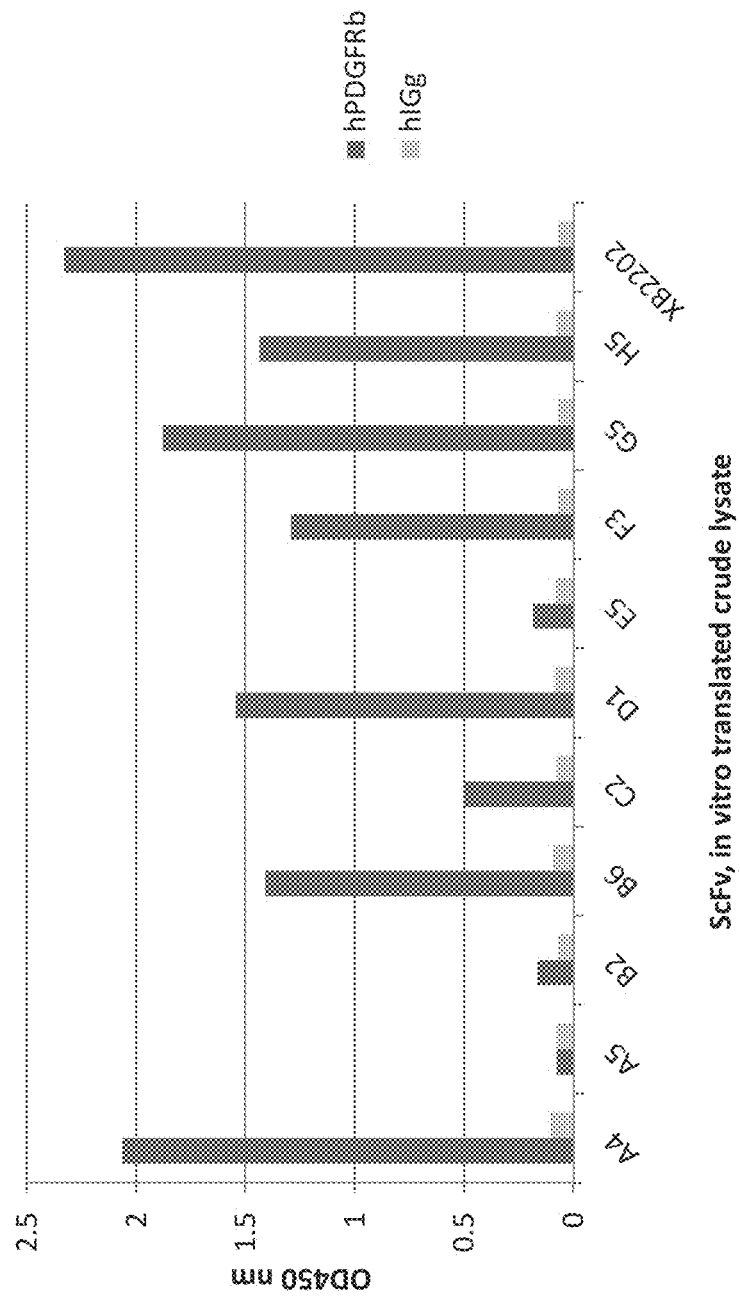
FIG. 6 is a schematic representation of the construction of exemplary VL nucleic acid display libraries for use in the disclosed methods.
Figure 7:
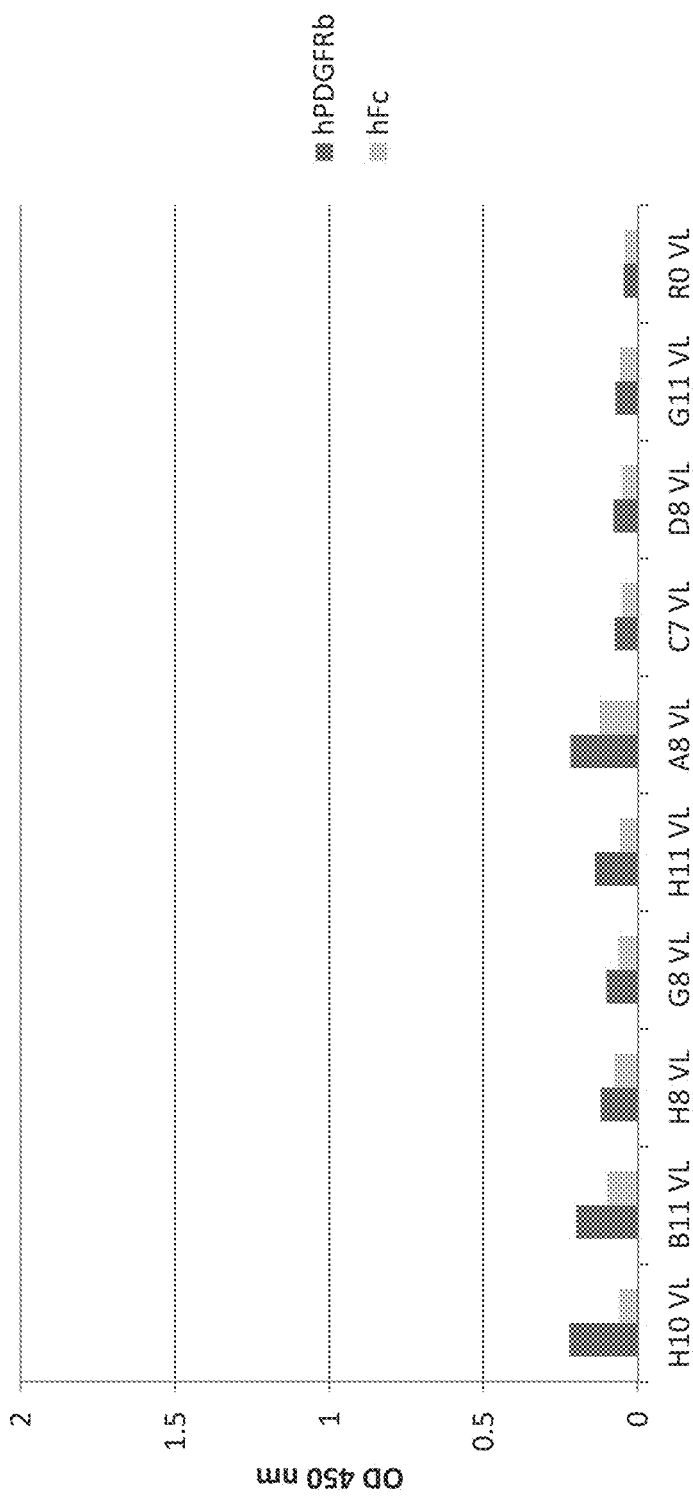
FIG. 7 depicts the results of ELISA assays measuring the binding to human PDGFRβ of XB1511/VL scFv comprising VL domains isolated from the second round screening pool of a VH/VL pairing DNA display screen.

A PDGFRβ binding ELISA assay was performed to assess the binding of the scFv to immobilized PDGFRβ and to determine the EC50. Specifically, 2 ug/mL of human PDGFRβ and human Fc or IgG in PBS was immobilized on Maxisorp plates at 4° C. overnight. The plate was then washed and blocked with superblock. In vitro translated crude scFv lysate was diluted 1:3 in 1×PBST. 100 ul of the diluted scFv lysate was loaded into each well of Maxisorp plates and incubated for 1 hour at room temperature. scFv that bound to immobilized PDGFRβ was detected by anti-flag antibody-HRP at 1:5000 dilution and a TMB substrate. The plate was read on a Molecular Device plate reader with end point assay at OD 450 nm. As shown in FIGS. 4, 5 and 6, in the ELISA binding assay, greater than 50% of the scFvs generated for XB1511 and XB2202 showed specific binding to PDGFRβ. In contrast, the unpaired VLs alone did not show binding to PDGFRβ (see FIG. 7).

Figure 8:
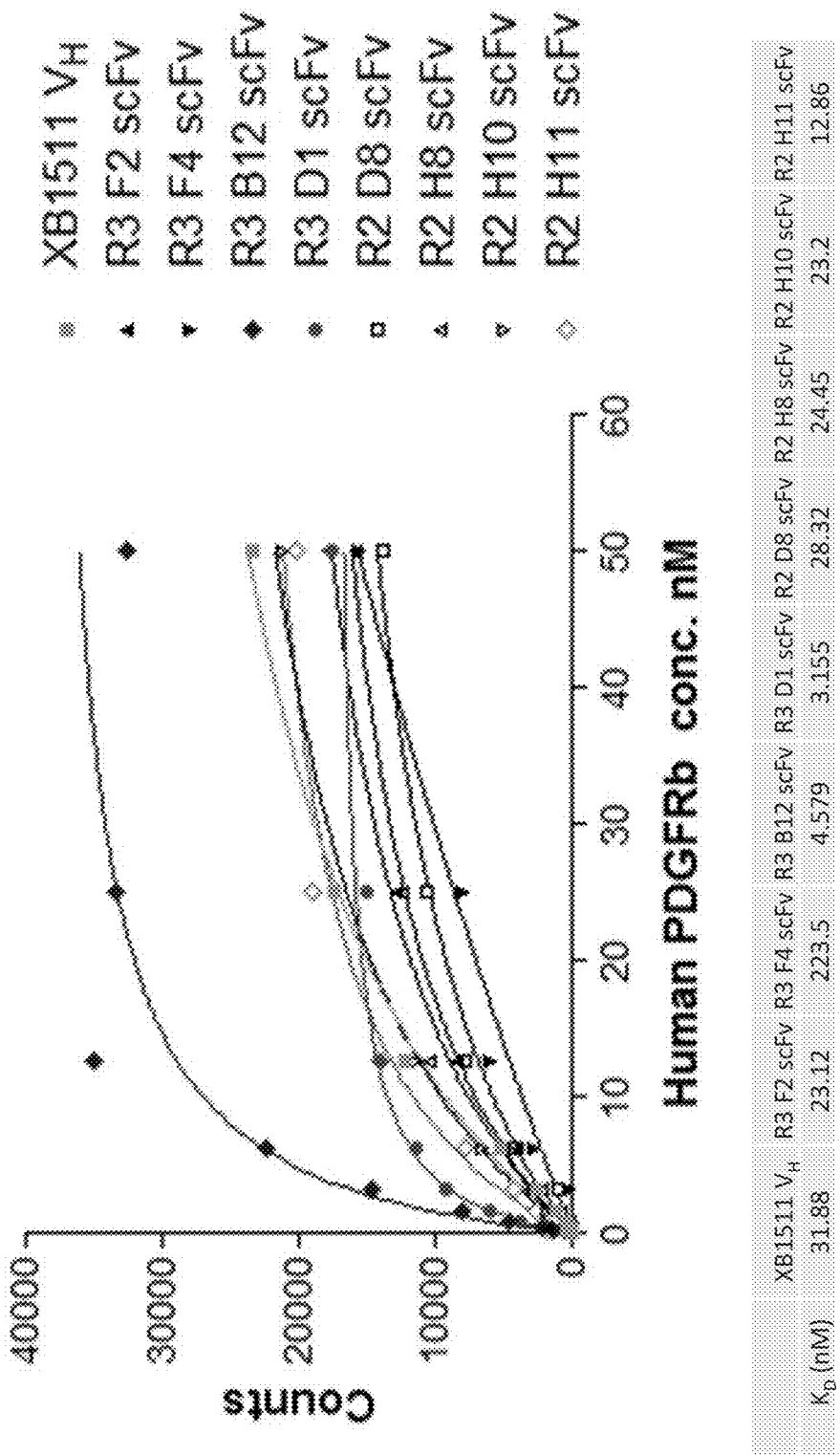
FIG. 8 depicts the results of ELISA assays measuring the binding to human PDGFRβ of XB1511/VL scFv comprising VL domains isolated from the third round screening pool of a VH/VL pairing DNA display screen.
Figure 9:
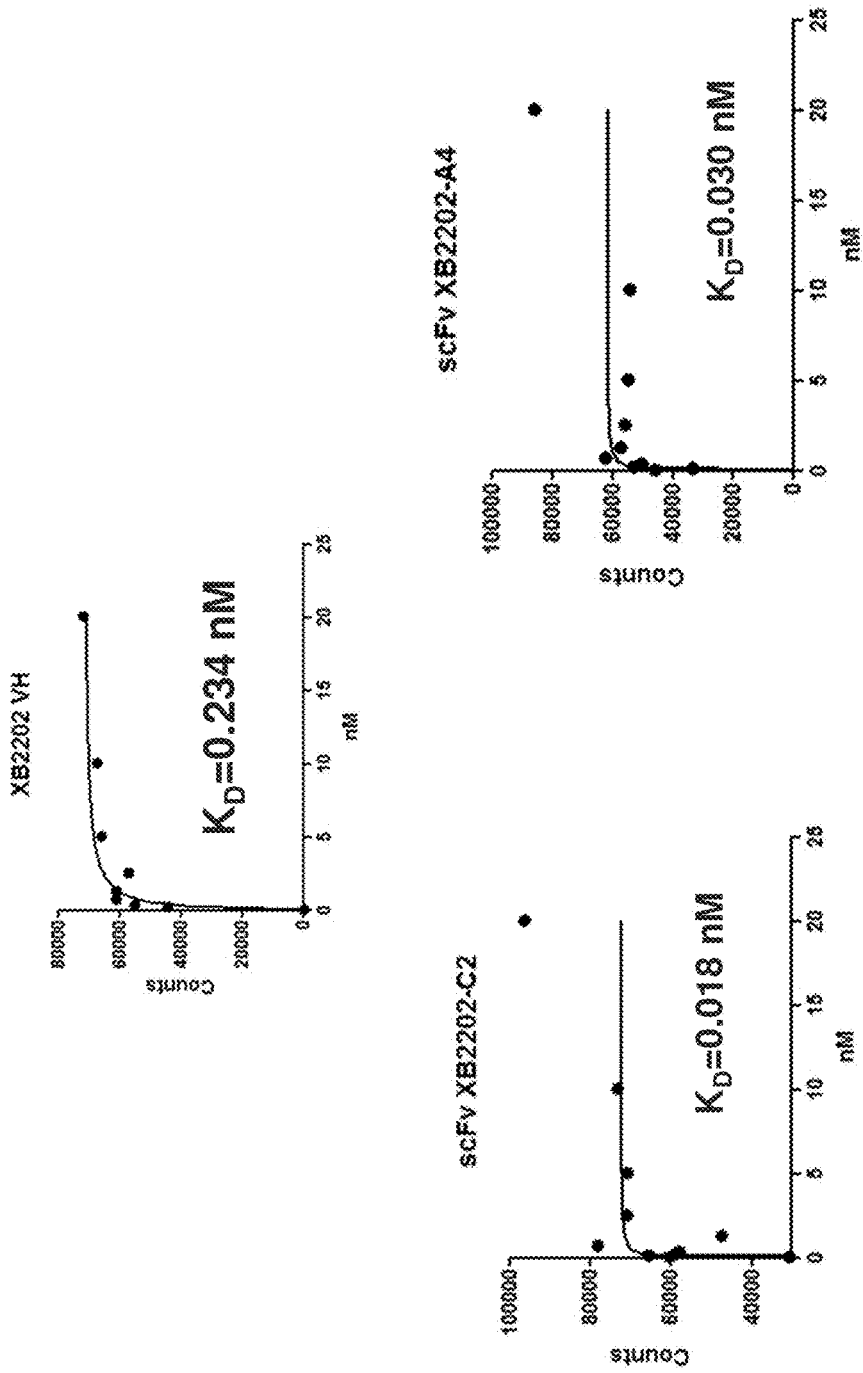
FIG. 9 depicts the results of ELISA assays measuring the binding to human PDGFRβ of XB2202/VL scFv comprising VL domains isolated from the second round screening pool of a VH/VL pairing DNA display screen.

The affinity of several scFvs was determined by solution based equilibrium binding assay. Specifically, 120 pmol of scFv RNA was translated into free protein with $^{35}$S Met incorporated. The translated reaction mixture was 3-fold diluted in binding buffer containing 1×PBS with 0.025% triton, 1 mg/mL BSA and 0.1 mg/mL sssDNA. Human PDGFRβ was diluted in the same binding buffer to final concentrations from 100 nM to 0 nM. The diluted scFv mixture was incubated with hPDGFRβ in final volume of 100 ul on Kingfisher plates (Thermofisher Scientific, 97002084). Following incubation, 25 ul of protein A magnetic beads (Invitrogen) were used to capture the PDGFRβ from solution. The captured PDGFRβ was washed and eluted in kingfisher Reader (Thermofisher Scientific). The amount of scFv (labeled with $^{35}$S Met) bound to the magnetic bead-immobilized hPDGFRβ was counted using a scintillation counter and the Kd was calculated with Graph Pad Prism 5. For the XB1511-derived scFv tested, 2 scFv showed an 8-10 fold higher Kd, 1 showed 2.5 fold higher Kd, and 4 showed a similar Kd when compared to XB1511 VH alone (FIG. 8). Only 1 scFv showed a lower $K_D$ than XB1511 VH alone. As shown in FIG. 9, both of the XB2202-derived scFv tested showed approximately an 8-10 fold better Kd when compared to XB2202 VH alone.

Example 4

Binding Affinity of Anti-PDGFRβ VH Domains to Human and Mouse PDGFRβ

Figure 10:
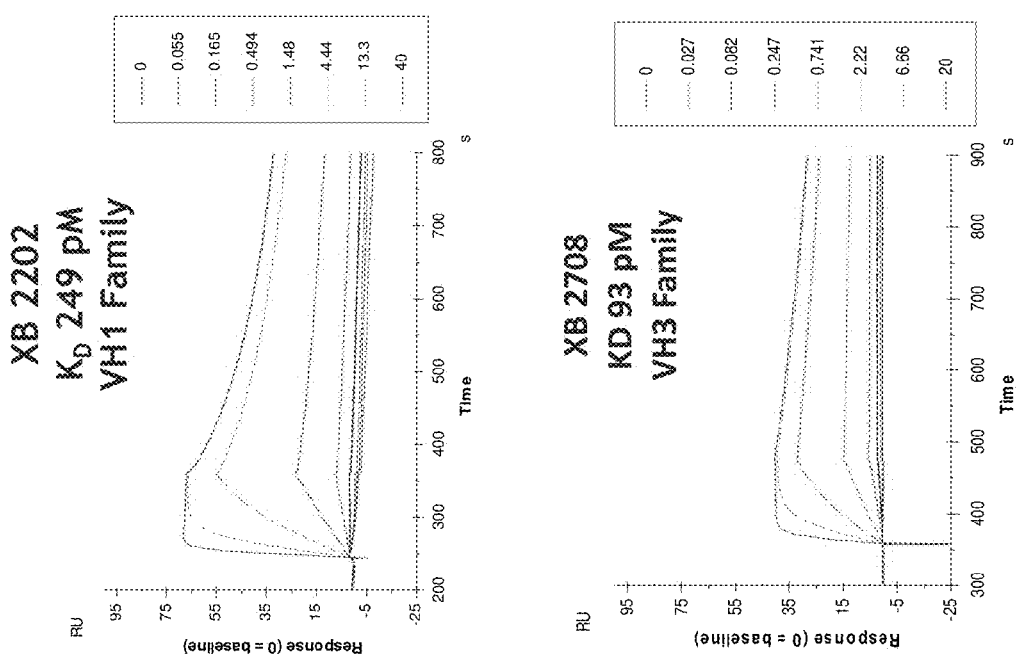
FIG. 10 depicts the results of ELISA assays measuring the binding to human PDGFRβ of unpaired VL domains from the XB1511/VL scFv set forth in FIG. 9.
Figure 10:
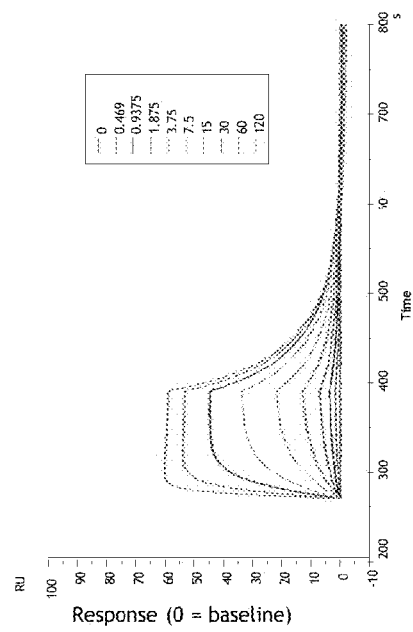
Figure 11:
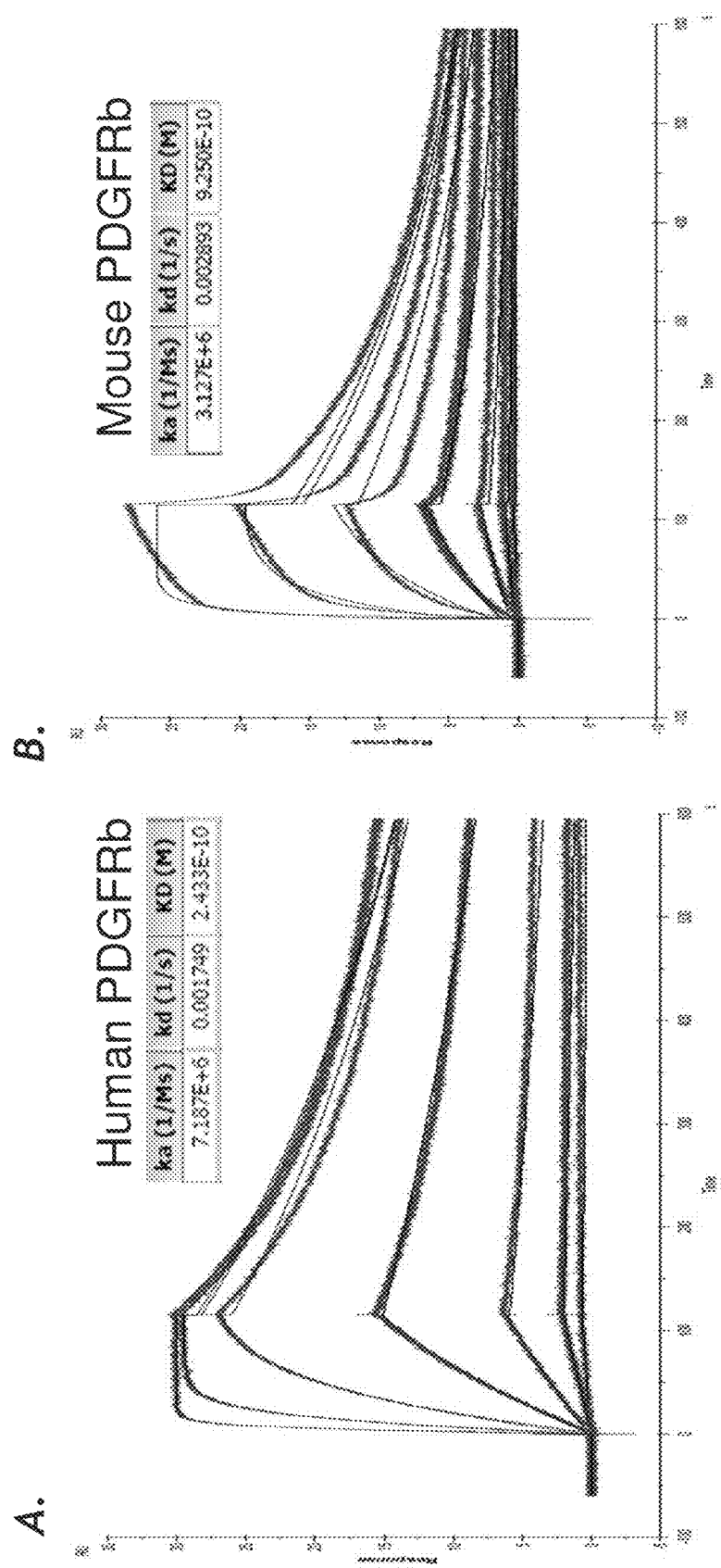
FIGS. 11A and B depict the results of solution binding affinity studies measuring the binding to human PDGFRβ of $^{35}$S Met labeled XB1511 VH domain and XB1511-containing scFV obtained from VH/VL pairing DNA display screens.
Figure 12:
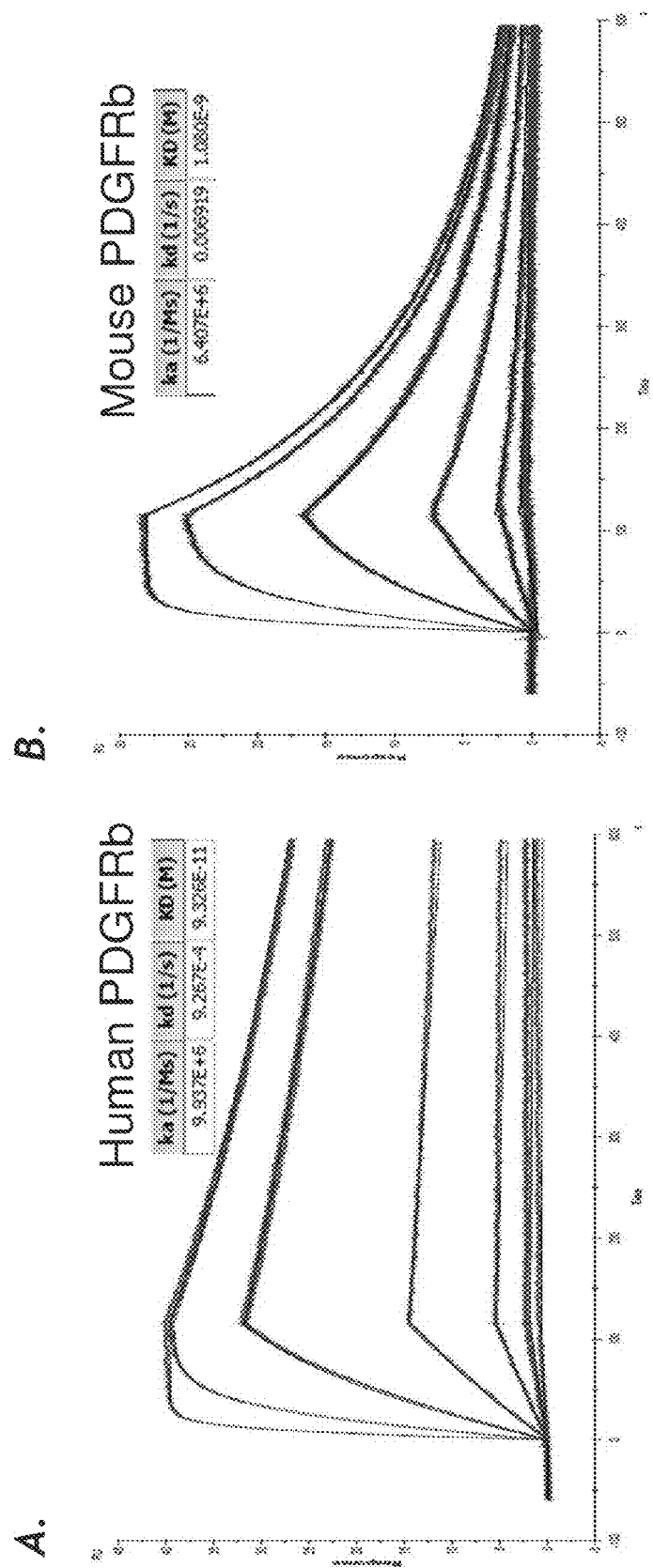
FIGS. 12A and B depict the results of solution binding affinity studies measuring the binding to human PDGFRβ of $^{35}$S Met labeled XB2202 VH domain and XB2202-containing scFV obtained from VH/VL pairing DNA display screens.

The R4 framework shuffled human and mouse PDGFRβ enriched VH domain pool selected in Example 2 was cloned into E. coli expression vectors, produced and purified. The binding kinetics of the VH domains to human and mouse PDFGR was determined using surface plasmon resonance on a Biacore T100. Briefly, human and mouse PDGFR-hIgG1-Fc chimeric fusion protein were separately immobilized using a Series CM5 sensorchip (CM5) coupled to anti-hIgG1 Fc monoclonal antibody. For each cycle, the PDGFR fusion protein was first captured, followed by the injection of VH for 115 seconds at a flow rate of 100 uL/min (association). Immediately following the association phase is a dissociation phase of 600 seconds. The surface was regenerated at each cycle with a single injection of 3M MgCl2 (10 uL/min, 60 seconds). Multiple concentrations of VH domain were injected (0.55 nM-40 nM) and the resulting sensorgram were analyzed with T100 Evaluation software. The binding kinetics was determined using 1:1 binding curve fitting. The binding kinetics of VH domain clones XB2202 and XB2708 to human and mouse PDGFRβ are shown in FIGS. 10, 11 and 12, respectively. These results show that XB2202 and XB2708 have a 50-150 fold affinity improvement compared to parental XB1511. Specifically, XB2202 and XB2708 have Kds of 249 pM and 93 pM, respectively and off rates (Koff) of $1.86 \times 10^{-3}$ and $9.267 \times 10^{-4}$, respectively. Both XB2202 and XB2708 bound to human and mouse PDGFRβ. It is of particular note that, although they shared the same HCDR3, XB2202 was derived from a VH1 family germline sequence and XB2708 was derived from VH3 family germline sequence.

Example 5

Inhibition of PDGFBB Binding to PDGFRβ

Figure 13:
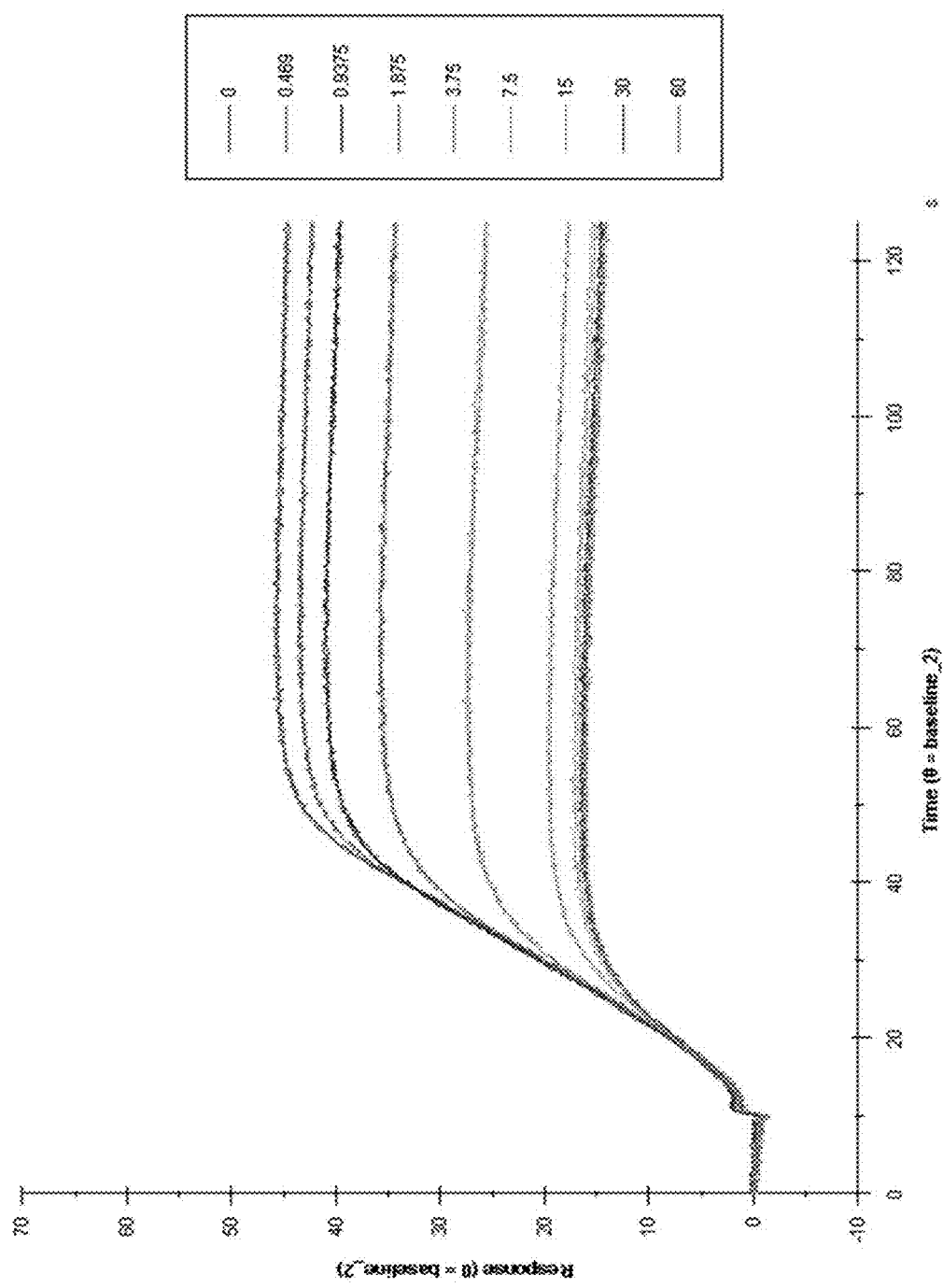
FIG. 13 depicts the results of surface plasmon resonance competition binding assays measuring the kinetics of binding of PDGF-BB to PDGFRβ at various concentrations of XB2202.

The ability of the XB2202 VH domain, disclosed herein, to antagonize the binding of PDGFBB ligand to the human PDFGRb was assessed using surface plasmon resonance on a Biacore T100. Briefly, human PDGFR-hIgG1-Fc chimeric fusion protein was immobilized using a Series CM5 sensorchip coupled with anti-hIgG1 Fc monoclonal antibody. 10 nM of human PDGFBB was injected to pre-captured human PDGFRβ obtain the 100% binding response unit to PDGFRβ in the absence VH. For each successive cycle, the PDGFR fusion protein was first captured then VH domain was then injected for 120 seconds. After washing away unbound VH domain, 10 nM of PDGFBB was then injected for 120 seconds. The surface was regenerated at each cycle with a single injection of 3M MgCl2 (10 uL/min, 60 seconds). Multiple concentrations of VH were injected (0.46 nM-60 nM), the resulting sensorgram were analyzed with T100 Evaluation software, and the PDGFBB binding inhibition was calculated. As shown in FIG. 13, XB2202 inhibits PDGFBB binding to human PDFGRb with an IC50 of less than 5 nM.

Example 6

Inhibition of Pericyte Cell Migration

Figure 14:
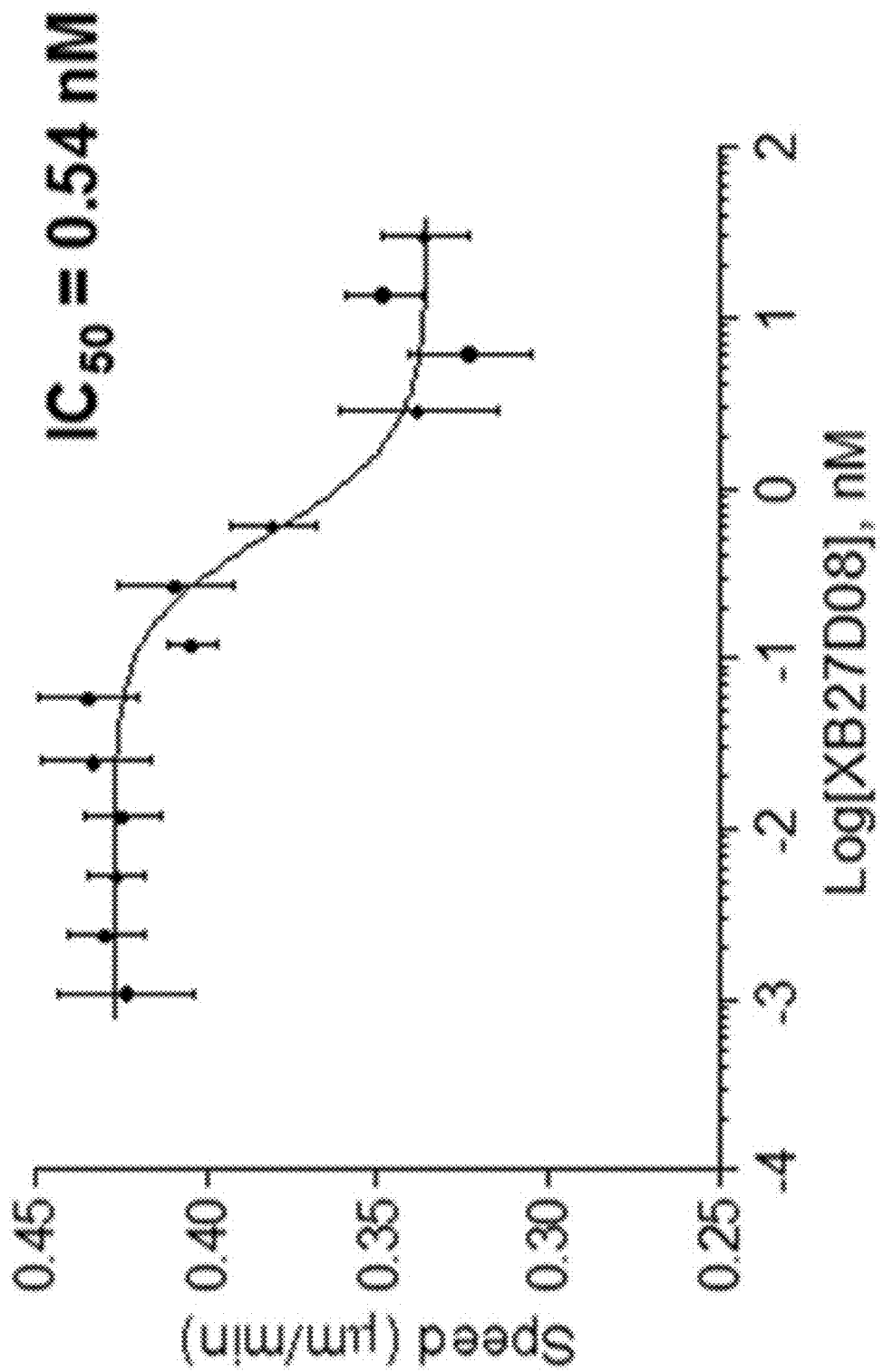
FIG. 14 depicts the results of in vitro cell migration assays measuring inhibition of pericyte migration by XB2708.

The ability of the XB2708 VH domain, disclosed herein, to antagonize PDGF-BB induced pericyte migration in vitro was determined Primary human retinal pericytes were obtained from Cell Systems Corporation (Kirkland, Wash.) and cultured according to the manufacturer's suggestions using CSC full growth medium. Approximately 125 cells (2-5 passages) were seeded in each well of 384-well BIND© biosensor plates coated with human plasma fibronectin (5 µg/ml in PBS) and blocked with BSA (1% in PBS) in serum-free medium containing 0.1% BSA. Cells were allowed to adhere and then serum-starve overnight. Following serum starvation, cells were incubated for 1 hour with various concentrations of VHs against human PDGFRβ receptor in a tissue culture incubator. Migration was stimulated at the end of antibody pre-incubation by PDGF-BB addition to a final concentration of 5 ng/ml in serum-free medium. Well images were acquired using a BIND© Scanner every 18 minutes for 20 hours in a tissue culture incubator at 37° C. with 5% $CO_2$ and >75% humidity. Collected data were analyzed using a Matlab-based centroid identification and tracking algorithm to calculate the speed of cells between the hours 10 and 16. The results set forth in FIG. 14 show that XB2708 can antagonize PDGF-BB-induced pericyte migration with an IC50 of 0.54 nM.

Example 7

Figure 15:
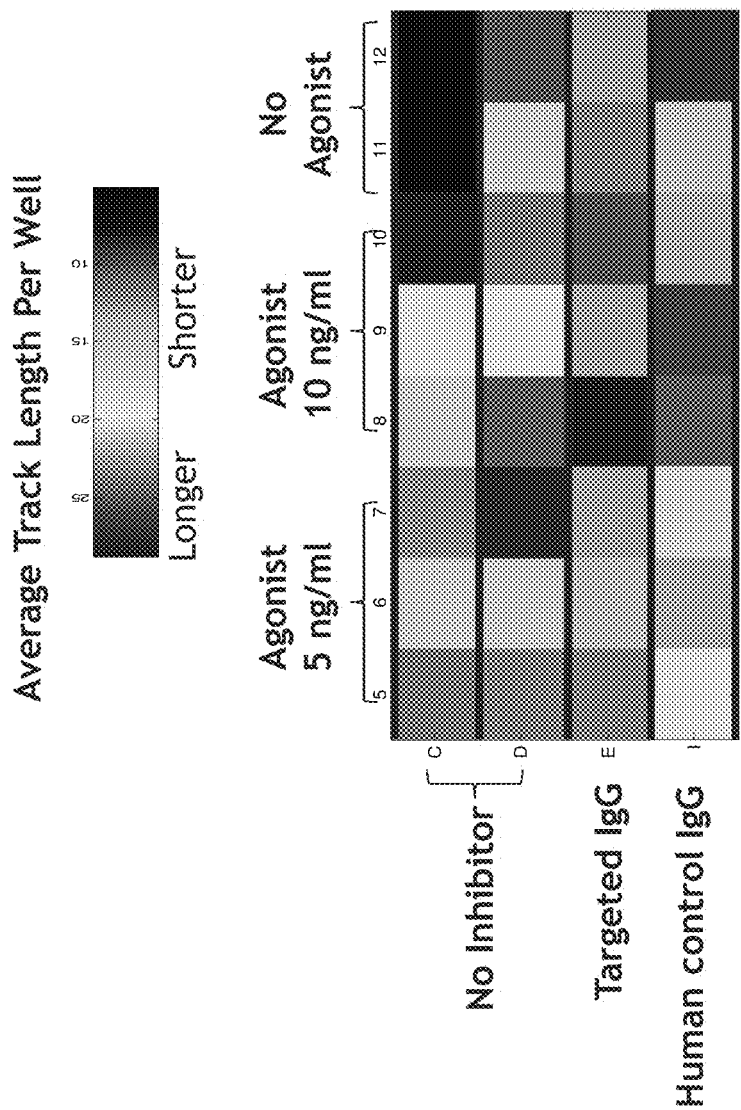
FIG. 15 depicts the results of label-free migration assays measuring the ability of an XB1511-containing IgG1 to inhibit the migration of human foreskin fibroblasts.

Conversion of VH-VL Pairs to Heterotetrameric IgG and Demonstration of Biological Activity XB1511 VH and D8 VL were expressed together in a heterotetrameric IgG in 293T cells. Cell culture supernatant was collected after 48 hours and 96 hours and the expressed IgG was purified with protein A agarose beads. The IgG was produced at 8 mg/L without any optimization. To evaluate the biological activity of the XB1511/D8 IgG, HFF-1 human foreskin fibroblasts were seeded in 384-well BIND biosensors and allowed to attach overnight in serum-free media. The fibroblast cells were then stimulated with 5 ng/mL or 10 ng/mL of PDGFBB ligand and allowed to migrate for 18 hours in the presence or absence of 100 nM XB1511/D8 IgG. BIND Scanner images were captured every 15 minutes and software analysis tools used to measure the track lengths of individual cell migration responses. Track length is represented by a "heat map" from blue (no migration) to red (maximal migration). As shown in FIG. 15, the XB1511/D8 IgG was able to completely block the PDGFBB-induced migration of human fibroblasts.

Example 8 scFv Thermostability

Figure 16:
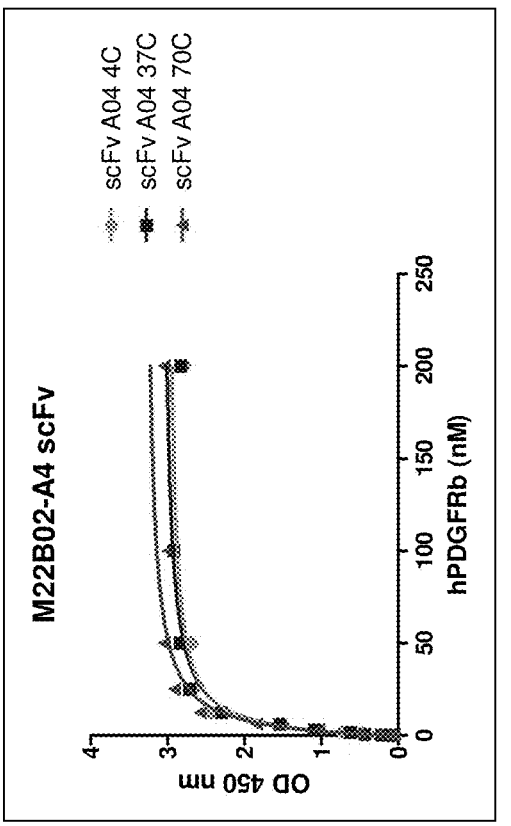
FIG. 16 depicts the results of ELISA assays measuring the binding to human PDGFRβ of XB2202 VH domain and XB2202/A4 scFv after incubation at various temperatures.
Figure 16:
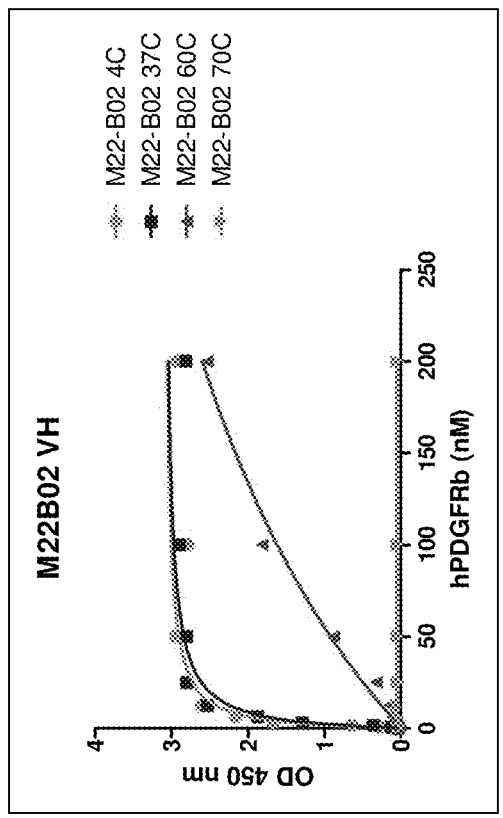

The thermostability of the XB2202 VH and XB2202/A4 scFv were determined. Specifically, 1 mg/mL of XB2202 and XB2202-A4 were incubated at 4° C., 37° C., 60° C. and 70° C. for 12 hours and a PDGFRβ binding ELISA was performed to test the binding activity of the protein after incubation. As shown in FIG. 16, the XB2202 VH domain lost significant PDGFRβ binding activity after incubation at 60° C. and completely lost binding activity after incubation at 70° C. The Tm of XB2202 was measured to be approximately 62° C. In contrast, the XB2202/A4 scFv was completely active after 12 hour incubation at 70° C., indicating that the Tm of the XB2202 scFv was greater than 70° C.

Example 9

Expression, Purification and Concentration of IgG1 Antibodies

XB1511/D8 and XB2202/A4 VH/VL pairs were separately expressed as full-length heterotetrameric IgG1 antibodies in 293T cells and purified. The amino acid sequences of the heavy and light chains of XB1511/D8 and XB2202/A4 IgG1 antibodies are set forth in Table 7, herein.

Cell culture supernatants were obtained by filtration and expressed antibodies purified using a two-step purification scheme. Specifically, Protein A affinity purification was performed, with antibody bound elution at pH3.5. The pH of the Protein A eluate was adjusted to pH 7 using 1M Tris, and purified further by ion exchange chromatography using a HiTrap Q XL column (GE Healthcare). The purified antibody was stored in PBS at pH7.

TABLE 7

Amino acid sequences of XB1511/D8 and XB2202/A4 VH/VL pairs formatted as full-length heterotetrameric IgG1 antibodies.

| Antibody chain | Amino Acid Sequence (Signal sequences underlined) | SEQ ID NO. |
|---|---|---|
| XB1511 IgG1 | <u>GWSLILLFLVAVATRVLS</u>QVQLVQSGAEVKKPGSSVKVSCKASGGTFSSYAIS WVRQAPGQGLEWMGGIIPIFGTANYAQKFQGRVTITADESTSTAYMELSSLRS EDTAVYYCAIHGGDRSYWGQGTLVTVSSASTKGPSVFPLAPSSKSTSGGTAAL GCLVKDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLY SKLTVDKSRWQQGNVFSCSVMHEALHNHYTQKSLSLSPGK | 505 |
| D8 Ckappa | <u>DFQVQIISFLLISASVIMSRG</u>EIVMTQSPGTLTLSPGEGATLSCRASQSVTSN YLAWYQQRPGQAPRLLIYDASNRATGIPDRFSGSGFGTDFTLTISRLEPEDFA VYYCQQYVNSRTFGQGTKVEIKRTVAAPSVFIFPPSDEQLKSGTKVEIKRTVA APSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC | 506 |
| XB2202 IgG1 | <u>GWSLILLFLVAVATRVLS</u>QVQLVQSGAEVKKPGSSVRVSCKASGGTFSRHAIS WVRQAPGQGLEWIGGILPILKTPNYAQRFQGRVTINADESTSTVYMEMSSLRS EDTAVYYCATHGGDRSYWGQGTLVTVSSASTKGPSVFPLAPSSKSTSGGTAAL GCLVKDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLY SKLTVDKSRWQQGNVFSCSVMHEALHNHYTQKSLSLSPGK | 507 |
| A4 Ckappa | <u>DFQVQIISFLLISASVIMSRG</u>DVVMTQSPSSLSASVGDRVTITCQASQDISNW LNWYQQKPGKAPKLLIYEASNLETGVPSRFSGSGSGTDFTFTISSLQPEDIAT YYCQQYNNVLRTFGQGTKVEIKRTVAAPSVFIFPPSDEQLKSGTKVEIKRTVA APSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC | 508 |

The antibody expression level and the antibody concentration after each purification step was determined by measuring the $A_{280}$ of the antibody solution. The purity and quality of the purified antibodies was determined by size-exclusion high-performance liquid chromatography (SEC-HPLC). The results of these experiments are set forth in Table 8, herein. These data show that when XB1511/D8 and XB2202/A4 VH/VL pairs are formatted as full-length heterotetrameric IgG1 antibodies, the resultant antibodies are highly manufacturable in that they are expressed at high levels, are easily purified to a high purity, and exhibit little aggregation.

TABLE 8

Analysis of expression and purification of XB1511/D8 and XB2202/A4 IgG1 antibodies.

| Antibody | Culture volume | Antibody Expression level | Amount of antibody after protein A purification | Amount of antibody after ion-exchange purification | Antibody % recovery after 2 step purification | Antibody % purity | % antibody aggregates |
|---|---|---|---|---|---|---|---|
| XB1511/D8 IgG1 | 2.0 L | 24 mg/L | 46 mg | 44 mg | 97.8% | 95.8% | 2.4% |
| XB2202/A4 IgG1 | 1.4 L | 47 mg/L | 62 mg | 54 mg | 87% | 96.9% | 2.5% |

The purified XB1511/D8 and XB2202/A4 IgG1 antibodies were further analysed for their ability to be concentrated. Specifically, solutions of each antibody were concentrated to 50 mg/ml using centricon ultra filtration spin columns with 10 kDa and 30 kDa cut-off limits. The integrity of the concentrated solution was analyzed by SEC-HPLC. From this analysis it was determined that the 50 mg/ml solution of XB1511/D8 IgG1 had a purity of about 96% and contained about 2.4% of antibody aggregates, whilst the 50 mg/ml solution of XB2202/A4 IgG1 had a purity of about 97.8% and contained about 2.2% of antibody aggregates. These data demonstrate that XB1511/D8 and XB2202/A4 IgG1 antibodies are highly stable in a concentrated solution.

Example 10

Thermostability of XB1511/D8 and XB2202/A4 IgG1 Antibodies

The thermostability of XB1511/D8 and XB2202/A4 IgG1 antibodies were determined using a fluorescence based assay. Specifically, 5 mg/ml of purified XB1511/D8 IgG1, XB2202/A4 IgG1, or human IgG1 control were mixed with Sypro orange dye (Sigma) and the temperature of the mixture increased in 1 degree increments from 25° C. to 95° C. The Sypro orange dye incorporates into the IgG when the temperature increases and the IgG unfolds. The fluorescent signal produced by the association of Sypro orange dye with the IgGs was monitored using a BioRad CFX96 instrument. In this assay, the negative regression of the Sypro orange signal was used to identify the peak melting (i.e. $T_m$) point for each protein.

From this analysis it was determined that XB1511/D8 and XB2202/A4 have melting temperatures ($T_m$) of 67° C. to 70° C., respectively. This compared well to the human IgG1 control antibody which exhibited a $T_m$ of 72° C. This data demonstrate that the VH and VH/VL pairs of the invention are capable of being formatted into highly thermostable full-length IgG molecules.

Example 11

Binding Affinities of XB2202 VH, scFv and IgG1 Antibodies to Human

The binding kinetics of XB2202 VH domain, XB2202/A4 scFv and XB2202/A4. IgG1 to human PDFGR were determined using surface plasmon resonance on a Biacore T100. Briefly, recombinant human PDGFR-hIgG1-Fc chimeric fusion protein (R&D, #385-PR-100/CF) was immobilized on a Series CM5 sensorchip coupled with anti-hIgG1 Fc monoclonal antibody (for the VH and ScFv assays) or anti-6His antibody (for the IgG assay). XB2202 VH domain, XB2202/A4 scFv and XB2202/A4 IgG1 were flown over the surface at 50 or 100 ul/min for 3 min at different concentrations (75, 50, 25, 10, 5, and 1 nM) and allowed to dissociate for 10 min. The data was analyzed using the Biacore T100 analysis software using a 1:1 model. Mass transport was checked and avoided to allow accurate measurements. All data was double referenced according to Biacore standard protocol.

The binding kinetics of XB2202 VH domain, XB2202/A4 scFv and XB2202/A4 IgG1 antibodies to human PDGFRβ are shown in Table 9, herein. These data show that XB2202 VH domain, XB2202/A4 scFv and XB2202/A4 IgG1 each have a high binding affinity for PDGFRβ. It is of particular note that XB2202/A4 scFv and XB2202/A4 IgG1 exhibit an improved off-rate ($1.54 \times 10^{-3}$ $s^{-1}$ and $1.56 \times 10^{-3}$ $s^{-1}$, respectively) compared to that of the unpaired XB2202 VH domain alone ($2.95 \times 10^{-3}$ $s^{-1}$).

TABLE 9

Binding Kinetics of XB2202 VH domain, XB2202/A4 scFv and XB2202/A4 IgG1 to human PDGFRβ

| Antibody | On-rate ($M^{-1}s^{-1}$) | Off-rate ($s^{-1}$) | Kd (M) |
|---|---|---|---|
| XB2202 VH | $1.30 \times 10^7$ | $2.95 \times 10^{-3}$ | $2.27 \times 10^{-10}$ |
| XB2202/A4 ScFv | $7.06 \times 10^5$ | $1.54 \times 10^{-3}$ | $2.18 \times 10^{-9}$ |
| XB2202/A4 IgG1 | $9.80 \times 10^5$ | $1.56 \times 10^{-3}$ | $1.59 \times 10^{-9}$ |

Example 12

Functional Analysis of Anti-PDGFRβ Antibodies Using In Vivo Mouse Models

The ability of the anti-PDGFRβ antibodies disclosed herein to inhibit PDGF-induced vascularization in vivo is evaluated using the developing retina vasculature model, the corneal neovascularization model, and/or the choroidal neovascularization model described in Nobuo et al. Am. J.

Path, (2006) 168(6), 2036-2052 (which is incorporated by reference herein in its entirety). In these assays antibodies are administered to mice as VH domains, scFv, and/or full length IgG.

We claim:

1. An isolated binding polypeptide that specifically binds to PDGFRβ, comprising a VH domain having the amino acid sequence selected from the group consisting of SEQ ID NOs: 318-368.

2. The binding polypeptide of claim 1, comprising a VL domain comprising a CDR3 comprising the amino acid sequence selected from the group consisting of SEQ ID NOs: 63-147.

3. The binding polypeptide of claim 2, wherein the VL domain comprises the amino acid sequence selected from the group consisting of SEQ ID NOs: 369-453.

4. The binding polypeptide of claim 1, wherein the VL domain further comprises a CDR2 comprising the amino acid sequence selected from the group consisting of SEQ ID NOs: 148-232.

5. The binding polypeptide of claim 1, wherein the VL domain further comprises a CDR1 comprising the amino acid sequence selected from the group consisting of SEQ ID NOs: 233-317.

6. The binding polypeptide of claim 1, which inhibits the activity of PDGFRβ.

7. The binding polypeptide of claim 6, wherein the activity of PDGFRβ is inhibited by antagonizing PDGF binding to PDGFRβ.

8. The binding polypeptide of claim 6, wherein the activity of PDGFRβ is inhibited by antagonizing PDGFRβ dimerization.

9. The binding polypeptide of claim 1, which binds to PDGFRβ with a Kd of less than 250 pM.

10. The binding polypeptide of claim 1, which binds to PDGFRβ with a Kd of less than 100 pM.

11. The binding polypeptide of claim 1, which binds to PDGFRβ with an off-rate of less than $10^{-3}$ s$^{-1}$.

12. The binding polypeptide of claim 1, which binds specifically to mouse and human PDGFRβ.

13. The binding polypeptide of claim 1, which antagonizes PDGF binding to the PDGFRβ with an IC50 of less than 5 nM.

14. The binding polypeptide of claim 1, which inhibits ligand induced tyrosine phosphorylation of PDGFRβ with an IC50 of less than 4 nM.

15. The binding polypeptide of claim 1, which inhibits retinal pericyte migration with an IC50 of less than 6 nM.

16. The binding polypeptide of claim 1, comprising a VH domain with a melting temperature (Tm) of at least 68° C.

17. The binding polypeptide of claim 1, which is an antibody.

18. The binding polypeptide of claim 1, which is an scFv.

19. A pharmaceutical composition comprising binding polypeptide of claim 1 and one or more pharmaceutically acceptable carrier.

20. A diverse library of unpaired VH domains wherein each member of the library binds to human PDGFRβ and wherein each member of the library comprises a VH domain comprising a CDR3, a CDR2, and a CDR1, and wherein:
    the CDR3 comprises the CDR3 amino acid sequence set forth in SEQ ID NO: 1;
    the CDR2 comprises a CDR2 amino acid sequence selected from the group consisting of SEQ ID NOs: 2-32; and
    the CDR 1 comprises a CDR1 amino acid sequence selected from the group consisting of SEQ ID NOs: 33-62.

21. A diverse library of stable VH/VL pairs wherein each member of the library binds to human PDGFRβ and wherein each member of the library comprises a VH domain comprising a CDR3, a CDR2, and a CDR1, and wherein:
    the CDR3 comprises the CDR3 amino acid sequence set forth in SEQ ID NO: 1;
    the CDR2 comprises a CDR2 amino acid sequence selected from the group consisting of SEQ ID NOs: 2-32; and
    the CDR 1 comprises a CDR1 amino acid sequence selected from the group consisting of SEQ ID NOs: 33-62.

22. The library of claim 21, wherein the VL domains are human VL domains.

23. An isolated binding polypeptide that specifically binds to PDGFRβ, comprising a VH domain having the CDR3, CDR2, and CDR1 amino acid sequences set forth in SEQ ID NOs: 1, 3, and 35, respectively.

24. The isolated binding polypeptide-of claim 23, wherein the VH domain comprises the amino acid sequence set forth in SEQ ID NO: 321.

25. The isolated binding polypeptide of claim 24, further comprising a VL domain having the CDR3, CDR2, and CDR1 amino acid sequences set forth in SEQ ID NOs: 119, 204, and 289, respectively.

26. An isolated binding polypeptide that specifically binds to PDGFRβ, comprising a VH domain having the amino acid sequence set forth in SEQ ID NO: 321, and a VL domain having the amino acid sequence set forth in SEQ ID NO: 425.

* * * * *

```
                              SEQUENCE LISTING

<160> NUMBER OF SEQ ID NOS: 508

<210> SEQ ID NO 1
<211> LENGTH: 7
<212> TYPE: PRT
<213> ORGANISM: Artificial Sequence
<220> FEATURE:
<223> OTHER INFORMATION: Synthetic Heavy chain CDR

<400> SEQUENCE: 1

His Gly Gly Asp Arg Ser Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Heavy chain CDR

<400> SEQUENCE: 2

Gly Ile Ile Pro Ile Phe Gly Thr Ala Asn Tyr Ala Gln Lys Phe Gln
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Synthetic Heavy chain CDR

<400> SEQUENCE: 3

Gly Ile Leu Pro Ile Leu Lys Thr Pro Asn Tyr Ala Gln Arg Phe Gln
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Synthetic Heavy chain CDR, clone: C05

<400> SEQUENCE: 4

Gly Val Leu Pro Ile Leu Lys Thr Pro Asn Tyr Ala Gln Arg Phe Gln
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic Heavy chain CDR, clone: E2

<400> SEQUENCE: 5

Trp Ile Asn Pro Asn Ser Gly Asn Thr Gly Tyr Ala Gln Lys Phe Gln
1               5                   10                  15
```

-continued

Gly

```
<210> SEQ ID NO 6
<211> LENGTH: 17
<212> TYPE: PRT
<213> ORGANISM: Artificial Sequence
<220> FEATURE:
<223> OTHER INFORMATION: Synthetic Heavy chain CDR, clone: A3

<400> SEQUENCE: 6
```

Trp Ile Asn Pro Asn Ser Gly Gly Thr Tyr Phe Ala Gln Lys Phe Gln
1               5                   10                  15

Gly

```
<210> SEQ ID NO 7
<211> LENGTH: 17
<212> TYPE: PRT
<213> ORGANISM: Artificial Sequence
<220> FEATURE:
<223> OTHER INFORMATION: Synthetic Heavy chain CDR, clone: F10

<400> SEQUENCE: 7
```

Trp Ile Asn Pro Asp Ser Gly Gly Thr Tyr Phe Ala Gln Lys Phe Gln
1               5                   10                  15

Gly

```
<210> SEQ ID NO 8
<211> LENGTH: 17
<212> TYPE: PRT
<213> ORGANISM: Artificial Sequence
<220> FEATURE:
<223> OTHER INFORMATION: Synthetic Heavy chain CDR, clone: C12

<400> SEQUENCE: 8
```

Trp Met Asn Pro Asp Ser Gly Gly Thr Ile Tyr Ala Gln Lys Phe Gln
1               5                   10                  15

Gly

```
<210> SEQ ID NO 9
<211> LENGTH: 17
<212> TYPE: PRT
<213> ORGANISM: Artificial Sequence
<220> FEATURE:
<223> OTHER INFORMATION: Synthetic Heavy chain CDR, clone: H2

<400> SEQUENCE: 9
```

Trp Leu Asn Pro Asn Ser Gly Asp Thr His Ser Ala Gln Lys Phe Gln
1               5                   10                  15

Gly

```
<210> SEQ ID NO 10
<211> LENGTH: 17
<212> TYPE: PRT
<213> ORGANISM: Artificial Sequence
<220> FEATURE:
<223> OTHER INFORMATION: Synthetic Heavy chain CDR, clone: B1

<400> SEQUENCE: 10
```

Trp Ile Asn Pro Asn Asn Gly Asn Thr Thr Tyr Ala Gln Lys Phe Gln
1               5                   10                  15

Gly

```
<210> SEQ ID NO 11
```

```
<211> LENGTH: 17
<212> TYPE: PRT
<213> ORGANISM: Artificial Sequence
<220> FEATURE:
<223> OTHER INFORMATION: Synthetic Heavy chain CDR, clone: H1

<400> SEQUENCE: 11

Trp Ile Asn Pro Asn Ser Gly Gly Thr Asn Ser Ala Pro Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic Heavy chain CDR, clone: E6

<400> SEQUENCE: 12

Trp Ile Asn Pro Asn Ser Gly Gly Thr Asn Tyr Ala Gln Lys Phe Gln
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Synthetic Heavy chain CDR

<400> SEQUENCE: 13

Trp Ile Val Val Gly Ser Gly Asn Thr Asn Tyr Ala Gln Lys Phe Gln
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: Synthetic Heavy chain CDR

<400> SEQUENCE: 14

Val Ile Asn Thr Gly Val Gly Ser Thr Asn Tyr Ala Gln Lys Phe Gln
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Synthetic Heavy chain CDR, clone: H3

<400> SEQUENCE: 15

Leu Ser Asn Pro Ser Gly Asp Tyr Thr Val Tyr Ala Pro Lys Phe Gln
1               5                   10                  15

Gly

<210> SEQ ID NO 16
<211> LENGTH: 17
<212> TYPE: PRT
<213> ORGANISM: Artificial Sequence
<220> FEATURE:
```

-continued

<223> OTHER INFORMATION: Synthetic Heavy chain CDR, clone: B4

<400> SEQUENCE: 16

Leu Ser Asn Pro Ser Gly Asp Tyr Thr Val Tyr Ala Pro Lys Leu Gln
1               5                   10                  15
Gly

<210> SEQ ID NO 17
<211> LENGTH: 17
<212> TYPE: PRT
<213> ORGANISM: Artificial Sequence
<220> FEATURE:
<223> OTHER INFORMATION: Synthetic Heavy chain CDR, clone: D06

<400> SEQUENCE: 17

Val Ile Ser Tyr Asp Gly Ser Asn Lys Tyr Tyr Ala Asp Ser Val Lys
1               5                   10                  15
Gly

<210> SEQ ID NO 18
<211> LENGTH: 17
<212> TYPE: PRT
<213> ORGANISM: Artificial Sequence
<220> FEATURE:
<223> OTHER INFORMATION: Synthetic Heavy chain CDR, clone: F3

<400> SEQUENCE: 18

Trp Ile Ser Ala Asp Asn Gly Asn Thr Asn Tyr Ala Gln Lys Phe Gln
1               5                   10                  15
Glu

<210> SEQ ID NO 19
<211> LENGTH: 17
<212> TYPE: PRT
<213> ORGANISM: Artificial Sequence
<220> FEATURE:
<223> OTHER INFORMATION: Synthetic Heavy chain CDR, clone: A12

<400> SEQUENCE: 19

Trp Ile Ser Ala Asp Asn Gly Asn Thr Lys Tyr Ala Gln Lys Phe Gln
1               5                   10                  15
Asp

<210> SEQ ID NO 20
<211> LENGTH: 17
<212> TYPE: PRT
<213> ORGANISM: Artificial Sequence
<220> FEATURE:
<223> OTHER INFORMATION: Synthetic Heavy chain CDR, clone: G3

<400> SEQUENCE: 20

Gly Phe Asp Pro Glu Asp Gly Glu Thr Ile Tyr Ala Gln Lys Phe Gln
1               5                   10                  15
Gly

<210> SEQ ID NO 21
<211> LENGTH: 17
<212> TYPE: PRT
<213> ORGANISM: Artificial Sequence
<220> FEATURE:
<223> OTHER INFORMATION: Synthetic Heavy chain CDR, clone: G12

<400> SEQUENCE: 21

```
Gly Ile Ile Pro Val Ser Gly Thr Pro Asn Tyr Ala Gln Lys Phe Gln
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Synthetic Heavy chain CDR, clone: E9

<400> SEQUENCE: 22

Ile Thr Tyr Pro Ala Asp Ser Thr Thr Val Tyr Ser Pro Ser Phe Gln
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: Synthetic Heavy chain CDR, clone: E11

<400> SEQUENCE: 23

Arg Ile Asn Asn Asp Gly Ser Ser Thr Ser Tyr Ala Asp Ser Val Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Synthetic Heavy chain CDR, clone: C08

<400> SEQUENCE: 24

Arg Ile Ser Ile Asp Gly Thr Thr Thr Thr Tyr Ala Asp Ser Val Gln
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Synthetic Heavy chain CDR, clone: XB2708

<400> SEQUENCE: 25

Phe Ile Leu Phe Asp Gly Asn Asn Lys Tyr Tyr Ala Asp Ser Val Lys
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Synthetic Heavy chain CDR, clone: D03

<400> SEQUENCE: 26

Arg Ile Asn Ala Asp Gly Thr Ser Thr Ala Tyr Ala Glu Ser Val Lys
1               5                   10                  15

Gly
```

<210> SEQ ID NO 27
<211> LENGTH: 16
<212> TYPE: PRT
<213> ORGANISM: Artificial Sequence
<220> FEATURE:
<223> OTHER INFORMATION: Synthetic Heavy chain CDR, clone: A10

<400> SEQUENCE: 27

Leu Ile Tyr Ser Asp Gly Ser Thr Tyr Tyr Ala Asp Ser Val Lys Gly
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Synthetic Heavy chain CDR, clone: C09

<400> SEQUENCE: 28

Ala Ile Asp Gly Ser Gly Gly Thr Thr Tyr Tyr Ala Gly Ser Val Lys
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Synthetic Heavy chain CDR, clone: A06

<400> SEQUENCE: 29

His Ile Ser Asn Asp Gly Ser Ile Thr Arg Tyr Ala Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic Heavy chain CDR, clone: C05

<400> SEQUENCE: 30

Arg Ile Lys Thr Asp Gly Ser Ser Thr Ser Tyr Ala Asp Ser Val Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic Heavy chain CDR, clone: H01

<400> SEQUENCE: 31

Arg Ile Ser Ser Asp Gly Ser Thr Thr Ala Tyr Ala Asp Ser Val Arg
1               5                   10                  15

Gly

<210> SEQ ID NO 32
<211> LENGTH: 17
<212> TYPE: PRT
<213> ORGANISM: Artificial Sequence

```
<220> FEATURE:
<223> OTHER INFORMATION: Synthetic Heavy chain CDR, clone: G07

<400> SEQUENCE: 32

Arg Ile Ser Ser Asp Gly Ser Ser Thr Ala Tyr Ala Asp Ser Val Lys
1               5                   10                  15
Gly

<210> SEQ ID NO 33
<211> LENGTH: 5
<212> TYPE: PRT
<213> ORGANISM: Artificial Sequence
<220> FEATURE:
<223> OTHER INFORMATION: Synthetic Heavy chain CDR

<400> SEQUENCE: 33

Ser Tyr Ala Ile Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Heavy chain CDR, clone: G2

<400> SEQUENCE: 34

Gly Tyr Ala Ile Ser
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Heavy chain CDR

<400> SEQUENCE: 35

Arg His Ala Ile Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Heavy chain CDR

<400> SEQUENCE: 36

Asp Tyr Tyr Ile Gln
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Heavy chain CDR, clone: H2

<400> SEQUENCE: 37

Ala Tyr Tyr Ile Gln
1               5

<210> SEQ ID NO 38
<211> LENGTH: 5
<212> TYPE: PRT
```

```
<213> ORGANISM: Artificial Sequence
<220> FEATURE:
<223> OTHER INFORMATION: Synthetic Heavy chain CDR

<400> SEQUENCE: 38

Asp Tyr Tyr Ile His
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Heavy chain CDR, clone: H1

<400> SEQUENCE: 39

Asp Tyr His Leu His
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Heavy chain CDR, clone: E6

<400> SEQUENCE: 40

Asp Tyr Tyr Leu His
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Heavy chain CDR, clone: A1

<400> SEQUENCE: 41

Ser Ser Ala Val Gln
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Heavy chain CDR, clone: H7

<400> SEQUENCE: 42

Ser Ser Ala Met Gln
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Heavy chain CDR, clone: B2

<400> SEQUENCE: 43

Asn Tyr Gln Val Gln
1               5

<210> SEQ ID NO 44
<211> LENGTH: 5
<212> TYPE: PRT
<213> ORGANISM: Artificial Sequence
```

```
<220> FEATURE:
<223> OTHER INFORMATION: Synthetic Heavy chain CDR, clone: A7

<400> SEQUENCE: 44

Asn Tyr Pro Val Gln
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Heavy chain CDR

<400> SEQUENCE: 45

Asn Ser Phe Met Gln
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Heavy chain CDR

<400> SEQUENCE: 46

Ser Tyr Gly Met His
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Heavy chain CDR

<400> SEQUENCE: 47

Ser His Gly Met Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Heavy chain CDR, clone: G3

<400> SEQUENCE: 48

Glu Leu Ser Met His
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Heavy chain CDR, clone: H12

<400> SEQUENCE: 49

Asp Asn Tyr Val His
1               5

<210> SEQ ID NO 50
<211> LENGTH: 5
<212> TYPE: PRT
<213> ORGANISM: Artificial Sequence
<220> FEATURE:
```

<223> OTHER INFORMATION: Synthetic Heavy chain CDR, clone: G12

<400> SEQUENCE: 50

Ala Tyr Pro Ile Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Heavy chain CDR, clone: C06

<400> SEQUENCE: 51

Gly His Tyr Ile His
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Heavy chain CDR, clone: C11

<400> SEQUENCE: 52

Asn Asp Tyr Ile His
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Heavy chain CDR, clone: F08

<400> SEQUENCE: 53

Ser Ser Tyr Ile His
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Heavy chain CDR, clone: E9

<400> SEQUENCE: 54

Asn Tyr Trp Ile Gly
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Heavy chain CDR, clone: E11

<400> SEQUENCE: 55

Ser Tyr Trp Met His
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Heavy chain CDR, clone: C08

<400> SEQUENCE: 56

Ala Phe Trp Met His
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Heavy chain CDR, clone: D03

<400> SEQUENCE: 57

Asn Asp Trp Met His
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Heavy chain CDR, clone: A10

<400> SEQUENCE: 58

Asp Tyr Ala Met Asn
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic Heavy chain CDR, clone: C09

<400> SEQUENCE: 59

Asn Asn Ala Met Ser
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Heavy chain CDR, clone: A06

<400> SEQUENCE: 60

Gly His Trp Met His
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic Heavy chain CDR, clone: C05

<400> SEQUENCE: 61

Ser Asn Trp Met His
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic Heavy chain CDR

```
<400> SEQUENCE: 62

Ser Asp Trp Met His
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Light chain CDR, clone: B10

<400> SEQUENCE: 63

His Gln Ser Ser Ser Leu Pro Trp Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Light chain CDR, clone: H10

<400> SEQUENCE: 64

His Gln Ser Ser Ser Leu Pro His Thr
1               5

<210> SEQ ID NO 65
<211> LENGTH: 11
<212> TYPE: PRT
<213> ORGANISM: Artificial Sequence
<220> FEATURE:
<223> OTHER INFORMATION: Synthetic Light chain CDR, clone: F10

<400> SEQUENCE: 65

Arg Ala Ser Gln Ser Ile Gly Ser Gly Leu His
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthetic Light chain CDR, clone: B12

<400> SEQUENCE: 66

His Gln Thr Ser Ser Leu Pro Leu Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Light chain CDR, clone: B11

<400> SEQUENCE: 67

Gln Gln Tyr Gly Ser Ser Pro Trp Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Light chain CDR, clone: E7

<400> SEQUENCE: 68
```

```
Gln Gln Tyr Gly Ser Ser Pro Gln Thr
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic Light chain CDR, clone: E8

<400> SEQUENCE: 69

Gln Gln Tyr Gly Ser Ser Pro Pro Tyr Thr
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Synthetic Light chain CDR, clone: H8

<400> SEQUENCE: 70

Gln Gln Tyr Ala Gly Ser Pro Phe Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Light chain CDR, clone: H12

<400> SEQUENCE: 71

Gln Gln Phe Gly Ser Ser Pro Trp Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Light chain CDR, clone: F8

<400> SEQUENCE: 72

Gln Gln Tyr Gly Ser Ser Pro Leu Thr
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Light chain CDR, clone: D11

<400> SEQUENCE: 73

Gln Gln Tyr Gly Ala Ser Pro Arg Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Light chain CDR, clone: G8

<400> SEQUENCE: 74
```

Gln Gln Tyr Gly Ser Ala Leu Leu Thr
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Light chain CDR, clone: H9

<400> SEQUENCE: 75

Gln Gln Tyr Gly Asn Ser Trp Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Light chain CDR, clone: H11

<400> SEQUENCE: 76

His Gln Ser Arg Asn Leu Pro Phe Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Light chain CDR, clone: G12

<400> SEQUENCE: 77

His Gln Ser Arg Ser Phe Pro Leu Thr
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic Light chain CDR, clone: E11

<400> SEQUENCE: 78

Gln Gln Tyr Glu Thr Ser Trp Thr
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic Light chain CDR, clone: F12

<400> SEQUENCE: 79

Arg Asp Gly Leu Asn His Leu Val
1               5

<210> SEQ ID NO 80
<211> LENGTH: 11
<212> TYPE: PRT
<213> ORGANISM: Artificial Sequence
<220> FEATURE:
<223> OTHER INFORMATION: Synthetic Light chain CDR, clone: C8

<400> SEQUENCE: 80

Gly Thr Trp Asp Ser Ser Leu Ser Val Val Ile

<210> SEQ ID NO 81
<211> LENGTH: 9
<212> TYPE: PRT
<213> ORGANISM: Artificial Sequence
<220> FEATURE:
<223> OTHER INFORMATION: Synthetic Light chain CDR, clone: A8

<400> SEQUENCE: 81

His Gln Thr Gly Ser Phe Pro Tyr Thr
1               5

<210> SEQ ID NO 82
<211> LENGTH: 10
<212> TYPE: PRT
<213> ORGANISM: Artificial Sequence
<220> FEATURE:
<223> OTHER INFORMATION: Synthetic Light chain CDR, clone: B8

<400> SEQUENCE: 82

Leu Leu Ser Tyr Ser Gly Pro Arg Val Val
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Synthetic Light chain CDR, clone: F7

<400> SEQUENCE: 83

Gln Gln Ser Tyr Arg Thr Pro Phe Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Light chain CDR, clone: B7

<400> SEQUENCE: 84

Gln Val Trp Asp Ser Ser Ser Val Ile
1               5

<210> SEQ ID NO 85
<211> LENGTH: 11
<212> TYPE: PRT
<213> ORGANISM: Artificial Sequence
<220> FEATURE:
<223> OTHER INFORMATION: Synthetic Light chain CDR, clone: G9

<400> SEQUENCE: 85

Lys Ser Arg Asp Ser Ser Ala Met Arg Trp Val
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Synthetic Light chain CDR, clone: A9

<400> SEQUENCE: 86

Leu Leu Tyr Phe Asn Pro Thr Arg Val
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Light chain CDR, clone: A11

<400> SEQUENCE: 87

Gly Ala Asp His Gly Arg Val
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Light chain CDR, clone: E12

<400> SEQUENCE: 88

Gln Val Trp His Ser Gly Val Ile
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic Light chain CDR, clone: H7

<400> SEQUENCE: 89

His Gln Ser Arg Ser Ser His Thr
1               5

<210> SEQ ID NO 90
<211> LENGTH: 11
<212> TYPE: PRT
<213> ORGANISM: Artificial Sequence
<220> FEATURE:
<223> OTHER INFORMATION: Synthetic Light chain CDR, clone: A10

<400> SEQUENCE: 90

Gln Ser Phe Asp Val Tyr Ser His Glu Val Val
1               5                   10

<210> SEQ ID NO 91
<211> LENGTH: 9
<212> TYPE: PRT
<213> ORGANISM: Artificial Sequence
<220> FEATURE:
<223> OTHER INFORMATION: Synthetic Light chain CDR, clone: C11

<400> SEQUENCE: 91

Met Gln Ser Thr His Phe Pro Phe Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Light chain CDR, clone: D10

<400> SEQUENCE: 92

Gln Gln Tyr Asp Ser Pro Pro Trp Thr
1               5

```
<210> SEQ ID NO 93
<211> LENGTH: 9
<212> TYPE: PRT
<213> ORGANISM: Artificial Sequence
<220> FEATURE:
<223> OTHER INFORMATION: Synthetic Light chain CDR, clone: D12

<400> SEQUENCE: 93

Gln Gln His Asp Thr Ser Gln Trp Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Light chain CDR, clone: C7

<400> SEQUENCE: 94

Met Gln Gly Leu His Ile Pro His Thr
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Light chain CDR, clone: D7

<400> SEQUENCE: 95

Met Gln Ser Thr His Gln Trp Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Light chain CDR, clone: C9

<400> SEQUENCE: 96

Gln Gln Tyr Asp Ser Tyr Ser Arg Thr
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic Light chain CDR, clone: C12

<400> SEQUENCE: 97

Gln Gln Ser Phe Ser Met Arg Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic Light chain CDR, clone: D8

<400> SEQUENCE: 98

Gln Gln Tyr Val Asn Ser Arg Thr
1               5
```

```
<210> SEQ ID NO 99
<211> LENGTH: 8
<212> TYPE: PRT
<213> ORGANISM: Artificial Sequence
<220> FEATURE:
<223> OTHER INFORMATION: Synthetic Light chain CDR, clone: D9

<400> SEQUENCE: 99

Gln Gln Tyr Asn Asp Phe Phe Thr
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Light chain CDR, clone: G7

<400> SEQUENCE: 100

Met Gln Ala Thr Gln Phe Pro Ser
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Light chain CDR, clone: G11

<400> SEQUENCE: 101

Gln Gln Tyr Gly Asp Ser Val Phe Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Light chain CDR, clone: F9

<400> SEQUENCE: 102

Gln Gln Ser Tyr Ser Thr Pro Arg Thr
1               5

<210> SEQ ID NO 103
<211> LENGTH: 10
<212> TYPE: PRT
<213> ORGANISM: Artificial Sequence
<220> FEATURE:
<223> OTHER INFORMATION: Synthetic Light chain CDR, clone: E9

<400> SEQUENCE: 103

Gln Glu Ser Tyr Ser Thr Leu Leu Tyr Thr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic Light chain CDR, clone: B1

<400> SEQUENCE: 104

Gln Val Trp Glu Ser Gly Ser Glu His Tyr Val
1               5                   10

<210> SEQ ID NO 105
```

```
<211> LENGTH: 11
<212> TYPE: PRT
<213> ORGANISM: Artificial Sequence
<220> FEATURE:
<223> OTHER INFORMATION: Synthetic Light chain CDR, clone: E6

<400> SEQUENCE: 105

Gln Val Trp Glu Ser Thr Ser Asp His Pro Thr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic Light chain CDR, clone: F3

<400> SEQUENCE: 106

Gln Val Trp Asp Ser Ser Ser Asp His Trp Val
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Synthetic Light chain CDR, clone: H4

<400> SEQUENCE: 107

Gln Val Trp Asp Ser Ser Ser Gly His Arg Gly Val
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic Light chain CDR, clone: H5

<400> SEQUENCE: 108

Gln Val Trp Asp Ser Ala Thr Asp His Val Val
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic Light chain CDR, clone: B5

<400> SEQUENCE: 109

Gln Val Trp Asp Ser Asp Arg His His Val Val
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic Light chain CDR, clone: G6

<400> SEQUENCE: 110

Gln Val Trp Asp Ile Asn Asp Asp Tyr Ala Val
1               5                   10

<210> SEQ ID NO 111
<211> LENGTH: 11
```

```
<212> TYPE: PRT
<213> ORGANISM: Artificial Sequence
<220> FEATURE:
<223> OTHER INFORMATION: Synthetic Light chain CDR, clone: C1

<400> SEQUENCE: 111

Gln Gln Tyr Val Ser Ser Pro Pro Met Tyr Thr
1               5                   10

<210> SEQ ID NO 112
<211> LENGTH: 9
<212> TYPE: PRT
<213> ORGANISM: Artificial Sequence
<220> FEATURE:
<223> OTHER INFORMATION: Synthetic Light chain CDR, clone: F1

<400> SEQUENCE: 112

Gln Gln Tyr Val Thr Tyr Pro Leu Thr
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic Light chain CDR, clone: A3

<400> SEQUENCE: 113

Gln Gln Tyr Asp Ser Val Pro Leu Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Light chain CDR, clone: B4

<400> SEQUENCE: 114

Gln Gln Tyr Glu Asp Leu Pro Ser Phe
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic Light chain CDR, clone: B6

<400> SEQUENCE: 115

Gln Gln Tyr Gly Ser Phe Pro Tyr Ser
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic Light chain CDR, clone: F2

<400> SEQUENCE: 116

Gln Gln Tyr Gln Asn Pro Pro Phe Thr
1               5

<210> SEQ ID NO 117
<211> LENGTH: 9
<212> TYPE: PRT
```

```
<213> ORGANISM: Artificial Sequence
<220> FEATURE:
<223> OTHER INFORMATION: Synthetic Light chain CDR, clone: D3

<400> SEQUENCE: 117

Gln Gln Tyr Lys Thr Phe Pro His Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic Light chain CDR, clone: G2

<400> SEQUENCE: 118

Gln Gln Tyr His Ser Tyr Pro Tyr Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic Light chain CDR, clone: A4

<400> SEQUENCE: 119

Gln Gln Tyr Asn Asn Val Leu Arg Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Light chain CDR, clone: G4

<400> SEQUENCE: 120

Gln Gln Tyr Asn Lys Trp Pro Thr Phe
1               5

<210> SEQ ID NO 121
<211> LENGTH: 10
<212> TYPE: PRT
<213> ORGANISM: Artificial Sequence
<220> FEATURE:
<223> OTHER INFORMATION: Synthetic Light chain CDR, clone: D5

<400> SEQUENCE: 121

Gln Gln Tyr Tyr Asn Trp Pro Pro Trp Thr
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Synthetic Light chain CDR, clone: A1

<400> SEQUENCE: 122

Gln Gln Arg Ser Asn Gly Val Thr Phe
1               5

<210> SEQ ID NO 123
<211> LENGTH: 9
<212> TYPE: PRT
<213> ORGANISM: Artificial Sequence
```

```
<220> FEATURE:
<223> OTHER INFORMATION: Synthetic Light chain CDR, clone: H2

<400> SEQUENCE: 123

Gln His Tyr His Thr Tyr Pro Phe Thr
1               5

<210> SEQ ID NO 124
<211> LENGTH: 12
<212> TYPE: PRT
<213> ORGANISM: Artificial Sequence
<220> FEATURE:
<223> OTHER INFORMATION: Synthetic Light chain CDR, clone: E2

<400> SEQUENCE: 124

Gln Gln Tyr Tyr Leu Thr Pro Thr Phe Thr Val Thr
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Synthetic Light chain CDR, clone: F4

<400> SEQUENCE: 125

Gln Gln Thr Asn Thr Phe Pro Leu Thr
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic Light chain CDR, clone: C5

<400> SEQUENCE: 126

Gln Gln Tyr His Thr Thr Pro Tyr Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic Light chain CDR, clone: E5

<400> SEQUENCE: 127

Gln Gln Ser Phe Ser Ser Pro Trp Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic Light chain CDR, clone: F6

<400> SEQUENCE: 128

Gln Gln Ser Phe Thr Thr Leu Val Thr
1               5

<210> SEQ ID NO 129
<211> LENGTH: 10
<212> TYPE: PRT
<213> ORGANISM: Artificial Sequence
<220> FEATURE:
```

<223> OTHER INFORMATION: Synthetic Light chain CDR, clone: G5

<400> SEQUENCE: 129

Cys Gln Gln Phe Asn Ser Tyr Pro Leu Ser
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Synthetic Light chain CDR, clone: A5

<400> SEQUENCE: 130

Gly Ala Asp His Gly Ser Gly Ser Asn Leu Val Tyr Val
1               5                   10

<210> SEQ ID NO 131
<211> LENGTH: 13
<212> TYPE: PRT
<213> ORGANISM: Artificial Sequence
<220> FEATURE:
<223> OTHER INFORMATION: Synthetic Light chain CDR, clone: D6

<400> SEQUENCE: 131

Gly Ala Asp His Gly Ser Gly Ser Asp Phe Val Tyr Val
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic Light chain CDR, clone: E4

<400> SEQUENCE: 132

Ala Ala Trp Asp Asp Ser Leu Asn Gly Pro Val
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic Light chain CDR, clone: F5

<400> SEQUENCE: 133

Ala Ala Trp Asp Asp Arg Leu Ser Gly Pro Val
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Synthetic Light chain CDR, clone: G1

<400> SEQUENCE: 134

Ala Thr Trp Asp Asp Asp Leu Ser Asn Pro Lys Trp Val
1               5                   10

<210> SEQ ID NO 135
<211> LENGTH: 9
<212> TYPE: PRT
<213> ORGANISM: Artificial Sequence
<220> FEATURE:
<223> OTHER INFORMATION: Synthetic Light chain CDR, clone: E3

<400> SEQUENCE: 135

Met Gln Ala Leu Gln Thr Ser Trp Thr
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic Light chain CDR, clone: A2

<400> SEQUENCE: 136

Met Gln Gly Thr His Trp Pro Tyr Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic Light chain CDR, clone: D1

<400> SEQUENCE: 137

Met Gln Ser Arg Asn Leu Pro Lys Thr
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic Light chain CDR, clone: C4

<400> SEQUENCE: 138

Met Val Trp Tyr Ser Ala Trp Val
1               5

<210> SEQ ID NO 139
<211> LENGTH: 10
<212> TYPE: PRT
<213> ORGANISM: Artificial Sequence
<220> FEATURE:
<223> OTHER INFORMATION: Synthetic Light chain CDR, clone: E1

<400> SEQUENCE: 139

His Val Leu Asp Ser Ser Thr Ile Val Ile
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Synthetic Light chain CDR, clone: A6

<400> SEQUENCE: 140

His Gln Tyr Asn Asn Trp Pro Leu Tyr Thr
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Synthetic Light chain CDR, clone: H1

```
<400> SEQUENCE: 141

Asn Ser Arg Asp Ser Ser Gly Tyr Leu Leu Leu
1               5                   10

<210> SEQ ID NO 142
<211> LENGTH: 9
<212> TYPE: PRT
<213> ORGANISM: Artificial Sequence
<220> FEATURE:
<223> OTHER INFORMATION: Synthetic Light chain CDR, clone: B2

<400> SEQUENCE: 142

Leu Leu Ser Tyr Ser Gly Ala Gly Val
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic Light chain CDR, clone: C2

<400> SEQUENCE: 143

Leu Gln Asp Tyr Ser Phe Pro Tyr Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic Light chain CDR, clone: G3

<400> SEQUENCE: 144

Gln Ala Trp Asp Ser Ser His Ala Val
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic Light chain CDR, clone: H3

<400> SEQUENCE: 145

Gln Ser Glu Asp Ser Arg Gly Pro Val
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic Light chain CDR, clone: D4

<400> SEQUENCE: 146

Val Gln Ala Thr His Phe Pro Val Thr
1               5

<210> SEQ ID NO 147
<211> LENGTH: 11
<212> TYPE: PRT
<213> ORGANISM: Artificial Sequence
<220> FEATURE:
<223> OTHER INFORMATION: Synthetic Light chain CDR, clone: C6

<400> SEQUENCE: 147
```

Cys Ser Tyr Thr Thr Gly Ser Thr Leu Tyr Leu
1               5                   10

<210> SEQ ID NO 148
<211> LENGTH: 6
<212> TYPE: PRT
<213> ORGANISM: Artificial Sequence
<220> FEATURE:
<223> OTHER INFORMATION: Synthetic Light chain CDR, clone: B10

<400> SEQUENCE: 148

Ala Tyr Gln Ser Val Ser
1               5

<210> SEQ ID NO 149
<211> LENGTH: 6
<212> TYPE: PRT
<213> ORGANISM: Artificial Sequence
<220> FEATURE:
<223> OTHER INFORMATION: Synthetic Light chain CDR, clone: H10

<400> SEQUENCE: 149

Ser Ser Gln Ser Phe Ser
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic Light chain CDR, clone: F10

<400> SEQUENCE: 150

Ala Ser Gln Ser Met Ser
1               5

<210> SEQ ID NO 151
<211> LENGTH: 6
<212> TYPE: PRT
<213> ORGANISM: Artificial Sequence
<220> FEATURE:
<223> OTHER INFORMATION: Synthetic Light chain CDR, clone: B12

<400> SEQUENCE: 151

Ala Ser Gln Pro Phe Ser
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic Light chain CDR, clone: B11

<400> SEQUENCE: 152

Gly Ala Ser Ser Arg Ala Ser
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic Light chain CDR, clone: E7

<400> SEQUENCE: 153

```
Gly Ala Ser Ser Arg Ala Thr
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic Light chain CDR, clone: E8

<400> SEQUENCE: 154

Gly Ala Ser Ser Arg Ala Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic Light chain CDR, clone: H8

<400> SEQUENCE: 155

Gly Ala Ser Ser Arg Ala Thr
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic Light chain CDR, clone: H12

<400> SEQUENCE: 156

Gly Ala Ser Arg Arg Ala Thr
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic Light chain CDR, clone: F8

<400> SEQUENCE: 157

Val Ala Ser Arg Arg Val Thr
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic Light chain CDR, clone: D11

<400> SEQUENCE: 158

Gly Ala Ser Ser Arg Ala Thr
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic Light chain CDR, clone: G8

<400> SEQUENCE: 159

Asp Ala Ser Asn Arg Ala Ala
```

```
<210> SEQ ID NO 160
<211> LENGTH: 7
<212> TYPE: PRT
<213> ORGANISM: Artificial Sequence
<220> FEATURE:
<223> OTHER INFORMATION: Synthetic Light chain CDR, clone: H9

<400> SEQUENCE: 160

Arg Ala Ser Thr Arg Ala Thr
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic Light chain CDR, clone: H11

<400> SEQUENCE: 161

Ala Ser Gln Ser Phe Ser
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic Light chain CDR, clone: G12

<400> SEQUENCE: 162

Ser Ser Gln Ser Ile Ser
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic Light chain CDR, clone: E11

<400> SEQUENCE: 163

Arg Ala Ser Thr Arg Ala Thr
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic Light chain CDR, clone: F12

<400> SEQUENCE: 164

Gly Glu Asn Asn Arg Pro Ser
1               5

<210> SEQ ID NO 165
<211> LENGTH: 8
<212> TYPE: PRT
<213> ORGANISM: Artificial Sequence
<220> FEATURE:
<223> OTHER INFORMATION: Synthetic Light chain CDR, clone: C8

<400> SEQUENCE: 165

Tyr Asp Asn Tyr Gln Arg Phe Ser
1               5
```

<210> SEQ ID NO 166
<211> LENGTH: 7
<212> TYPE: PRT
<213> ORGANISM: Artificial Sequence
<220> FEATURE:
<223> OTHER INFORMATION: Synthetic Light chain CDR, clone: A8

<400> SEQUENCE: 166

Leu Ala Ser Gln Ser Phe Ser
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic Light chain CDR, clone: B8

<400> SEQUENCE: 167

Asp Thr Ser Asn Lys Gln Ser
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic Light chain CDR, clone: F7

<400> SEQUENCE: 168

Trp Ala Ser Thr Arg Glu Ser
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic Light chain CDR, clone: B7

<400> SEQUENCE: 169

Arg Asp Ser Asn Arg Pro Ser
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic Light chain CDR, clone: G9

<400> SEQUENCE: 170

Gly Lys Asp Asn Arg Pro Ser
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic Light chain CDR, clone: A9

<400> SEQUENCE: 171

Asp Thr His Asn Arg His Ser
1               5

```
<210> SEQ ID NO 172
<211> LENGTH: 8
<212> TYPE: PRT
<213> ORGANISM: Artificial Sequence
<220> FEATURE:
<223> OTHER INFORMATION: Synthetic Light chain CDR, clone: A11

<400> SEQUENCE: 172

Gly Ile Val Gly Ser Lys Gly Asp
 1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic Light chain CDR, clone: E12

<400> SEQUENCE: 173

Phe Asp Ser Asp Arg Pro Ser
 1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic Light chain CDR, clone: H7

<400> SEQUENCE: 174

Tyr Ala Ser Gln Ser Phe Ser
 1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic Light chain CDR, clone: A10

<400> SEQUENCE: 175

Gly Asn Asn Gln Arg Pro Ser
 1               5

<210> SEQ ID NO 176
<211> LENGTH: 7
<212> TYPE: PRT
<213> ORGANISM: Artificial Sequence
<220> FEATURE:
<223> OTHER INFORMATION: Synthetic Light chain CDR, clone: C11

<400> SEQUENCE: 176

Glu Val Ser Lys Arg Phe Ser
 1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic Light chain CDR, clone: D10

<400> SEQUENCE: 177

Asp Ala Ser His Leu Glu Ala
 1               5
```

```
<210> SEQ ID NO 178
<211> LENGTH: 7
<212> TYPE: PRT
<213> ORGANISM: Artificial Sequence
<220> FEATURE:
<223> OTHER INFORMATION: Synthetic Light chain CDR, clone: D12

<400> SEQUENCE: 178

Gly Ala Ser Ser Arg Ala Ala
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic Light chain CDR, clone: C7

<400> SEQUENCE: 179

Glu Val Ser Gly Arg Phe Ser
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic Light chain CDR, clone: D7

<400> SEQUENCE: 180

Ser Val Ser Lys Arg Asp Ser
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic Light chain CDR, clone: C9

<400> SEQUENCE: 181

Glu Ala Ser Arg Leu Glu Ser
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic Light chain CDR, clone: C12

<400> SEQUENCE: 182

Gly Ala Ser Gly Leu Gln Ser
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic Light chain CDR, clone: D8

<400> SEQUENCE: 183

Asp Ala Ser Asn Arg Ala Thr
1               5

<210> SEQ ID NO 184
```

```
<211> LENGTH: 7
<212> TYPE: PRT
<213> ORGANISM: Artificial Sequence
<220> FEATURE:
<223> OTHER INFORMATION: Synthetic Light chain CDR, clone: D9

<400> SEQUENCE: 184

Gly Ala Ser Thr Arg Ala Thr
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic Light chain CDR, clone: G7

<400> SEQUENCE: 185

Lys Ile Ser Asn Arg Met Ser
1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic Light chain CDR, clone: G11

<400> SEQUENCE: 186

Gly Gly Ser Ile Arg Ala Ser
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic Light chain CDR, clone: F9

<400> SEQUENCE: 187

Ala Ala Ser Thr Leu His Tyr
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic Light chain CDR, clone: E9

<400> SEQUENCE: 188

Ala Ala Ser Arg Leu Gln Ser
1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic Light chain CDR, clone: B1

<400> SEQUENCE: 189

Asp Asp Ser Asp Arg Pro Ser
1               5

<210> SEQ ID NO 190
<211> LENGTH: 7
```

```
<212> TYPE: PRT
<213> ORGANISM: Artificial Sequence
<220> FEATURE:
<223> OTHER INFORMATION: Synthetic Light chain CDR, clone: E6

<400> SEQUENCE: 190

Tyr Asp Asn Asp Arg Pro Ser
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic Light chain CDR, clone: F3

<400> SEQUENCE: 191

Tyr Asp Ser Asp Arg Pro Ser
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic Light chain CDR, clone: H4

<400> SEQUENCE: 192

Asp Asp Ser Asp Arg Pro Ser
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic Light chain CDR, clone: H5

<400> SEQUENCE: 193

Ser Asp Arg Asp Arg Pro Ser
1               5

<210> SEQ ID NO 194
<211> LENGTH: 7
<212> TYPE: PRT
<213> ORGANISM: Artificial Sequence
<220> FEATURE:
<223> OTHER INFORMATION: Synthetic Light chain CDR, clone: B5

<400> SEQUENCE: 194

Asp Asp Tyr Gly Arg Pro Ser
1               5

<210> SEQ ID NO 195
<211> LENGTH: 7
<212> TYPE: PRT
<213> ORGANISM: Artificial Sequence
<220> FEATURE:
<223> OTHER INFORMATION: Synthetic Light chain CDR, clone: G6

<400> SEQUENCE: 195

Gln Asp Thr Lys Arg Pro Ser
1               5

<210> SEQ ID NO 196
<211> LENGTH: 7
<212> TYPE: PRT
```

```
<213> ORGANISM: Artificial Sequence
<220> FEATURE:
<223> OTHER INFORMATION: Synthetic Light chain CDR, clone: C1

<400> SEQUENCE: 196

Gly Ala Ser Ser Arg Ala Thr
1               5

<210> SEQ ID NO 197
<211> LENGTH: 7
<212> TYPE: PRT
<213> ORGANISM: Artificial Sequence
<220> FEATURE:
<223> OTHER INFORMATION: Synthetic Light chain CDR, clone: F1

<400> SEQUENCE: 197

Gly Ala Ser Asn Leu Glu Gly
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic Light chain CDR, clone: A3

<400> SEQUENCE: 198

Gly Ala Ser Thr Leu Glu Ser
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic Light chain CDR, clone: B4

<400> SEQUENCE: 199

Glu Ala Ser Asn Leu Glu Thr
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic Light chain CDR, clone: B6

<400> SEQUENCE: 200

Ala Ala Ser Asn Arg Ala Thr
1               5

<210> SEQ ID NO 201
<211> LENGTH: 7
<212> TYPE: PRT
<213> ORGANISM: Artificial Sequence
<220> FEATURE:
<223> OTHER INFORMATION: Synthetic Light chain CDR, clone: F2

<400> SEQUENCE: 201

Gly Ala Ser Asn Leu Glu Arg
1               5

<210> SEQ ID NO 202
<211> LENGTH: 7
<212> TYPE: PRT
<213> ORGANISM: Artificial Sequence
```

```
<220> FEATURE:
<223> OTHER INFORMATION: Synthetic Light chain CDR, clone: D3

<400> SEQUENCE: 202

Ala Ala Ser Tyr Leu Gln Thr
1               5

<210> SEQ ID NO 203
<211> LENGTH: 7
<212> TYPE: PRT
<213> ORGANISM: Artificial Sequence
<220> FEATURE:
<223> OTHER INFORMATION: Synthetic Light chain CDR, clone: G2

<400> SEQUENCE: 203

Lys Val Ser Thr Leu Glu Ser
1               5

<210> SEQ ID NO 204
<211> LENGTH: 7
<212> TYPE: PRT
<213> ORGANISM: Artificial Sequence
<220> FEATURE:
<223> OTHER INFORMATION: Synthetic Light chain CDR, clone: A4

<400> SEQUENCE: 204

Glu Ala Ser Asn Leu Glu Thr
1               5

<210> SEQ ID NO 205
<211> LENGTH: 7
<212> TYPE: PRT
<213> ORGANISM: Artificial Sequence
<220> FEATURE:
<223> OTHER INFORMATION: Synthetic Light chain CDR, clone: G4

<400> SEQUENCE: 205

Gly Ala Ser Thr Arg Ala Thr
1               5

<210> SEQ ID NO 206
<211> LENGTH: 7
<212> TYPE: PRT
<213> ORGANISM: Artificial Sequence
<220> FEATURE:
<223> OTHER INFORMATION: Synthetic Light chain CDR, clone: D5

<400> SEQUENCE: 206

Ala Ala Ser Thr Leu His Tyr
1               5

<210> SEQ ID NO 207
<211> LENGTH: 7
<212> TYPE: PRT
<213> ORGANISM: Artificial Sequence
<220> FEATURE:
<223> OTHER INFORMATION: Synthetic Light chain CDR, clone: A1

<400> SEQUENCE: 207

Glu Ala Ser Thr Arg Ala Thr
1               5

<210> SEQ ID NO 208
<211> LENGTH: 7
<212> TYPE: PRT
<213> ORGANISM: Artificial Sequence
<220> FEATURE:
```

<223> OTHER INFORMATION: Synthetic Light chain CDR, clone: H2

<400> SEQUENCE: 208

Gln Ala Ser Ser Leu Lys Thr
1               5

<210> SEQ ID NO 209
<211> LENGTH: 7
<212> TYPE: PRT
<213> ORGANISM: Artificial Sequence
<220> FEATURE:
<223> OTHER INFORMATION: Synthetic Light chain CDR, clone: E2

<400> SEQUENCE: 209

Trp Ala Ser Thr Arg Glu Ser
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic Light chain CDR, clone: F4

<400> SEQUENCE: 210

Arg Ala Thr Asn Leu Gln Ser
1               5

<210> SEQ ID NO 211
<211> LENGTH: 7
<212> TYPE: PRT
<213> ORGANISM: Artificial Sequence
<220> FEATURE:
<223> OTHER INFORMATION: Synthetic Light chain CDR, clone: C5

<400> SEQUENCE: 211

Trp Ala Ser Thr Arg Glu Ser
1               5

<210> SEQ ID NO 212
<211> LENGTH: 7
<212> TYPE: PRT
<213> ORGANISM: Artificial Sequence
<220> FEATURE:
<223> OTHER INFORMATION: Synthetic Light chain CDR, clone: E5

<400> SEQUENCE: 212

Ala Ala Ser Asn Leu Gln Ser
1               5

<210> SEQ ID NO 213
<211> LENGTH: 7
<212> TYPE: PRT
<213> ORGANISM: Artificial Sequence
<220> FEATURE:
<223> OTHER INFORMATION: Synthetic Light chain CDR, clone: F6

<400> SEQUENCE: 213

Ser Ala Ser Thr Leu Gln Ser
1               5

<210> SEQ ID NO 214
<211> LENGTH: 7
<212> TYPE: PRT
<213> ORGANISM: Artificial Sequence
<220> FEATURE:
<223> OTHER INFORMATION: Synthetic Light chain CDR, clone: G5

<400> SEQUENCE: 214

Asp Ala Ser Thr Leu Gln Thr
1               5

<210> SEQ ID NO 215
<211> LENGTH: 12
<212> TYPE: PRT
<213> ORGANISM: Artificial Sequence
<220> FEATURE:
<223> OTHER INFORMATION: Synthetic Light chain CDR, clone: A5

<400> SEQUENCE: 215

Val Gly Thr Gly Gly Ile Val Gly Ser Arg Gly Asp
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Synthetic Light chain CDR, clone: D6

<400> SEQUENCE: 216

Val Gly Thr Gly Gly Ile Val Gly Ser Arg Gly Asp
1               5                   10

<210> SEQ ID NO 217
<211> LENGTH: 7
<212> TYPE: PRT
<213> ORGANISM: Artificial Sequence
<220> FEATURE:
<223> OTHER INFORMATION: Synthetic Light chain CDR, clone: E4

<400> SEQUENCE: 217

Thr Asn Asn Gln Arg Pro Ser
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetic Light chain CDR, clone: F5

<400> SEQUENCE: 218

Thr Thr Asp Arg Arg Pro Ser
1               5

<210> SEQ ID NO 219
<211> LENGTH: 7
<212> TYPE: PRT
<213> ORGANISM: Artificial Sequence
<220> FEATURE:
<223> OTHER INFORMATION: Synthetic Light chain CDR, clone: G1

<400> SEQUENCE: 219

Thr Thr Asn Gln Arg Pro Ser
1               5

<210> SEQ ID NO 220
<211> LENGTH: 7
<212> TYPE: PRT
<213> ORGANISM: Artificial Sequence
<220> FEATURE:
<223> OTHER INFORMATION: Synthetic Light chain CDR, clone: E3

```
<400> SEQUENCE: 220

Leu Gly Ser Asn Arg Ala Ser
1               5

<210> SEQ ID NO 221
<211> LENGTH: 7
<212> TYPE: PRT
<213> ORGANISM: Artificial Sequence
<220> FEATURE:
<223> OTHER INFORMATION: Synthetic Light chain CDR, clone: A2

<400> SEQUENCE: 221

Gln Val Ser Thr Arg Asp Ser
1               5

<210> SEQ ID NO 222
<211> LENGTH: 7
<212> TYPE: PRT
<213> ORGANISM: Artificial Sequence
<220> FEATURE:
<223> OTHER INFORMATION: Synthetic Light chain CDR, clone: D1

<400> SEQUENCE: 222

Glu Ala Ser Ser Arg Phe Ser
1               5

<210> SEQ ID NO 223
<211> LENGTH: 10
<212> TYPE: PRT
<213> ORGANISM: Artificial Sequence
<220> FEATURE:
<223> OTHER INFORMATION: Synthetic Light chain CDR, clone: C4

<400> SEQUENCE: 223

Arg Ser Asp Ser Asp Arg His Gln Gly Ser
1               5                   10

<210> SEQ ID NO 224
<211> LENGTH: 7
<212> TYPE: PRT
<213> ORGANISM: Artificial Sequence
<220> FEATURE:
<223> OTHER INFORMATION: Synthetic Light chain CDR, clone: E1

<400> SEQUENCE: 224

Arg Asp Thr Asn Arg Pro Ser
1               5

<210> SEQ ID NO 225
<211> LENGTH: 7
<212> TYPE: PRT
<213> ORGANISM: Artificial Sequence
<220> FEATURE:
<223> OTHER INFORMATION: Synthetic Light chain CDR, clone: A6

<400> SEQUENCE: 225

Gly Ala Ser Thr Arg Ala Thr
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic Light chain CDR, clone: H1

<400> SEQUENCE: 226
```

Gly Lys Asn Thr Arg Pro Ser
1               5

<210> SEQ ID NO 227
<211> LENGTH: 7
<212> TYPE: PRT
<213> ORGANISM: Artificial Sequence
<220> FEATURE:
<223> OTHER INFORMATION: Synthetic Light chain CDR, clone: B2

<400> SEQUENCE: 227

Asp Ala Ser Asn Lys His Ser
1               5

<210> SEQ ID NO 228
<211> LENGTH: 7
<212> TYPE: PRT
<213> ORGANISM: Artificial Sequence
<220> FEATURE:
<223> OTHER INFORMATION: Synthetic Light chain CDR, clone: C2

<400> SEQUENCE: 228

Asp Ser Ser Thr Leu Gln Ser
1               5

<210> SEQ ID NO 229
<211> LENGTH: 7
<212> TYPE: PRT
<213> ORGANISM: Artificial Sequence
<220> FEATURE:
<223> OTHER INFORMATION: Synthetic Light chain CDR, clone: G3

<400> SEQUENCE: 229

Gln Asp Thr Lys Arg Pro Ser
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic Light chain CDR, clone: H3

<400> SEQUENCE: 230

Lys Asp Thr Glu Arg Pro Ser
1               5

<210> SEQ ID NO 231
<211> LENGTH: 7
<212> TYPE: PRT
<213> ORGANISM: Artificial Sequence
<220> FEATURE:
<223> OTHER INFORMATION: Synthetic Light chain CDR, clone: D4

<400> SEQUENCE: 231

Lys Ile Ser Asn Arg Phe Ser
1               5

<210> SEQ ID NO 232
<211> LENGTH: 7
<212> TYPE: PRT
<213> ORGANISM: Artificial Sequence
<220> FEATURE:
<223> OTHER INFORMATION: Synthetic Light chain CDR, clone: C6

<400> SEQUENCE: 232

Asp Val Asn Arg Arg Pro Ser
1               5

<210> SEQ ID NO 233
<211> LENGTH: 11
<212> TYPE: PRT
<213> ORGANISM: Artificial Sequence
<220> FEATURE:
<223> OTHER INFORMATION: Synthetic Light chain CDR, clone: B10

<400> SEQUENCE: 233

Arg Ala Ser Gln Thr Ile Gly Ser Thr Leu His
1               5                   10

<210> SEQ ID NO 234
<211> LENGTH: 11
<212> TYPE: PRT
<213> ORGANISM: Artificial Sequence
<220> FEATURE:
<223> OTHER INFORMATION: Synthetic Light chain CDR, clone: H10

<400> SEQUENCE: 234

Arg Ala Ser Gln Ser Ile Gly Ser Ser Leu His
1               5                   10

<210> SEQ ID NO 235
<211> LENGTH: 9
<212> TYPE: PRT
<213> ORGANISM: Artificial Sequence
<220> FEATURE:
<223> OTHER INFORMATION: Synthetic Light chain CDR, clone: F10

<400> SEQUENCE: 235

His Gln Ser Ser Ser Leu Pro Trp Thr
1               5

<210> SEQ ID NO 236
<211> LENGTH: 11
<212> TYPE: PRT
<213> ORGANISM: Artificial Sequence
<220> FEATURE:
<223> OTHER INFORMATION: Synthetic Light chain CDR, clone: B12

<400> SEQUENCE: 236

Arg Ala Ser Gln Ser Ile Gly Ile Lys Leu His
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Synthetic Light chain CDR, clone: B11

<400> SEQUENCE: 237

Arg Ala Ser Gln Ser Val Ser Ser Asn Tyr Leu Ala
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Synthetic Light chain CDR, clone: E7

<400> SEQUENCE: 238

Arg Ala Ser Gln Ser Val Ser Ser Ser Tyr Leu Ala

-continued

```
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Synthetic Light chain CDR, clone: E8

<400> SEQUENCE: 239

Arg Ala Ser Gln Ser Val Ser Ser Ser Tyr Leu Ala
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Synthetic Light chain CDR, clone: H8

<400> SEQUENCE: 240

Arg Ala Ser Gln Ser Val Ser Ser Asn Tyr Leu Ala
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Synthetic Light chain CDR, clone: H12

<400> SEQUENCE: 241

Arg Ala Ser Gln Ser Val Arg Ser Ser Tyr Val Ala
1               5                   10

<210> SEQ ID NO 242
<211> LENGTH: 13
<212> TYPE: PRT
<213> ORGANISM: Artificial Sequence
<220> FEATURE:
<223> OTHER INFORMATION: Synthetic Light chain CDR, clone: F8

<400> SEQUENCE: 242

Ser Gly Gly Arg Ser Asn Ile Gly Gly Asn Ala Val Asn
1               5                   10

<210> SEQ ID NO 243
<211> LENGTH: 12
<212> TYPE: PRT
<213> ORGANISM: Artificial Sequence
<220> FEATURE:
<223> OTHER INFORMATION: Synthetic Light chain CDR, clone: D11

<400> SEQUENCE: 243

Arg Ala Ser Gln Asn Ile Thr Ser Asn Phe Phe Ala
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Synthetic Light chain CDR, clone: G8

<400> SEQUENCE: 244

Arg Ala Ser Gln Ser Leu Ser Gly Thr Tyr Leu Ala
1               5                   10
```

```
<210> SEQ ID NO 245
<211> LENGTH: 12
<212> TYPE: PRT
<213> ORGANISM: Artificial Sequence
<220> FEATURE:
<223> OTHER INFORMATION: Synthetic Light chain CDR, clone: H9

<400> SEQUENCE: 245

Arg Ala Ser Glu Asp Ile Tyr Asn Asn Tyr Leu Ala
1               5                   10

<210> SEQ ID NO 246
<211> LENGTH: 11
<212> TYPE: PRT
<213> ORGANISM: Artificial Sequence
<220> FEATURE:
<223> OTHER INFORMATION: Synthetic Light chain CDR, clone: H11

<400> SEQUENCE: 246

Arg Ala Ser Gln Ser Ile Gly Ser Ser Leu His
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Synthetic Light chain CDR, clone: G12

<400> SEQUENCE: 247

Arg Ala Ser Glu Ser Ile Gly Thr Ala Leu His
1               5                   10

<210> SEQ ID NO 248
<211> LENGTH: 12
<212> TYPE: PRT
<213> ORGANISM: Artificial Sequence
<220> FEATURE:
<223> OTHER INFORMATION: Synthetic Light chain CDR, clone: E11

<400> SEQUENCE: 248

Arg Thr Ser Gln Ile Leu His Ser Gln Tyr Leu Ala
1               5                   10

<210> SEQ ID NO 249
<211> LENGTH: 11
<212> TYPE: PRT
<213> ORGANISM: Artificial Sequence
<220> FEATURE:
<223> OTHER INFORMATION: Synthetic Light chain CDR, clone: F12

<400> SEQUENCE: 249

Gln Gly Asp Thr Leu Arg Thr Cys Tyr Ala Ser
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Synthetic Light chain CDR, clone: C8

<400> SEQUENCE: 250

Ser Gly Ser Thr Ser Asn Ile Gly Lys Asn Phe Val Ser
1               5                   10
```

```
<210> SEQ ID NO 251
<211> LENGTH: 11
<212> TYPE: PRT
<213> ORGANISM: Artificial Sequence
<220> FEATURE:
<223> OTHER INFORMATION: Synthetic Light chain CDR, clone: A8

<400> SEQUENCE: 251

Arg Ala Ser Arg Tyr Ile Gly Ser Asn Leu His
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Synthetic Light chain CDR, clone: B8

<400> SEQUENCE: 252

Gly Ser Ser Thr Gly Ala Val Thr Ser Gly His Ser Pro Phe
1               5                   10

<210> SEQ ID NO 253
<211> LENGTH: 17
<212> TYPE: PRT
<213> ORGANISM: Artificial Sequence
<220> FEATURE:
<223> OTHER INFORMATION: Synthetic Light chain CDR, clone: F7
<220> FEATURE:
<221> NAME/KEY: misc_feature
<222> LOCATION: (4)..(4)
<223> OTHER INFORMATION: Xaa can be any naturally occurring amino acid

<400> SEQUENCE: 253

Lys Ser Ser Xaa Ser Leu Leu Tyr Arg Ser Asn Asn Lys Asn Tyr Leu
1               5                   10                  15

Ala

<210> SEQ ID NO 254
<211> LENGTH: 11
<212> TYPE: PRT
<213> ORGANISM: Artificial Sequence
<220> FEATURE:
<223> OTHER INFORMATION: Synthetic Light chain CDR, clone: B7

<400> SEQUENCE: 254

Gly Gly Ala Asn Ile Ala Asn Lys Asn Val His
1               5                   10

<210> SEQ ID NO 255
<211> LENGTH: 11
<212> TYPE: PRT
<213> ORGANISM: Artificial Sequence
<220> FEATURE:
<223> OTHER INFORMATION: Synthetic Light chain CDR, clone: G9

<400> SEQUENCE: 255

Gln Gly Asp Ser Leu Arg Thr Tyr Tyr Ala Ser
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Synthetic Light chain CDR, clone: A9
```

```
<400> SEQUENCE: 256

Gly Ser Ser Thr Gly Ala Val Thr Ser Gly His Tyr Pro Tyr
1               5                   10

<210> SEQ ID NO 257
<211> LENGTH: 12
<212> TYPE: PRT
<213> ORGANISM: Artificial Sequence
<220> FEATURE:
<223> OTHER INFORMATION: Synthetic Light chain CDR, clone: A11

<400> SEQUENCE: 257

Thr Leu Ser Ser Gly Tyr Ser Asn Tyr Lys Val Asp
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Synthetic Light chain CDR, clone: E12

<400> SEQUENCE: 258

Gly Gly Asn Asn Ile Gly Ser Lys Ser Val His
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Synthetic Light chain CDR, clone: H7

<400> SEQUENCE: 259

Arg Ala Ser Gln Asn Ile Gly Asn Ser Leu His
1               5                   10

<210> SEQ ID NO 260
<211> LENGTH: 13
<212> TYPE: PRT
<213> ORGANISM: Artificial Sequence
<220> FEATURE:
<223> OTHER INFORMATION: Synthetic Light chain CDR, clone: A10

<400> SEQUENCE: 260

Thr Arg Cys Thr Gly Asn Ile Ala Ser His Phe Val Gln
1               5                   10

<210> SEQ ID NO 261
<211> LENGTH: 17
<212> TYPE: PRT
<213> ORGANISM: Artificial Sequence
<220> FEATURE:
<223> OTHER INFORMATION: Synthetic Light chain CDR, clone: C11

<400> SEQUENCE: 261

Lys Ser Ser Gln Ser Leu Leu Asn Ser Asp Asp Gly Lys Thr Tyr Leu
1               5                   10                  15

Tyr

<210> SEQ ID NO 262
<211> LENGTH: 11
<212> TYPE: PRT
<213> ORGANISM: Artificial Sequence
<220> FEATURE:
<223> OTHER INFORMATION: Synthetic Light chain CDR, clone: D10
```

```
<400> SEQUENCE: 262

Gln Ala Ser His Asp Ile Ser Asn Tyr Leu Asn
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Synthetic Light chain CDR, clone: D12

<400> SEQUENCE: 263

Arg Ala Ser Gln Ser Val Ser Arg Thr Tyr Leu Ala
1               5                   10

<210> SEQ ID NO 264
<211> LENGTH: 16
<212> TYPE: PRT
<213> ORGANISM: Artificial Sequence
<220> FEATURE:
<223> OTHER INFORMATION: Synthetic Light chain CDR, clone: C7

<400> SEQUENCE: 264

Lys Ser Ser Gln Ser Leu Leu His Ser Asp Gly Lys Thr His Leu Phe
1               5                   10                  15

<210> SEQ ID NO 265
<211> LENGTH: 16
<212> TYPE: PRT
<213> ORGANISM: Artificial Sequence
<220> FEATURE:
<223> OTHER INFORMATION: Synthetic Light chain CDR, clone: D7

<400> SEQUENCE: 265

Arg Ser Ser His Ser Leu Val His Ser Asp Gly Asn Ile Tyr Leu Asn
1               5                   10                  15

<210> SEQ ID NO 266
<211> LENGTH: 11
<212> TYPE: PRT
<213> ORGANISM: Artificial Sequence
<220> FEATURE:
<223> OTHER INFORMATION: Synthetic Light chain CDR, clone: C9

<400> SEQUENCE: 266

Arg Ala Ser Gln Ser Ile Ser Ser Trp Leu Ala
1               5                   10

<210> SEQ ID NO 267
<211> LENGTH: 11
<212> TYPE: PRT
<213> ORGANISM: Artificial Sequence
<220> FEATURE:
<223> OTHER INFORMATION: Synthetic Light chain CDR, clone: C12

<400> SEQUENCE: 267

Arg Thr Ser Gln Gly Ile Arg Asn Tyr Leu Ser
1               5                   10

<210> SEQ ID NO 268
<211> LENGTH: 12
<212> TYPE: PRT
<213> ORGANISM: Artificial Sequence
<220> FEATURE:
<223> OTHER INFORMATION: Synthetic Light chain CDR, clone: D8
```

```
<400> SEQUENCE: 268

Arg Ala Ser Gln Ser Val Thr Ser Asn Tyr Leu Ala
1               5                   10

<210> SEQ ID NO 269
<211> LENGTH: 11
<212> TYPE: PRT
<213> ORGANISM: Artificial Sequence
<220> FEATURE:
<223> OTHER INFORMATION: Synthetic Light chain CDR, clone: D9

<400> SEQUENCE: 269

Arg Ala Ser Gln Ser Val Ser Ser Lys Leu Ala
1               5                   10

<210> SEQ ID NO 270
<211> LENGTH: 16
<212> TYPE: PRT
<213> ORGANISM: Artificial Sequence
<220> FEATURE:
<223> OTHER INFORMATION: Synthetic Light chain CDR, clone: G7

<400> SEQUENCE: 270

Arg Ser Ser Glu Ser Pro Val His Ser Asp Gly Asn Ile Tyr Leu Ser
1               5                   10                  15

<210> SEQ ID NO 271
<211> LENGTH: 12
<212> TYPE: PRT
<213> ORGANISM: Artificial Sequence
<220> FEATURE:
<223> OTHER INFORMATION: Synthetic Light chain CDR, clone: G11

<400> SEQUENCE: 271

Arg Ala Ser Gln Ser Val Ser Ser Arg Asn Leu Ala
1               5                   10

<210> SEQ ID NO 272
<211> LENGTH: 11
<212> TYPE: PRT
<213> ORGANISM: Artificial Sequence
<220> FEATURE:
<223> OTHER INFORMATION: Synthetic Light chain CDR, clone: F9

<400> SEQUENCE: 272

Arg Ala Ser Asp Asn Ile Gly Asn Tyr Leu Asn
1               5                   10

<210> SEQ ID NO 273
<211> LENGTH: 11
<212> TYPE: PRT
<213> ORGANISM: Artificial Sequence
<220> FEATURE:
<223> OTHER INFORMATION: Synthetic Light chain CDR, clone: E9

<400> SEQUENCE: 273

Arg Ala Ser Glu Ser Ile Ser Asn Tyr Leu Asn
1               5                   10

<210> SEQ ID NO 274
<211> LENGTH: 11
<212> TYPE: PRT
<213> ORGANISM: Artificial Sequence
<220> FEATURE:
<223> OTHER INFORMATION: Synthetic Light chain CDR, clone: B1

<400> SEQUENCE: 274
```

```
Gly Gly Asn Asn Ile Gly Tyr Asp Ser Val His
1               5                   10
```

<210> SEQ ID NO 275
<211> LENGTH: 10
<212> TYPE: PRT
<213> ORGANISM: Artificial Sequence
<220> FEATURE:
<223> OTHER INFORMATION: Synthetic Light chain CDR, clone: E6

<400> SEQUENCE: 275

```
Gly Gly Asn Asn Ile Gly Ala Thr Thr Val
1               5                   10
```

<210> SEQ ID NO 276
<211> LENGTH: 11
<212> TYPE: PRT
<213> ORGANISM: Artificial Sequence
<220> FEATURE:
<223> OTHER INFORMATION: Synthetic Light chain CDR, clone: F3

<400> SEQUENCE: 276

```
Gly Gly Asn Asn Ile Gly Ser Lys Ser Val His
1               5                   10
```

<210> SEQ ID NO 277
<211> LENGTH: 11
<212> TYPE: PRT
<213> ORGANISM: Artificial Sequence
<220> FEATURE:
<223> OTHER INFORMATION: Synthetic Light chain CDR, clone: H4

<400> SEQUENCE: 277

```
Gly Gly Asn Asn Ile Val Ser Lys Gly Val His
1               5                   10
```

<210> SEQ ID NO 278
<211> LENGTH: 11
<212> TYPE: PRT
<213> ORGANISM: Artificial Sequence
<220> FEATURE:
<223> OTHER INFORMATION: Synthetic Light chain CDR, clone: H5

<400> SEQUENCE: 278

```
Gly Gly Asn Asn Leu Gly Ser Lys Ile Val His
1               5                   10
```

<210> SEQ ID NO 279
<211> LENGTH: 11
<212> TYPE: PRT
<213> ORGANISM: Artificial Sequence
<220> FEATURE:
<223> OTHER INFORMATION: Synthetic Light chain CDR, clone: B5

<400> SEQUENCE: 279

```
Ala Gly Asn Asn Ile Gly Gly Lys Ser Val Gln
1               5                   10
```

<210> SEQ ID NO 280
<211> LENGTH: 11
<212> TYPE: PRT
<213> ORGANISM: Artificial Sequence
<220> FEATURE:
<223> OTHER INFORMATION: Synthetic Light chain CDR, clone: G6

<400> SEQUENCE: 280

```
Ser Gly Asp Asn Leu Gly His Thr Asn Ala Cys
1               5                   10

<210> SEQ ID NO 281
<211> LENGTH: 12
<212> TYPE: PRT
<213> ORGANISM: Artificial Sequence
<220> FEATURE:
<223> OTHER INFORMATION: Synthetic Light chain CDR, clone: C1

<400> SEQUENCE: 281

Thr Ala Ser Gln Ser Val Ser Ser Thr Tyr Leu Thr
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Synthetic Light chain CDR, clone: F1

<400> SEQUENCE: 282

Arg Ala Ser Gln Asn Ile Asp Tyr Asp Leu Ala
1               5                   10

<210> SEQ ID NO 283
<211> LENGTH: 11
<212> TYPE: PRT
<213> ORGANISM: Artificial Sequence
<220> FEATURE:
<223> OTHER INFORMATION: Synthetic Light chain CDR, clone: A3

<400> SEQUENCE: 283

Gln Ala Ser Gln Val Ile Asp Lys Tyr Val Asn
1               5                   10

<210> SEQ ID NO 284
<211> LENGTH: 11
<212> TYPE: PRT
<213> ORGANISM: Artificial Sequence
<220> FEATURE:
<223> OTHER INFORMATION: Synthetic Light chain CDR, clone: B4

<400> SEQUENCE: 284

Gln Ala Ser Gln Asp Ile Phe His Tyr Leu Asn
1               5                   10

<210> SEQ ID NO 285
<211> LENGTH: 12
<212> TYPE: PRT
<213> ORGANISM: Artificial Sequence
<220> FEATURE:
<223> OTHER INFORMATION: Synthetic Light chain CDR, clone: B6

<400> SEQUENCE: 285

Arg Ala Ser Gln Ser Phe Gly Ser Asn Tyr Leu Ala
1               5                   10

<210> SEQ ID NO 286
<211> LENGTH: 11
<212> TYPE: PRT
<213> ORGANISM: Artificial Sequence
<220> FEATURE:
<223> OTHER INFORMATION: Synthetic Light chain CDR, clone: F2

<400> SEQUENCE: 286

Gln Ala Ser Gln Phe Ile His Ile Tyr Leu Asn
```

```
1               5                   10
```

<210> SEQ ID NO 287
<211> LENGTH: 11
<212> TYPE: PRT
<213> ORGANISM: Artificial Sequence
<220> FEATURE:
<223> OTHER INFORMATION: Synthetic Light chain CDR, clone: D3

<400> SEQUENCE: 287

```
Arg Ala Ser Gln Asp Val Gly Ile Tyr Val Ala
1               5                   10
```

<210> SEQ ID NO 288
<211> LENGTH: 11
<212> TYPE: PRT
<213> ORGANISM: Artificial Sequence
<220> FEATURE:
<223> OTHER INFORMATION: Synthetic Light chain CDR, clone: G2

<400> SEQUENCE: 288

```
Arg Ala Ser Gln Asp Ile Asn Thr Trp Leu Ala
1               5                   10
```

<210> SEQ ID NO 289
<211> LENGTH: 11
<212> TYPE: PRT
<213> ORGANISM: Artificial Sequence
<220> FEATURE:
<223> OTHER INFORMATION: Synthetic Light chain CDR, clone: A4

<400> SEQUENCE: 289

```
Gln Ala Ser Gln Asp Ile Ser Asn Trp Leu Asn
1               5                   10
```

<210> SEQ ID NO 290
<211> LENGTH: 11
<212> TYPE: PRT
<213> ORGANISM: Artificial Sequence
<220> FEATURE:
<223> OTHER INFORMATION: Synthetic Light chain CDR, clone: G4

<400> SEQUENCE: 290

```
Arg Val Ser Gln Asn Val Phe Ser Asp Leu Ala
1               5                   10
```

<210> SEQ ID NO 291
<211> LENGTH: 11
<212> TYPE: PRT
<213> ORGANISM: Artificial Sequence
<220> FEATURE:
<223> OTHER INFORMATION: Synthetic Light chain CDR, clone: D5

<400> SEQUENCE: 291

```
Arg Ala Ser Asp Asn Ile Gly Asn Tyr Leu Asn
1               5                   10
```

<210> SEQ ID NO 292
<211> LENGTH: 11
<212> TYPE: PRT
<213> ORGANISM: Artificial Sequence
<220> FEATURE:
<223> OTHER INFORMATION: Synthetic Light chain CDR, clone: A1

<400> SEQUENCE: 292

```
Arg Ala Ser Gln Ser Val Ser Ser Phe Leu Ala
1               5                   10
```

<210> SEQ ID NO 293
<211> LENGTH: 11
<212> TYPE: PRT
<213> ORGANISM: Artificial Sequence
<220> FEATURE:
<223> OTHER INFORMATION: Synthetic Light chain CDR, clone: H2

<400> SEQUENCE: 293

Arg Ala Thr Glu Ser Ile Ser Ile Trp Leu Ala
1               5                   10

<210> SEQ ID NO 294
<211> LENGTH: 17
<212> TYPE: PRT
<213> ORGANISM: Artificial Sequence
<220> FEATURE:
<223> OTHER INFORMATION: Synthetic Light chain CDR, clone: E2

<400> SEQUENCE: 294

Lys Ser Ser Gln Ser Val Leu Tyr Ser Ser Asn Asn Lys Asn Tyr Leu
1               5                   10                  15

Ala

<210> SEQ ID NO 295
<211> LENGTH: 11
<212> TYPE: PRT
<213> ORGANISM: Artificial Sequence
<220> FEATURE:
<223> OTHER INFORMATION: Synthetic Light chain CDR, clone: F4

<400> SEQUENCE: 295

Arg Ala Ser Gln Asp Ile Ser Ser Trp Leu Ala
1               5                   10

<210> SEQ ID NO 296
<211> LENGTH: 17
<212> TYPE: PRT
<213> ORGANISM: Artificial Sequence
<220> FEATURE:
<223> OTHER INFORMATION: Synthetic Light chain CDR, clone: C5

<400> SEQUENCE: 296

Lys Ser Ser Gln Ser Val Leu Tyr Ser Ser Asn Asn Arg Asn Tyr Leu
1               5                   10                  15

Ala

<210> SEQ ID NO 297
<211> LENGTH: 11
<212> TYPE: PRT
<213> ORGANISM: Artificial Sequence
<220> FEATURE:
<223> OTHER INFORMATION: Synthetic Light chain CDR, clone: E5

<400> SEQUENCE: 297

Arg Ala Ser Gln Thr Phe Thr Ser His Leu Asn
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Synthetic Light chain CDR, clone: F6

<400> SEQUENCE: 298

Arg Ala Ser Gln Ser Val Asn Val Tyr Leu Asn
1               5                   10

<210> SEQ ID NO 299
<211> LENGTH: 11
<212> TYPE: PRT
<213> ORGANISM: Artificial Sequence
<220> FEATURE:
<223> OTHER INFORMATION: Synthetic Light chain CDR, clone: G5

<400> SEQUENCE: 299

Arg Ala Ser Gln Asp Ile Ser Ser Ser Leu Ala
1               5                   10

<210> SEQ ID NO 300
<211> LENGTH: 12
<212> TYPE: PRT
<213> ORGANISM: Artificial Sequence
<220> FEATURE:
<223> OTHER INFORMATION: Synthetic Light chain CDR, clone: A5

<400> SEQUENCE: 300

Thr Val Ser Ser Gly Tyr Arg Ser Tyr Glu Val Asp
1               5                   10

<210> SEQ ID NO 301
<211> LENGTH: 12
<212> TYPE: PRT
<213> ORGANISM: Artificial Sequence
<220> FEATURE:
<223> OTHER INFORMATION: Synthetic Light chain CDR, clone: D6

<400> SEQUENCE: 301

Thr Leu Ser Ser Asp Tyr Ser Ser Tyr Asn Val Asp
1               5                   10

<210> SEQ ID NO 302
<211> LENGTH: 13
<212> TYPE: PRT
<213> ORGANISM: Artificial Sequence
<220> FEATURE:
<223> OTHER INFORMATION: Synthetic Light chain CDR, clone: E4

<400> SEQUENCE: 302

Ser Gly Ser Ser Thr Asn Ile Gly Ser Asn Ala Val Asn
1               5                   10

<210> SEQ ID NO 303
<211> LENGTH: 13
<212> TYPE: PRT
<213> ORGANISM: Artificial Sequence
<220> FEATURE:
<223> OTHER INFORMATION: Synthetic Light chain CDR, clone: F5

<400> SEQUENCE: 303

Ser Gly Gly Gly Ser Asn Ile Gly Ser Asn Phe Gly Tyr
1               5                   10

<210> SEQ ID NO 304
<211> LENGTH: 13
<212> TYPE: PRT
<213> ORGANISM: Artificial Sequence
<220> FEATURE:
<223> OTHER INFORMATION: Synthetic Light chain CDR, clone: G1

<400> SEQUENCE: 304

```
Ser Gly Ser Ser Ser Asn Ile Gly Ser Asn Ser Val Asp
1               5                   10
```

<210> SEQ ID NO 305
<211> LENGTH: 16
<212> TYPE: PRT
<213> ORGANISM: Artificial Sequence
<220> FEATURE:
<223> OTHER INFORMATION: Synthetic Light chain CDR, clone: E3

<400> SEQUENCE: 305

```
Arg Ser Ser Gln Ser Leu Leu His Ser Asn Gly Tyr Asn Phe Leu Asp
1               5                   10                  15
```

<210> SEQ ID NO 306
<211> LENGTH: 13
<212> TYPE: PRT
<213> ORGANISM: Artificial Sequence
<220> FEATURE:
<223> OTHER INFORMATION: Synthetic Light chain CDR, clone: A2

<400> SEQUENCE: 306

```
Cys Asp Asp Thr Val Ser Thr Leu Pro Ala Arg His Pro
1               5                   10
```

<210> SEQ ID NO 307
<211> LENGTH: 16
<212> TYPE: PRT
<213> ORGANISM: Artificial Sequence
<220> FEATURE:
<223> OTHER INFORMATION: Synthetic Light chain CDR, clone: D1

<400> SEQUENCE: 307

```
Lys Ser Ser Gln Ser Leu Val His Arg Asp Gly Lys Thr Tyr Leu Tyr
1               5                   10                  15
```

<210> SEQ ID NO 308
<211> LENGTH: 14
<212> TYPE: PRT
<213> ORGANISM: Artificial Sequence
<220> FEATURE:
<223> OTHER INFORMATION: Synthetic Light chain CDR, clone: C4

<400> SEQUENCE: 308

```
Thr Leu Ser Ser Gly Phe Asn Val Val Ser Tyr Asn Ile Tyr
1               5                   10
```

<210> SEQ ID NO 309
<211> LENGTH: 11
<212> TYPE: PRT
<213> ORGANISM: Artificial Sequence
<220> FEATURE:
<223> OTHER INFORMATION: Synthetic Light chain CDR, clone: E1

<400> SEQUENCE: 309

```
Ala Gly Asn Asn Ile Gly Thr Tyr Tyr Val His
1               5                   10
```

<210> SEQ ID NO 310
<211> LENGTH: 11
<212> TYPE: PRT
<213> ORGANISM: Artificial Sequence
<220> FEATURE:
<223> OTHER INFORMATION: Synthetic Light chain CDR, clone: A6

<400> SEQUENCE: 310

```
Arg Ala Ser Gln Ser Val Ser Ser Asn Leu Ala
```

<210> SEQ ID NO 311
<211> LENGTH: 11
<212> TYPE: PRT
<213> ORGANISM: Artificial Sequence
<220> FEATURE:
<223> OTHER INFORMATION: Synthetic Light chain CDR, clone: H1

<400> SEQUENCE: 311

Gln Gly Asp Ser Leu Arg Thr Tyr Tyr Ala Ser
1               5                   10

<210> SEQ ID NO 312
<211> LENGTH: 14
<212> TYPE: PRT
<213> ORGANISM: Artificial Sequence
<220> FEATURE:
<223> OTHER INFORMATION: Synthetic Light chain CDR, clone: B2

<400> SEQUENCE: 312

Gly Ser Ser Thr Gly Ala Val Thr Ser Gly His Tyr Pro Tyr
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Synthetic Light chain CDR, clone: C2

<400> SEQUENCE: 313

Arg Pro Ser Gln Asp Ile Gly Thr Asp Leu Gly
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthetic Light chain CDR, clone: G3

<400> SEQUENCE: 314

Ser Gly Asp Glu Leu Lys Tyr Lys Tyr Thr Cys
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Synthetic Light chain CDR, clone: H3

<400> SEQUENCE: 315

Ser Gly Ser Thr Phe Pro Lys Leu Tyr Ser Phe
1               5                   10

<210> SEQ ID NO 316
<211> LENGTH: 16
<212> TYPE: PRT
<213> ORGANISM: Artificial Sequence
<220> FEATURE:
<223> OTHER INFORMATION: Synthetic Light chain CDR, clone: D4

<400> SEQUENCE: 316

Arg Ser Ser Glu Ser Val Val His Asp Asp Gly Asn Thr Tyr Leu Ser
1               5                   10                  15

<210> SEQ ID NO 317
<211> LENGTH: 14
<212> TYPE: PRT
<213> ORGANISM: Artificial Sequence
<220> FEATURE:
<223> OTHER INFORMATION: Synthetic Light chain CDR, clone: C6

<400> SEQUENCE: 317

Thr Gly Thr Ser Asp Asp Val Gly Arg Tyr Asp Tyr Val Ser
1               5                   10

<210> SEQ ID NO 318
<211> LENGTH: 116
<212> TYPE: PRT
<213> ORGANISM: Artificial Sequence
<220> FEATURE:
<223> OTHER INFORMATION: Synthetic Heavy chain, clone: A4 XB1511

<400> SEQUENCE: 318

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile His Gly Gly Asp Arg Ser Tyr Trp Gly Gln Gly Thr Leu Val
            100                 105                 110

Thr Val Ser Ser
        115

<210> SEQ ID NO 319
<211> LENGTH: 116
<212> TYPE: PRT
<213> ORGANISM: Artificial Sequence
<220> FEATURE:
<223> OTHER INFORMATION: Synthetic Heavy chain, clone: B4

<400> SEQUENCE: 319

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile His Gly Gly Asp Arg Ser Tyr Trp Gly Gln Gly Thr Leu Val
            100                 105                 110

```
Thr Val Ser Ser
        115

<210> SEQ ID NO 320
<211> LENGTH: 116
<212> TYPE: PRT
<213> ORGANISM: Artificial Sequence
<220> FEATURE:
<223> OTHER INFORMATION: Synthetic Heavy chain, clone:  G2

<400> SEQUENCE: 320

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Lys Asp Thr Ala Val Tyr Tyr Cys
                85                  90                  95

Ala Ile His Gly Gly Asp Arg Ser Tyr Trp Gly Gln Gly Thr Leu Val
            100                 105                 110

Thr Val Ser Ser
        115

<210> SEQ ID NO 321
<211> LENGTH: 116
<212> TYPE: PRT
<213> ORGANISM: Artificial Sequence
<220> FEATURE:
<223> OTHER INFORMATION: Synthetic Heavy chain, clone:  XB2202

<400> SEQUENCE: 321

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 322
<211> LENGTH: 116
<212> TYPE: PRT
<213> ORGANISM: Artificial Sequence
<220> FEATURE:
<223> OTHER INFORMATION: Synthetic Heavy chain, clone:  C4
```

```
<400> SEQUENCE: 322

Gln Met Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Gly Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 323
<211> LENGTH: 116
<212> TYPE: PRT
<213> ORGANISM: Artificial Sequence
<220> FEATURE:
<223> OTHER INFORMATION: Synthetic Heavy chain, clone: B12

<400> SEQUENCE: 323

Gln Met Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Glu Asn Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 324
<211> LENGTH: 116
<212> TYPE: PRT
<213> ORGANISM: Artificial Sequence
<220> FEATURE:
<223> OTHER INFORMATION: Synthetic Heavy chain, clone: D07

<400> SEQUENCE: 324

Gln Met Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45
```

Gly Gly Ile Leu Pro Ile Leu Lys Thr Pro Asn Tyr Ala Gln Arg Phe
        50                  55                  60

Gln Gly Arg Val Thr Ile Asn Ala Asp Glu Ser Thr Ser Thr Val Tyr
 65                  70                  75                  80

Met Glu Met Ser Ser Leu Arg Ser Asp Asp Thr Ala Val Tyr Tyr Cys
                     85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 325
<211> LENGTH: 116
<212> TYPE: PRT
<213> ORGANISM: Artificial Sequence
<220> FEATURE:
<223> OTHER INFORMATION: Synthetic Heavy chain, clone: C05

<400> SEQUENCE: 325

Gln Met Gln Leu Val Gln Ser Gly Ala Glu Val Lys Lys Pro Gly Ser
 1               5                  10                  15

Ser Val Arg Val Ser Cys Lys Ala Ser Gly Gly Thr Phe Ser Arg His
                20                  25                  30

Ala Ile Ser Trp Val Arg Gln Ala Pro Gly Gln Gly Leu Glu Trp Ile
            35                  40                  45

Gly Gly Val Leu Pro Ile Leu Lys Thr Pro Asn Tyr Ala Gln Arg Phe
        50                  55                  60

Gln Gly Arg Val Thr Ile Asn Ala Asp Glu Ser Thr Ser Thr Val Tyr
 65                  70                  75                  80

Met Glu Leu Ser Ser Leu Arg Ser Glu Asp Thr Ala Val Tyr Tyr Cys
                     85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 326
<211> LENGTH: 116
<212> TYPE: PRT
<213> ORGANISM: Artificial Sequence
<220> FEATURE:
<223> OTHER INFORMATION: Synthetic Heavy chain, clone: E05

<400> SEQUENCE: 326

Gln Val Gln Leu Val Gln Ser Gly Pro Lys Val Lys Lys Pro Gly Ser
 1               5                  10                  15

Ser Val Arg Val Ser Cys Lys Ala Ser Gly Gly Thr Phe Ser Arg His
                20                  25                  30

Ala Ile Ser Trp Val Arg Gln Ala Pro Gly Gln Gly Leu Glu Trp Ile
            35                  40                  45

Gly Gly Ile Leu Pro Ile Leu Lys Thr Pro Asn Tyr Ala Gln Arg Phe
        50                  55                  60

Gln Gly Arg Val Thr Ile Asn Ala Asp Glu Ser Thr Ser Thr Val Tyr
 65                  70                  75                  80

Met Glu Met Ser Ser Leu Arg Ser Glu Asp Thr Ala Val Tyr Tyr Cys
                     85                  90                  95

Ala Thr His Gly Gly Asp Arg Ser Tyr Trp Gly Gln Gly Thr Leu Val
                100                 105                 110

```
Thr Val Ser Ser
        115

<210> SEQ ID NO 327
<211> LENGTH: 116
<212> TYPE: PRT
<213> ORGANISM: Artificial Sequence
<220> FEATURE:
<223> OTHER INFORMATION: Synthetic Heavy chain, clone: E2

<400> SEQUENCE: 327

Gln Met Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Asp Tyr
            20                  25                  30

Tyr Ile Gln Trp Val Arg Gln Ala Pro Gly Gln Gly Leu Glu Trp Val
        35                  40                  45

Gly Trp Ile Asn Pro Asn Ser Gly Asn Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Tyr Ser Tyr Trp Gly Gln Gly Thr Leu Val
            100                 105                 110

Thr Val Ser Ser
        115

<210> SEQ ID NO 328
<211> LENGTH: 116
<212> TYPE: PRT
<213> ORGANISM: Artificial Sequence
<220> FEATURE:
<223> OTHER INFORMATION: Synthetic Heavy chain, clone: A3

<400> SEQUENCE: 328

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Ser Asp Tyr
            20                  25                  30

Tyr Ile Gln Trp Val Arg Gln Ala Pro Gly Gln Gly Leu Glu Trp Met
        35                  40                  45

Gly Trp Ile Asn Pro Asn Ser Gly Gly Thr Tyr Phe Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Thr Ser Asp Asp Thr Ala Val Tyr Tyr Cys
                85                  90                  95

Ala Thr His Gly Gly Asp Arg Gly Tyr Trp Gly Gln Gly Thr Leu Val
            100                 105                 110

Thr Val Ser Ser
        115

<210> SEQ ID NO 329
<211> LENGTH: 116
<212> TYPE: PRT
<213> ORGANISM: Artificial Sequence
<220> FEATURE:
<223> OTHER INFORMATION: Synthetic Heavy chain, clone: C3
```

<400> SEQUENCE: 329

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Gln Trp Val Arg Gln Ala Pro Gly Gln Gly Leu Glu Trp Ile
            35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
                100                 105                 110

Thr Val Ser Ser
            115
```

<210> SEQ ID NO 330
<211> LENGTH: 116
<212> TYPE: PRT
<213> ORGANISM: Artificial Sequence
<220> FEATURE:
<223> OTHER INFORMATION: Synthetic Heavy chain, clone: F10

<400> SEQUENCE: 330

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Gln Trp Val Arg Gln Ala Pro Gly Gln Gly Leu Glu Trp Met
            35                  40                  45

Gly Trp Ile Asn Pro Asp Ser Gly Gly Thr Tyr Phe Ala Gln Lys Phe
    50                  55                  60

Gln Gly Arg Val Ala Met Thr Arg Asp Thr Ser Ile Asn Thr Ala Tyr
65                  70                  75                  80

Met Glu Leu Ser Ser Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
                100                 105                 110

Thr Val Ser Ser
            115
```

<210> SEQ ID NO 331
<211> LENGTH: 116
<212> TYPE: PRT
<213> ORGANISM: Artificial Sequence
<220> FEATURE:
<223> OTHER INFORMATION: Synthetic Heavy chain, clone: C12

<400> SEQUENCE: 331

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Gln Trp Val Arg Gln Ala Pro Gly Glu Gly Leu Glu Trp Met
            35                  40                  45
```

```
Gly Trp Met Asn Pro Asp Ser Gly Gly Thr Ile Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Pro Asp Thr Ala Val Tyr Tyr Cys
                 85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 332
<211> LENGTH: 116
<212> TYPE: PRT
<213> ORGANISM: Artificial Sequence
<220> FEATURE:
<223> OTHER INFORMATION: Synthetic Heavy chain, clone:  H2

<400> SEQUENCE: 332

Gln Met Gln Leu Val Gln Ser Gly Ala Glu Val Lys Asn Pro Gly Ala
 1               5                  10                  15

Ser Val Lys Val Ser Cys Lys Ala Ser Gly Tyr Pro Phe Ser Ala Tyr
                 20                  25                  30

Tyr Ile Gln Trp Val Arg Gln Ala Pro Gly Gln Gly Leu Glu Trp Met
             35                  40                  45

Gly Trp Leu Asn Pro Asn Ser Gly Asp Thr His Ser Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Gly Leu Thr Ser Asp Asp Thr Ala Val Tyr Tyr Cys
                 85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 333
<211> LENGTH: 116
<212> TYPE: PRT
<213> ORGANISM: Artificial Sequence
<220> FEATURE:
<223> OTHER INFORMATION: Synthetic Heavy chain, clone:  F11

<400> SEQUENCE: 333

Gln Met Gln Leu Val Gln Ser Gly Ala Glu Val Lys Asn Pro Gly Ala
 1               5                  10                  15

Ser Val Lys Val Ser Cys Lys Ala Ser Gly Tyr Pro Phe Ser Ala Tyr
                 20                  25                  30

Tyr Ile Gln Trp Val Arg Gln Ala Pro Gly Gln Gly Leu Glu Trp Met
             35                  40                  45

Gly Trp Leu Asn Pro Asn Ser Gly Asp Thr His Ser Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Gly Pro Thr Ser Asp Asp Thr Ala Val Tyr Tyr Cys
                 85                  90                  95

Ala Thr His Gly Gly Asp Arg Ser Tyr Trp Gly Gln Gly Thr Leu Val
```

Thr Val Ser Ser
        115

<210> SEQ ID NO 334
<211> LENGTH: 116
<212> TYPE: PRT
<213> ORGANISM: Artificial Sequence
<220> FEATURE:
<223> OTHER INFORMATION: Synthetic Heavy chain, clone: B1

<400> SEQUENCE: 334

Gln Met Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Ser Asp Tyr
            20                  25                  30

Tyr Ile His Trp Val Arg Gln Ala Pro Gly Gln Gly Leu Glu Trp Ile
        35                  40                  45

Gly Trp Ile Asn Pro Asn Asn Gly Asn Thr Thr Tyr Ala Gln Lys Phe
    50                  55                  60

Gln Gly Arg Val Thr Met Ile Arg Asp Thr Ser Ile Ser Thr Ala Tyr
65                  70                  75                  80

Met Glu Leu Ser Glu Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 335
<211> LENGTH: 116
<212> TYPE: PRT
<213> ORGANISM: Artificial Sequence
<220> FEATURE:
<223> OTHER INFORMATION: Synthetic Heavy chain, clone: E11

<400> SEQUENCE: 335

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Arg Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 336
<211> LENGTH: 116
<212> TYPE: PRT
<213> ORGANISM: Artificial Sequence
<220> FEATURE:

<223> OTHER INFORMATION: Synthetic Heavy chain, clone: H1

<400> SEQUENCE: 336

```
Glu Val Gln Leu Leu Glu Ser Gly Ala Glu Val Lys Gln Pro Gly Ala
1               5                   10                  15
Ser Val Lys Val Ser Cys Lys Thr Ser Gly Tyr Thr Phe Thr Asp Tyr
            20                  25                  30
His Leu His Trp Val Arg Gln Ala Pro Gly Gln Gly Leu Glu Trp Met
        35                  40                  45
Gly Trp Ile Asn Pro Asn Ser Gly Gly Thr Asn Ser Ala Pro Lys Phe
    50                  55                  60
Gln Gly Arg Val Thr Met Thr Arg Asp Thr Ser Ile Ser Thr Ala Tyr
65                  70                  75                  80
Met Glu Leu Ser Gly Leu Thr Ser Asp Asp Thr Ala Val Tyr Tyr Cys
                85                  90                  95
Ala Thr His Gly Gly Asp Arg Ser Tyr Trp Gly Gln Gly Thr Leu Val
            100                 105                 110
Thr Val Ser Ser
        115
```

<210> SEQ ID NO 337
<211> LENGTH: 116
<212> TYPE: PRT
<213> ORGANISM: Artificial Sequence
<220> FEATURE:
<223> OTHER INFORMATION: Synthetic Heavy chain, clone: E6

<400> SEQUENCE: 337

```
Gln Met Gln Leu Val Gln Ser Gly Ala Glu Val Lys Arg Pro Gly Ala
1               5                   10                  15
Ser Val Lys Val Pro Cys Lys Ala Ser Gly Tyr Thr Phe Thr Asp Tyr
            20                  25                  30
Tyr Leu His Trp Val Arg Gln Ala Pro Gly Gln Gly Leu Lys Trp Met
        35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Glu Asp Thr Ala Val Tyr Tyr Cys
                85                  90                  95
Ala Thr His Gly Gly Asp Arg Ser Tyr Trp Gly Gln Gly Thr Leu Val
            100                 105                 110
Thr Val Ser Ser
        115
```

<210> SEQ ID NO 338
<211> LENGTH: 116
<212> TYPE: PRT
<213> ORGANISM: Artificial Sequence
<220> FEATURE:
<223> OTHER INFORMATION: Synthetic Heavy chain, clone: A1

<400> SEQUENCE: 338

```
Gln Val Gln Leu Val Gln Ser Gly Pro Glu Val Lys Lys Pro Gly Thr
1               5                   10                  15
Ser Val Lys Val Ser Cys Lys Ala Ser Gly Phe Thr Phe Thr Ser Ser
            20                  25                  30
Ala Val Gln Trp Val Arg Gln Ala Arg Gly Gln Arg Leu Glu Trp Ile
```

```
                35                  40                  45
Gly Trp Ile Val Val Gly Ser Gly Asn Thr Asn Tyr Ala Gln Lys Phe
 50                  55                  60

Gln Glu Arg Val Thr Ile Thr Arg Asp Met Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 339
<211> LENGTH: 116
<212> TYPE: PRT
<213> ORGANISM: Artificial Sequence
<220> FEATURE:
<223> OTHER INFORMATION: Synthetic Heavy chain, clone: H7

<400> SEQUENCE: 339

Gln Val Gln Leu Val Gln Ser Gly Pro Glu Val Lys Lys Pro Gly Thr
 1               5                  10                  15

Ser Val Lys Val Ser Cys Lys Ala Ser Gly Phe Thr Phe Thr Ser Ser
                20                  25                  30

Ala Met Gln Trp Val Arg Gln Ala Arg Gly Gln Arg Leu Glu Trp Ile
                35                  40                  45

Gly Trp Ile Val Val Gly Ser Gly Asn Thr Asn Tyr Ala Gln Lys Phe
 50                  55                  60

Gln Glu Arg Val Thr Ile Thr Arg Asp Met Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 340
<211> LENGTH: 116
<212> TYPE: PRT
<213> ORGANISM: Artificial Sequence
<220> FEATURE:
<223> OTHER INFORMATION: Synthetic Heavy chain, clone: G04

<400> SEQUENCE: 340

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Ser Tyr
                20                  25                  30

Ala Ile Ser Trp Val Arg Gln Ala Arg Gly Gln Arg Leu Glu Trp Ile
                35                  40                  45

Gly Trp Ile Val Val Gly Ser Gly Asn Thr Asn Tyr Ala Gln Lys Phe
 50                  55                  60

Gln Glu Arg Val Thr Ile Thr Arg Asp Met Ser Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Thr His Gly Gly Asp Arg Ser Tyr Trp Gly Gln Gly Thr Leu Val
            100                 105                 110

Thr Val Ser Ser
        115

<210> SEQ ID NO 341
<211> LENGTH: 116
<212> TYPE: PRT
<213> ORGANISM: Artificial Sequence
<220> FEATURE:
<223> OTHER INFORMATION: Synthetic Heavy chain, clone:  B2

<400> SEQUENCE: 341

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Gln Val Gln Trp Val Arg Gln Ala Pro Gly Gln Gly Leu Glu Trp Leu
        35                  40                  45

Gly Val Ile Asn Thr Gly Val Gly Ser Thr Asn Tyr Ala Gln Lys Phe
    50                  55                  60

Gln Gly Arg Val Thr Met Thr Arg Asp Thr Ala Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 342
<211> LENGTH: 116
<212> TYPE: PRT
<213> ORGANISM: Artificial Sequence
<220> FEATURE:
<223> OTHER INFORMATION: Synthetic Heavy chain, clone:  A7

<400> SEQUENCE: 342

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Pro Val Gln Trp Val Arg Gln Ala Pro Gly Gln Gly Leu Glu Trp Leu
        35                  40                  45

Gly Val Ile Asn Thr Gly Val Gly Ser Thr Asn Tyr Ala Gln Lys Phe
    50                  55                  60

Gln Gly Arg Val Thr Met Thr Arg Asp Thr Ala Thr Ser Ile Val Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 343
<211> LENGTH: 116
<212> TYPE: PRT
<213> ORGANISM: Artificial Sequence
```

```
<220> FEATURE:
<223> OTHER INFORMATION: Synthetic Heavy chain, clone: H3

<400> SEQUENCE: 343

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Asn Ser
            20                  25                  30

Phe Met Gln Trp Val Arg Gln Val Pro Gly Gln Arg Leu Glu Trp Val
        35                  40                  45

Gly Leu Ser Asn Pro Ser Gly Asp Tyr Thr Val Tyr Ala Pro Lys Phe
    50                  55                  60

Gln Gly Arg Val Thr Met Thr Thr Asp Thr Ala Thr Ser Thr Phe Tyr
65                  70                  75                  80

Met Glu Leu Phe Ser Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 344
<211> LENGTH: 116
<212> TYPE: PRT
<213> ORGANISM: Artificial Sequence
<220> FEATURE:
<223> OTHER INFORMATION: Synthetic Heavy chain, clone: B4

<400> SEQUENCE: 344

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Asn Ser
            20                  25                  30

Phe Met Gln Trp Val Arg Gln Val Pro Gly Gln Arg Leu Glu Trp Val
        35                  40                  45

Gly Leu Ser Asn Pro Ser Gly Asp Tyr Thr Val Tyr Ala Pro Lys Leu
    50                  55                  60

Gln Gly Arg Val Thr Met Thr Thr Asp Thr Ala Thr Gly Thr Phe Tyr
65                  70                  75                  80

Met Glu Leu Phe Ser Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 345
<211> LENGTH: 116
<212> TYPE: PRT
<213> ORGANISM: Artificial Sequence
<220> FEATURE:
<223> OTHER INFORMATION: Synthetic Heavy chain, clone: H05

<400> SEQUENCE: 345

Glu Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30
```

```
Gly Met His Trp Val Arg Gln Ala Pro Gly Lys Gly Leu Glu Trp Val
            35                  40                  45

Ala Phe Ile Leu Phe Asp Gly Asn Asn Lys Tyr Tyr Ala Asp Ser Val
 50                      55                  60

Lys Gly Arg Phe Thr Ile Ser Ser Asp Asn Ser Lys Asn Thr Leu Tyr
 65                      70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
                100                 105                 110

Thr Val Ser Ser
            115
```

<210> SEQ ID NO 346
<211> LENGTH: 116
<212> TYPE: PRT
<213> ORGANISM: Artificial Sequence
<220> FEATURE:
<223> OTHER INFORMATION: Synthetic Heavy chain, clone: D06

<400> SEQUENCE: 346

```
Gln Val Gln Leu Val Gln Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                      70                  75                  80

Leu Gln Met Asn Ser Leu Arg Ala Glu Asp Thr Ala Val Tyr Tyr Cys
                85                  90                  95

Ala Lys His Gly Gly Asp Arg Ser Tyr Trp Gly Gln Gly Thr Leu Val
                100                 105                 110

Thr Val Ser Ser
            115
```

<210> SEQ ID NO 347
<211> LENGTH: 116
<212> TYPE: PRT
<213> ORGANISM: Artificial Sequence
<220> FEATURE:
<223> OTHER INFORMATION: Synthetic Heavy chain, clone: F3

<400> SEQUENCE: 347

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ile Ser His
                20                  25                  30

Gly Met Ser Trp Val Arg Gln Ala Pro Gly Gln Gly Leu Glu Trp Met
            35                  40                  45

Gly Trp Ile Ser Ala Asp Asn Gly Asn Thr Asn Tyr Ala Gln Lys Phe
 50                      55                  60

Gln Glu Arg Val Thr Ile Thr Arg Asp Met Ser Thr Ser Thr Ala Tyr
 65                      70                  75                  80

Met Glu Leu Ser Ser Leu Arg Ser Glu Asp Thr Ala Val Tyr Tyr Cys
                85                  90                  95
```

Ala Thr His Gly Gly Asp Arg Ser Tyr Trp Gly Gln Gly Thr Leu Val
            100                 105                 110

Thr Val Ser Ser
        115

<210> SEQ ID NO 348
<211> LENGTH: 116
<212> TYPE: PRT
<213> ORGANISM: Artificial Sequence
<220> FEATURE:
<223> OTHER INFORMATION: Synthetic Heavy chain, clone: A12

<400> SEQUENCE: 348

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser His
            20                  25                  30

Gly Met Ser Trp Val Arg Gln Ala Pro Gly Gln Gly Leu Glu Trp Met
        35                  40                  45

Gly Trp Ile Ser Ala Asp Asn Gly Asn Thr Lys Tyr Ala Gln Lys Phe
    50                  55                  60

Gln Asp Arg Val Thr Leu Thr Thr Asp Thr Ser Ser Thr Ala Tyr
65                  70                  75                  80

Leu Glu Leu Arg Ser Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 349
<211> LENGTH: 116
<212> TYPE: PRT
<213> ORGANISM: Artificial Sequence
<220> FEATURE:
<223> OTHER INFORMATION: Synthetic Heavy chain, clone: G3

<400> SEQUENCE: 349

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 350
<211> LENGTH: 116
<212> TYPE: PRT

<213> ORGANISM: Artificial Sequence
<220> FEATURE:
<223> OTHER INFORMATION: Synthetic Heavy chain, clone: F05

<400> SEQUENCE: 350

Gln Val Gln Leu Val Gln Ser Gly Ala Glu Val Lys Arg Pro Gly Ala
1               5                   10                  15
Ser Val Lys Val Ser Cys Lys Ala Ser Gly Tyr Thr Leu Thr Glu Leu
            20                  25                  30
Ser Met His Trp Val Arg Gln Ala Pro Gly Lys Gly Leu Glu Trp Met
        35                  40                  45
Gly Gly Phe Asp Pro Glu Asp Gly Glu Thr Ile Tyr Ala Gln Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr His Gly Gly Asp Arg Ser Tyr Trp Gly Gln Gly Thr Leu Val
            100                 105                 110
Thr Val Ser Ser
        115

<210> SEQ ID NO 351
<211> LENGTH: 116
<212> TYPE: PRT
<213> ORGANISM: Artificial Sequence
<220> FEATURE:
<223> OTHER INFORMATION: Synthetic Heavy chain, clone: H12

<400> SEQUENCE: 351

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Asn
            20                  25                  30
Tyr Val His Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Thr His Gly Gly Asp Arg Ser Tyr Trp Gly Gln Gly Thr Leu Val
            100                 105                 110
Thr Val Ser Ser
        115

<210> SEQ ID NO 352
<211> LENGTH: 116
<212> TYPE: PRT
<213> ORGANISM: Artificial Sequence
<220> FEATURE:
<223> OTHER INFORMATION: Synthetic Heavy chain, clone: G12

<400> SEQUENCE: 352

Gln Val Gln Leu Val Gln Ser Gly Ala Glu Val Lys Lys Pro Gly Ser
1               5                   10                  15
Ser Val Lys Val Ser Cys Lys Ala Ser Gly Gly Ala Phe Asn Ala Tyr
            20                  25                  30

```
Pro Ile Ser Trp Val Arg Gln Ala Pro Gly Gln Gly Leu Glu Trp Met
        35                  40                  45

Gly Gly Ile Ile Pro Val Ser Gly Thr Pro Asn Tyr Ala Gln Lys Phe
50                  55                  60

Gln Gly Arg Val Thr Ile Thr Ala Asp Lys Ser Thr Tyr Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 353
<211> LENGTH: 116
<212> TYPE: PRT
<213> ORGANISM: Artificial Sequence
<220> FEATURE:
<223> OTHER INFORMATION: Synthetic Heavy chain, clone: C06

<400> SEQUENCE: 353

Gln Met Gln Leu Val Gln Ser Gly Ala Glu Val Lys Lys Pro Gly Ala
1               5                   10                  15

Ser Val Lys Val Ser Cys Met Ala Ser Gly Tyr Thr Phe Thr Gly His
            20                  25                  30

Tyr Ile His Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Thr Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 354
<211> LENGTH: 116
<212> TYPE: PRT
<213> ORGANISM: Artificial Sequence
<220> FEATURE:
<223> OTHER INFORMATION: Synthetic Heavy chain, clone: C11

<400> SEQUENCE: 354

Gln Val Gln Leu Val Gln Ser Gly Ala Ala Val Lys Lys Pro Gly Ala
1               5                   10                  15

Ser Val Lys Val Ser Arg Lys Ala Ser Gly Tyr Thr Phe Thr Asn Asp
            20                  25                  30

Tyr Ile His Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95
Ala Thr His Gly Gly Asp Arg Ser Tyr Trp Gly Gln Gly Thr Leu Val
            100                 105                 110

Thr Val Ser Ser
        115

<210> SEQ ID NO 355
<211> LENGTH: 116
<212> TYPE: PRT
<213> ORGANISM: Artificial Sequence
<220> FEATURE:
<223> OTHER INFORMATION: Synthetic Heavy chain, clone: F08

<400> SEQUENCE: 355

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile His Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 356
<211> LENGTH: 116
<212> TYPE: PRT
<213> ORGANISM: Artificial Sequence
<220> FEATURE:
<223> OTHER INFORMATION: Synthetic Heavy chain, clone: E9

<400> SEQUENCE: 356

Gln Val Gln Leu Val Glu Ser Gly Ala Glu Val Arg Lys Pro Gly Glu
1               5                   10                  15

Ser Leu Gln Ile Ser Cys Lys Ala Ser Gly Tyr Arg Phe Thr Asn Tyr
                20                  25                  30

Trp Ile Gly Trp Val Arg Gln Met Pro Gly Lys Gly Leu Glu Trp Met
            35                  40                  45

Gly Ile Thr Tyr Pro Ala Asp Ser Thr Thr Val Tyr Ser Pro Ser Phe
        50                  55                  60

Gln Gly Gln Val Thr Ile Ser Ala Asp Lys Ser Ile Ser Thr Val Phe
65                  70                  75                  80

Leu Gln Trp Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 357
<211> LENGTH: 116
```

```
<212> TYPE: PRT
<213> ORGANISM: Artificial Sequence
<220> FEATURE:
<223> OTHER INFORMATION: Synthetic Heavy chain, clone: E11

<400> SEQUENCE: 357

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Asn Asp Gly Ser Thr Ser Tyr Ala Asp Ser Val
    50                  55                  60

Lys Gly Arg Phe Thr Ile Ser Arg Asp Thr Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 358
<211> LENGTH: 116
<212> TYPE: PRT
<213> ORGANISM: Artificial Sequence
<220> FEATURE:
<223> OTHER INFORMATION: Synthetic Heavy chain, clone: H11

<400> SEQUENCE: 358

Gln Val Gln Leu Leu Glu Ser Gly Ala Glu Val Lys Asn Pro Gly Ala
1               5                   10                  15

Ser Val Lys Val Ser Cys Lys Ala Ser Gly Tyr Pro Phe Ser Ala Tyr
            20                  25                  30

Tyr Ile Gln Trp Val Arg Gln Ala Pro Gly Gln Gly Leu Glu Trp Met
        35                  40                  45

Gly Trp Leu Asn Pro Asn Ser Gly Asp Thr His Ser Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Thr Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 359
<211> LENGTH: 116
<212> TYPE: PRT
<213> ORGANISM: Artificial Sequence
<220> FEATURE:
<223> OTHER INFORMATION: Synthetic Heavy chain, clone: C08

<400> SEQUENCE: 359

Glu Val Gln Leu Leu Glu Ser Glu Gly Gly Leu Val Gln Pro Gly Gly
1               5                   10                  15

Ser Leu Arg Leu Ser Cys Thr Ala Ser Gly Phe Ser Phe Asn Ala Phe
```

```
                     20                  25                  30

Trp Met His Trp Val Arg Gln Ala Pro Gly Lys Gly Leu Glu Trp Val
            35                  40                  45

Ser Arg Ile Ser Ile Asp Gly Thr Thr Thr Tyr Ala Asp Ser Val
    50                  55                  60

Gln Gly Arg Phe Thr Ile Ser Arg Asp Asn Ala Arg Asn Thr Leu Tyr
65                  70                  75                  80

Leu Gln Met Asn Ser Leu Arg Ala Glu Asp Ala Ala Val Tyr Tyr Cys
                85                  90                  95

Ala Thr His Gly Gly Asp Arg Ser Tyr Trp Ser Gln Gly Thr Leu Val
                100                 105                 110

Thr Val Ser Ser
        115

<210> SEQ ID NO 360
<211> LENGTH: 116
<212> TYPE: PRT
<213> ORGANISM: Artificial Sequence
<220> FEATURE:
<223> OTHER INFORMATION: Synthetic Heavy chain, clone: XB2708

<400> SEQUENCE: 360

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Ser Arg Ser Tyr
                20                  25                  30

Gly Met His Trp Val Arg Gln Ala Pro Gly Lys Gly Leu Glu Trp Val
            35                  40                  45

Ala Phe Ile Leu Phe Asp Gly Asn Asn Lys Tyr Tyr Ala Asp Ser Val
    50                  55                  60

Lys Gly Arg Phe Thr Ile Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 361
<211> LENGTH: 116
<212> TYPE: PRT
<213> ORGANISM: Artificial Sequence
<220> FEATURE:
<223> OTHER INFORMATION: Synthetic Heavy chain, clone: D03

<400> SEQUENCE: 361

Gln Val Gln Leu Val Gln Ser Gly Gly Gly Leu Val Gln Pro Gly Gly
1               5                   10                  15

Ser Leu Arg Leu Ser Cys Val Ala Ser Gly Phe Thr Phe Gly Asn Asp
                20                  25                  30

Trp Met His Trp Val Arg Gln Ala Pro Gly Lys Gly Leu Val Trp Val
            35                  40                  45

Ser Arg Ile Asn Ala Asp Gly Thr Ser Thr Ala Tyr Ala Glu Ser Val
    50                  55                  60

Lys Gly Arg Phe Thr Val Ser Arg Asp Asn Ala Lys Asn Thr Leu Tyr
65                  70                  75                  80
```

```
Leu Gln Met Asn Gly Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 362
<211> LENGTH: 115
<212> TYPE: PRT
<213> ORGANISM: Artificial Sequence
<220> FEATURE:
<223> OTHER INFORMATION: Synthetic Heavy chain, clone: A10

<400> SEQUENCE: 362

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Asn Trp Val Arg Gln Ala Pro Gly Lys Gly Leu Glu Trp Val
        35                  40                  45

Ser Leu Ile Tyr Ser Asp Gly Ser Thr Tyr Tyr Ala Asp Ser Val Lys
    50                  55                  60

Gly Arg Phe Thr Ile Ser Arg Asp Asn Ser Lys Lys Thr Leu Tyr Leu
65                  70                  75                  80

Gln Met Asn Asn Leu Arg Val Glu Asp Thr Ala Val Tyr Tyr Cys Ala
                85                  90                  95

Thr His Gly Gly Asp Arg Ser Tyr Trp Gly Gln Gly Thr Leu Val Thr
            100                 105                 110

Val Ser Ser
        115

<210> SEQ ID NO 363
<211> LENGTH: 116
<212> TYPE: PRT
<213> ORGANISM: Artificial Sequence
<220> FEATURE:
<223> OTHER INFORMATION: Synthetic Heavy chain, clone: C09

<400> SEQUENCE: 363

Gln Val Gln Leu Val Gln Ser Gly Gly Ala Leu Val Gln Pro Gly Gly
1               5                   10                  15

Ser Leu Arg Leu Ser Cys Ala Ser Gly Phe Thr Leu Ser Asn Asn
            20                  25                  30

Ala Met Ser Trp Val Arg Gln Ala Pro Gly Lys Arg Leu Glu Trp Val
        35                  40                  45

Ser Ala Ile Asp Gly Ser Gly Thr Thr Tyr Tyr Ala Gly Ser Val
    50                  55                  60

Lys Gly Arg Phe Thr Ile Ser Ser Asp Asn Ser Lys Asn Thr Val Phe
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 364
```

```
<211> LENGTH: 116
<212> TYPE: PRT
<213> ORGANISM: Artificial Sequence
<220> FEATURE:
<223> OTHER INFORMATION: Synthetic Heavy chain, clone: A06

<400> SEQUENCE: 364

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Gly His
            20                  25                  30

Trp Met His Trp Val Arg Gln Val Pro Gly Lys Gly Leu Val Trp Val
        35                  40                  45

Ser His Ile Ser Asn Asp Gly Ser Ile Thr Arg Tyr Ala Asp Ser Val
    50                  55                  60

Lys Gly Arg Phe Thr Val Ala Arg Asp Asn Ala Lys Asn Thr Met Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 365
<211> LENGTH: 116
<212> TYPE: PRT
<213> ORGANISM: Artificial Sequence
<220> FEATURE:
<223> OTHER INFORMATION: Synthetic Heavy chain, clone: C05

<400> SEQUENCE: 365

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ile Phe Ser Ser Asn
            20                  25                  30

Trp Met His Trp Val Arg Gln Val Pro Gly Lys Gly Leu Glu Trp Val
        35                  40                  45

Ser Arg Ile Lys Thr Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 366
<211> LENGTH: 116
<212> TYPE: PRT
<213> ORGANISM: Artificial Sequence
<220> FEATURE:
<223> OTHER INFORMATION: Synthetic Heavy chain, clone: H01

<400> SEQUENCE: 366

Gln Val Gln Leu Val Gln Ser Gly Gly Gly Leu Val Gln Pro Gly Gly
1               5                   10                  15
```

Ser Leu Arg Leu Ser Cys Ala Ala Ser Gly Phe Thr Leu Ser Ser Asp
            20                  25                  30

Trp Met His Trp Val Arg Gln Ala Pro Gly Lys Gly Leu Val Trp Val
            35                  40                  45

Ser Arg Ile Ser Ser Asp Gly Ser Thr Thr Ala Tyr Ala Asp Ser Val
        50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 367
<211> LENGTH: 116
<212> TYPE: PRT
<213> ORGANISM: Artificial Sequence
<220> FEATURE:
<223> OTHER INFORMATION: Synthetic Heavy chain, clone: G04

<400> SEQUENCE: 367

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Leu Ser Ser Asp
            20                  25                  30

Trp Met His Trp Val Arg Gln Ala Pro Gly Lys Gly Leu Val Trp Val
            35                  40                  45

Ser Arg Ile Ser Ser Asp Gly Ser Thr Thr Ala Tyr Ala Asp Ser Val
        50                  55                  60

Arg Gly Arg Phe Thr Ile Ser Arg Asp Asn Thr Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 368
<211> LENGTH: 116
<212> TYPE: PRT
<213> ORGANISM: Artificial Sequence
<220> FEATURE:
<223> OTHER INFORMATION: Synthetic Heavy chain, clone: G07

<400> SEQUENCE: 368

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Trp Met His Trp Val Arg Gln Ala Pro Gly Glu Gly Leu Val Trp Val
            35                  40                  45

Ser Arg Ile Ser Ser Asp Gly Ser Ser Thr Ala Tyr Ala Asp Ser Val
        50                  55                  60

Lys Gly Arg Phe Thr Ile Ser Arg Asp Asn Ala Lys Asn Thr Val Ser
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 369
<211> LENGTH: 107
<212> TYPE: PRT
<213> ORGANISM: Artificial Sequence
<220> FEATURE:
<223> OTHER INFORMATION: Synthetic Light chain, clone: B10

<400> SEQUENCE: 369

Gln Ser Val Leu Thr Gln Ser Pro Asp Leu Ser Val Thr Pro Arg
1               5                   10                  15

Glu Lys Leu Thr Ile Thr Cys Arg Ala Ser Gln Thr Ile Gly Ser Thr
                20                  25                  30

Leu His Trp Tyr Gln Gln Lys Pro Gly Gln Ser Pro Arg Leu Val Ile
            35                  40                  45

Lys Tyr Ala Tyr Gln Ser Val Ser Gly Val Pro Ser Arg Phe Ser Gly
50                  55                  60

Ser Gly Ser Gly Thr Glu Phe Thr Leu Thr Ile Asn Gly Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Leu Thr Val Leu
            100                 105

<210> SEQ ID NO 370
<211> LENGTH: 107
<212> TYPE: PRT
<213> ORGANISM: Artificial Sequence
<220> FEATURE:
<223> OTHER INFORMATION: Synthetic Light chain, clone: H10

<400> SEQUENCE: 370

Gln Ser Val Leu Thr Gln Ser Pro Asp Phe Gln Ser Val Ser Pro Lys
1               5                   10                  15

Asp Lys Val Thr Ile Thr Cys Arg Ala Ser Gln Ser Ile Gly Ser Ser
                20                  25                  30

Leu His Trp Tyr Gln Gln Lys Pro Gly Gln Ser Pro Lys Leu Leu Ile
            35                  40                  45

Lys Tyr Ser Ser Gln Ser Phe Ser Gly Val Pro Ser Arg Phe Ser Gly
50                  55                  60

Ser Ala Ser Gly Thr Glu Phe Thr Leu Thr Ile Thr Gly Leu Glu Ala
65                  70                  75                  80

Glu Asp Ala Ala Thr Tyr Tyr Cys His Gln Ser Ser Ser Leu Pro His
                85                  90                  95

Thr Phe Gly Gln Gly Thr Lys Val Thr Val Leu
            100                 105

<210> SEQ ID NO 371
<211> LENGTH: 107
<212> TYPE: PRT
<213> ORGANISM: Artificial Sequence
<220> FEATURE:
<223> OTHER INFORMATION: Synthetic Light chain, clone: F10

<400> SEQUENCE: 371

Gln Ser Val Leu Thr Gln Ser Pro Glu Phe Gln Ser Val Thr Pro Lys
1               5                   10                  15

Glu Lys Val Thr Ile Thr Cys Arg Ala Ser Gln Ser Ile Gly Ser Gly
            20                  25                  30

Leu His Trp Tyr Gln Gln Lys Pro His Gln Ser Pro Lys Leu Leu Ile
        35                  40                  45

Arg Tyr Ala Ser Gln Ser Met Ser Gly Val Pro Ser Arg Phe Ser Gly
    50                  55                  60

Ser Gly Ser Gly Thr Asp Phe Thr Leu Thr Ile Ser Arg Leu Glu Val
65                  70                  75                  80

Glu Asp Ala Ala Met Tyr Tyr Cys His Gln Ser Ser Ser Leu Pro Trp
                85                  90                  95

Thr Phe Gly Gln Gly Thr Lys Val Thr Val Leu
            100                 105

<210> SEQ ID NO 372
<211> LENGTH: 107
<212> TYPE: PRT
<213> ORGANISM: Artificial Sequence
<220> FEATURE:
<223> OTHER INFORMATION: Synthetic Light chain, clone: B12

<400> SEQUENCE: 372

Gln Ser Val Leu Thr Gln Ser Pro Asp Phe Gln Ser Val Thr Pro Lys
1               5                   10                  15

Gln Asn Val Thr Phe Thr Cys Arg Ala Ser Gln Ser Ile Gly Ile Lys
            20                  25                  30

Leu His Trp Tyr Gln Gln Lys Pro Asp Gln Ser Pro Lys Val Leu Ile
        35                  40                  45

Lys Tyr Ala Ser Gln Pro Phe Ser Gly Val Pro Ser Arg Phe Ser Gly
    50                  55                  60

Arg Gly Ser Gly Thr Asp Phe Thr Leu Thr Ile Asn Ser Leu Glu Ala
65                  70                  75                  80

Glu Asp Ala Ala Thr Tyr Tyr Cys His Gln Thr Ser Ser Leu Pro Leu
                85                  90                  95

Thr Phe Gly Gly Gly Thr Lys Val Thr Val Leu
            100                 105

<210> SEQ ID NO 373
<211> LENGTH: 108
<212> TYPE: PRT
<213> ORGANISM: Artificial Sequence
<220> FEATURE:
<223> OTHER INFORMATION: Synthetic Light chain, clone: B11

<400> SEQUENCE: 373

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ser Gly Ile Pro Val Arg Val Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

Trp Thr Phe Gly Gln Gly Thr Lys Leu Thr Val Leu
            100                 105

<210> SEQ ID NO 374
<211> LENGTH: 108
<212> TYPE: PRT
<213> ORGANISM: Artificial Sequence
<220> FEATURE:
<223> OTHER INFORMATION: Synthetic Light chain, clone: E7

<400> SEQUENCE: 374

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

Gln Thr Phe Gly Gln Gly Thr Lys Leu Thr Val Leu
            100                 105

<210> SEQ ID NO 375
<211> LENGTH: 109
<212> TYPE: PRT
<213> ORGANISM: Artificial Sequence
<220> FEATURE:
<223> OTHER INFORMATION: Synthetic Light chain, clone: E8

<400> SEQUENCE: 375

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

Pro Tyr Thr Phe Gly Gln Gly Thr Lys Leu Thr Val Leu
            100                 105

<210> SEQ ID NO 376
<211> LENGTH: 108
<212> TYPE: PRT
<213> ORGANISM: Artificial Sequence
<220> FEATURE:
<223> OTHER INFORMATION: Synthetic Light chain, clone: H8

<400> SEQUENCE: 376

```
Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Leu Gln Lys Pro Gly Gln Ala Pro Arg Leu Leu
        35                  40                  45

Ile Ser Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Pro
                85                  90                  95

Phe Thr Phe Gly Pro Gly Thr Lys Leu Thr Val Leu
                100                 105
```

<210> SEQ ID NO 377
<211> LENGTH: 108
<212> TYPE: PRT
<213> ORGANISM: Artificial Sequence
<220> FEATURE:
<223> OTHER INFORMATION: Synthetic Light chain, clone: H12

<400> SEQUENCE: 377

```
Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Val Ala Trp Tyr Gln Gln Lys Pro Gly Gln Ala Pro Arg Leu Leu
        35                  40                  45

Ile Ser Gly Ala Ser Arg Arg Ala Thr Gly Ile Pro Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr His Cys Gln Gln Phe Gly Ser Ser Pro
                85                  90                  95

Trp Thr Phe Gly Gln Gly Thr Lys Leu Thr Val Leu
                100                 105
```

<210> SEQ ID NO 378
<211> LENGTH: 108
<212> TYPE: PRT
<213> ORGANISM: Artificial Sequence
<220> FEATURE:
<223> OTHER INFORMATION: Synthetic Light chain, clone: F8

<400> SEQUENCE: 378

```
Gln Ser Val Leu Thr Gln Pro Pro Ser Ala Ser Gly Thr Pro Gly Gln
1               5                   10                  15

Arg Val Thr Ile Ser Cys Ser Gly Gly Arg Ser Asn Ile Gly Gly Asn
            20                  25                  30

Ala Val Asn Trp Tyr Gln Gln Lys Pro Gly Gln Ala Pro Arg Leu Leu
        35                  40                  45

Ile His Val Ala Ser Arg Arg Val Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Ile Tyr Tyr Cys Gln Gln Tyr Gly Ser Ser Pro
                85                  90                  95
```

```
Leu Thr Phe Gly Gly Gly Thr Lys Leu Thr Val Leu
            100                 105

<210> SEQ ID NO 379
<211> LENGTH: 108
<212> TYPE: PRT
<213> ORGANISM: Artificial Sequence
<220> FEATURE:
<223> OTHER INFORMATION: Synthetic Light chain, clone:  D11

<400> SEQUENCE: 379

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Asn Ile Thr Ser Asn
            20                  25                  30

Phe Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Ile Ser
    50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln Gln Tyr Gly Ala Ser Pro
                85                  90                  95

Arg Thr Phe Gly Gln Gly Thr Gln Leu Thr Val Leu
            100                 105

<210> SEQ ID NO 380
<211> LENGTH: 108
<212> TYPE: PRT
<213> ORGANISM: Artificial Sequence
<220> FEATURE:
<223> OTHER INFORMATION: Synthetic Light chain, clone:  G8

<400> SEQUENCE: 380

Gln Ser Val Leu Thr Gln Ser Pro Gly Thr Leu Ser Leu Ser Pro Gly
1               5                   10                  15

Asp Arg Ala Thr Leu Ser Cys Arg Ala Ser Gln Ser Leu Ser Gly Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Asn Arg Ala Ala Gly Ile Pro Lys Arg Phe Ser
    50                  55                  60

Gly Ser Gly Ser Arg Thr Asp Phe Thr Leu Thr Ile Ser Arg Val Asp
65                  70                  75                  80

Pro Ala Asp Ser Ala Val Tyr Tyr Cys Gln Gln Tyr Gly Ser Ala Leu
                85                  90                  95

Leu Thr Phe Gly Gly Gly Thr Lys Val Thr Val Leu
            100                 105

<210> SEQ ID NO 381
<211> LENGTH: 107
<212> TYPE: PRT
<213> ORGANISM: Artificial Sequence
<220> FEATURE:
<223> OTHER INFORMATION: Synthetic Light chain, clone:  H9

<400> SEQUENCE: 381

Gln Ser Val Leu Thr Gln Ser Pro Gly Thr Leu Ser Leu Ser Pro Gly
1               5                   10                  15
```

```
Glu Ser Ala Thr Leu Ser Cys Arg Ala Ser Glu Asp Ile Tyr Asn Asn
                20                  25                  30

Tyr Leu Ala Trp Tyr Gln His Lys Arg Gly Gln Pro Pro Arg Leu Leu
            35                  40                  45

Ile Phe Arg Ala Ser Thr Arg Ala Thr Gly Ile Pro Thr Arg Phe Ser
50                  55                  60

Gly Ser Gly Ser Gly Arg Asp Phe Val Leu Thr Ile Asn Arg Leu Glu
65                  70                  75                  80

Pro Glu Asp Phe Ala Val Tyr Tyr Cys Gln Gln Tyr Gly Asn Ser Trp
                85                  90                  95

Thr Phe Gly Gln Gly Thr Lys Leu Thr Val Leu
            100                 105

<210> SEQ ID NO 382
<211> LENGTH: 107
<212> TYPE: PRT
<213> ORGANISM: Artificial Sequence
<220> FEATURE:
<223> OTHER INFORMATION: Synthetic Light chain, clone: H11

<400> SEQUENCE: 382

Gln Ser Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Thr Phe Ala Ser Gln Ser Phe Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Arg Asn Leu Pro Phe
                85                  90                  95

Thr Phe Gly Pro Gly Thr Lys Leu Thr Val Leu
            100                 105

<210> SEQ ID NO 383
<211> LENGTH: 107
<212> TYPE: PRT
<213> ORGANISM: Artificial Sequence
<220> FEATURE:
<223> OTHER INFORMATION: Synthetic Light chain, clone: G12

<400> SEQUENCE: 383

Gln Ser Val Leu Thr Gln Ser Pro Asp Phe Gln Ser Val Thr Pro Lys
1               5                   10                  15

Glu Glu Val Thr Ile Thr Cys Arg Ala Ser Glu Ser Ile Gly Thr Ala
                20                  25                  30

Leu His Trp Tyr Gln Gln Lys Pro Asp Gln Ser Pro Lys Leu Leu Ile
            35                  40                  45

Lys Tyr Ser Ser Gln Ser Ile Ser Gly Val Pro Ser Arg Phe Val Gly
50                  55                  60

Arg Gly Ser Glu Thr Glu Phe Thr Leu Thr Ile Asn Ser Leu Glu Ala
65                  70                  75                  80

Glu Asn Ala Ala Thr Tyr Tyr Cys His Gln Ser Arg Ser Phe Pro Leu
                85                  90                  95

Thr Phe Gly Gln Gly Thr Gln Leu Thr Val Leu
            100                 105
```

<210> SEQ ID NO 384
<211> LENGTH: 107
<212> TYPE: PRT
<213> ORGANISM: Artificial Sequence
<220> FEATURE:
<223> OTHER INFORMATION: Synthetic Light chain, clone: E11

<400> SEQUENCE: 384

Gln Ser Val Leu Thr Gln Ser Pro Gly Thr Leu Ser Leu Ser Pro Gly
1               5                   10                  15

Glu Arg Ala Thr Leu Ser Cys Arg Thr Ser Gln Ile Leu His Ser Gln
            20                  25                  30

Tyr Leu Ala Trp Tyr Gln Gln Lys Arg Gly Gln Ala Pro Arg Leu Leu
        35                  40                  45

Ile Phe Arg Ala Ser Thr Arg Ala Thr Gly Ile Pro Glu Arg Phe Ser
    50                  55                  60

Gly Ser Gly Ser Gly Arg Asp Phe Val Leu Thr Ile Ser Arg Leu Glu
65                  70                  75                  80

Pro Glu Asp Ser Ala Val Tyr Tyr Cys Gln Gln Tyr Glu Thr Ser Trp
                85                  90                  95

Thr Phe Gly Gln Gly Thr Lys Val Thr Val Leu
            100                 105

<210> SEQ ID NO 385
<211> LENGTH: 107
<212> TYPE: PRT
<213> ORGANISM: Artificial Sequence
<220> FEATURE:
<223> OTHER INFORMATION: Synthetic Light chain, clone: F12

<400> SEQUENCE: 385

Gln Ser Val Leu Thr Gln Asp Pro Val Val Ser Val Ala Leu Gly Gln
1               5                   10                  15

Thr Val Arg Ile Thr Cys Gln Gly Asp Thr Leu Arg Thr Cys Tyr Ala
            20                  25                  30

Ser Trp Tyr Gln Gln Arg Pro Arg Gln Ala Pro Ile Leu Val Ile Tyr
        35                  40                  45

Gly Glu Asn Asn Arg Pro Ser Gly Ile Pro Ala Arg Phe Ser Gly Ser
    50                  55                  60

Ser Ser Gly Ser Thr Ala Ser Leu Thr Ile Thr Gly Ala Gln Ala Glu
65                  70                  75                  80

Asp Glu Gly Asp Tyr Tyr Cys His Cys Arg Asp Gly Leu Asn His Leu
                85                  90                  95

Val Phe Gly Gly Gly Thr Lys Val Thr Val Leu
            100                 105

<210> SEQ ID NO 386
<211> LENGTH: 110
<212> TYPE: PRT
<213> ORGANISM: Artificial Sequence
<220> FEATURE:
<223> OTHER INFORMATION: Synthetic Light chain, clone: C8

<400> SEQUENCE: 386

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Lys Asn
            20                  25                  30

```
Phe Val Ser Trp Tyr Gln His Leu Pro Gly Thr Ala Pro Lys Leu Leu
            35                  40                  45

Ile Tyr Asp Asn Tyr Gln Arg Phe Ser Gly Ile Pro Asp Arg Phe Ser
 50                  55                  60

Gly Phe Lys Ser Gly Thr Ser Ala Thr Leu Ser Ile Thr Gly Leu Gln
 65                  70                  75                  80

Thr Ala Asp Glu Ala Asp Tyr Tyr Cys Gly Thr Trp Asp Ser Ser Leu
                 85                  90                  95

Ser Val Val Ile Phe Gly Gly Gly Thr Lys Leu Thr Val Leu
            100                 105                 110

<210> SEQ ID NO 387
<211> LENGTH: 107
<212> TYPE: PRT
<213> ORGANISM: Artificial Sequence
<220> FEATURE:
<223> OTHER INFORMATION: Synthetic Light chain, clone: A8

<400> SEQUENCE: 387

Gln Ala Gly Leu Thr Gln Ser Pro Asp Phe Gln Ser Val Thr Pro Lys
 1               5                  10                  15

Glu Arg Val Thr Ile Thr Cys Arg Ala Ser Arg Tyr Ile Gly Ser Asn
            20                  25                  30

Leu His Trp Tyr Gln Gln Lys Pro Asp Gln Pro Pro Lys Leu Leu Ile
            35                  40                  45

Lys Leu Ala Ser Gln Ser Phe Ser Gly Val Pro Pro Arg Phe Ser Gly
 50                  55                  60

Gly Gly Ser Gly Thr Asp Phe Thr Leu Thr Ile Asn Gly Leu Glu Ala
 65                  70                  75                  80

Glu Asp Ala Ala Thr Tyr Tyr Cys His Gln Thr Gly Ser Phe Pro Tyr
                 85                  90                  95

Thr Phe Gly Gln Gly Thr Lys Leu Thr Val Leu
            100                 105

<210> SEQ ID NO 388
<211> LENGTH: 110
<212> TYPE: PRT
<213> ORGANISM: Artificial Sequence
<220> FEATURE:
<223> OTHER INFORMATION: Synthetic Light chain, clone: B8

<400> SEQUENCE: 388

Gln Ala Val Leu Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
            20                  25                  30

His Ser Pro Phe Trp Phe Gln Gln Arg Pro Gly Gln Ala Pro Arg Thr
            35                  40                  45

Leu Ile Tyr Asp Thr Ser Asn Lys Gln Ser Trp Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Leu Leu Ser Tyr Ser Gly
                 85                  90                  95

Pro Arg Val Val Phe Gly Gly Gly Thr Lys Val Thr Val Leu
            100                 105                 110

<210> SEQ ID NO 389
```

<211> LENGTH: 113
<212> TYPE: PRT
<213> ORGANISM: Artificial Sequence
<220> FEATURE:
<223> OTHER INFORMATION: Synthetic Light chain, clone: F7
<220> FEATURE:
<221> NAME/KEY: misc_feature
<222> LOCATION: (27)..(27)
<223> OTHER INFORMATION: Xaa can be any naturally occurring amino acid

<400> SEQUENCE: 389

Gln Ala Val Val Thr Gln Ser Pro Asp Ser Leu Ala Val Ser Leu Gly
1               5                   10                  15

Glu Arg Ala Thr Ile Ser Cys Lys Ser Xaa Ser Leu Leu Tyr Arg
            20                  25                  30

Ser Asn Asn Lys Asn Tyr Leu Ala Trp Tyr Gln Gln Lys Pro Gly Gln
        35                  40                  45

Pro Pro Arg Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Val Ser Arg Leu Arg Ala Glu Asp Ala Ala Val Tyr Tyr Cys Gln Gln
                85                  90                  95

Ser Tyr Arg Thr Pro Phe Ser Phe Gly Pro Gly Thr Lys Val Thr Val
            100                 105                 110

Leu

<210> SEQ ID NO 390
<211> LENGTH: 106
<212> TYPE: PRT
<213> ORGANISM: Artificial Sequence
<220> FEATURE:
<223> OTHER INFORMATION: Synthetic Light chain, clone: B7

<400> SEQUENCE: 390

Ser Tyr Val Leu Thr Gln Pro Leu Ser Val Ser Val Ala Leu Gly Gln
1               5                   10                  15

Thr Ala Arg Ile Ser Cys Gly Gly Ala Asn Ile Ala Asn Lys Asn Val
            20                  25                  30

His Trp Tyr Gln Leu Gln Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Thr Arg Ala Gln Ala Arg
65                  70                  75                  80

Asp Glu Ala Asp Tyr Tyr Cys Gln Val Trp Asp Ser Ser Val Ile
                85                  90                  95

Ile Gly Gly Gly Thr Lys Val Thr Val Leu
            100                 105

<210> SEQ ID NO 391
<211> LENGTH: 108
<212> TYPE: PRT
<213> ORGANISM: Artificial Sequence
<220> FEATURE:
<223> OTHER INFORMATION: Synthetic Light chain, clone: G9

<400> SEQUENCE: 391

Ser Tyr Val Leu Thr Gln Asp Pro Ala Val Ser Val Ala Leu Gly Gln
1               5                   10                  15

```
Thr Val Arg Ile Thr Cys Gln Gly Asp Ser Leu Arg Thr Tyr Tyr Ala
            20                  25                  30

Ser Trp Tyr Arg Gln Lys Pro Gly Gln Ala Pro Val Leu Val Phe Tyr
            35                  40                  45

Gly Lys Asp Asn Arg Pro Ser Gly Ile Pro Asp Arg Phe Ser Gly Ser
50                      55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Ala Met Arg
                85                  90                  95

Trp Val Phe Gly Gly Gly Thr Lys Leu Thr Val Leu
            100                 105
```

<210> SEQ ID NO 392
<211> LENGTH: 108
<212> TYPE: PRT
<213> ORGANISM: Artificial Sequence
<220> FEATURE:
<223> OTHER INFORMATION: Synthetic Light chain, clone: A9

<400> SEQUENCE: 392

```
Asn Phe Met Leu Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Val Pro Arg Thr
            35                  40                  45

Phe Ile Tyr Asp Thr His Asn Arg His Ser Trp Thr Pro Val Arg Phe
50                  55                  60

Ser Gly Ser Leu Phe Gly Gly Lys Ala Ala Leu Thr Leu Ser Gly Ala
65                  70                  75                  80

Gln Pro Glu Asp Glu Ala Glu Tyr Tyr Cys Leu Leu Tyr Phe Asn Pro
                85                  90                  95

Thr Arg Val Phe Gly Gly Gly Thr Lys Leu Thr Val
            100                 105
```

<210> SEQ ID NO 393
<211> LENGTH: 110
<212> TYPE: PRT
<213> ORGANISM: Artificial Sequence
<220> FEATURE:
<223> OTHER INFORMATION: Synthetic Light chain, clone: A11

<400> SEQUENCE: 393

```
Asn Phe Met Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Pro Arg Phe Val Met
            35                  40                  45

Arg Val Gly Thr Gly Gly Ile Val Gly Ser Lys Gly Asp Gly Ile Pro
50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Arg Val Phe Gly Gly Gly Thr Lys Leu Thr Val Leu
            100                 105                 110
```

<210> SEQ ID NO 394
<211> LENGTH: 105
<212> TYPE: PRT
<213> ORGANISM: Artificial Sequence
<220> FEATURE:
<223> OTHER INFORMATION: Synthetic Light chain, clone: E12

<400> SEQUENCE: 394

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr His Leu Arg Pro Gly Gln Ala Pro Val Leu Val Ile Tyr
        35                  40                  45

Phe Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp His Ser Gly Val Ile Phe
                85                  90                  95

Gly Gly Gly Thr Lys Leu Thr Val Leu
            100                 105

<210> SEQ ID NO 395
<211> LENGTH: 106
<212> TYPE: PRT
<213> ORGANISM: Artificial Sequence
<220> FEATURE:
<223> OTHER INFORMATION: Synthetic Light chain, clone: H7

<400> SEQUENCE: 395

Gln Pro Val Leu Thr Gln Ser Leu Asp Phe Gln Ser Val Thr Pro Lys
1               5                   10                  15

Glu Lys Val Thr Ile Thr Cys Arg Ala Ser Gln Asn Ile Gly Asn Ser
            20                  25                  30

Leu His Trp Tyr Gln Gln Lys Pro Asn Gln Ser Pro Lys Val Leu Ile
        35                  40                  45

Lys Tyr Ala Ser Gln Ser Phe Ser Gly Val Pro Ser Arg Phe Ser Gly
    50                  55                  60

Ser Gly Phe Gly Thr Asp Phe Thr Leu Thr Ile Asn Ser Leu Glu Pro
65                  70                  75                  80

Glu Asp Ala Ala Thr Tyr Tyr Cys His Gln Ser Arg Ser Ser His Thr
                85                  90                  95

Phe Gly Gln Gly Thr Lys Leu Thr Val Leu
            100                 105

<210> SEQ ID NO 396
<211> LENGTH: 113
<212> TYPE: PRT
<213> ORGANISM: Artificial Sequence
<220> FEATURE:
<223> OTHER INFORMATION: Synthetic Light chain, clone: A10

<400> SEQUENCE: 396

Glu Ile Val Leu Thr Gln Ser Pro Gly Asn Leu Ser Leu Ser Pro Gly
1               5                   10                  15

Glu Arg Ala Thr Leu Ser Cys Thr Arg Cys Thr Gly Asn Ile Ala Ser
            20                  25                  30

His Phe Val Gln Trp Tyr Gln Gln Arg Pro Gly Ser Ser Pro Thr Thr
            35                  40                  45

Val Ile Phe Gly Asn Asn Gln Arg Pro Ser Gly Val Ser Asp Arg Phe
 50                  55                  60

Ser Gly Ser Ile Asp Ser Ser Asn Ser Ala Ser Leu Thr Ile Ser
 65                  70                  75                  80

Arg Leu Lys Thr Glu Asp Glu Ala Asp Tyr Tyr Cys Gln Ser Phe Asp
                 85                  90                  95

Val Tyr Ser His Glu Val Val Phe Gly Gly Gly Thr Lys Leu Thr Val
                100                 105                 110

Leu

<210> SEQ ID NO 397
<211> LENGTH: 113
<212> TYPE: PRT
<213> ORGANISM: Artificial Sequence
<220> FEATURE:
<223> OTHER INFORMATION: Synthetic Light chain, clone: C11

<400> SEQUENCE: 397

Gln Thr Val Val Thr Gln Thr Pro Val Ser Leu Ser Val Thr Pro Gly
 1               5                  10                  15

Gln Pro Ala Ser Ile Ser Cys Lys Ser Ser Gln Ser Leu Leu Asn Ser
                 20                  25                  30

Asp Asp Gly Lys Thr Tyr Leu Tyr Trp Tyr Leu Gln Arg Pro Gly Gln
                 35                  40                  45

Pro Pro His Leu Leu Ile Tyr Glu Val Ser Lys Arg Phe Ser Gly Val
 50                  55                  60

Pro Asp Arg Phe Ser Gly Ser Gly Ser Gly Thr Asp Phe Thr Leu Arg
 65                  70                  75                  80

Ile Ser Arg Val Glu Ala Glu Asp Val Gly Val Phe Tyr Cys Met Gln
                 85                  90                  95

Ser Thr His Phe Pro Phe Thr Phe Gly Pro Gly Thr Lys Val Thr Val
                100                 105                 110

Leu

<210> SEQ ID NO 398
<211> LENGTH: 107
<212> TYPE: PRT
<213> ORGANISM: Artificial Sequence
<220> FEATURE:
<223> OTHER INFORMATION: Synthetic Light chain, clone: D10

<400> SEQUENCE: 398

Asn Ile Gln Met Thr Gln Ser Pro Val Ser Leu Ser Ala Ser Leu Gly
 1               5                  10                  15

Asp Thr Val Ser Ile Thr Cys Gln Ala Ser His Asp Ile Ser Asn Tyr
                 20                  25                  30

Leu Asn Trp Tyr Gln Gln Lys Pro Gly Lys Ala Pro Lys Leu Leu Ile
                 35                  40                  45

Tyr Asp Ala Ser His Leu Glu Ala Gly Val Pro Ser Arg Phe Arg Gly
 50                  55                  60

Ser Gly Ser Gly Thr Asp Phe Thr Leu Thr Ile Asn Arg Leu Glu Pro
 65                  70                  75                  80

Glu Asp Phe Ala Val Tyr Tyr Cys Gln Gln Tyr Asp Ser Pro Pro Trp
                 85                  90                  95

Thr Phe Gly Gln Gly Thr Lys Leu Thr Val Leu

<210> SEQ ID NO 399
<211> LENGTH: 108
<212> TYPE: PRT
<213> ORGANISM: Artificial Sequence
<220> FEATURE:
<223> OTHER INFORMATION: Synthetic Light chain, clone: D12

<400> SEQUENCE: 399

Asp Val Val Leu Thr Gln Ser Pro Gly Thr Met Ser Leu Ser Pro Gly
1               5                   10                  15

Glu Arg Ala Thr Leu Ser Cys Arg Ala Ser Gln Ser Val Ser Arg Thr
            20                  25                  30

Tyr Leu Ala Trp His Gln Gln Lys Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Ser Ile Ser Arg Leu Glu
65                  70                  75                  80

Pro Glu Asp Phe Ala Val Tyr Tyr Cys Gln Gln His Asp Thr Ser Gln
                85                  90                  95

Trp Thr Phe Gly Gln Gly Thr Lys Leu Thr Val Leu
            100                 105

<210> SEQ ID NO 400
<211> LENGTH: 112
<212> TYPE: PRT
<213> ORGANISM: Artificial Sequence
<220> FEATURE:
<223> OTHER INFORMATION: Synthetic Light chain, clone: C7

<400> SEQUENCE: 400

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr His Leu Phe Trp Tyr Leu Gln Arg Pro Gly Gln Ser
        35                  40                  45

Pro Gln Leu Leu Ile Tyr Glu Val Ser Arg Phe Ser Gly Val Ser
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Ile Pro His Thr Phe Gly Gln Gly Thr Lys Val Glu Ile Lys
            100                 105                 110

<210> SEQ ID NO 401
<211> LENGTH: 111
<212> TYPE: PRT
<213> ORGANISM: Artificial Sequence
<220> FEATURE:
<223> OTHER INFORMATION: Synthetic Light chain, clone: D7

<400> SEQUENCE: 401

Asp Ile Val Met Thr Gln Ser Pro Leu Ser Leu Pro Val Thr Leu Gly
1               5                   10                  15

Gln Pro Ala Ser Ile Ser Cys Arg Ser Ser His Ser Leu Val His Ser
            20                  25                  30

```
Asp Gly Asn Ile Tyr Leu Asn Trp Tyr His Gln Arg Pro Gly Gln Ser
        35                  40                  45

Pro Arg Leu Ile Tyr Ser Val Ser Lys Arg Asp Ser Gly Val Pro
 50                  55                  60

Asp Arg Phe Ser Gly Ser Gly Ser Arg Thr Asp Phe Thr Leu Lys Ile
 65                  70                  75                  80

Ser Arg Val Glu Ala Glu Asp Val Gly Val Tyr Phe Cys Met Gln Ser
                 85                  90                  95

Thr His Gln Trp Thr Phe Gly Gln Gly Thr Lys Val Glu Ile Lys
                100                 105                 110

<210> SEQ ID NO 402
<211> LENGTH: 107
<212> TYPE: PRT
<213> ORGANISM: Artificial Sequence
<220> FEATURE:
<223> OTHER INFORMATION: Synthetic Light chain, clone: C9
<220> FEATURE:
<221> NAME/KEY: misc_feature
<222> LOCATION: (75)..(75)
<223> OTHER INFORMATION: Xaa can be any naturally occurring amino acid

<400> SEQUENCE: 402

Val Ile Trp Met Thr Gln Ser Pro Ser Thr Val Ser Ala Ser Val Gly
 1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Asn Leu Leu Ile
        35                  40                  45

Tyr Glu Ala Ser Arg Leu Glu Ser Gly Ile Pro Ser Arg Phe Ser Gly
 50                  55                  60

Ser Gly Ser Gly Thr Glu Phe Thr Leu Thr Xaa Ser Ser Leu Gln Pro
 65                  70                  75                  80

Asp Asp Phe Ala Thr Tyr Tyr Cys Gln Gln Tyr Asp Ser Tyr Ser Arg
                 85                  90                  95

Thr Phe Gly Gln Gly Thr Lys Val Ala Ile Lys
                100                 105

<210> SEQ ID NO 403
<211> LENGTH: 106
<212> TYPE: PRT
<213> ORGANISM: Artificial Sequence
<220> FEATURE:
<223> OTHER INFORMATION: Synthetic Light chain, clone: C12

<400> SEQUENCE: 403

Asp Val Val Met Thr Gln Ser Pro Ser Ser Leu Ser Ala Ser Val Gly
 1               5                  10                  15

Asp Arg Val Thr Ile Thr Cys Arg Thr Ser Gln Gly Ile Arg Asn Tyr
                 20                  25                  30

Leu Ser Trp Tyr Gln Gln Lys Pro Ala Lys Ala Pro Lys Leu Leu Ile
        35                  40                  45

His Gly Ala Ser Gly Leu Gln Ser Gly Val Pro Ser Arg Phe Ser Gly
 50                  55                  60

Ser Gly Ser Gly Thr Asn Phe Thr Leu Thr Ile Ser Ser Leu Gln Pro
 65                  70                  75                  80

Glu Asp Phe Ala Thr Tyr Tyr Cys Gln Gln Ser Phe Ser Met Arg Thr
                 85                  90                  95
```

Phe Gly Gln Gly Thr Lys Val Glu Ile Lys
            100                 105

<210> SEQ ID NO 404
<211> LENGTH: 114
<212> TYPE: PRT
<213> ORGANISM: Artificial Sequence
<220> FEATURE:
<223> OTHER INFORMATION: Synthetic Light chain, clone: D8

<400> SEQUENCE: 404

Glu Ile Val Met Thr Gln Ser Pro Gly Thr Leu Thr Leu Ser Pro Gly
1               5                   10                  15

Glu Gly Ala Thr Leu Ser Cys Arg Ala Ser Gln Ser Val Thr Ser Asn
            20                  25                  30

Tyr Leu Ala Trp Tyr Gln Gln Arg Pro Gly Ala Ser Ser Leu Gln Ser
        35                  40                  45

Gly Gln Ala Pro Arg Leu Leu Ile Tyr Asp Ala Ser Asn Arg Ala Thr
    50                  55                  60

Gly Ile Pro Asp Arg Phe Ser Gly Ser Gly Phe Gly Thr Asp Phe Thr
65                  70                  75                  80

Leu Thr Ile Ser Arg Leu Glu Pro Glu Asp Phe Ala Val Tyr Tyr Cys
                85                  90                  95

Gln Gln Tyr Val Asn Ser Arg Thr Phe Gly Gln Gly Thr Lys Val Glu
            100                 105                 110

Ile Lys

<210> SEQ ID NO 405
<211> LENGTH: 106
<212> TYPE: PRT
<213> ORGANISM: Artificial Sequence
<220> FEATURE:
<223> OTHER INFORMATION: Synthetic Light chain, clone: D9

<400> SEQUENCE: 405

Glu Ile Val Met Thr Gln Ser Pro Val Thr Leu Ser Val Ser Pro Gly
1               5                   10                  15

Glu Arg Ala Thr Leu Ser Cys Arg Ala Ser Gln Ser Val Ser Ser Lys
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asn Asp Phe Phe Thr
                85                  90                  95

Phe Gly Pro Gly Thr Lys Val Asp Ile Lys
            100                 105

<210> SEQ ID NO 406
<211> LENGTH: 111
<212> TYPE: PRT
<213> ORGANISM: Artificial Sequence
<220> FEATURE:
<223> OTHER INFORMATION: Synthetic Light chain, clone: G7

<400> SEQUENCE: 406

Glu Ile Val Leu Thr Gln Thr Pro Leu Ser Ser Pro Val Thr Leu Gly
1               5                   10                  15

Gln Pro Ala Ser Ile Ser Cys Arg Ser Ser Glu Ser Pro Val His Ser
                20                  25                  30

Asp Gly Asn Ile Tyr Leu Ser Trp Leu His Gln Arg Pro Gly Gln Pro
            35                  40                  45

Pro Arg Leu Leu Leu Tyr Lys Ile Ser Asn Arg Met Ser Gly Val Pro
50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Ser Phe Gly Gly Gly Thr Lys Leu Glu Ile Lys
            100                 105                 110

<210> SEQ ID NO 407
<211> LENGTH: 108
<212> TYPE: PRT
<213> ORGANISM: Artificial Sequence
<220> FEATURE:
<223> OTHER INFORMATION: Synthetic Light chain, clone: G11

<400> SEQUENCE: 407

Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Arg
                20                  25                  30

Asn Leu Ala Trp Tyr Gln Gln Lys Pro Gly Gln Ala Pro Arg Leu Leu
            35                  40                  45

Ile Tyr Gly Gly Ser Ile Arg Ala Ser Gly Thr Ser Thr Arg Phe Ser
50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Tyr Gly Asp Ser Val
                85                  90                  95

Phe Thr Phe Gly Pro Gly Thr Lys Val Asp Ile Lys
            100                 105

<210> SEQ ID NO 408
<211> LENGTH: 107
<212> TYPE: PRT
<213> ORGANISM: Artificial Sequence
<220> FEATURE:
<223> OTHER INFORMATION: Synthetic Light chain, clone: F9

<400> SEQUENCE: 408

Asn Ile Gln Met Thr Gln Ser Pro Ser Ser Leu Ser Ala Ser Val Gly
1               5                   10                  15

Asp Arg Val Asn Ile Thr Cys Arg Ala Ser Asp Asn Ile Gly Asn Tyr
                20                  25                  30

Leu Asn Trp Tyr Gln His Lys Pro Gly Lys Ala Pro Thr Val Leu Ile
            35                  40                  45

Tyr Ala Ala Ser Thr Leu His Tyr Gly Val Pro Ser Arg Phe Ser Gly
50                  55                  60

Arg Gly Ser Gly Thr Asp Phe Thr Val Thr Ile Ser Ser Leu Gln Pro
65                  70                  75                  80

Glu Asp Ser Ala Thr Tyr Tyr Cys Gln Gln Ser Tyr Ser Thr Pro Arg
                85                  90                  95

Thr Phe Gly Gln Gly Thr Arg Val Glu Leu Lys

<210> SEQ ID NO 409
<211> LENGTH: 108
<212> TYPE: PRT
<213> ORGANISM: Artificial Sequence
<220> FEATURE:
<223> OTHER INFORMATION: Synthetic Light chain, clone: E9

<400> SEQUENCE: 409

Ala Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Asn Tyr
            20                  25                  30

Leu Asn Trp Tyr Gln Gln Lys Pro Gly Lys Ala Pro Lys Leu Leu Leu
        35                  40                  45

Ser Ala Ala Ser Arg Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Leu Ala Thr Tyr Tyr Cys Gln Glu Ser Tyr Ser Thr Leu Leu
                85                  90                  95

Tyr Thr Phe Gly Gln Gly Thr Lys Leu Glu Ile Lys
            100                 105

<210> SEQ ID NO 410
<211> LENGTH: 108
<212> TYPE: PRT
<213> ORGANISM: Artificial Sequence
<220> FEATURE:
<223> OTHER INFORMATION: Synthetic Light chain, clone: B1

<400> SEQUENCE: 410

Ser Tyr Glu Leu Thr Gln Pro Pro Ser Val Ser Val Ala Pro Gly Lys
1               5                   10                  15

Thr Ala Ser Ile Thr Cys Gly Gly Asn Asn Ile Gly Tyr Asp Ser Val
            20                  25                  30

His Trp Tyr Gln Gln Lys Pro Gly Gln Ala Pro Val Leu Val Val Phe
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Ser Gly Ser Glu His
                85                  90                  95

Tyr Val Phe Gly Thr Gly Thr Gln Leu Thr Val Leu
            100                 105

<210> SEQ ID NO 411
<211> LENGTH: 108
<212> TYPE: PRT
<213> ORGANISM: Artificial Sequence
<220> FEATURE:
<223> OTHER INFORMATION: Synthetic Light chain, clone: E6

<400> SEQUENCE: 411

Leu Pro Val Leu Thr Gln Pro Pro Ser Val Ser Val Ala Pro Gly Gln
1               5                   10                  15

Thr Ala Arg Ile Ser Cys Gly Gly Asn Asn Ile Gly Ala Thr Thr Val
            20                  25                  30

```
His Trp Tyr Gln His Arg Pro Gly Gln Ala Pro Val Ser Val Ile Phe
         35                  40                  45

Tyr Asp Asn Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Glu Ser Thr Ser Asp His
                 85                  90                  95

Pro Thr Phe Gly Gly Gly Thr Gln Leu Thr Val Leu
            100                 105

<210> SEQ ID NO 412
<211> LENGTH: 108
<212> TYPE: PRT
<213> ORGANISM: Artificial Sequence
<220> FEATURE:
<223> OTHER INFORMATION: Synthetic Light chain, clone:  F3

<400> SEQUENCE: 412

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Ile Tyr
         35                  40                  45

Tyr Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Trp Val Phe Gly Gly Gly Thr Lys Leu Thr Val Leu
            100                 105

<210> SEQ ID NO 413
<211> LENGTH: 109
<212> TYPE: PRT
<213> ORGANISM: Artificial Sequence
<220> FEATURE:
<223> OTHER INFORMATION: Synthetic Light chain, clone:  H4

<400> SEQUENCE: 413

Ser Tyr Glu Leu Thr Gln Ser Pro Ser Val Ser Val Pro Pro Gly Gln
1               5                   10                  15

Thr Ala Arg Ile Thr Cys Gly Gly Asn Asn Ile Val Ser Lys Gly Val
             20                  25                  30

His Trp Tyr Gln Gln Arg Pro Gly Gln Ala Pro Val Leu Val Val Tyr
         35                  40                  45

Asp Asp Ser Asp Arg Pro Ser Gly Ile Pro Glu Arg Phe Ala Gly Phe
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Gly His
                 85                  90                  95

Arg Gly Val Phe Gly Gly Gly Thr Lys Val Thr Val Leu
            100                 105
```

```
<210> SEQ ID NO 414
<211> LENGTH: 108
<212> TYPE: PRT
<213> ORGANISM: Artificial Sequence
<220> FEATURE:
<223> OTHER INFORMATION: Synthetic Light chain, clone: H5

<400> SEQUENCE: 414
```

Ser Tyr Glu Leu Thr Gln Pro Pro Ser Val Ser Met Ala Pro Gly Lys
1               5                   10                  15

Thr Ala Arg Ile Thr Cys Gly Gly Asn Asn Leu Gly Ser Lys Ile Val
            20                  25                  30

His Trp Tyr Gln Gln Lys Pro Gly Gln Ala Pro Val Val Val Ile Tyr
        35                  40                  45

Ser Asp Arg Asp Arg Pro Ser Gly Val Pro Glu Arg Phe Ser Gly Ser
    50                  55                  60

Asn Ser Gly Asn Ser Ala Thr Leu Thr Ile Ser Gly Val Glu Ala Gly
65                  70                  75                  80

Asp Glu Ala Asp Tyr Tyr Cys Gln Val Trp Asp Ser Ala Thr Asp His
                85                  90                  95

Val Val Phe Gly Gly Gly Thr Lys Leu Thr Val Leu
            100                 105

```
<210> SEQ ID NO 415
<211> LENGTH: 108
<212> TYPE: PRT
<213> ORGANISM: Artificial Sequence
<220> FEATURE:
<223> OTHER INFORMATION: Synthetic Light chain, clone: B5

<400> SEQUENCE: 415
```

Ser Tyr Glu Leu Thr Gln Pro Pro Ser Val Ser Val Ala Pro Gly Gln
1               5                   10                  15

Thr Ala Thr Ile Thr Cys Ala Gly Asn Asn Ile Gly Gly Lys Ser Val
            20                  25                  30

Gln Trp Tyr Gln Gln Lys Pro Gly Gln Ala Pro Val Val Val Val Tyr
        35                  40                  45

Asp Asp Tyr Gly Arg Pro Ser Gly Ile Pro Glu Arg Val Ser Gly Ser
    50                  55                  60

Asn Ser Gly Asn Thr Ala Thr Leu Thr Leu Thr Arg Val Glu Ala Gly
65                  70                  75                  80

Asp Glu Ala Asp Tyr Tyr Cys Gln Val Trp Asp Ser Asp Arg His His
                85                  90                  95

Val Val Phe Gly Gly Gly Thr Lys Leu Thr Val Leu
            100                 105

```
<210> SEQ ID NO 416
<211> LENGTH: 108
<212> TYPE: PRT
<213> ORGANISM: Artificial Sequence
<220> FEATURE:
<223> OTHER INFORMATION: Synthetic Light chain, clone: G6
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (104)..(104)
```

<223> OTHER INFORMATION: Xaa can be any naturally occurring amino acid

<400> SEQUENCE: 416

Gln Leu Val Leu Thr Gln Pro Pro Ser Val Ser Val Ser Pro Gly Gln
1               5                   10                  15

Thr Ala Ser Ile Thr Cys Ser Gly Asp Asn Leu Gly His Thr Asn Ala
            20                  25                  30

Cys Trp Tyr Gln Gln Asn Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Pro Ala Thr Leu Thr Ile Xaa Arg Val Xaa Ala Gly
65                  70                  75                  80

Asp Glu Ala Asn Tyr Tyr Cys Gln Val Trp Asp Ile Asn Asp Asp Tyr
                85                  90                  95

Ala Val Phe Gly Thr Gly Thr Xaa Leu Thr Val Leu
            100                 105

<210> SEQ ID NO 417
<211> LENGTH: 104
<212> TYPE: PRT
<213> ORGANISM: Artificial Sequence
<220> FEATURE:
<223> OTHER INFORMATION: Synthetic Light chain, clone: C1

<400> SEQUENCE: 417

Gln Ser Val Leu Thr Gln Ser Pro Gly Thr Leu Ser Leu Ser Pro Gly
1               5                   10                  15

Glu Arg Ala Thr Leu Ser Cys Thr Ala Ser Gln Ser Val Ser Ser Thr
            20                  25                  30

Tyr Leu Thr Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Ser Ser Pro
                85                  90                  95

Pro Met Tyr Thr Phe Gly Gln Leu
            100

<210> SEQ ID NO 418
<211> LENGTH: 107
<212> TYPE: PRT
<213> ORGANISM: Artificial Sequence
<220> FEATURE:
<223> OTHER INFORMATION: Synthetic Light chain, clone: F1
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid

```
<220> FEATURE:
<221> NAME/KEY: misc_feature
<222> LOCATION: (82)..(82)
<223> OTHER INFORMATION: Xaa can be any naturally occurring amino acid

<400> SEQUENCE: 418

Asp Ile Gln Met Thr Gln Ser Pro Ser Thr Leu Ser Ala Ser Val Gly
1               5                   10                  15

Asp Arg Val Thr Ile Ser Cys Arg Ala Ser Gln Asn Ile Asp Tyr Asp
            20                  25                  30

Leu Ala Trp Tyr Gln Xaa Lys Pro Gly Lys Ala Pro Xaa Leu Leu Ile
        35                  40                  45

Tyr Gly Ala Ser Asn Leu Glu Gly Gly Val Pro Ser Xaa Phe Ser Gly
50                  55                  60

Xaa Gly Ser Gly Thr Glu Phe Thr Leu Thr Ile Ser Ser Leu Gln Pro
65                  70                  75                  80

Asp Xaa Ser Ala Thr Tyr Tyr Cys Gln Gln Tyr Val Thr Tyr Pro Leu
            85                  90                  95

Thr Phe Gly Gln Gly Thr Arg Leu Glu Ile Lys
            100                 105

<210> SEQ ID NO 419
<211> LENGTH: 111
<212> TYPE: PRT
<213> ORGANISM: Artificial Sequence
<220> FEATURE:
<223> OTHER INFORMATION: Synthetic Light chain, clone: A3

<400> SEQUENCE: 419

Ala Ile Gln Met Thr Gln Ser Pro Ser Ser Leu Ser Ala Ser Val Gly
1               5                   10                  15

Asp Arg Val Thr Met Thr Cys Gln Ala Ser Gln Val Ile Asp Lys Tyr
            20                  25                  30

Val Asn Trp Tyr Arg Gln Arg Pro Gly Lys Ala Pro Glu Leu Leu Ile
        35                  40                  45

Tyr Gly Ala Ser Thr Leu Glu Ser Gly Val Pro Ser Arg Phe Ser Gly
50                  55                  60

Ser Gly Ser Gly Thr Gln Phe Thr Phe Ser Ile Thr Ser Val Gln Pro
65                  70                  75                  80

Glu Asp Phe Ala Thr Tyr Ile Cys Gln Gln Tyr Asp Ser Val Pro Leu
            85                  90                  95

Thr Phe Gly Pro Gly Thr Ile Leu Asp Val Lys Arg Thr Val Ala
            100                 105                 110

<210> SEQ ID NO 420
<211> LENGTH: 110
<212> TYPE: PRT
<213> ORGANISM: Artificial Sequence
<220> FEATURE:
<223> OTHER INFORMATION: Synthetic Light chain, clone: B4

<400> SEQUENCE: 420

Asp Ile Gln Leu Thr Gln Ser Pro Ser Ser Leu Ser Ala Ser Ile Gly
1               5                   10                  15

Asp Arg Val Thr Ile Thr Cys Gln Ala Ser Gln Asp Ile Phe His Tyr
            20                  25                  30

Leu Asn Trp Phe Gln Gln Lys Pro Gly Lys Ala Pro Lys Leu Leu Ile
        35                  40                  45

Tyr Glu Ala Ser Asn Leu Glu Thr Gly Val Pro Ser Arg Phe Ser Gly
```

```
                       50                  55                  60
Ser Gly Ser Val Thr Asp Phe Thr Phe Thr Ile Ser Ser Leu Gln Pro
 65                  70                  75                  80

Glu Asp Ile Ala Thr Tyr Tyr Cys Gln Gln Tyr Glu Asp Leu Pro Ser
                     85                  90                  95

Phe Gly Gly Gly Thr Lys Val Asp Ile Lys Arg Thr Val Ala
                100                 105                 110

<210> SEQ ID NO 421
<211> LENGTH: 108
<212> TYPE: PRT
<213> ORGANISM: Artificial Sequence
<220> FEATURE:
<223> OTHER INFORMATION: Synthetic Light chain, clone:  B6

<400> SEQUENCE: 421

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Phe Gly Ser Asn
                 20                  25                  30

Tyr Leu Ala Trp Tyr Gln His Lys Pro Gly Gln Ala Pro Arg Leu Leu
             35                  40                  45

Ile Phe Ala Ala Ser Asn Arg Ala Thr Gly Ile Pro Asp Arg Phe Thr
 50                  55                  60

Gly Ser Ala Ser Gly Thr Asp Phe Thr Leu Thr Ile Asn Arg Val Glu
 65                  70                  75                  80

Pro Glu Asp Leu Ala Val Tyr Tyr Cys Gln Gln Tyr Gly Ser Phe Pro
                 85                  90                  95

Tyr Ser Phe Gly Gln Gly Thr Lys Leu Glu Ile Lys
                100                 105

<210> SEQ ID NO 422
<211> LENGTH: 111
<212> TYPE: PRT
<213> ORGANISM: Artificial Sequence
<220> FEATURE:
<223> OTHER INFORMATION: Synthetic Light chain, clone:  F2

<400> SEQUENCE: 422

Asn Ile Gln Met Thr Gln Ser Pro Ser Ser Leu Ser Ala Ser Val Gly
  1               5                  10                  15

Asp Arg Val Thr Ile Thr Cys Gln Ala Ser Gln Phe Ile His Ile Tyr
                 20                  25                  30

Leu Asn Trp Tyr Gln Gln Lys Leu Gly Lys Ala Pro Lys Leu Leu Ile
             35                  40                  45

Tyr Gly Ala Ser Asn Leu Glu Arg Gly Val Pro Ser Arg Phe Ser Gly
         50                  55                  60

Arg Gly Ser Glu Thr Asp Phe Thr Phe Thr Ile Asp Ser Leu Gln Pro
 65                  70                  75                  80

Glu Asp Ile Ala Thr Tyr Phe Cys Gln Gln Tyr Gln Asn Pro Pro Phe
                 85                  90                  95

Thr Phe Gly Gly Gly Thr Lys Val Glu Ile Asn Gly Thr Val Ala
                100                 105                 110

<210> SEQ ID NO 423
<211> LENGTH: 111
<212> TYPE: PRT
<213> ORGANISM: Artificial Sequence
<220> FEATURE:
```

<223> OTHER INFORMATION: Synthetic Light chain, clone: D3

<400> SEQUENCE: 423

Ala Ile Arg Met Thr Gln Ser Pro Ser Ser Leu Ser Ala Ser Ile Gly
1               5                   10                  15

Asp Arg Ile Ser Val Thr Cys Arg Ala Ser Gln Asp Val Gly Ile Tyr
            20                  25                  30

Val Ala Trp Phe Gln Gln Lys Pro Gly Lys Pro Pro Arg Ser Leu Ile
        35                  40                  45

Tyr Ala Ala Ser Tyr Leu Gln Thr Ala Val Pro Pro Lys Phe Arg Gly
    50                  55                  60

Ser Gly Ser Gly Thr Asp Phe Thr Leu Thr Ile Ser Asp Leu Gln Pro
65                  70                  75                  80

Asp Asp Phe Ala Thr Tyr Tyr Cys Gln Gln Tyr Lys Thr Phe Pro His
                85                  90                  95

Thr Phe Gly Gln Gly Thr Lys Leu Asp Phe Lys Arg Thr Val Ala
            100                 105                 110

<210> SEQ ID NO 424
<211> LENGTH: 107
<212> TYPE: PRT
<213> ORGANISM: Artificial Sequence
<220> FEATURE:
<223> OTHER INFORMATION: Synthetic Light chain, clone: G2

<400> SEQUENCE: 424

Val Ile Trp Met Thr Gln Ser Pro Ser Thr Leu Ser Ala Ser Val Gly
1               5                   10                  15

Asp Arg Val Thr Ile Thr Cys Arg Ala Ser Gln Asp Ile Asn Thr Trp
            20                  25                  30

Leu Ala Trp Tyr Gln Gln Lys Pro Gly Lys Ala Pro Lys Leu Leu Met
        35                  40                  45

Phe Lys Val Ser Thr Leu Glu Ser Gly Asp Phe Ser Arg Phe Ser Gly
    50                  55                  60

Ser Gly Ser Gly Thr Glu Phe Thr Leu Thr Val Ser Ser Leu Gln Pro
65                  70                  75                  80

Asp Asp Ser Ala Ile Tyr Tyr Cys Gln Gln Tyr His Ser Tyr Pro Tyr
                85                  90                  95

Thr Phe Gly Gln Gly Thr Arg Leu Glu Ile Lys
            100                 105

<210> SEQ ID NO 425
<211> LENGTH: 107
<212> TYPE: PRT
<213> ORGANISM: Artificial Sequence
<220> FEATURE:
<223> OTHER INFORMATION: Synthetic Light chain, clone: A4

<400> SEQUENCE: 425

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Trp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro

```
                65                  70                  75                  80
Glu Asp Ile Ala Thr Tyr Tyr Cys Gln Gln Tyr Asn Asn Val Leu Arg
                    85                  90                  95

Thr Phe Gly Gln Gly Thr Lys Val Glu Ile Lys
                100                 105

<210> SEQ ID NO 426
<211> LENGTH: 106
<212> TYPE: PRT
<213> ORGANISM: Artificial Sequence
<220> FEATURE:
<223> OTHER INFORMATION: Synthetic Light chain, clone: G4
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 426

Glu Ile Val Met Thr Xaa Ser Pro Ala Thr Leu Ser Val Ser Pro Gly
1               5                   10                  15

Glu Arg Val Thr Leu Ser Cys Arg Val Ser Gln Asn Val Phe Ser Asp
                20                  25                  30

Leu Ala Trp Tyr Gln Arg Lys Thr Gly Gln Ser Pro Arg Leu Leu Ile
            35                  40                  45

His Gly Ala Ser Thr Arg Ala Thr Gly Ile Pro Thr Arg Phe Ser Gly
        50                  55                  60

Ser Gly Ser Gly Thr Glu Phe Thr Leu Thr Ile Ser Ser Leu Xaa Ser
65                  70                  75                  80

Asp Asp Phe Ala Val Tyr Tyr Cys Gln Gln Tyr Asn Lys Trp Pro Thr
                85                  90                  95

Phe Gly Gln Gly Thr Lys Val Glu Ile Lys
                100                 105

<210> SEQ ID NO 427
<211> LENGTH: 112
<212> TYPE: PRT
<213> ORGANISM: Artificial Sequence
<220> FEATURE:
<223> OTHER INFORMATION: Synthetic Light chain, clone: D5

<400> SEQUENCE: 427

Ala Ile Gln Leu Thr Gln Ser Pro Ser Ser Leu Ser Ala Ser Val Gly
1               5                   10                  15

Asp Arg Val Asn Ile Thr Cys Arg Ala Ser Asp Asn Ile Gly Asn Tyr
                20                  25                  30

Leu Asn Trp Tyr Gln His Lys Pro Gly Lys Ala Pro Thr Val Leu Ile
            35                  40                  45

Tyr Ala Ala Ser Thr Leu His Tyr Gly Val Pro Ser Arg Phe Ser Gly
        50                  55                  60

Arg Gly Ser Gly Thr Asp Phe Thr Val Thr Ile Ser Ser Leu Arg Ser
65                  70                  75                  80

Asp Asp Phe Ala Val Tyr Tyr Cys Gln Gln Tyr Tyr Asn Trp Pro Pro
                85                  90                  95

Trp Thr Phe Gly Gln Gly Thr Thr Val Asp Ile Lys Arg Thr Val Ala
                100                 105                 110
```

```
<210> SEQ ID NO 428
<211> LENGTH: 106
<212> TYPE: PRT
<213> ORGANISM: Artificial Sequence
<220> FEATURE:
<223> OTHER INFORMATION: Synthetic Light chain, clone: A1

<400> SEQUENCE: 428

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Tyr Gln Gln Lys Pro Gly Gln Ala Pro Arg Leu Leu Ile
        35                  40                  45

Phe Glu Ala Ser Thr Arg Ala Thr Gly Ile Ser Ala Arg Phe Ser Gly
    50                  55                  60

Ser Gly Ser Gly Thr Asp Phe Thr Leu Thr Ile Ser Thr Leu Glu Pro
65                  70                  75                  80

Glu Asp Phe Ala Val Tyr Tyr Cys Gln Gln Arg Ser Asn Gly Val Thr
                85                  90                  95

Phe Gly Gln Gly Thr Arg Leu Glu Ile Lys
            100                 105

<210> SEQ ID NO 429
<211> LENGTH: 111
<212> TYPE: PRT
<213> ORGANISM: Artificial Sequence
<220> FEATURE:
<223> OTHER INFORMATION: Synthetic Light chain, clone: H2

<400> SEQUENCE: 429

Asp Ile Gln Met Thr Gln Ser Pro Ser Thr Leu Ser Ala Ser Val Gly
1               5                   10                  15

Asp Thr Val Thr Ile Thr Cys Arg Ala Thr Glu Ser Ile Ser Ile Trp
            20                  25                  30

Leu Ala Trp Tyr Gln Gln Glu Pro Gly Lys Ala Pro Asn Leu Leu Val
        35                  40                  45

Ser Gln Ala Ser Ser Leu Lys Thr Gly Val Pro Ser Arg Phe Ser Ala
    50                  55                  60

Ser Gly Ser Gly Thr Glu Phe Thr Leu Thr Ile Ser Ser Leu His Pro
65                  70                  75                  80

Asp Asp Phe Ala Thr Tyr Val Cys Gln His Tyr His Thr Tyr Pro Phe
                85                  90                  95

Thr Phe Gly Pro Gly Thr Lys Val Asp Met Lys Arg Thr Val Ala
            100                 105                 110

<210> SEQ ID NO 430
<211> LENGTH: 116
<212> TYPE: PRT
<213> ORGANISM: Artificial Sequence
<220> FEATURE:
<223> OTHER INFORMATION: Synthetic Light chain, clone: E2
<220> FEATURE:
<221> NAME/KEY: misc_feature
<222> LOCATION: (11)..(11)
<223> OTHER INFORMATION: Xaa can be any naturally occurring amino acid

<400> SEQUENCE: 430

Glu Ile Val Leu Thr Gln Ser Pro Asp Ser Xaa Ala Val Ser Leu Gly
1               5                   10                  15

Glu Arg Ala Thr Ile Asn Cys Lys Ser Ser Gln Ser Val Leu Tyr Ser
```

```
                    20                  25                  30
Ser Asn Asn Lys Asn Tyr Leu Ala Trp Tyr Gln Gln Lys Pro Gly Gln
            35                  40                  45

Pro Pro Arg Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Arg Leu Gln Ala Glu Asp Val Ala Val Tyr Tyr Cys Gln Gln
                85                  90                  95

Tyr Tyr Leu Thr Pro Thr Phe Thr Val Thr Phe Gly Gln Gly Thr Lys
            100                 105                 110

Leu Glu Ile Lys
        115

<210> SEQ ID NO 431
<211> LENGTH: 111
<212> TYPE: PRT
<213> ORGANISM: Artificial Sequence
<220> FEATURE:
<223> OTHER INFORMATION: Synthetic Light chain, clone:  F4

<400> SEQUENCE: 431

Asp Ile Gln Leu Thr Gln Ser Pro Ser Ser Val Ser Ala Ser Val Gly
 1               5                  10                  15

Asp Arg Val Thr Ile Thr Cys Arg Ala Ser Gln Asp Ile Ser Ser Trp
                20                  25                  30

Leu Ala Trp Tyr Gln Gln Lys Pro Gly Lys Ala Pro Lys Phe Leu Ile
            35                  40                  45

Tyr Arg Ala Thr Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Gly Asp Phe Ala Thr Tyr Tyr Cys Gln Gln Thr Asn Thr Phe Pro Leu
                85                  90                  95

Thr Phe Gly Gly Gly Thr Lys Val Glu Val Lys Arg Thr Val Ala
            100                 105                 110

<210> SEQ ID NO 432
<211> LENGTH: 113
<212> TYPE: PRT
<213> ORGANISM: Artificial Sequence
<220> FEATURE:
<223> OTHER INFORMATION: Synthetic Light chain, clone:  C5

<400> SEQUENCE: 432

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Arg Asn Tyr Leu Ala Trp Tyr Gln Lys Lys Pro Gly Gln
            35                  40                  45

Pro Pro Lys Leu Leu Phe Tyr Trp Ala Ser Thr Arg Glu Ser Gly Val
        50                  55                  60

Ser Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95
```

Tyr His Thr Thr Pro Tyr Thr Phe Gly Gln Gly Thr Lys Leu Glu Ile
                100                 105                 110

Lys

<210> SEQ ID NO 433
<211> LENGTH: 111
<212> TYPE: PRT
<213> ORGANISM: Artificial Sequence
<220> FEATURE:
<223> OTHER INFORMATION: Synthetic Light chain, clone: E5

<400> SEQUENCE: 433

Val Ile Trp Met Thr Gln Ser Pro Ser Ser Leu Ser Ala Ser Val Gly
1               5                   10                  15

Asp Arg Val Ser Ile Thr Cys Arg Ala Ser Gln Thr Phe Thr Ser His
            20                  25                  30

Leu Asn Trp Tyr Gln Gln Lys Pro Gly Gln Pro Pro Lys Leu Leu Ile
        35                  40                  45

Phe Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Gly Leu Gln Ala
65                  70                  75                  80

Thr Asp Phe Ala Thr Tyr Tyr Cys Gln Gln Ser Phe Ser Ser Pro Trp
                85                  90                  95

Thr Phe Gly Gln Gly Thr Thr Val Asp Val Lys Gly Thr Val Ala
                100                 105                 110

<210> SEQ ID NO 434
<211> LENGTH: 111
<212> TYPE: PRT
<213> ORGANISM: Artificial Sequence
<220> FEATURE:
<223> OTHER INFORMATION: Synthetic Light chain, clone: F6

<400> SEQUENCE: 434

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asn Val Tyr
            20                  25                  30

Leu Asn Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Thr Gly
    50                  55                  60

Ser Gly Ser Arg Thr Asp Phe Thr Leu Thr Ile Asn Gly Leu Gln Pro
65                  70                  75                  80

Glu Asp Phe Ala Thr Tyr Tyr Cys Gln Gln Ser Phe Thr Thr Leu Val
                85                  90                  95

Thr Phe Gly Pro Gly Thr Arg Val Asp Val Thr Arg Thr Val Ala
                100                 105                 110

<210> SEQ ID NO 435
<211> LENGTH: 111
<212> TYPE: PRT
<213> ORGANISM: Artificial Sequence
<220> FEATURE:
<223> OTHER INFORMATION: Synthetic Light chain, clone: G5

<400> SEQUENCE: 435

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Ser Ser Ser
            20                  25                  30

Leu Ala Trp Tyr Gln Gln Lys Pro Gly Lys Ala Pro Lys Pro Leu Ile
        35                  40                  45

Tyr Asp Ala Ser Thr Leu Gln Thr Gly Val Pro Ser Arg Phe Ser Gly
    50                  55                  60

Arg Ala Ser Gly Thr Asp Phe Thr Leu Thr Ile Asp Ser Leu Gln Pro
65                  70                  75                  80

Glu Asp Phe Ala Thr Tyr Cys Cys Gln Gln Phe Asn Ser Tyr Pro Leu
                85                  90                  95

Ser Phe Gly Gly Gly Thr Lys Val Glu Leu Lys Arg Thr Val Ala
            100                 105                 110

<210> SEQ ID NO 436
<211> LENGTH: 116
<212> TYPE: PRT
<213> ORGANISM: Artificial Sequence
<220> FEATURE:
<223> OTHER INFORMATION: Synthetic Light chain, clone: A5

<400> SEQUENCE: 436

Ser Tyr Glu Leu Thr Gln Pro Pro Ser Ala Ser Ala Ser Leu Gly Ala
1               5                   10                  15

Ser Val Thr Leu Thr Cys Thr Val Ser Ser Gly Tyr Arg Ser Tyr Glu
            20                  25                  30

Val Asp Trp Phe Gln Gln Arg Pro Gly Lys Gly Pro Arg Phe Val Met
        35                  40                  45

Arg Val Gly Thr Gly Gly Ile Val Gly Ser Arg Gly Asp Gly Ile Pro
    50                  55                  60

Asp Arg Phe Ser Val Trp Gly Ser Gly Leu Asn Arg Tyr Leu Thr Ile
65                  70                  75                  80

Glu Asp Ile Gln Glu Glu Asp Glu Ser Asp Tyr Tyr Cys Gly Ala Asp
                85                  90                  95

His Gly Ser Gly Ser Asn Leu Val Tyr Val Phe Gly Thr Gly Thr Lys
            100                 105                 110

Val Thr Val Leu
        115

<210> SEQ ID NO 437
<211> LENGTH: 116
<212> TYPE: PRT
<213> ORGANISM: Artificial Sequence
<220> FEATURE:
<223> OTHER INFORMATION: Synthetic Light chain, clone: D6

<400> SEQUENCE: 437

Gln Leu Val Leu Thr Gln Pro Pro Ser Ala Ser Ala Ser Leu Gly Ala
1               5                   10                  15

Ser Val Thr Leu Thr Cys Thr Leu Ser Ser Asp Tyr Ser Ser Tyr Asn
            20                  25                  30

Val Asp Trp Tyr Gln Gln Arg Pro Gly Met Gly Pro Arg Phe Leu Met
        35                  40                  45

Arg Val Gly Thr Gly Gly Ile Val Gly Ser Arg Gly Asp Gly Ile Pro
    50                  55                  60

Asp Arg Phe Ser Val Lys Gly Ser Gly Leu Asn Arg Tyr Leu Thr Ile
65                  70                  75                  80

Lys Asn Ile Gln Glu Glu Asp Glu Ser Asp Tyr Tyr Cys Gly Ala Asp
```

```
                    85                  90                  95

His Gly Ser Gly Ser Asp Phe Val Tyr Val Phe Gly Ile Gly Thr Lys
                100                 105                 110

Leu Thr Val Leu
        115

<210> SEQ ID NO 438
<211> LENGTH: 110
<212> TYPE: PRT
<213> ORGANISM: Artificial Sequence
<220> FEATURE:
<223> OTHER INFORMATION: Synthetic Light chain, clone: E4

<400> SEQUENCE: 438

Gln Ser Val Leu Thr Gln Pro Pro Ser Ala Ser Gly Thr Pro Gly Gln
1               5                   10                  15

Arg Val Thr Ile Ser Cys Ser Gly Ser Ser Thr Asn Ile Gly Ser Asn
                20                  25                  30

Ala Val Asn Trp Tyr Gln Gln Leu Pro Arg Thr Ala Pro Lys Leu Leu
            35                  40                  45

Ile Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asn Tyr Tyr Cys Ala Ala Trp Asp Asp Ser Leu
                85                  90                  95

Asn Gly Pro Val Phe Gly Gly Gly Thr Gln Leu Thr Val Leu
                100                 105                 110

<210> SEQ ID NO 439
<211> LENGTH: 110
<212> TYPE: PRT
<213> ORGANISM: Artificial Sequence
<220> FEATURE:
<223> OTHER INFORMATION: Synthetic Light chain, clone: F5

<400> SEQUENCE: 439

Gln Ser Val Leu Thr Gln Pro Pro Ser Ala Ser Gly Thr Pro Gly Gln
1               5                   10                  15

Thr Val Ile Ile Ser Cys Ser Gly Gly Gly Ser Asn Ile Gly Ser Asn
                20                  25                  30

Phe Gly Tyr Trp Tyr Gln Gln Phe Pro Gly Thr Ala Pro Lys Leu Leu
            35                  40                  45

Ile Tyr Thr Thr Asp Arg Arg Pro Ser Gly Val Pro Asp Arg Phe Ser
        50                  55                  60

Gly Ser Lys Ser Gly Thr Thr Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Pro Val Phe Gly Gly Gly Thr Gln Leu Thr Val Leu
                100                 105                 110

<210> SEQ ID NO 440
<211> LENGTH: 112
<212> TYPE: PRT
<213> ORGANISM: Artificial Sequence
<220> FEATURE:
<223> OTHER INFORMATION: Synthetic Light chain, clone: G1

<400> SEQUENCE: 440
```

```
Gln Thr Val Val Thr Gln Pro Pro Ser Val Ser Gly Thr Pro Gly Gln
1               5                   10                  15

Arg Val Thr Ile Ser Cys Ser Gly Ser Ser Asn Ile Gly Ser Asn
            20                  25                  30

Ser Val Asp Trp Tyr Gln Gln Phe Pro Gly Ser Ala Pro Lys Leu Leu
        35                  40                  45

Ile Tyr Thr Thr Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Leu
                85                  90                  95

Ser Asn Pro Lys Trp Val Phe Gly Gly Gly Thr Lys Leu Thr Val Leu
            100                 105                 110
```

<210> SEQ ID NO 441
<211> LENGTH: 112
<212> TYPE: PRT
<213> ORGANISM: Artificial Sequence
<220> FEATURE:
<223> OTHER INFORMATION: Synthetic Light chain, clone: E3

<400> SEQUENCE: 441

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Ser Trp Thr Phe Gly Gln Gly Thr Lys Leu Glu Ile Lys
            100                 105                 110
```

<210> SEQ ID NO 442
<211> LENGTH: 114
<212> TYPE: PRT
<213> ORGANISM: Artificial Sequence
<220> FEATURE:
<223> OTHER INFORMATION: Synthetic Light chain, clone: A2

<400> SEQUENCE: 442

```
Asp Ile Cys Arg Ile Arg Pro Leu Ile Arg Leu Thr Ile Gly Thr Ile
1               5                   10                  15

Thr Ile Tyr Asn Tyr Asn Gly Cys Cys Asp Asp Thr Val Ser Thr Leu
            20                  25                  30

Pro Ala Arg His Pro Trp Thr Ala Gly Leu His Leu Gln Ser Pro Arg
        35                  40                  45

Arg Leu Met Tyr Gln Val Ser Thr Arg Asp Ser Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Glu Asp Val Gly Val Tyr Tyr Cys Met Gln Gly Thr His
```

85                  90                  95

Trp Pro Tyr Thr Phe Gly Gln Gly Thr Lys Leu Glu Ile Arg Arg Thr
                100                 105                 110

Val Ala

<210> SEQ ID NO 443
<211> LENGTH: 112
<212> TYPE: PRT
<213> ORGANISM: Artificial Sequence
<220> FEATURE:
<223> OTHER INFORMATION: Synthetic Light chain, clone: D1

<400> SEQUENCE: 443

Asp Ile Val Met Thr Gln Thr Pro Leu Ser Leu Ser Val Thr Pro Gly
1               5                   10                  15

Gln Pro Ala Ala Ile Ser Cys Lys Ser Ser Gln Ser Leu Val His Arg
                20                  25                  30

Asp Gly Lys Thr Tyr Leu Tyr Trp Tyr Leu Gln Lys Pro Gly His Ser
            35                  40                  45

Pro Gln Leu Leu Val Tyr Glu Ala Ser Ser Arg Phe Ser Gly Val Pro
        50                  55                  60

Asp Arg Ile Ser Gly Ser Ala Ser Gly Thr Gln Phe Thr Leu Asn Ile
65                  70                  75                  80

Ser Arg Val Glu Ala Glu Asp Val Gly Leu Tyr Tyr Cys Met Gln Ser
                85                  90                  95

Arg Asn Leu Pro Lys Thr Phe Gly Gln Gly Thr Lys Val Glu Ile Lys
                100                 105                 110

<210> SEQ ID NO 444
<211> LENGTH: 108
<212> TYPE: PRT
<213> ORGANISM: Artificial Sequence
<220> FEATURE:
<223> OTHER INFORMATION: Synthetic Light chain, clone: C4

<400> SEQUENCE: 444

Ser Tyr Glu Leu Thr Gln Pro Thr Ser Leu Ser Ala Ser Pro Gly Ala
1               5                   10                  15

Ser Ala Ser Leu Thr Cys Thr Leu Ser Ser Gly Phe Asn Val Val Ser
                20                  25                  30

Tyr Asn Ile Tyr Trp Tyr Gln Gln Lys Pro Gly Ser Pro Pro Gln Tyr
            35                  40                  45

Leu Leu Arg Tyr Arg Ser Asp Ser Asp Arg His Gln Gly Ser Gly Val
        50                  55                  60

Pro Ser Arg Phe Ser Gly Ser Lys Asp Ala Ser Ala Asn Ala Gly Ile
65                  70                  75                  80

Leu Val Ile Ser Ala Leu Gln Ser Asp Glu Ala Asp Tyr Tyr Cys
                85                  90                  95

Met Val Trp Tyr Ser Ala Trp Val Phe Gly Gly Gly
                100                 105

<210> SEQ ID NO 445
<211> LENGTH: 107
<212> TYPE: PRT
<213> ORGANISM: Artificial Sequence
<220> FEATURE:
<223> OTHER INFORMATION: Synthetic Light chain, clone: E1

<400> SEQUENCE: 445

Ser Tyr Glu Leu Thr Gln Pro Leu Ser Val Ser Ala Leu Gly Gln
1               5                   10                  15

Thr Ala Thr Ile Thr Cys Ala Gly Asn Asn Ile Gly Thr Tyr Tyr Val
            20                  25                  30

His Trp Tyr Gln Gln Arg Pro Gly Gln Ala Pro Val Leu Val Met Tyr
        35                  40                  45

Arg Asp Thr Asn Arg Pro Ser Gly Ile Ser Asp Arg Phe Ser Gly Ser
    50                  55                  60

Asn Ser Gly Asp Thr Ala Thr Leu Thr Ile Cys Gly Val Gln Val Gly
65                  70                  75                  80

Asp Glu Ala Asp Tyr Tyr Cys His Val Leu Asp Ser Ser Thr Ile Val
                85                  90                  95

Ile Phe Gly Gly Gly Thr Gln Leu Thr Val Leu
                100                 105

<210> SEQ ID NO 446
<211> LENGTH: 108
<212> TYPE: PRT
<213> ORGANISM: Artificial Sequence
<220> FEATURE:
<223> OTHER INFORMATION: Synthetic Light chain, clone: A6

<400> SEQUENCE: 446

Gln Ser Val Leu Thr Gln Ser Pro Ala Thr Leu Ser Val Ser Pro Gly
1               5                   10                  15

Glu Arg Ala Ser Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Asn Asn Trp Pro Leu
                85                  90                  95

Tyr Thr Phe Gly Gln Gly Thr Lys Leu Thr Val Leu
                100                 105

<210> SEQ ID NO 447
<211> LENGTH: 108
<212> TYPE: PRT
<213> ORGANISM: Artificial Sequence
<220> FEATURE:
<223> OTHER INFORMATION: Synthetic Light chain, clone: H1

<400> SEQUENCE: 447

Gln Ser Val Leu Thr Gln Asp Pro Ala Val Pro Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Leu Leu Val Ile Tyr
        35                  40                  45

Gly Lys Asn Thr Arg Pro Ser Gly Ile Pro Val Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Tyr Leu
                85                  90                  95

Leu Leu Phe Gly Thr Gly Thr Lys Leu Thr Val Leu
            100                 105

<210> SEQ ID NO 448
<211> LENGTH: 109
<212> TYPE: PRT
<213> ORGANISM: Artificial Sequence
<220> FEATURE:
<223> OTHER INFORMATION: Synthetic Light chain, clone: B2

<400> SEQUENCE: 448

Gln Ala Val Leu Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Ala Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Gly Val Phe Gly Thr Gly Thr Lys Val Thr Val Leu
            100                 105

<210> SEQ ID NO 449
<211> LENGTH: 111
<212> TYPE: PRT
<213> ORGANISM: Artificial Sequence
<220> FEATURE:
<223> OTHER INFORMATION: Synthetic Light chain, clone: C2

<400> SEQUENCE: 449

Asp Ile Gln Met Thr Gln Ser Pro Ser Ser Leu Ser Ala Ser Val Gly
1               5                   10                  15

Asp Arg Val Ala Ile Ala Cys Arg Pro Ser Gln Asp Ile Gly Thr Asp
            20                  25                  30

Leu Gly Trp Tyr Gln Gln Lys Pro Gly Lys Ala Pro Lys Leu Leu Ile
        35                  40                  45

Phe Asp Ser Ser Thr Leu Gln Ser Gly Val Pro Ser Arg Phe Ser Gly
    50                  55                  60

Ser Leu Ser Gly Thr Asp Phe Ile Leu Thr Ile Thr Asn Leu Gln Pro
65                  70                  75                  80

Glu Asp Phe Ala Thr Tyr Tyr Cys Leu Gln Asp Tyr Ser Phe Pro Tyr
                85                  90                  95

Thr Phe Gly Gln Gly Thr Lys Leu Gln Ile Lys Arg Thr Val Ala
            100                 105                 110

<210> SEQ ID NO 450
<211> LENGTH: 106
<212> TYPE: PRT
<213> ORGANISM: Artificial Sequence
<220> FEATURE:
<223> OTHER INFORMATION: Synthetic Light chain, clone: G3

<400> SEQUENCE: 450

Ser Tyr Val Leu Thr Gln Pro Pro Ser Val Ser Val Ser Pro Gly Gln
1               5                   10                  15

```
Thr Ala Ser Ile Thr Cys Ser Gly Asp Glu Leu Lys Tyr Lys Tyr Thr
            20                  25                  30

Cys Trp Tyr His Gln Lys Pro Gly Gln Ser Pro Val Leu Leu Ile Tyr
        35                  40                  45

Gln Asp Thr Lys Arg Pro Ser Gly Ile Pro Glu Arg Phe Ser Gly Ser
 50                  55                  60

Arg Ser Glu Asn Thr Ala Thr Leu Thr Ile Ser Gly Thr Gln Ala Met
 65              70                  75                  80

Asp Glu Ala Asp Tyr Tyr Cys Gln Ala Trp Asp Ser Ser His Ala Val
                85                  90                  95

Phe Gly Arg Gly Thr Gln Leu Thr Val Leu
            100                 105

<210> SEQ ID NO 451
<211> LENGTH: 107
<212> TYPE: PRT
<213> ORGANISM: Artificial Sequence
<220> FEATURE:
<223> OTHER INFORMATION: Synthetic Light chain, clone: H3

<400> SEQUENCE: 451

His Ser Tyr Val Leu Thr Gln Pro Pro Ser Val Ser Val Phe Pro Gly
 1               5                  10                  15

Gln Thr Ala Arg Ile Thr Cys Ser Gly Ser Thr Phe Pro Lys Leu Tyr
            20                  25                  30

Ser Phe Trp Tyr Gln Gln Lys Thr Gly Gln Ala Pro Leu Leu Val Ile
        35                  40                  45

Tyr Lys Asp Thr Glu Arg Pro Ser Gly Ile Pro Glu Arg Phe Ser Gly
 50                  55                  60

Ser Thr Ser Gly Thr Thr Val Thr Leu Ile Ile Ser Gly Val Gln Pro
 65              70                  75                  80

Glu Asp Asp Ala Asp Tyr Tyr Cys Gln Ser Glu Asp Ser Arg Gly Pro
                85                  90                  95

Val Phe Gly Gly Gly Thr Lys Val Thr Val Leu
            100                 105

<210> SEQ ID NO 452
<211> LENGTH: 112
<212> TYPE: PRT
<213> ORGANISM: Artificial Sequence
<220> FEATURE:
<223> OTHER INFORMATION: Synthetic Light chain, clone: D4

<400> SEQUENCE: 452

Gly Val Val Met Thr Gln Thr Pro Leu Ser Ser Leu Val Thr Leu Gly
 1               5                  10                  15

Gln Pro Ala Ser Ile Ser Cys Arg Ser Ser Glu Ser Val Val His Asp
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
 65              70                  75                  80

Ser Arg Val Glu Pro Glu Asp Val Gly Val Tyr Tyr Cys Val Gln Ala
                85                  90                  95

Thr His Phe Pro Val Thr Phe Gly Gly Gly Thr Arg Val Glu Ile Lys
            100                 105                 110
```

<210> SEQ ID NO 453
<211> LENGTH: 111
<212> TYPE: PRT
<213> ORGANISM: Artificial Sequence
<220> FEATURE:
<223> OTHER INFORMATION: Synthetic Light chain, clone: C6

<400> SEQUENCE: 453

Gln Ser Ala Leu Thr Gln Pro Ala Ser Val Ser Ala Ser Pro Gly Gln
1               5                   10                  15

Ser Val Thr Ile Ser Cys Thr Gly Thr Ser Asp Asp Val Gly Arg Tyr
            20                  25                  30

Asp Tyr Val Ser Trp Tyr Gln Gln His Pro Gly Gly Ala Pro Lys Leu
        35                  40                  45

Ile Leu Tyr Asp Val Asn Arg Arg Pro Ser Gly Val Ser Asp Arg Phe
    50                  55                  60

Ser Gly Ser Lys Ser Ala Asn Lys Ala Ser Leu Thr Ile Ser Gly Leu
65                  70                  75                  80

Gln Ala Asp Asp Glu Gly Asp Tyr Tyr Cys Cys Ser Tyr Thr Thr Gly
                85                  90                  95

Ser Thr Leu Tyr Leu Phe Gly Thr Gly Thr Gln Leu Thr Val Leu
            100                 105                 110

<210> SEQ ID NO 454
<211> LENGTH: 18
<212> TYPE: DNA
<213> ORGANISM: Artificial Sequence
<220> FEATURE:
<223> OTHER INFORMATION: Synthetic Oligonucleotide: FR3 Reverse

<400> SEQUENCE: 454
cgcacagtaa tacacggc                                                 18

<210> SEQ ID NO 455
<211> LENGTH: 46
<212> TYPE: DNA
<213> ORGANISM: Artificial Sequence
<220> FEATURE:
<223> OTHER INFORMATION: Synthetic Oligonucleotide: VH1a

<400> SEQUENCE: 455
caattactat ttacaattac aatgcaggtk cagctggtgc agtctg                  46

<210> SEQ ID NO 456
<211> LENGTH: 46
<212> TYPE: DNA
<213> ORGANISM: Artificial Sequence
<220> FEATURE:
<223> OTHER INFORMATION: Synthetic Oligonucleotide: VH1b

<400> SEQUENCE: 456
caattactat ttacaattac aatgcaggtc cagcttgtgc agtctg                  46

<210> SEQ ID NO 457
<211> LENGTH: 46
<212> TYPE: DNA
<213> ORGANISM: Artificial Sequence
<220> FEATURE:
<223> OTHER INFORMATION: Synthetic Oligonucleotide: VH1c

<400> SEQUENCE: 457
caattactat ttacaattac aatgsaggtc cagctggtac agtctg                  46

<210> SEQ ID NO 458
<211> LENGTH: 46
<212> TYPE: DNA
<213> ORGANISM: Artificial Sequence
<220> FEATURE:
<223> OTHER INFORMATION: Synthetic Oligonucleotide: VH1d

<400> SEQUENCE: 458
caattactat ttacaattac aatgcaratg cagctggtgc agtctg          46

<210> SEQ ID NO 459
<211> LENGTH: 46
<212> TYPE: DNA
<213> ORGANISM: Artificial Sequence
<220> FEATURE:
<223> OTHER INFORMATION: Synthetic Oligonucleotide: VH2

<400> SEQUENCE: 459
caattactat ttacaattac aatgcagrtc accttgaagg agtctg          46

<210> SEQ ID NO 460
<211> LENGTH: 46
<212> TYPE: DNA
<213> ORGANISM: Artificial Sequence
<220> FEATURE:
<223> OTHER INFORMATION: Synthetic Oligonucleotide: VH3a

<400> SEQUENCE: 460
caattactat ttacaattac aatggargtg cagctggtgg agtctg          46

<210> SEQ ID NO 461
<211> LENGTH: 46
<212> TYPE: DNA
<213> ORGANISM: Artificial Sequence
<220> FEATURE:
<223> OTHER INFORMATION: Synthetic Oligonucleotide: VH3b

<400> SEQUENCE: 461
caattactat ttacaattac aatgcaggtg cagctggtgg agtctg          46

<210> SEQ ID NO 462
<211> LENGTH: 46
<212> TYPE: DNA
<213> ORGANISM: Artificial Sequence
<220> FEATURE:
<223> OTHER INFORMATION: Synthetic Oligonucleotide: VH3c

<400> SEQUENCE: 462
caattactat ttacaattac aatggaggtg cagctgttgg agtctg          46

<210> SEQ ID NO 463
<211> LENGTH: 42
<212> TYPE: DNA
<213> ORGANISM: Artificial Sequence
<220> FEATURE:
<223> OTHER INFORMATION: Synthetic Oligonucleotide: VH4a

<400> SEQUENCE: 463
caattactat ttacaattac aatgcagstg cagctgcagg ag              42

<210> SEQ ID NO 464
<211> LENGTH: 45
<212> TYPE: DNA
<213> ORGANISM: Artificial Sequence
<220> FEATURE:

```
<223> OTHER INFORMATION: Synthetic Oligonucleotide: VH4b

<400> SEQUENCE: 464
caattactat ttacaattac aatgcaggtg cagctacagc agtgg          45

<210> SEQ ID NO 465
<211> LENGTH: 46
<212> TYPE: DNA
<213> ORGANISM: Artificial Sequence
<220> FEATURE:
<223> OTHER INFORMATION: Synthetic Oligonucleotide: VH5

<400> SEQUENCE: 465
caattactat ttacaattac aatggargtg cagctggtgc agtctg         46

<210> SEQ ID NO 466
<211> LENGTH: 46
<212> TYPE: DNA
<213> ORGANISM: Artificial Sequence
<220> FEATURE:
<223> OTHER INFORMATION: Synthetic Oligonucleotide: VH6

<400> SEQUENCE: 466
caattactat ttacaattac aatgcaggta cagctgcagc agtcag         46

<210> SEQ ID NO 467
<211> LENGTH: 46
<212> TYPE: DNA
<213> ORGANISM: Artificial Sequence
<220> FEATURE:
<223> OTHER INFORMATION: Synthetic Oligonucleotide: VH7

<400> SEQUENCE: 467
caattactat ttacaattac aatgcaggtg cagctggtgc aatctg         46

<210> SEQ ID NO 468
<211> LENGTH: 42
<212> TYPE: DNA
<213> ORGANISM: Artificial Sequence
<220> FEATURE:
<223> OTHER INFORMATION: Synthetic Oligonucleotide: T7TMVUTR

<400> SEQUENCE: 468
taatacgact cactataggg acaattacta tttacaatta ca             42

<210> SEQ ID NO 469
<211> LENGTH: 75
<212> TYPE: DNA
<213> ORGANISM: Artificial Sequence
<220> FEATURE:
<223> OTHER INFORMATION: Synthetic Oligonucleotide: XB1511 FR3CDR3FR4
      Reverse

<400> SEQUENCE: 469
tgaggagacg gtgaccaggg ttccctggcc ccagtagctc ctgtcgcccc catgtktcgc   60
acagtaatac acggc                                                   75

<210> SEQ ID NO 470
<211> LENGTH: 39
<212> TYPE: DNA
<213> ORGANISM: Artificial Sequence
<220> FEATURE:
<223> OTHER INFORMATION: Synthetic Oligonucleotide: FR4 Cu3 Reverse

<400> SEQUENCE: 470
```

```
ggagacgagg gggaaaaggg ttgaggagac ggtgaccag                           39

<210> SEQ ID NO 471
<211> LENGTH: 87
<212> TYPE: DNA
<213> ORGANISM: Artificial Sequence
<220> FEATURE:
<223> OTHER INFORMATION: Synthetic Oligonucleotide: Y109

<400> SEQUENCE: 471
tttttttttt tttttttttt aaatagcgga tgctaaggac gacttgtcgt cgtcgtcctt   60
gtagtcggag acgaggggga aagggt                                        87

<210> SEQ ID NO 472
<211> LENGTH: 21
<212> TYPE: DNA
<213> ORGANISM: Artificial Sequence
<220> FEATURE:
<223> OTHER INFORMATION: Synthetic Oligonucleotide: Ck1

<400> SEQUENCE: 472
caactgctca tcagatggcg g                                             21

<210> SEQ ID NO 473
<211> LENGTH: 21
<212> TYPE: DNA
<213> ORGANISM: Artificial Sequence
<220> FEATURE:
<223> OTHER INFORMATION: Synthetic Oligonucleotide: Cl1

<400> SEQUENCE: 473
cagtgtggcc ttgttggctt g                                             21

<210> SEQ ID NO 474
<211> LENGTH: 21
<212> TYPE: DNA
<213> ORGANISM: Artificial Sequence
<220> FEATURE:
<223> OTHER INFORMATION: Synthetic Oligonucleotide: Ck2

<400> SEQUENCE: 474
agatggtgca gccacagttc g                                             21

<210> SEQ ID NO 475
<211> LENGTH: 41
<212> TYPE: DNA
<213> ORGANISM: Artificial Sequence
<220> FEATURE:
<223> OTHER INFORMATION: Synthetic Oligonucleotide: Jl1-3Ck2

<400> SEQUENCE: 475
agatggtgca gccacagttc gtagacggts ascttggtcc c                       41

<210> SEQ ID NO 476
<211> LENGTH: 41
<212> TYPE: DNA
<213> ORGANISM: Artificial Sequence
<220> FEATURE:
<223> OTHER INFORMATION: Synthetic Oligonucleotide: Jl7Ck2

<400> SEQUENCE: 476
agatggtgca gccacagttc ggagacggtc agctgggtgc c                       41

<210> SEQ ID NO 477
<211> LENGTH: 42
```

```
<212> TYPE: DNA
<213> ORGANISM: Artificial Sequence
<220> FEATURE:
<223> OTHER INFORMATION: Synthetic Oligonucleotide: T7TMVUTR

<400> SEQUENCE: 477
taatacgact cactataggg acaattacta tttacaatta ca                              42

<210> SEQ ID NO 478
<211> LENGTH: 42
<212> TYPE: DNA
<213> ORGANISM: Artificial Sequence
<220> FEATURE:
<223> OTHER INFORMATION: Synthetic Oligonucleotide: UTRVk1a

<400> SEQUENCE: 478
caattactat ttacaattac aatgracatc cagatgaccc ag                              42

<210> SEQ ID NO 479
<211> LENGTH: 42
<212> TYPE: DNA
<213> ORGANISM: Artificial Sequence
<220> FEATURE:
<223> OTHER INFORMATION: Synthetic Oligonucleotide: UTRVk1b

<400> SEQUENCE: 479
caattactat ttacaattac aatggmcatc cagttgaccc ag                              42

<210> SEQ ID NO 480
<211> LENGTH: 42
<212> TYPE: DNA
<213> ORGANISM: Artificial Sequence
<220> FEATURE:
<223> OTHER INFORMATION: Synthetic Oligonucleotide: UTRVk1c

<400> SEQUENCE: 480
caattactat ttacaattac aatggccatc crgatgaccc ag                              42

<210> SEQ ID NO 481
<211> LENGTH: 42
<212> TYPE: DNA
<213> ORGANISM: Artificial Sequence
<220> FEATURE:
<223> OTHER INFORMATION: Synthetic Oligonucleotide: UTRVk1d

<400> SEQUENCE: 481
caattactat ttacaattac aatggtcatc tggatgaccc ag                              42

<210> SEQ ID NO 482
<211> LENGTH: 42
<212> TYPE: DNA
<213> ORGANISM: Artificial Sequence
<220> FEATURE:
<223> OTHER INFORMATION: Synthetic Oligonucleotide: UTRVk2a

<400> SEQUENCE: 482
caattactat ttacaattac aatggatatt gtgatgaccc ag                              42

<210> SEQ ID NO 483
<211> LENGTH: 42
<212> TYPE: DNA
<213> ORGANISM: Artificial Sequence
<220> FEATURE:
<223> OTHER INFORMATION: Synthetic Oligonucleotide: UTRVk2b

<400> SEQUENCE: 483
```
caattactat ttacaattac aatggatrtt gtgatgactc ag         42

<210> SEQ ID NO 484
<211> LENGTH: 42
<212> TYPE: DNA
<213> ORGANISM: Artificial Sequence
<220> FEATURE:
<223> OTHER INFORMATION: Synthetic Oligonucleotide: UTRVk3a

<400> SEQUENCE: 484
caattactat ttacaattac aatggaaatt gtgttgacrc ag         42

<210> SEQ ID NO 485
<211> LENGTH: 42
<212> TYPE: DNA
<213> ORGANISM: Artificial Sequence
<220> FEATURE:
<223> OTHER INFORMATION: Synthetic Oligonucleotide: UTRVk3b

<400> SEQUENCE: 485
caattactat ttacaattac aatggaaata gtgatgacgc ag         42

<210> SEQ ID NO 486
<211> LENGTH: 42
<212> TYPE: DNA
<213> ORGANISM: Artificial Sequence
<220> FEATURE:
<223> OTHER INFORMATION: Synthetic Oligonucleotide: UTRVk3c

<400> SEQUENCE: 486
caattactat ttacaattac aatggaaatt gtaatgacac ag         42

<210> SEQ ID NO 487
<211> LENGTH: 42
<212> TYPE: DNA
<213> ORGANISM: Artificial Sequence
<220> FEATURE:
<223> OTHER INFORMATION: Synthetic Oligonucleotide: UTRVk4a

<400> SEQUENCE: 487
caattactat ttacaattac aatggacatc gtgatgaccc ag         42

<210> SEQ ID NO 488
<211> LENGTH: 42
<212> TYPE: DNA
<213> ORGANISM: Artificial Sequence
<220> FEATURE:
<223> OTHER INFORMATION: Synthetic Oligonucleotide: UTRVk5a

<400> SEQUENCE: 488
caattactat ttacaattac aatggaaacg acactcacgc ag         42

<210> SEQ ID NO 489
<211> LENGTH: 42
<212> TYPE: DNA
<213> ORGANISM: Artificial Sequence
<220> FEATURE:
<223> OTHER INFORMATION: Synthetic Oligonucleotide: UTRVk6a

<400> SEQUENCE: 489
caattactat ttacaattac aatggaaatt gtgctgactc ag         42

<210> SEQ ID NO 490
<211> LENGTH: 42
<212> TYPE: DNA
<213> ORGANISM: Artificial Sequence
<220> FEATURE:
<223> OTHER INFORMATION: Synthetic Oligonucleotide: UTRVk6b

<400> SEQUENCE: 490
caattactat ttacaattac aatggatgtt gtgatgacac ag        42

<210> SEQ ID NO 491
<211> LENGTH: 42
<212> TYPE: DNA
<213> ORGANISM: Artificial Sequence
<220> FEATURE:
<223> OTHER INFORMATION: Synthetic Oligonucleotide: UTRVL1a

<400> SEQUENCE: 491
caattactat ttacaattac aatgcagtct gtgctgackc ag        42

<210> SEQ ID NO 492
<211> LENGTH: 42
<212> TYPE: DNA
<213> ORGANISM: Artificial Sequence
<220> FEATURE:
<223> OTHER INFORMATION: Synthetic Oligonucleotide: UTRVL1b

<400> SEQUENCE: 492
caattactat ttacaattac aatgcagtct gtgytgacgc ag        42

<210> SEQ ID NO 493
<211> LENGTH: 42
<212> TYPE: DNA
<213> ORGANISM: Artificial Sequence
<220> FEATURE:
<223> OTHER INFORMATION: Synthetic Oligonucleotide: UTRVL2

<400> SEQUENCE: 493
caattactat ttacaattac aatgcagtct gccctgactc ag        42

<210> SEQ ID NO 494
<211> LENGTH: 42
<212> TYPE: DNA
<213> ORGANISM: Artificial Sequence
<220> FEATURE:
<223> OTHER INFORMATION: Synthetic Oligonucleotide: UTRVL3a

<400> SEQUENCE: 494
caattactat ttacaattac aatgtcctat gwgctgactc ag        42

<210> SEQ ID NO 495
<211> LENGTH: 42
<212> TYPE: DNA
<213> ORGANISM: Artificial Sequence
<220> FEATURE:
<223> OTHER INFORMATION: Synthetic Oligonucleotide: UTRVL3b

<400> SEQUENCE: 495
caattactat ttacaattac aatgtcctat gagctgacac ag        42

<210> SEQ ID NO 496
<211> LENGTH: 42
<212> TYPE: DNA
<213> ORGANISM: Artificial Sequence
<220> FEATURE:
<223> OTHER INFORMATION: Synthetic Oligonucleotide: UTRVL3c

<400> SEQUENCE: 496
caattactat ttacaattac aatgtcttct gagctgactc ag        42

<210> SEQ ID NO 497
<211> LENGTH: 42
<212> TYPE: DNA
<213> ORGANISM: Artificial Sequence
<220> FEATURE:
<223> OTHER INFORMATION: Synthetic Oligonucleotide: UTRVL3d

<400> SEQUENCE: 497
caattactat ttacaattac aatgtcctat gagctgatgc ag     42

<210> SEQ ID NO 498
<211> LENGTH: 42
<212> TYPE: DNA
<213> ORGANISM: Artificial Sequence
<220> FEATURE:
<223> OTHER INFORMATION: Synthetic Oligonucleotide: UTRVL4

<400> SEQUENCE: 498
caattactat ttacaattac aatgcagcyt gtgctgactc aa     42

<210> SEQ ID NO 499
<211> LENGTH: 42
<212> TYPE: DNA
<213> ORGANISM: Artificial Sequence
<220> FEATURE:
<223> OTHER INFORMATION: Synthetic Oligonucleotide: UTRVL5

<400> SEQUENCE: 499
caattactat ttacaattac aatgcagsct gtgctgactc ag     42

<210> SEQ ID NO 500
<211> LENGTH: 42
<212> TYPE: DNA
<213> ORGANISM: Artificial Sequence
<220> FEATURE:
<223> OTHER INFORMATION: Synthetic Oligonucleotide: UTRVL6

<400> SEQUENCE: 500
caattactat ttacaattac aatgaatttt atgctgactc ag     42

<210> SEQ ID NO 501
<211> LENGTH: 42
<212> TYPE: DNA
<213> ORGANISM: Artificial Sequence
<220> FEATURE:
<223> OTHER INFORMATION: Synthetic Oligonucleotide: UTRVL7

<400> SEQUENCE: 501
caattactat ttacaattac aatgcagrct gtggtgactc ag     42

<210> SEQ ID NO 502
<211> LENGTH: 42
<212> TYPE: DNA
<213> ORGANISM: Artificial Sequence
<220> FEATURE:
<223> OTHER INFORMATION: Synthetic Oligonucleotide: UTRVL8

<400> SEQUENCE: 502
caattactat ttacaattac aatgcagact gtggtgaccc ag     42

<210> SEQ ID NO 503
<211> LENGTH: 42
<212> TYPE: DNA
<213> ORGANISM: Artificial Sequence
<220> FEATURE:
<223> OTHER INFORMATION: Synthetic Oligonucleotide: UTRVL4/9

<400> SEQUENCE: 503
caattactat ttacaattac aatgcwgcct gtgctgactc ag         42

<210> SEQ ID NO 504
<211> LENGTH: 42
<212> TYPE: DNA
<213> ORGANISM: Artificial Sequence
<220> FEATURE:
<223> OTHER INFORMATION: Synthetic Oligonucleotide: UTRVL10

<400> SEQUENCE: 504
caattactat ttacaattac aatgcaggca gggctgactc ag         42

<210> SEQ ID NO 505
<211> LENGTH: 464
<212> TYPE: PRT
<213> ORGANISM: Artificial Sequence
<220> FEATURE:
<223> OTHER INFORMATION: Synthetic Antibody chain: XB1511 IgG1

<400> SEQUENCE: 505

Gly Trp Ser Leu Ile Leu Leu Phe Leu Val Ala Val Ala Thr Arg Val
1               5                   10                  15

Leu Ser Gln Val Gln Leu Val Gln Ser Gly Ala Glu Val Lys Lys Pro
            20                  25                  30

Gly Ser Ser Val Lys Val Ser Cys Lys Ala Ser Gly Gly Thr Phe Ser
        35                  40                  45

Ser Tyr Ala Ile Ser Trp Val Arg Gln Ala Pro Gly Gln Gly Leu Glu
    50                  55                  60

Trp Met Gly Gly Ile Ile Pro Ile Phe Gly Thr Ala Asn Tyr Ala Gln
65                  70                  75                  80

Lys Phe Gln Gly Arg Val Thr Ile Thr Ala Asp Glu Ser Thr Ser Thr
                85                  90                  95

Ala Tyr Met Glu Leu Ser Ser Leu Arg Ser Glu Asp Thr Ala Val Tyr
            100                 105                 110

Tyr Cys Ala Ile His Gly Gly Asp Arg Ser Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro

```
            275                 280                 285
Glu Val Lys Phe Asn Trp Tyr Val Asp Gly Val Glu Val His Asn Ala
290                 295                 300
Lys Thr Lys Pro Arg Glu Glu Gln Tyr Asn Ser Thr Tyr Arg Val Val
305                 310                 315                 320
Ser Val Leu Thr Val Leu His Gln Asp Trp Leu Asn Gly Lys Glu Tyr
            325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
            355                 360                 365
Pro Pro Ser Arg Asp Glu Leu Thr Lys Asn Gln Val Ser Leu Thr Cys
370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
            405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
            435                 440                 445
Leu His Asn His Tyr Thr Gln Lys Ser Leu Ser Leu Ser Pro Gly Lys
            450                 455                 460

<210> SEQ ID NO 506
<211> LENGTH: 262
<212> TYPE: PRT
<213> ORGANISM: Artificial Sequence
<220> FEATURE:
<223> OTHER INFORMATION: Synthetic Antibody chain: D8 Ckappa

<400> SEQUENCE: 506

Asp Phe Gln Val Gln Ile Ile Ser Phe Leu Leu Ile Ser Ala Ser Val
1               5                   10                  15
Ile Met Ser Arg Gly Glu Ile Val Met Thr Gln Ser Pro Gly Thr Leu
            20                  25                  30
Thr Leu Ser Pro Gly Glu Gly Ala Thr Leu Ser Cys Arg Ala Ser Gln
        35                  40                  45
Ser Val Thr Ser Asn Tyr Leu Ala Trp Tyr Gln Gln Arg Pro Gly Gln
    50                  55                  60
Ala Pro Arg Leu Leu Ile Tyr Asp Ala Ser Asn Arg Ala Thr Gly Ile
65                  70                  75                  80
Pro Asp Arg Phe Ser Gly Ser Gly Phe Gly Thr Asp Phe Thr Leu Thr
                85                  90                  95
Ile Ser Arg Leu Glu Pro Glu Asp Phe Ala Val Tyr Tyr Cys Gln Gln
            100                 105                 110
Tyr Val Asn Ser Arg Thr Phe Gly Gln Gly Thr Lys Val Glu Ile Lys
        115                 120                 125
Arg Thr Val Ala Ala Pro Ser Val Phe Ile Phe Pro Pro Ser Asp Glu
    130                 135                 140
Gln Leu Lys Ser Gly Thr Lys Val Glu Ile Lys Arg Thr Val Ala Ala
145                 150                 155                 160
Pro Ser Val Phe Ile Phe Pro Pro Ser Asp Glu Gln Leu Lys Ser Gly
                165                 170                 175
Thr Ala Ser Val Val Cys Leu Leu Asn Asn Phe Tyr Pro Arg Glu Ala
```

```
                180                 185                 190
Lys Val Gln Trp Lys Val Asp Asn Ala Leu Gln Ser Gly Asn Ser Gln
            195                 200                 205

Glu Ser Val Thr Glu Gln Asp Ser Lys Asp Ser Thr Tyr Ser Leu Ser
            210                 215                 220

Ser Thr Leu Thr Leu Ser Lys Ala Asp Tyr Glu Lys His Lys Val Tyr
225                 230                 235                 240

Ala Cys Glu Val Thr His Gln Gly Leu Ser Ser Pro Val Thr Lys Ser
                245                 250                 255

Phe Asn Arg Gly Glu Cys
                260

<210> SEQ ID NO 507
<211> LENGTH: 464
<212> TYPE: PRT
<213> ORGANISM: Artificial Sequence
<220> FEATURE:
<223> OTHER INFORMATION: Synthetic Antibody chain: XB2202 IgG1

<400> SEQUENCE: 507

Gly Trp Ser Leu Ile Leu Leu Phe Leu Val Ala Val Ala Thr Arg Val
1               5                   10                  15

Leu Ser Gln Val Gln Leu Val Gln Ser Gly Ala Glu Val Lys Lys Pro
            20                  25                  30

Gly Ser Ser Val Arg Val Ser Cys Lys Ala Ser Gly Gly Thr Phe Ser
        35                  40                  45

Arg His Ala Ile Ser Trp Val Arg Gln Ala Pro Gly Gln Gly Leu Glu
    50                  55                  60

Trp Ile Gly Gly Ile Leu Pro Ile Leu Lys Thr Pro Asn Tyr Ala Gln
65                  70                  75                  80

Arg Phe Gln Gly Arg Val Thr Ile Asn Ala Asp Glu Ser Thr Ser Thr
                85                  90                  95

Val Tyr Met Glu Met Ser Ser Leu Arg Ser Glu Asp Thr Ala Val Tyr
            100                 105                 110

Tyr Cys Ala Thr His Gly Gly Asp Arg Ser Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
```

```
                275                 280                 285
Glu Val Lys Phe Asn Trp Tyr Val Asp Gly Val Glu Val His Asn Ala
        290                 295                 300
Lys Thr Lys Pro Arg Glu Glu Gln Tyr Asn Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
                355                 360                 365
Pro Pro Ser Arg Asp Glu Leu Thr Lys Asn Gln Val Ser Leu Thr Cys
370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
                435                 440                 445
Leu His Asn His Tyr Thr Gln Lys Ser Leu Ser Leu Ser Pro Gly Lys
            450                 455                 460

<210> SEQ ID NO 508
<211> LENGTH: 262
<212> TYPE: PRT
<213> ORGANISM: Artificial Sequence
<220> FEATURE:
<223> OTHER INFORMATION: Synthetic Antibody chain: A4 Ckappa

<400> SEQUENCE: 508

Asp Phe Gln Val Gln Ile Ile Ser Phe Leu Leu Ile Ser Ala Ser Val
1               5                   10                  15
Ile Met Ser Arg Gly Asp Val Val Met Thr Gln Ser Pro Ser Ser Leu
            20                  25                  30
Ser Ala Ser Val Gly Asp Arg Val Thr Ile Thr Cys Gln Ala Ser Gln
        35                  40                  45
Asp Ile Ser Asn Trp Leu Asn Trp Tyr Gln Gln Lys Pro Gly Lys Ala
    50                  55                  60
Pro Lys Leu Leu Ile Tyr Glu Ala Ser Asn Leu Glu Thr Gly Val Pro
65                  70                  75                  80
Ser Arg Phe Ser Gly Ser Gly Ser Gly Thr Asp Phe Thr Phe Thr Ile
                85                  90                  95
Ser Ser Leu Gln Pro Glu Asp Ile Ala Thr Tyr Tyr Cys Gln Gln Tyr
            100                 105                 110
Asn Asn Val Leu Arg Thr Phe Gly Gln Gly Thr Lys Val Glu Ile Lys
        115                 120                 125
Arg Thr Val Ala Ala Pro Ser Val Phe Ile Phe Pro Pro Ser Asp Glu
    130                 135                 140
Gln Leu Lys Ser Gly Thr Lys Val Glu Ile Lys Arg Thr Val Ala Ala
145                 150                 155                 160
Pro Ser Val Phe Ile Phe Pro Pro Ser Asp Glu Gln Leu Lys Ser Gly
                165                 170                 175
Thr Ala Ser Val Val Cys Leu Leu Asn Asn Phe Tyr Pro Arg Glu Ala
```

-continued

```
                180                   185                   190
Lys Val Gln Trp Lys Val Asp Asn Ala Leu Gln Ser Gly Asn Ser Gln
            195                   200                   205

Glu Ser Val Thr Glu Gln Asp Ser Lys Asp Ser Thr Tyr Ser Leu Ser
        210                   215                   220

Ser Thr Leu Thr Leu Ser Lys Ala Asp Tyr Glu Lys His Lys Val Tyr
225                 230                   235                   240

Ala Cys Glu Val Thr His Gln Gly Leu Ser Ser Pro Val Thr Lys Ser
                245                   250                   255

Phe Asn Arg Gly Glu Cys
            260
```